US011760977B2

(12) United States Patent
Evans et al.

(10) Patent No.: US 11,760,977 B2
(45) Date of Patent: Sep. 19, 2023

(54) COMPOSITIONS AND METHODS FOR ORGANOID GENERATION AND DISEASE MODELING

(71) Applicant: SALK INSTITUTE FOR BIOLOGICAL STUDIES, La Jolla, CA (US)

(72) Inventors: Ronald Evans, La Jolla, CA (US); Michael Downes, La Jolla, CA (US); Annette Atkins, La Jolla, CA (US); Eiji Yoshihara, La Jolla, CA (US); Ruth Yu, La Jolla, CA (US)

(73) Assignee: SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 837 days.

(21) Appl. No.: 16/301,671

(22) PCT Filed: May 24, 2017

(86) PCT No.: PCT/US2017/034278
§ 371 (c)(1),
(2) Date: Nov. 14, 2018

(87) PCT Pub. No.: WO2017/205511
PCT Pub. Date: Nov. 30, 2017

(65) Prior Publication Data
US 2019/0211310 A1 Jul. 11, 2019

Related U.S. Application Data
(60) Provisional application No. 62/341,461, filed on May 25, 2016.

(51) Int. Cl.
C12N 5/071 (2010.01)
G01N 33/50 (2006.01)
A61K 35/39 (2015.01)

(52) U.S. Cl.
CPC ............ *C12N 5/0677* (2013.01); *A61K 35/39* (2013.01); *G01N 33/5088* (2013.01); *C12N 2501/117* (2013.01); *C12N 2501/16* (2013.01); *C12N 2501/385* (2013.01); *C12N 2501/395* (2013.01); *C12N 2501/415* (2013.01); *C12N 2501/727* (2013.01); *C12N 2501/999* (2013.01); *C12N 2502/1382* (2013.01); *C12N 2502/28* (2013.01); *C12N 2503/02* (2013.01); *C12N 2506/02* (2013.01); *C12N 2506/45* (2013.01); *C12N 2513/00* (2013.01); *C12N 2533/52* (2013.01); *C12N 2533/54* (2013.01); *C12N 2533/90* (2013.01); *G01N 2800/04* (2013.01); *G01N 2800/7028* (2013.01)

(58) Field of Classification Search
CPC .................................................. C12N 5/0677
See application file for complete search history.

(56) References Cited

U.S. PATENT DOCUMENTS

| 4,683,202 | A | 7/1987 | Mullis |
| 5,399,346 | A | 3/1995 | Anderson et al. |
| 5,854,033 | A | 12/1998 | Lizardi |
| 5,942,435 | A | 8/1999 | Wheeler |
| 9,102,920 | B2 | 8/2015 | Feng et al. |
| 9,546,379 | B2 | 1/2017 | Evans et al. |
| 10,520,494 | B2 | 12/2019 | Zentrum |
| 10,912,800 | B2 | 2/2021 | Evans et al. |
| 10,920,199 | B2 | 2/2021 | Evans et al. |
| 2009/0281191 | A1 | 11/2009 | Rangwala et al. |
| 2010/0145470 | A1* | 6/2010 | Cohen ...................... A61L 27/56 435/325 |
| 2011/0028401 | A1 | 2/2011 | Minchiotti et al. |
| 2011/0165570 | A1 | 7/2011 | Feng et al. |
| 2012/0039919 | A1 | 2/2012 | Yang et al. |
| 2012/0302491 | A1 | 11/2012 | Narkar et al. |
| 2013/0195811 | A1 | 8/2013 | Wang et al. |
| 2014/0289877 | A1* | 9/2014 | Taniguchi ........... A61L 27/3886 435/1.1 |
| 2015/0203818 | A1 | 7/2015 | Mountford et al. |
| 2015/0368667 | A1 | 12/2015 | Evans et al. |
| 2016/0083693 | A1* | 3/2016 | Xu ......................... A61K 35/39 424/499 |

(Continued)

FOREIGN PATENT DOCUMENTS

| CA | 2937882 A1 | 9/2015 |
| EP | 2878664 A1 | 6/2015 |

(Continued)

OTHER PUBLICATIONS

Raikwar et al. (2015, PLOS One, vol. 10(1), e0116582, pp. 1-15). (Year: 2015).*
Bosnak et al. (2002, Diabetes Care, vol. 25(3), pp. 629-630).*
Yoshihara et al. (Apr. 2016, Cell Metabolism, vol. 23, pp. 622-634) (Year: 2016).*
Mandel, et al., "SERKAL Syndrome: An Autosomal-Recessive Disorder Caused by a Loss-of-Function Mutation in WNT4," Am. J. Hum. Genet., Jan. 2008, vol. 82, No. 1, p. 39-47.
Raikwar, et al., "Human iPS Cell-Derived Insulin Producing Cells Form Vascularized Organoids under the Kidney Capsules of Diabetic Mice," PLos One, Jan. 28, 2015, vol. 10, No. 1, p. e0116582.
International Search Report for corresponding PCT Patent Application No. PCT/US17/34278, dated Oct. 31, 2017, (16 pages).

(Continued)

*Primary Examiner* — Peter Paras, Jr.
*Assistant Examiner* — David A Montanari
(74) *Attorney, Agent, or Firm* — Melissa Hunter-Ensor; Leslie Serunion; Greenberg Traurig, LLP

(57) ABSTRACT

The invention features pancreatic islet and pancreatic organoids, and cell cultures and methods that are useful for the rapid and reliable generation of pancreatic islet and pancreatic islet organoids. The invention also features methods of treating pancreatic diseases and methods of identifying agents that are useful for treatment of pancreatic diseases, such as type 2 diabetes and pancreatic cancer, using the pancreatic islet and pancreatic organoids of the invention.

16 Claims, 38 Drawing Sheets
Specification includes a Sequence Listing.

(56) References Cited

U.S. PATENT DOCUMENTS

| | | |
|---|---|---|
| 2017/0087189 A1 | 3/2017 | Evans et al. |
| 2018/0044642 A1 | 2/2018 | Evans et al. |
| 2021/0283187 A1 | 9/2021 | Evans et al. |
| 2021/0363490 A1 | 11/2021 | Yoshihara et al. |
| 2022/0220446 A1 | 7/2022 | Evans et al. |

FOREIGN PATENT DOCUMENTS

| | | |
|---|---|---|
| EP | 2940127 A1 | 11/2015 |
| JP | 2009533017 A | 9/2009 |
| JP | 2011522520 A | 8/2011 |
| JP | 2016514481 A | 5/2016 |
| WO | 2001015755 A2 | 3/2001 |
| WO | 2006063733 A1 | 6/2006 |
| WO | 2006063734 A2 | 6/2006 |
| WO | 2006063735 A1 | 6/2006 |
| WO | 2006063736 A1 | 6/2006 |
| WO | 2006119886 A1 | 11/2006 |
| WO | 2006119887 A1 | 11/2006 |
| WO | 2006119888 A2 | 11/2006 |
| WO | 2009136867 A1 | 11/2009 |
| WO | 2011160066 A1 | 12/2011 |
| WO | 2012044486 A1 | 4/2012 |
| WO | 2013159103 A1 | 10/2013 |
| WO | 2014017513 A1 | 1/2014 |
| WO | 2014104364 A1 | 7/2014 |
| WO | 2014145625 A1 | 9/2014 |
| WO | 2015148832 A1 | 10/2015 |
| WO | 2016015158 A1 | 2/2016 |
| WO | 2016100898 A1 | 6/2016 |
| WO | 2016100909 A1 | 6/2016 |
| WO | 2016100921 A1 | 6/2016 |
| WO | 2016100925 A1 | 6/2016 |
| WO | 2016100930 A1 | 6/2016 |
| WO | 2017205511 A1 | 11/2017 |
| WO | 2018156955 A1 | 8/2018 |

OTHER PUBLICATIONS

Extended European Search Report issued in corresponding European Patent Application No. 17803511.9, dated Jul. 9, 2020 (12 pages).

Zhang et al., "Esrrb Activates Oct4 Transcription and Sustains Self-renewal and Pluripotency in Embryonic Stem Cells," Molecular Basis of Cell and Developmental Biology, Dec. 19, 2008, vol. 283, No. 51, pp. 35825-35833.

Zhang et al., "Metabolic Regulation in Pluripotent Stem Cells during Reprogramming and Self-Renewal," Cell Stem Cell, Nov. 2, 2012, vol. 11, pp. 589-595.

Zhao et al., "Overexpression of lactate dehydrogenase A attenuates glucose-induced insulin secretion in stable MIN-6 β-cell lines," FEBS Letters, 1998, vol. 430, pp. 213-216.

Zuckermann et al., "Discovery of Nanomolar Ligands for 7-Transmembrane G-Protein-Coupled Receptors from a Diverse N-(Substituted)glycine Peptoid Library," Journal of Medicinal Chemistry, 1994, vol. 37, pp. 2678-2685.

Extended European Search Report dated Dec. 1, 2021 in European Patent Application No. 21180343.2 (9 pages).

Saito et al., "Generation of Glucose-Responsive Functional Islets with a Three-Dimensional Structure from Mouse Fetal Pancreatic Cells and iPS Cells In Vitro," PLoS One, Dec. 1, 2011, vol. 6, No. 12, p. e28209 (7 pages).

Takebe et al., "Vascularized and functional human liver from an iPSC-derived organ bud transplant," Nature, Jul. 1, 2013, vol. 499, No. 7459, pp. 481-485 (5 pages).

Partial Supplementary European Search Report in corresponding European Patent Application No. 17803511.9, dated Apr. 7, 2020 (13 pages).

Yoshihara et al., "Disruption of TBP-2 ameliorates insulin sensitivity and secretion without affecting obesity," Nature Communications, 2010, vol. 1, Article No. 127, pp. 1-12.

Examination Report dated Jul. 26, 2021 in corresponding European Patent Application No. 17803511.9 (4 pages).

International Search Report and Written Opinion dated Oct. 31, 2017 in corresponding International PCT Patent Application No. PCT/US2017/034278 (22 pages).

Akinci et al., "Reprogramming of Various Cell Types to a Beta-Like State by Pdx1, Ngn3 and MafA," PLOS one, Nov. 2013, vol. 8, No. 11, pp. e82424.

Alaynick et al., "ERRγ Directs and Maintains the Transition to Oxidative Metabolism in the Postnatal Heart," Cell Metabolism, Jul. 2007, vol. 6, pp. 13-24.

Anderson, W. French, "Prospects for Human Gene Therapy," Science, Oct. 26, 1984, vol. 226, No. 4673, pp. 401-409.

Anello et al., "Functional and morphological alterations of mitochondria in pancreatic beta cells from type 2 diabetic patients," Diabetologia, 2005, vol. 48, pp. 282-289.

Ansari et al., "The Programmed Death-1 (PD-1) Pathway Regulates Autoimmune Diabetes in Nonobese Diabetic (NOD) Mice," Journal of Experimental Medicine, Jul. 7, 2003, vol. 198, No. 1, pp. 63-69.

Bader et al., "Identification of proliferative and mature β-cells in the islets of Langerhans," Nature, Jul. 21, 2016, vol. 535, pp. 430-434.

Barany, F., "Genetic disease detection and DNA amplification using cloned thermostable ligase," PNAS, Jan. 1991, vol. 88, pp. 189-193.

Bar-Ephraim et al., "Modelling cancer immunomodulation using epithelial organoid cultures," BioRxiv, 2018.

Blomer et al., "Highly efficient and sustained gene transfer in adult neurons with a lentivirus vector," Journal of Virology, Sep. 1997, vol. 71, No. 9, pp. 6641-6649.

Brevini et al., "No shortcuts to pig embryonic stem cells," Theriogenology, 2010, vol. 74, pp. 544-550.

Buenrostro et al., "ATAC-seq: A Method for Assaying Chromatin Accessibility Genome-Wide," Current Protocols in Molecular Biology, 2016, vol. 109, pp. 21.29.1-21.29.9.

Buganim et al., "Single-Cell Expression Analyses during Cellular Reprogramming Reveal an Early Stochastic and a Late Hierarchic Phase," Cell, Sep. 14, 2012, vol. 150, pp. 1209-1222.

Buganim et al., "The Developmental Potential of iPSCs Is Greatly Influenced by Reprogramming Factor Selection," Cell Stem Cell, Sep. 4, 2014, vol. 15, pp. 295-309.

Carey et al., "Single-gene transgenic mouse strains for reprogramming adult somatic cells," Nature Methods, Jan. 2010, vol. 7, No. 1, pp. 56-59.

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy, Mar. 1, 1997, vol. 8, pp. 423-430.

Chen et al., "Integration of External Signaling Pathways with the Core Transcriptional Network in Embryonic Stem Cells," Cell, Jun. 13, 2008, vol. 133, pp. 1106-1117.

Chen et al., "PDGF signalling controls age-dependent proliferation in pancreatic β-cells," Nature, 2012, vol. 478, No. 7369, pp. 349-355.

Colli et al., "PDL1 is expressed in the islets of people with type 1 diabetes and is up-regulated by interferons-α and-γ via IRF1 induction," EBioMedicine, 2018, vol. 36, pp. 367-375.

Conrad et al., "Revealing transcription factors during human pancreatic β cell development," Trends in Endocrinology & Metabolism, Aug. 2014, vol. 25, No. 8, pp. 407-414.

Crunkhorn, Sarah, "Human iPSC-derived β-like cells rescue diabetic mice," Nature Reviews Drug Discovery, 2016. vol. 15, No. 383.

Ding et al., "Activation of CD4+ T cells by delivery of the B7 costimulatory signal on bystander antigen-presenting cells (transcostimulation)," European Journal of Immunology, 1994, vol. 24, pp. 859-866.

Dobin et al., "STAR: ultrafast universal RNA-seq aligner," Bioinformatics, 2013, vol. 29, No. 1, pp. 15-21.

Dor et al., "Adult pancreatic β-cells are formed by self-duplication rather than stem-cell differentiation," Nature, May 6, 2004, vol. 429, pp. 41-46.

Dufour et al., "Genome-wide Orchestration of Cardiac Functions by the Orphan Nuclear Receptors ERRα and γ," Cell Metabolism, May 2007, vol. 5, pp. 345-356.

(56) References Cited

OTHER PUBLICATIONS

Felgner et al., "Lipofection: a highly efficient, lipid-mediated DNA-transfection procedure," PNAS, Nov. 1987, vol. 84, pp. 7413-7417.
Feng et al., "Reprogramming of fibroblasts into induced pluripotent stem cells with orphan nuclear receptor Esrrb," Nature Cell Biology, Feb. 2009, vol. 11, No. 2, pp. 197-203.
Festuccia et al., "Esrrb Is a Direct Nanog Target Gene that Can Substitute for Nanog Function in Pluripotent Cells," Cell Stem Cell, Oct. 5, 2012, vol. 11, pp. 477-490.
Foks et al., "Immune checkpoint proteins: exploring their therapeutic potential to regulate atherosclerosis," British journal of Pharmacology, 2017, vol. 174, pp. 3940-3955.
Folmes et al., "Somatic Oxidative Bioenergetics Transitions into Pluripotency-Dependent Glycolysis to Facilitate Nuclear Reprogramming," Cell Metabolism, Aug. 3, 2011, vol. 14, pp. 264-271.
Friedmann, Theodore, "Progress Toward Human Gene Therapy," Science, Jun. 16, 1989, vol. 244, No. 4910, pp. 1275-1281.
Guatelli et al., "Isothermal, in vitro amplification of nucleic acids by a multienzyme reaction modeled after retroviral replication," PNAS, Mar. 1990, vol. 87, pp. 1874-1878.
Hackenbrock, Charles R., "Ultrastructural Bases for Metabolically Linked Mechanical Activity in Mitochondria : I. Reversible Ultrastructural Changes with Change in Metabolic Steady State in Isolated Liver Mitochondria," Journal of Cell Biology, 1966, vol. 30, pp. 269-297.
Hart et al., "Attenuation of FGF signalling in mouse β-cells leads to diabetes," Nature, Dec. 14, 2000, vol. 408, pp. 864-868.
Heinz et al., "Simple Combinations of Lineage-Determining Transcription Factors Prime cis-Regulatory Elements Required for Macrophage and B Cell Identities," Molecular Cell, May 28, 2010, vol. 38, pp. 576-589.
Hickey et al., "Generation of islet-like cells from mouse gall bladder by direct ex vivo reprogramming," Stem Cell Research, 2013, vol. 11, pp. 503-515.
Hrvatin et al., "Differentiated human stem cells resemble fetal, not adult, β cells," PNAS, Feb. 25, 2014, vol. 111, No. 8, pp. 3038-3043.
Huang et al., "Enhanced Differentiation of Three-Gene-Reprogrammed Induced Pluripotent Stem Cells into Adipocytes via Adenoviral-Mediated PGC-1α Overexpression," International Journal of Molecular Sciences, 2011, vol. 12, pp. 7554-7568.
Huang et al., "Systematic and integrative analysis of large gene lists using DAVID bioinformatics resources," Nature Protocols, 2009, vol. 4, pp. 44-57.
Johnson, Larry G., "Gene Therapy for Cystic Fibrosis," Chest, Feb. 1995, vol. 107, pp. 77S-83S.
Kapturczak et al., "Transduction of Human and Mouse Pancreatic Islet Cells Using a Bicistronic Recombinant Adeno-associated Viral Vector," Molecular Therapy, Feb. 2002, vol. 5, No. 2, pp. 154-160.
Kawaguchi et al., "Generation of Naive Bovine Induced Pluripotent Stem Cells Using PiggyBac Transposition of Doxycycline-Inducible Transcription Factors," PLOS one, Aug. 19, 2015, vol. 10, pp. 1-18.
Kawamure et al., "Linking the p53 tumour suppressor pathway to somatic cell reprogramming," Nature, Aug. 27, 2009, vol. 460, No. 7259, pp. 1140-1144.
Kida et al., "ERRs Mediate a Metabolic Switch Required for Somatic Cell Reprogramming to Pluripotency," Cell Stem Cell, May 7, 2015, vol. 16, pp. 547-555.
Kwoh et al., "Transcription-based amplification system and detection of amplified human immunodeficiency virus type 1 with a bead-based sandwich hybridization format," PNAS, Feb. 1989, vol. 86, pp. 1173-1177.
Le Gal La Salle et al., "An Adenovirus Vector for Gene Transfer into Neurons and Glia in the Brain," Science, Feb. 12, 1993, vol. 259, No. 5097, pp. 988-990.
Lee et al., "Decoding the Pluripotency Network: The Emergence of New Transcription Factors," Biomedicines, 2013, vol. 1, pp. 49-78.

Li et al., "Small Molecules Facilitate the Reprogramming of Mouse Fibroblasts into Pancreatic Lineages," Cell Stem Cell, Feb. 6, 2014, vol. 14, pp. 228-236.
Liu et al., "Cells that present both specific ligand and costimulatory activity are the most efficient inducers of clonal expansion of normal CD4 T cells," PNAS, May 1992, vol. 89, pp. 3845-3849.
Ludwig et al., "Feeder-independent culture of human embryonic stem cells," Nature Methods, Aug. 2006, vol. 3, No. 8, pp. 637-646.
Ludwig et al., "Transplantation of human islets without immuno-suppression," PNAS, Nov. 19, 2013, vol. 110, No. 47, pp. 19054-19058.
Baidal et al., "Bioengineering of an Intraabdominal Endocrine Pancreas," The New England Journal of Medicine, May 11, 2017, vol. 376, No. 19, pp. 1887-1889 (5 pages).
Burns et al., "High-Throughput Luminescent Reporter of Insulin Secretion for Discovering Regulators of Pancreatic Beta-Cell Function," Cell Metabolism, Jan. 6, 2015, vol. 21, pp. 126-137 (24 pages).
D'Amour et al., "Production of pancreatic hormone-expressing endocrine cells from human embryonic stem cells," Nature Biotechnology, Nov. 2006, vol. 24, No. 11, pp. 1392-1401 (11 pages).
Kroon et al., "Pancreatic endoderm derived from human embryonic stem cells generates glucose-responsive insulin-secreting cells in vivo," Nature Biotechnology, Apr. 2008, vol. 26, No. 4, pp. 443-452 (11 pages).
Pagliuca et al., "Generation of Functional Human Pancreatic β Cells In Vitro," Cell, Oct. 9, 2014, vol. 159, pp. 428-439 (12 pages).
Rezania et al., "Reversal of diabetes with insulin-producing cells derived in vitro from human pluripotent stem cells," Nature Biotechnology, Nov. 2014, vol. 32, No. 11, pp. 1121-1133 (14 pages).
Russ et al., "Controlled induction of human pancreatic progenitors produces functional beta-like cells in vitro," The EMBO Journal, 2015, vol. 34, No. 13, pp. 1759-1772 (14 pages).
Vegas et al., "Combinatorial hydrogel library enables identification of materials that mitigate the foreign body response in primates," Nature Biotechnology, Mar. 2016, vol. 34, No. 3, pp. 345-352 (32 pages).
Vegas et al., "Long term Glycemic Control Using Polymer Encapsulated, Human Stem-Cell Derived β-cells in Immune Competent mice," Nature Medicine, Mar. 2016, vol. 22, No. 3, pp. 306-311 (21 pages).
Willert et al., "Wnt Proteins," Cold Spring Harbor Perspectives in Biology, Sep. 1, 2012, vol. 4, No. 9, a007864, pp. 1-13 (13 pages).
Yoshihara et al., "ERRγ Is Required for the Metabolic Maturation of Therapeutically Functional Glucose-Responsive β Cells," Cell Metabolism, Apr. 12, 2016, vol. 23, pp. 622-634 (14 pages).
Yu et al., "Human induced pluripotent stem cells free of vector and transgene sequences," Science, May 8, 2009 [Corrected: Jun. 5, 2009], vol. 324, No. 5928, pp. 797-801 (8 pages).
Sneddon et al., "Self-renewal of embryonic-stem-cell-derived progenitors by organ-matched mesenchyme," Nature, Nov. 29, 2012, vol. 491, No. 7426, pp. 765-768.
Soltanian et al., "Morphogenesis of Human Pluripotent Stem Cell Aggregates toward Pancreatic Progenitors in Suspension Culture," Cell Journal (Yakhteh), 2015, vol. 17, Suppl. 1, Ps-86, p. 59.
Office Action dated Apr. 30, 2021 in corresponding Japanese Patent Application No. 2018-561550 (9 pages).
English translation of the Office Action dated Apr. 30, 2021 in corresponding Japanese Patent Application No. 2018-561550 (6 pages).
Examination Report dated Aug. 18, 2022 in corresponding Australian Patent Application No. 2017269364 (4 pages).
Office Action dated Mar. 30, 2022 in corresponding Japanese Patent Application No. 2018-561550 (4 pages).
English translation of the Office Action dated Mar. 30, 2022 in corresponding Japanese Patent Application No. 2018-561550 (4 pages).
Jaramillo et al., "Potential for Pancreatic Maturation of Differentiating Human Embryonic Stem Cells Is Sensitive to the Specific Pathway of Definitive Endoderm Commitment," PLoS One, Apr. 2014, vol. 9, No. 4, e94307, pp. 1-14.
Liu et al., "All mixed up: defining roles for β-cell subtypes in mature islets," Genes & Development, 2017, vol. 31, pp. 228-240.

(56) References Cited

OTHER PUBLICATIONS

Kemp et al., "Transplantation of Isolated Pancreatic Islets into the Portal Vein of Diabetic Rats," Nature, 1973, vol. 244, p. 447.
Office Action dated Feb. 20, 2023 in corresponding European Patent Application No. 17803511.9 (5 pages).
Mangelsdorf et al., "The Nuclear Receptor Superfamily: The Second Decade," Cell, Dec. 15, 1995, vol. 83, No. 6, pp. 835-839.
Mao et al., "Automated genome annotation and pathway identification using the KEGG Orthology (KO) as a controlled vocabulary," Bioinformatics, 2005, vol. 21, No. 19, pp. 3787-3793.
Mao et al., "Lentiviral Vectors Mediate Long-Term and High Efficiency Transgene Expression in HEK 293T cells," International Journal of Medical Sciences, 2015, vol. 12, No. 5, pp. 407-415.
Martello et al., "Esrrb Is a Pivotal Target of the Gsk3/Tcf3 Axis Regulating Embryonic Stem Cell Self-Renewal," Cell Stem Cell, Oct. 5, 2012, vol. 11, pp. 491-504.
Mathieu et al., "Investigating the real role of HIF-1 and HIF-2 in iron recycling by macrophages," Haematologica, 2014, vol. 99, pp. e112-e114.
Miller et al., "Improved Retroviral Vectors for Gene Transfer and Expression," Biotechniques, Oct. 1989, vol. 7, No. 9, pp. 980-990.
Miller, Dusty A., "Retrovirus Packaging Cells," Human Gene Therapy, 1990, vol. 1, pp. 5-14.
Miyoshi et al., "Stable and efficient gene transfer into the retina using an HIV-based lentiviral vector," PNAS, Sep. 1997, vol. 94, pp. 10319-10323.
Morizane et al., "MHC matching improves engraftment of iPSC-derived neurons in non-human primates," Nature Communications, 2017, vol. 8, No. 385, pp. 1-12.
Munoz et al., "Conventional pluripotency markers are unspecific for bovine embryonic-derived cell-lines," Theriogenology, 2008, vol. 69, pp. 1159-1164.
Naldini et al., "In Vivo Gene Delivery and Stable Transduction of Nondividing Cells by a Lentiviral Vector," Science, Apr. 12, 1996, vol. 272, pp. 263-267.
Narkar et al., "Exercise and PGC-1α-Independent Synchronization of Type I Muscle Metabolism and Vasculature by ERRγ," Cell Metabolism, Mar. 2, 2011, vol. 13, pp. 283-293.
Nasr et al., "PD-L1 genetic overexpression or pharmacological restoration in hematopoietic stem and progenitor cells reverses autoimmune diabetes," Science Translational Medicine, Nov. 15, 2017, vol. 9, No. 416, pp. 1-14.
Nemajerova et al., "Two-factor reprogramming of somatic cells to pluripotent stem cells reveals partial functional redundancy of Sox2 and Klf4," Cell Death & Differentiation, 2012, vol. 19, pp. 1268-1276.
Nichols et al., "Adult tissue sources for new β cells," Translational Research, Apr. 2014, vol. 163, No. 4, pp. 418-431.
Ono et al., "Plasmid DNAs directly injected into mouse brain with lipofectin can be incorporated and expressed by brain cells," Neuroscience Letters, 1990, vol. 117, pp. 259-263.
Osum et al., "Interferon-gamma drives programmed death-ligand 1 expression on islet β cells to limit T cell function during autoimmune diabetes," Scientific Reports, 2018, vol. 8, No. 8295, pp. 1-12.
Pagliuca et al., "How to make a functional β-cell," Development, 2013, vol. 140, No. 12, pp. 2472-2483.
Panopoulos et al., "The metabolome of induced pluripotent stem cells reveals metabolic changes occurring in somatic cell reprogramming," Cell Research, 2012, vol. 22, pp. 168-177.
Paris et al., "Equine embryos and embryonic stem cells: Defining reliable markers of pluripotency," Theriogenology, Sep. 1, 2010, vol. 74, No. 4, pp. 516-524.
Ravassard et al., "A genetically engineered human pancreatic β cell line exhibiting glucose-inducible insulin secretion," The Journal of Clinical Investigation, 2011, vol. 121, No. 9, pp. 3589-3597.
Roberts et al., "Identification of novel transcripts in annotated genomes using RNA-Seq," Bioinformatics, 2011, vol. 27, No. 17, pp. 2325-2329.
Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, vol. 323, No. 9, pp. 570-578.
Roska et al., "Dissection of the functions of antigen-presenting cells in the induction of T cell activation." The Journal of Immunology, 1985, vol. 135, pp. 2953-2961.
Said et al., "Programmed death-1-induced interleukin-10 production by monocytes impairs CD4+ T cell activation during HIV infection," Nature Medicine, Apr. 2010, vol. 16, No. 4, pp. 452-459.
Schulz et al., "A Scalable System for Production of Functional Pancreatic Progenitors from Human Embryonic Stem Cells," PLOS one, May 2012, vol. 7, No. 5, pp. e37004.
Shyh-Chang et al., "Influence of Threonine Metabolism on S-Adenosylmethionine and Histone Methylation," Science, Jan. 11, 2013, vol. 339, No. 6116, pp. 222-226.
Subudhi et al., "Local expression of B7-H1 promotes organ-specific autoimmunity and transplant rejection," The Journal of Clinical Investigation, 2004, vol. 113, No. 5, pp. 694-700.
Sugii et al., "Human and mouse adipose-derived cells support feeder-independent induction of pluripotent stem cells," PNAS, Feb. 23, 2010, vol. 107, No. 8, pp. 3558-3563.
Sutton et al., "Isolation of Rat Pancreatic Islets by Ductal Injection of Collagenase," Transplantation, Dec. 1986, vol. 42, No. 6, pp. 689-690.
Takahashi et al., "Induction of Pluripotent Stem Cells from Adult Human Fibroblasts by Defined Factors," Cell, Nov. 30, 2007, vol. 131, pp. 861-872.
Takahashi et al., "Induction of Pluripotent Stem Cells from Mouse Embryonic and Adult Fibroblast Cultures by Defined Factors," Cell, Aug. 25, 2006, vol. 126, pp. 663-676.
Tang et al., "Desnutrin/ATGL Activates PPARδ to Promote Mitochondrial Function for Insulin Secretion in Islet β Cells," Cell Metabolism, Dec. 3, 2013, vol. 18, pp. 883-895.
Teta et al., "Very Slow Turnover of β-Cells in Aged Adult Mice," Diabetes, Sep. 2005, vol. 54, pp. 2557-2567.
Tolstoshev et al., "Gene expression using retroviral vectors," Current Opinion in Biotechnology, 1990, vol. 1, pp. 55-61.
Trapnell et al., "Differential analysis of gene regulation at transcript resolution with RNA-seq," Nature Biotechnology, Jan. 2013, vol. 31, No. 1, pp. 1-19.
Tsonkova et al., "The EndoC-βH1 cell line is a valid model of human beta cells and applicable for screenings to identify novel drug target candidates," Molecular Metabolism, 2018, vol. 8, pp. 144-157.
Vaithilingam et al., "Co-encapsulation and co-transplantation of mesenchymal stem cells reduces pericapsular fibrosis and improves encapsulated islet survival and function when allografted," Scientific Reports, 2017, vol. 7, No. 10059, pp. 1-13.
Vethe et al., "The Effect of Wnt Pathway Modulators on Human iPSC-Derived Pancreatic Beta Cell Maturation," Frontiers in Endocrinology, May 2019, vol. 10, No. 293, pp. 1-13.
Wei et al., "Klf4 Interacts Directly with Oct4 and Sox2 to Promote Reprogramming," Stem Cells, 2009, vol. 27, No. 12, pp. 2969-2978.
Wei et al., "Klf4 Organizes Long-Range Chromosomal Interactions with the Oct4 Locus in Reprogramming and Pluripotency," Cell Stem Cell, Jul. 3, 2013, vol. 13, pp. 36-47.
Wendeln et al., "Innate immune memory in the brain shapes neurological disease hallmarks," Nature, Apr. 2018, vol. 556, No. 7701, pp. 332-338.
Wolff et al., "Direct Gene Transfer into Mouse Muscle in Vivo," Science, Mar. 23, 1990, vol. 247, pp. 1465-1468.
Wu et al., "Receptor-mediated Gene Delivery and Expression in Vivo," Journal of Biological Chemistry, Oct. 15, 1988, vol. 263, No. 29, pp. 14621-14624.
Wu et al., "Targeting Genes: Delivery and Persistent Expression of a Foreign Gene Driven by Mammalian Regulatory Elements in Vivo," Journal of Biological Chemistry, Oct. 15, 1989, vol. 264, No. 29, pp. 16985-16987.
Wulfing et al., "A Receptor/Cytoskeletal Movement Triggered by Costimulation During T Cell Activation," Science, Dec. 18, 1998, vol. 282, pp. 2266-2269.

(56) References Cited

OTHER PUBLICATIONS

Xu et al., "The role of pyruvate carboxylase in insulin secretion and proliferation in rat pancreatic beta cells," Diabetologia, 2008, vol. 51, pp. 2022-2030.
Yang et al., "Nuclear Receptor Expression Links the Circadian Clock to Metabolism," Cell, Aug. 25, 2006, vol. 126, pp. 801-810.
Yu et al., "Induced Pluripotent Stem Cell Lines Derived from Human Somatic Cells," Science, 2007, vol. 318, pp. 1917-1920.
Zhang et al., "Efficient Reprogramming of Naïve-Like Induced Pluripotent Stem Cells from Porcine Adipose-Derived Stem Cells with a Feeder-Independent and Serum-Free System," PLOS one, Jan. 2014, vol. 9, No. 1, pp. e85089.

\* cited by examiner

Human ADSC 3D culture

Systematic Self-organization to sphere formation

Cell number in 1well of 24well with 30μl Matrigel

FIG. 2D-1
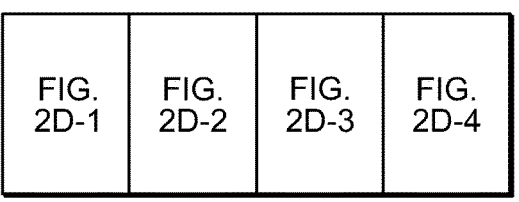
FIG. 2D
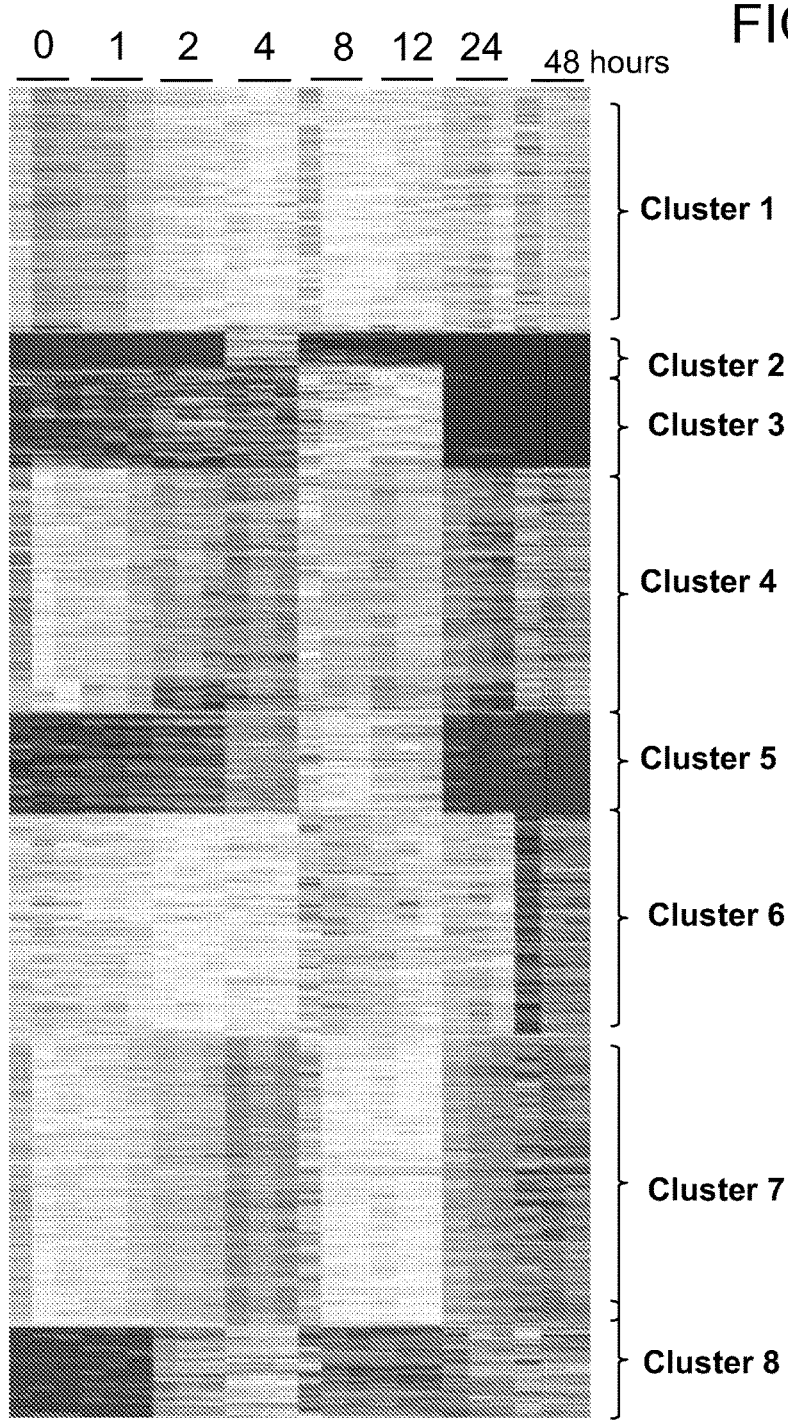
8448 genes by one-way ANOVA
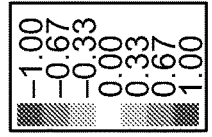

FIG. 2D-2

Cluster 1

| Term | Count | P-Value |
|---|---|---|
| Pyrimidine metabolism | 16 | 3.80E-03 |
| Endocytosis | 25 | 4.20E-03 |
| Pathways in cancer | 36 | 1.60E-02 |
| Propanoate metabolism | 7 | 2.70E-02 |
| Aminoacyl-tRNA biosynthesis | 8 | 2.90E-02 |
| Spliceosome | 16 | 4.40E-02 |
| DNA replication | 7 | 4.60E-02 |
| Lysosome | 15 | 4.90E-02 |

Cluster 2

| Term | Count | P-Value |
|---|---|---|
| Cytokine-cytokine receptor interaction | 14 | 2.40E-04 |
| Bladder cancer | 5 | 4.40E-03 |
| Pathways in cancer | 12 | 1.50E-02 |
| Fructose and mannose metabolism | 4 | 1.70E-02 |
| Neurotrophin signaling pathway | 6 | 4.90E-02 |
| Hematopoietic cell lineage | 5 | 4.90E-02 |

Cluster 3

| Term | Count | P-Value |
|---|---|---|
| Calcium signaling pathway | 15 | 1.00E-03 |
| NOD-like receptor signaling pathway | 8 | 2.90E-03 |
| p53 signaling pathway | 8 | 4.80E-03 |
| MAPK signaling pathway | 17 | 8.30E-03 |
| Pathways in cancer | 18 | 2.50E-02 |
| Inositol phosphate metabolism | 6 | 2.50E-02 |
| Cytokine-cytokine receptor interaction | 15 | 3.20E-02 |
| Melanogenesis | 8 | 3.40E-02 |
| Dorso-ventral axis formation | 4 | 4.10E-02 |

FIG. 2D-3

Cluster 4

| Term | Count | P-Value |
|---|---|---|
| TGF-beta signaling pathway | 16 | 2.30E-04 |
| Adherens junction | 14 | 7.50E-04 |
| Axon guidance | 19 | 8.50E-04 |
| Chronic myeloid leukemia | 13 | 1.90E-03 |
| ErbB signaling pathway | 14 | 2.40E-03 |
| Pathways in cancer | 34 | 3.20E-03 |
| Pancreatic cancer | 12 | 4.20E-03 |
| Lysine degradation | 9 | 4.80E-03 |
| Wnt signaling pathway | 19 | 5.10E-03 |
| Neurotrophin signaling pathway | 16 | 8.90E-03 |

Cluster 5

| Term | Count | P-Value |
|---|---|---|
| Cell cycle | 17 | 4.60E-06 |
| Oocyte meiosis | 14 | 8.70E-05 |
| Terpenoid backbone biosynthesis | 5 | 1.40E-03 |
| Progesterone-mediated oocyte maturation | 10 | 2.60E-03 |
| Valine, leucine and isoleucine degradation | 7 | 3.60E-03 |
| Biosynthesis of unsaturated fatty acids | 5 | 6.10E-03 |
| Pathogenic Escherichia coli infection | 7 | 1.30E-03 |
| Butanoate metabolism | 5 | 2.80E-02 |
| p53 signaling pathway | 7 | 2.90E-02 |
| Gap junction | 8 | 3.30E-02 |

Cluster 6

| Term | Count | P-Value |
|---|---|---|
| Lysosome | 20 | 5.00E-04 |
| ErbB signaling pathway | 14 | 7.80E-03 |
| MAPK signaling pathway | 30 | 1.30E-02 |
| Basal cell carcinoma | 10 | 1.40E-02 |
| Adipocytokine signaling pathway | 11 | 1.90E-02 |
| Acute myeloid leukemia | 10 | 2.00E-02 |
| Complement and coagulation cascades | 11 | 2.30E-02 |

FIG. 2D-4

Cluster 7

| Term | Count | P-Value |
|---|---|---|
| Parkinson's disease | 51 | 1.90E-16 |
| Huntington's disease | 60 | 5.50E-15 |
| Oxidative phosphorylation | 46 | 1.30E-12 |
| Proteasome | 26 | 2.20E-12 |
| Spliceosome | 43 | 3.10E-11 |
| Alzheimer's disease | 45 | 1.90E-08 |
| Citrate cycle (TCA cycle) | 16 | 3.20E-07 |
| Pathogenic Escherichia coli infection | 19 | 3.50E-05 |
| Glyoxylate and dicarboxylate metabolism | 8 | 6.80E-04 |
| Pyruvate metabolism | 12 | 4.00E-03 |

Cluster 8

| Term | Count | P-Value |
|---|---|---|
| Cytokine-cytokine receptor interaction | 25 | 9.00E-06 |
| Hematopoietic cell lineage | 11 | 6.90E-04 |
| Pathways in cancer | 24 | 8.20E-04 |
| Jak-STAT signaling pathway | 15 | 8.60E-04 |
| Dorso-ventral axis formation | 6 | 1.40E-03 |
| Melanoma | 9 | 2.90E-03 |
| VEGF signaling pathway | 9 | 4.10E-03 |
| MAPK signaling pathway | 19 | 4.70E-03 |
| Fructose and mannose metabolism | 6 | 5.80E-03 |
| Natural killer cell mediated cytotoxicity | 12 | 6.00E-03 |

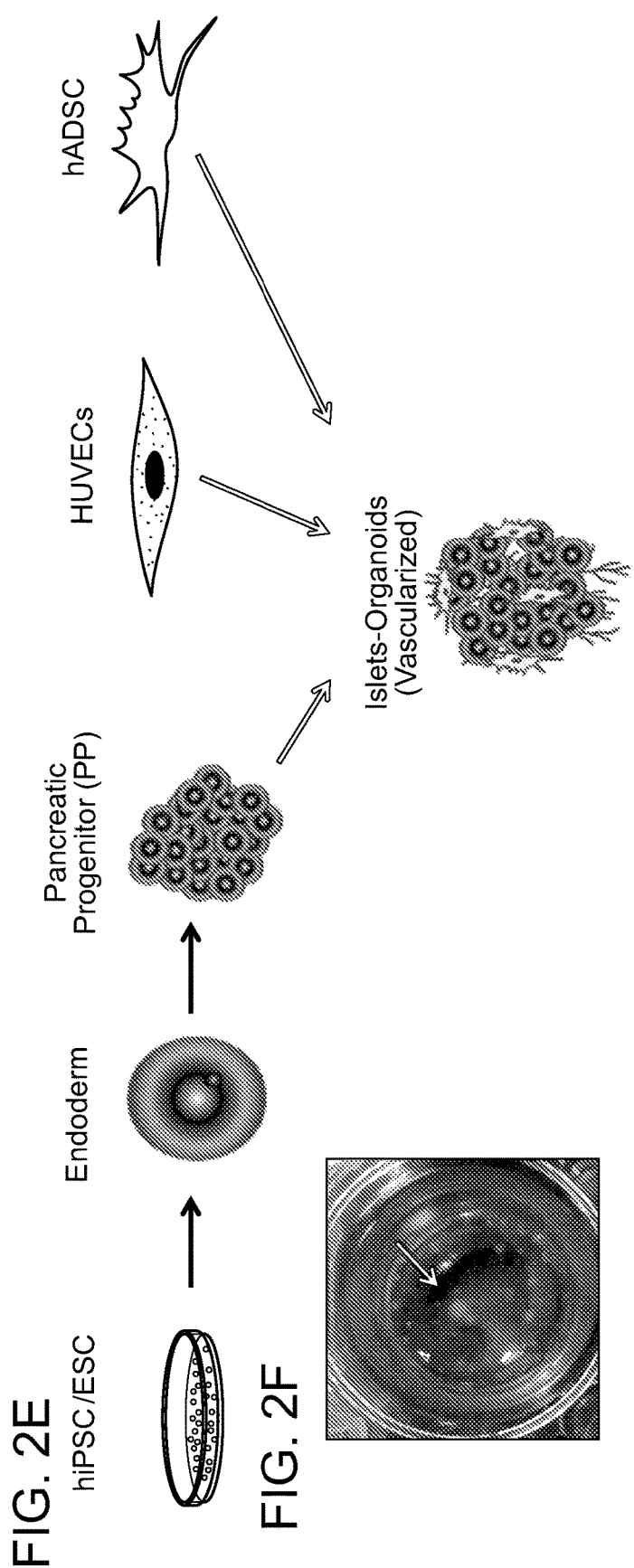
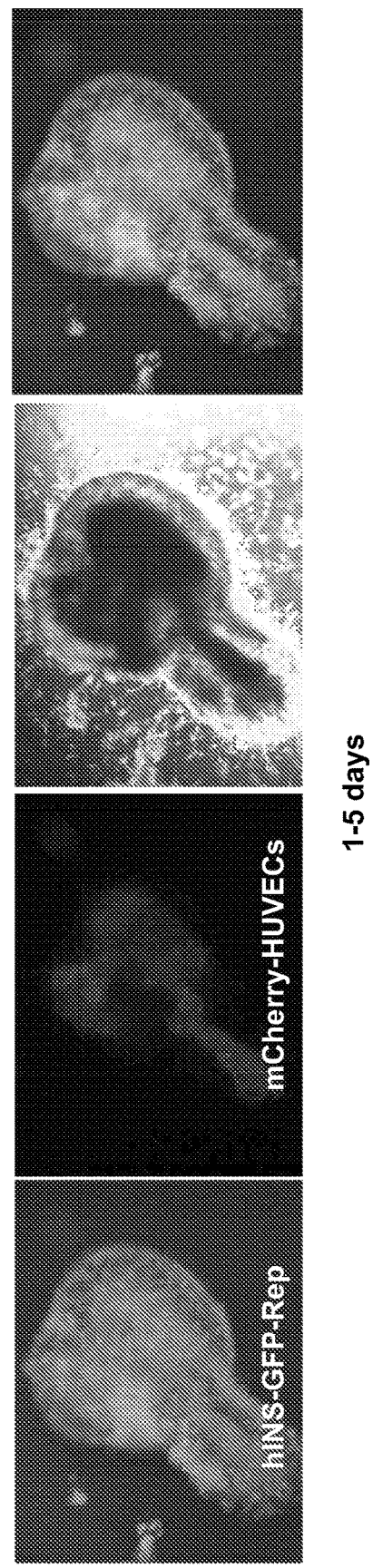

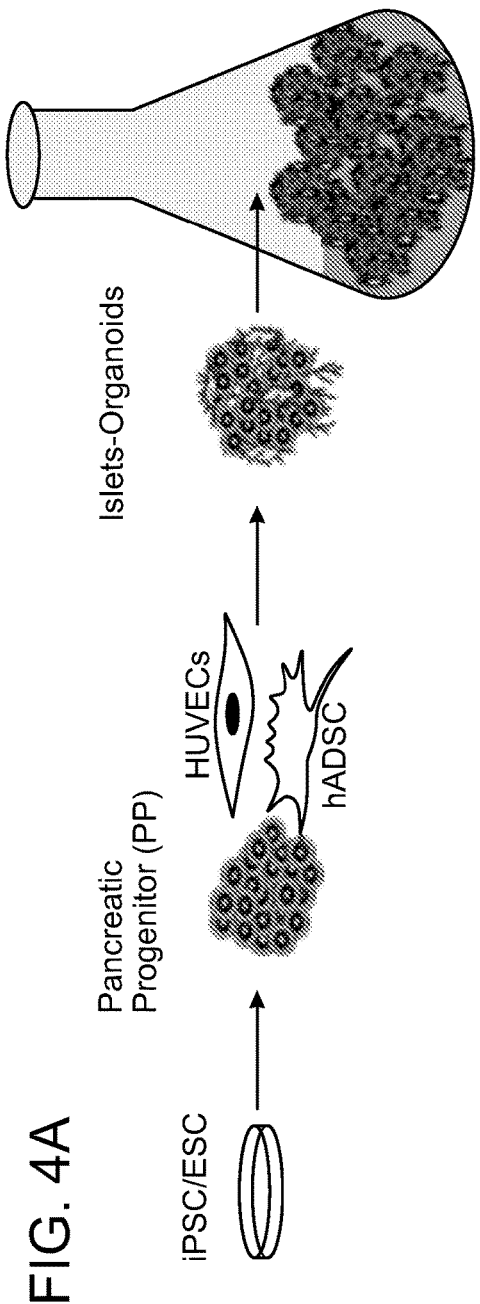
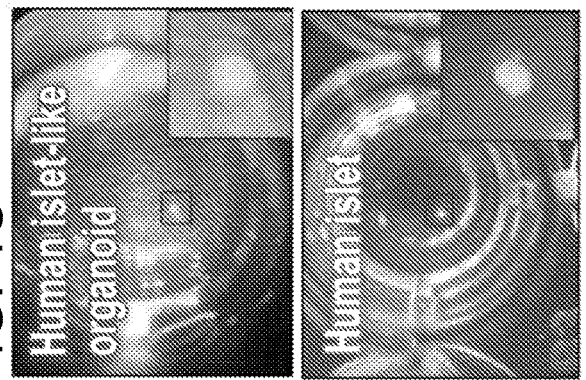
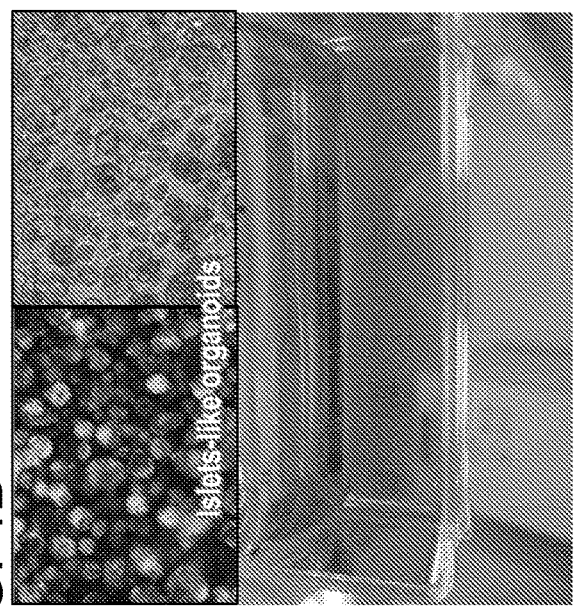
FIG. 4A
FIG. 4B
FIG. 4C

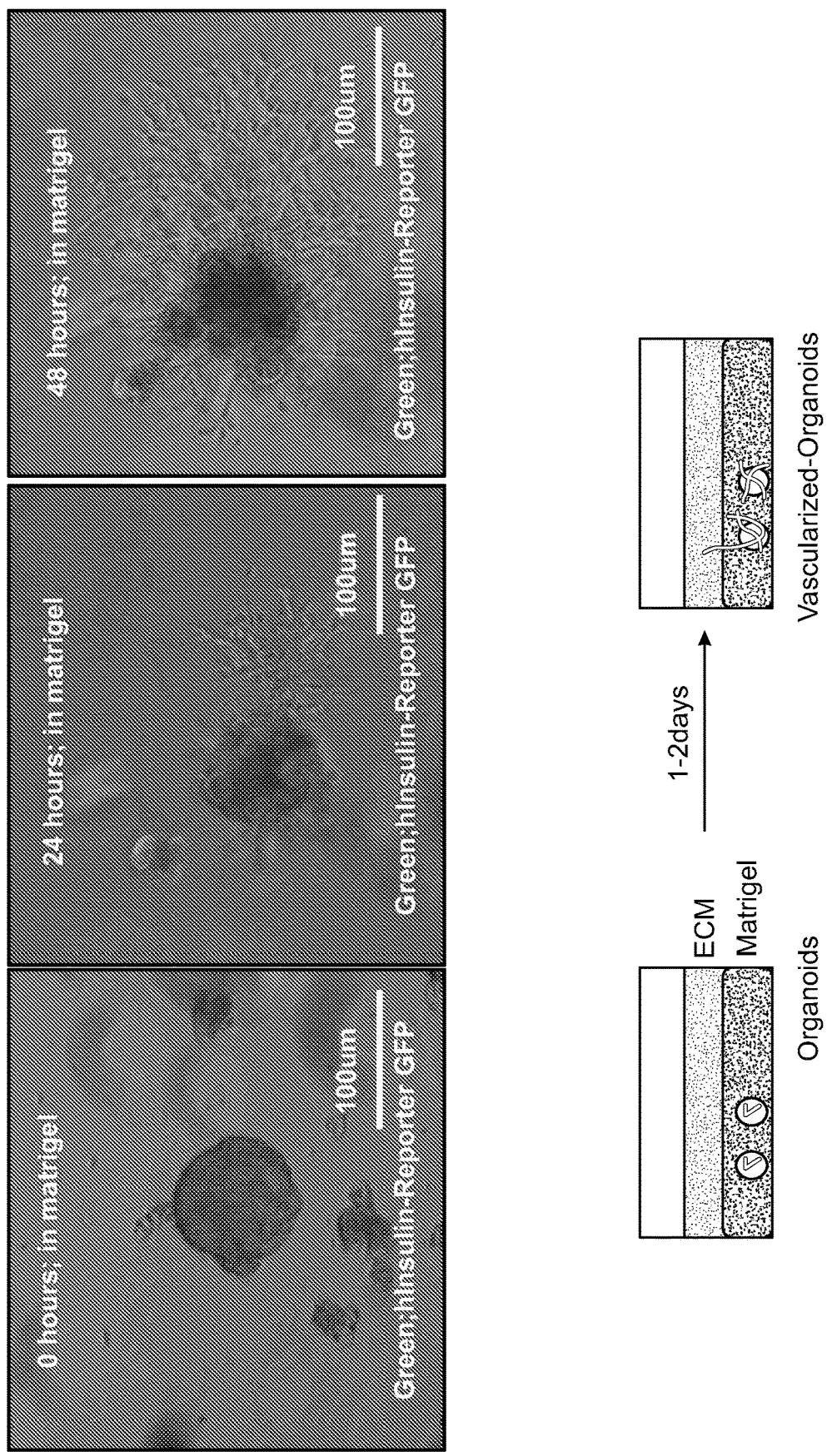
FIG. 4G *In vitro* Vascularization

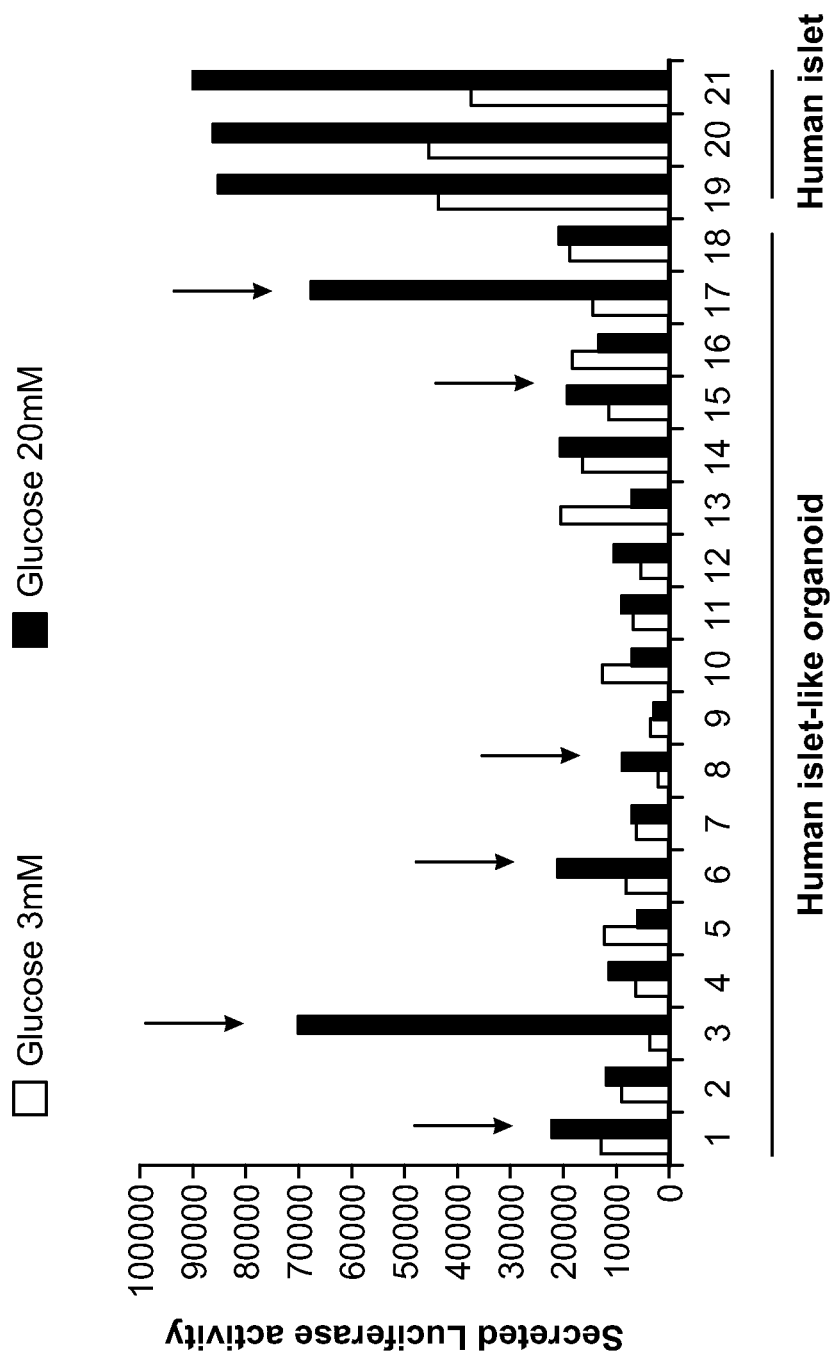

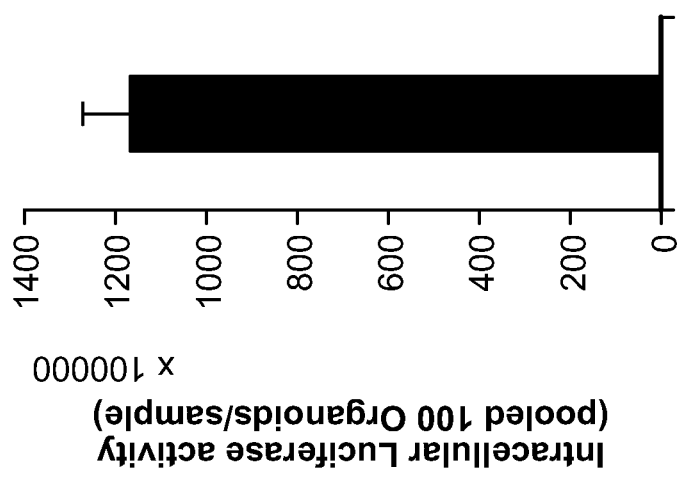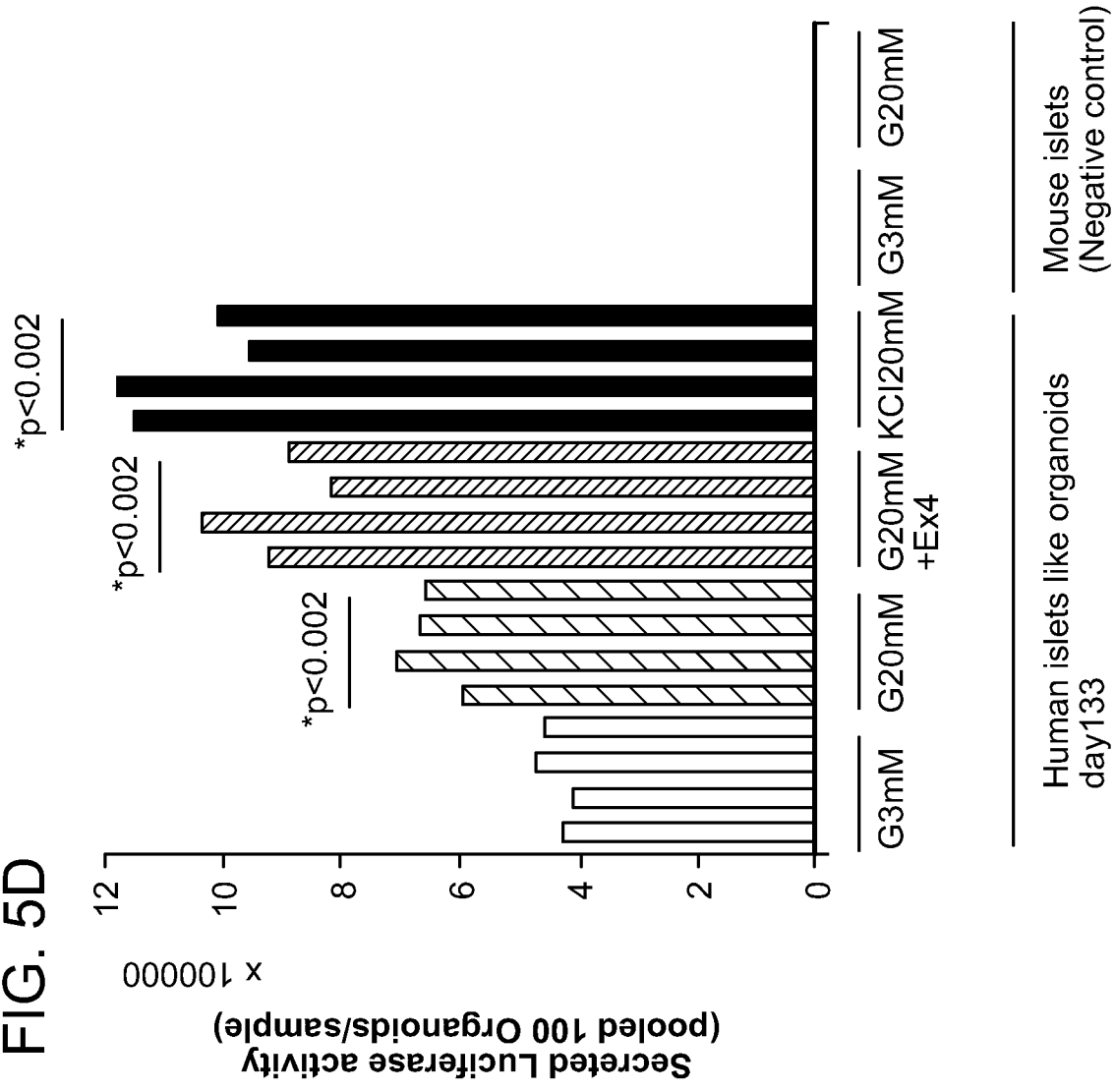

FIG. 6B
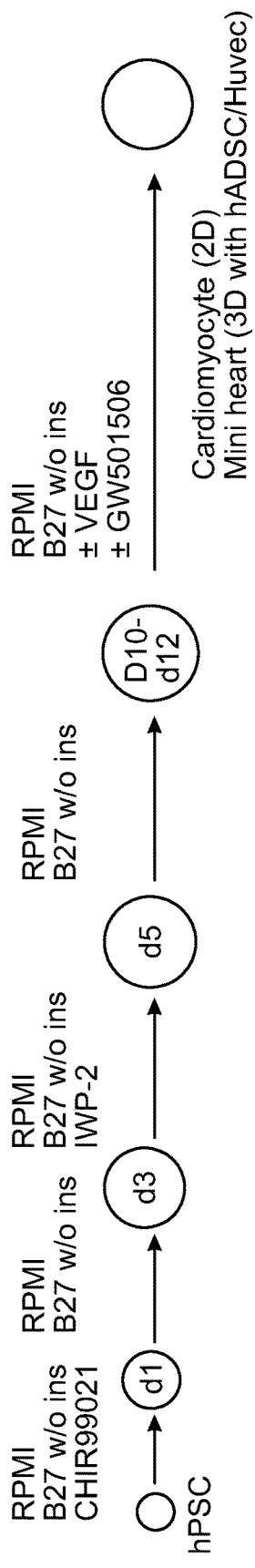
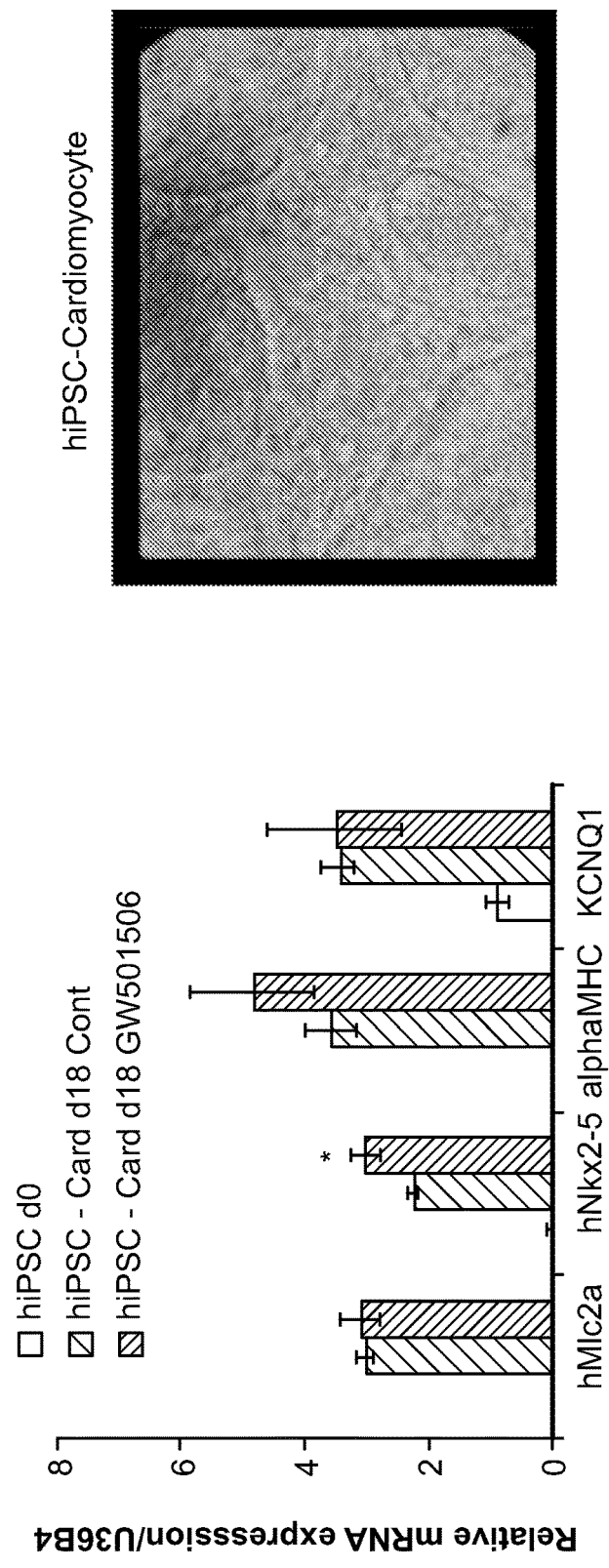

FIG. 6C
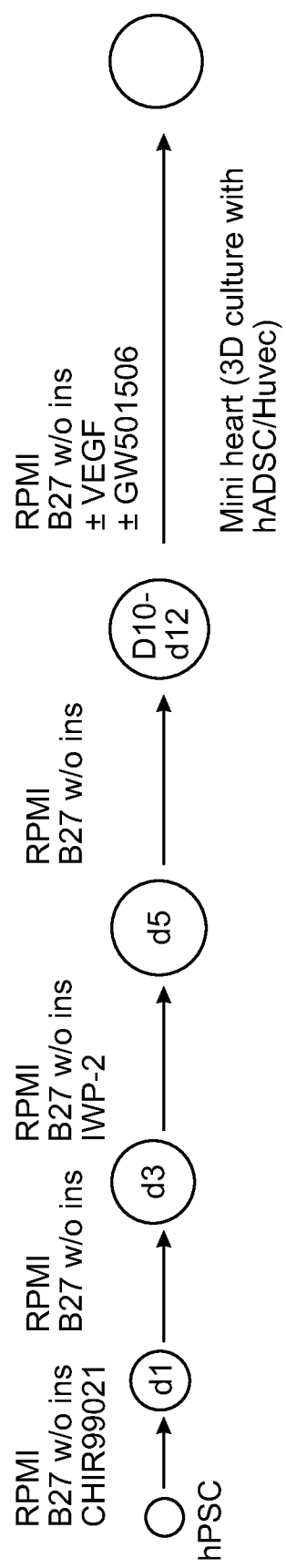
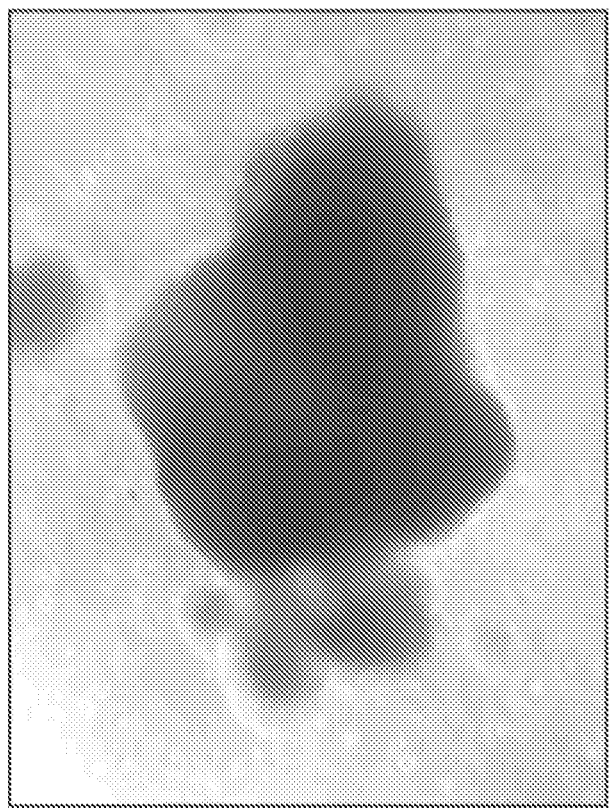

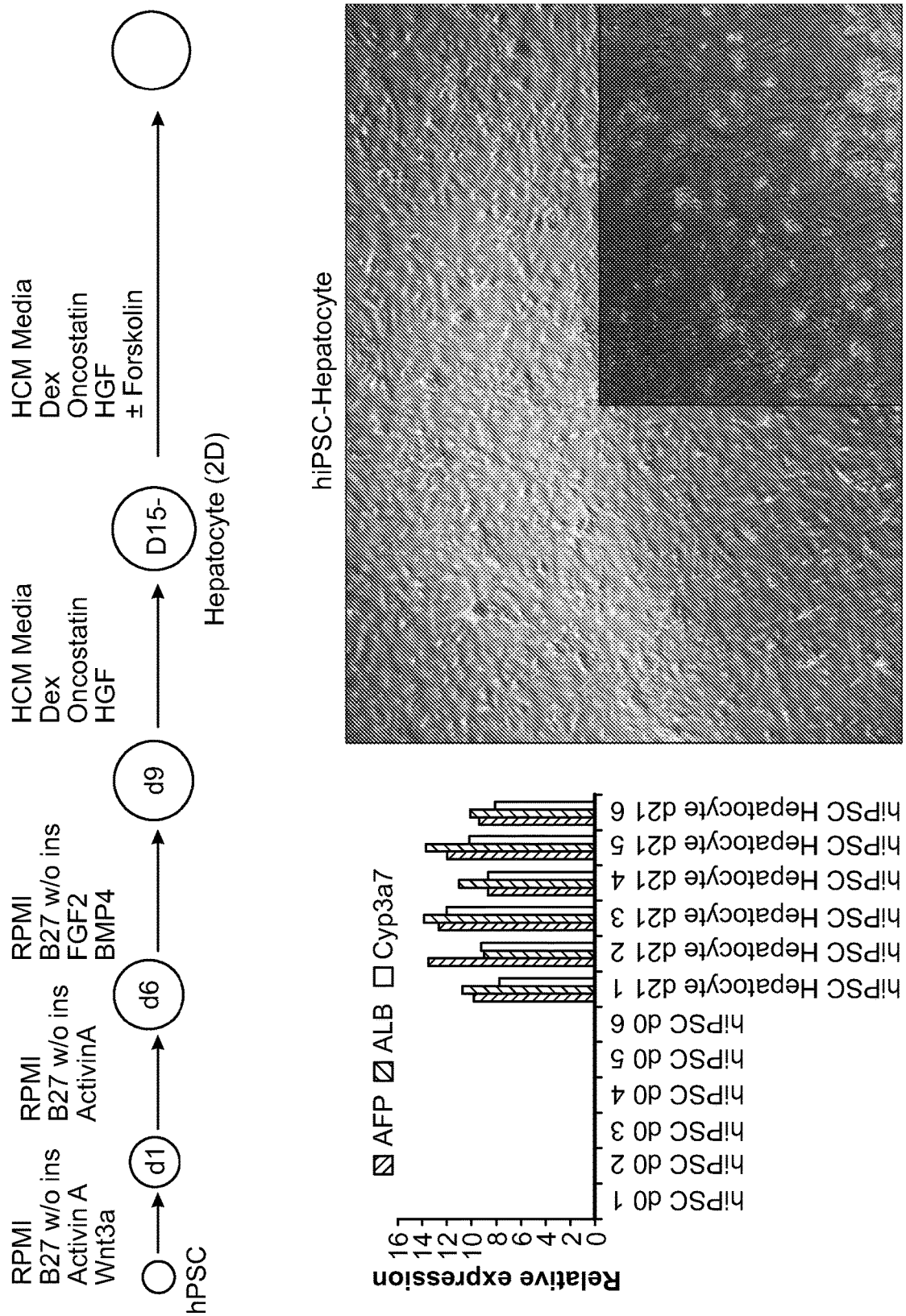

FIG. 6F
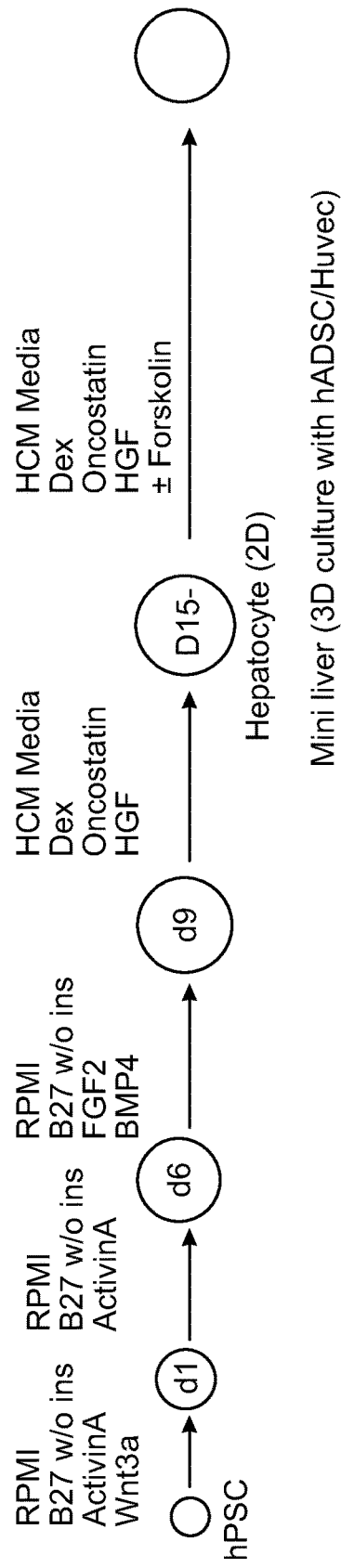
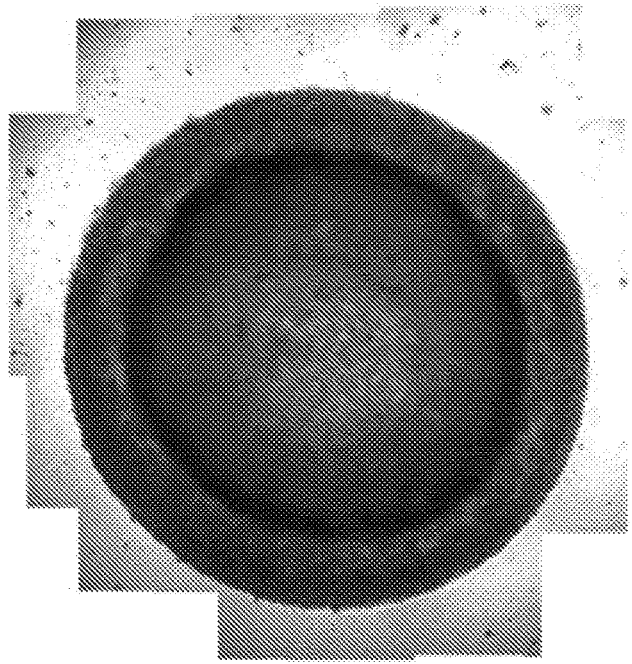
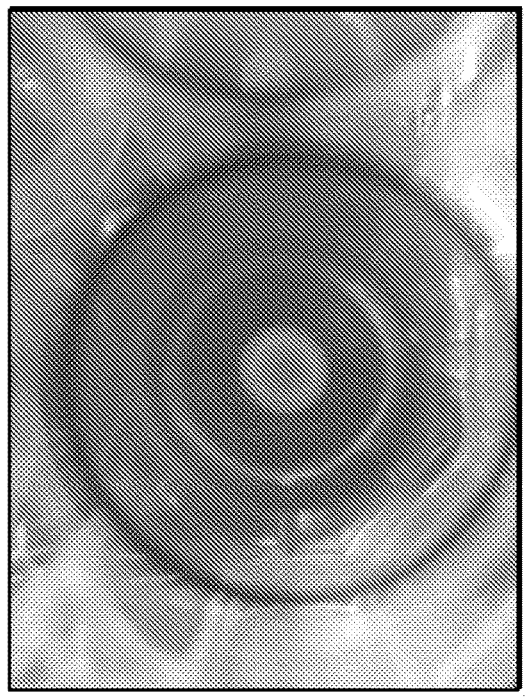

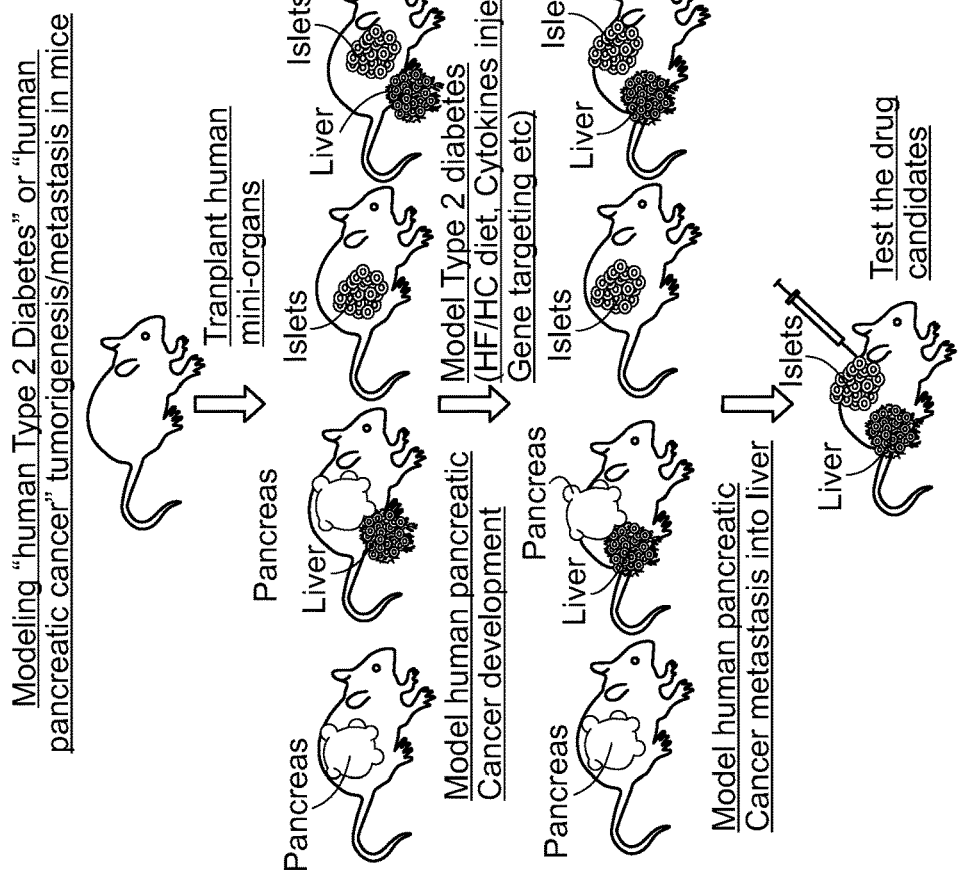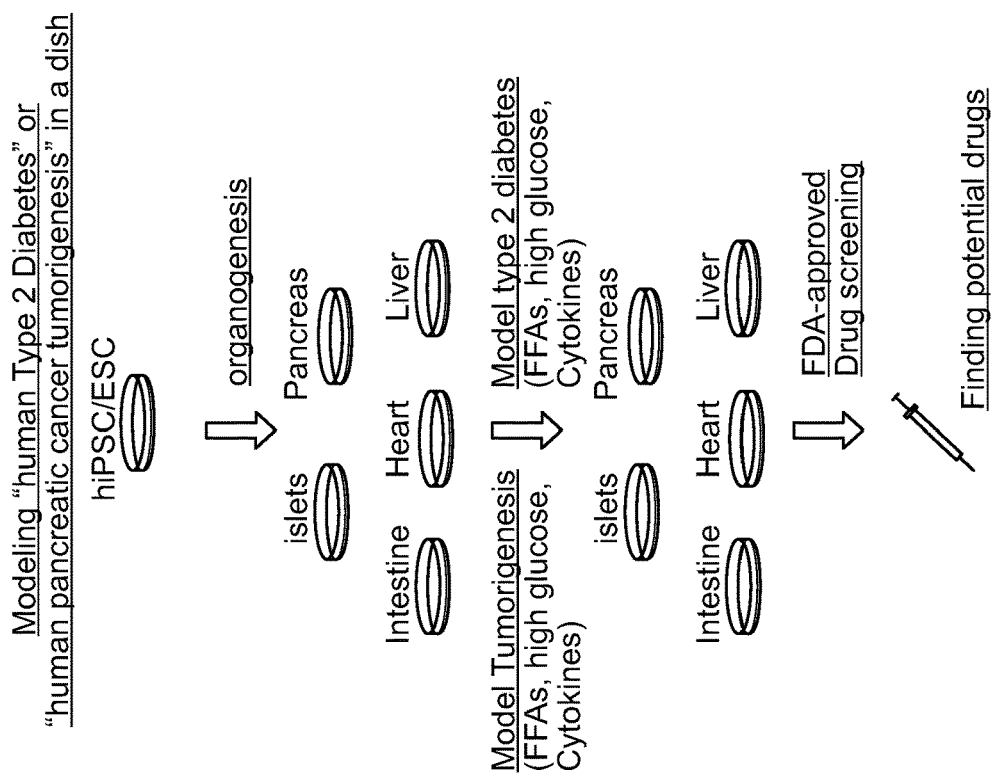

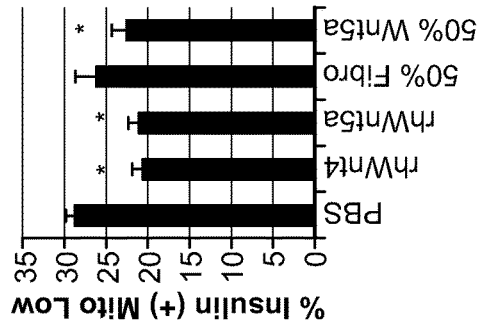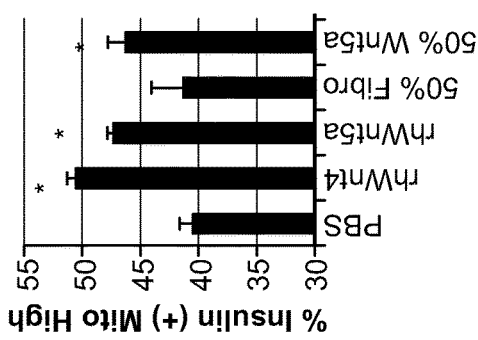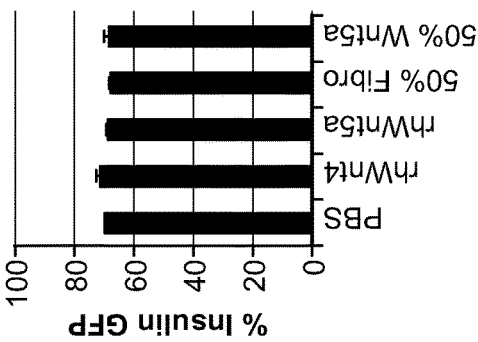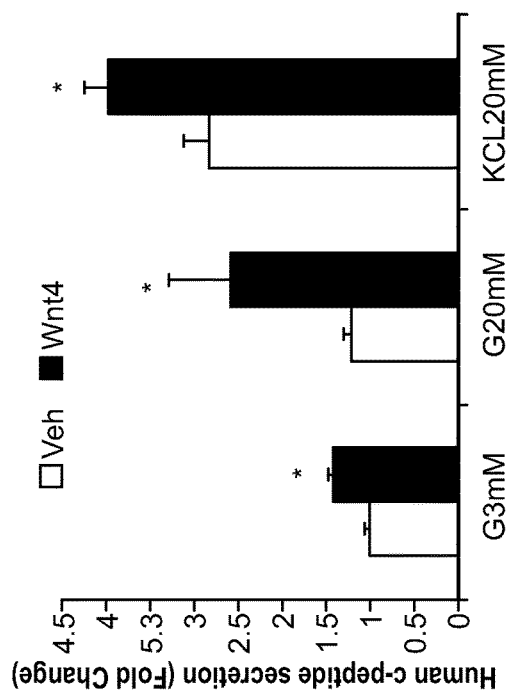

COMPOSITIONS AND METHODS FOR ORGANOID GENERATION AND DISEASE MODELING

CROSS REFERENCE TO RELATED APPLICATION

This application is the U.S. national phase application, pursuant to 35 U.S.C. § 371, of PCT International Application Ser. No.: PCT/US2017/034278, filed May 24, 2017, designating the United States and published in English, which claims the benefit of U.S. Provisional Application No. 62/341,461, filed on May 25, 2016, the entire contents of which are hereby incorporated by reference herein.

SEQUENCE LISTING

The application contains a Sequence Listing which has been submitted electronically in ASCII format and is hereby incorporated by reference in its entirety. The ASCII copy, created on Jun. 26, 2017, is named 167776_010901PCT_SL.txt and is 262,334 bytes in size.

STATEMENT OF RIGHTS TO INVENTIONS MADE UNDER FEDERALLY SPONSORED RESEARCH

This invention was made with government support under Grant Nos. DK057978 and DK0909962 awarded by the National Institutes of Health. The government has certain rights in the invention.

BACKGROUND OF THE INVENTION

Although animal disease models can yield insight into the pathogenesis of diseases, drugs screened and selected using animal models often fail to be adopted in human patients. Because evolutionary biology, molecular biology, and genetic studies show animals and humans can profoundly differ, recapitulating human disease using human cells and generation of functional human organs is urgently needed.

SUMMARY OF THE INVENTION

As described below, the present invention features compositions and methods for generating an organoid, including a pancreatic islet organoid or a pancreatic organoid.

In one aspect, the invention provides a method of generating a pancreatic islet organoid, the method involving culturing an induced pluripotent stem cell (iPSC)-derived beta-like cell in a 3-dimensional matrix containing gellan gum, thereby generating a pancreatic islet organoid.

In another aspect, the invention provides a cell culture including an iPSC-derived beta-like cell in a three-dimensional matrix containing gellan gum.

In another aspect, the invention provides a cell culture including a human iPSC-derived beta-like cell, a human adipose-derived stem cell (hADSC), and a human umbilical vein endothelial cell (HUVEC) in a three-dimensional matrix containing gellan gum.

In various embodiments of any aspect delineated herein, the cell culture includes an adipose-derived stem cell and/or an endothelial cell.

In another aspect, the invention provides a pancreatic islet organoid containing an iPSC-derived beta-like cell, where the organoid is vascularized and exhibits glucose-stimulated insulin secretion (GSIS).

In another aspect, the invention provides a pancreatic islet organoid containing an iPSC-derived beta-like cell, an iPSC-derived alpha cell, an iPSC-derived delta cell, an iPSC-derived duct cell, an adipose-derived stem cell (hADSC), and an endothelial cell where the organoid is vascularized and exhibits glucose-stimulated insulin secretion (GSIS), KCl-stimulated insulin secretion, GLP-1 stimulated insulin secretion, somatostatin secretion, and glucagon secretion.

In a related aspect, the invention provides a non-human organism transplanted with the organoid of any aspect delineated herein.

In another aspect, the invention provides a method of identifying an agent that modulates pancreatic activity and/or treats a pancreatic disease involving contacting a candidate agent with a pancreatic islet organoid or a pancreatic organoid; and measuring an activity of the organoid contacted with the candidate agent, where the candidate agent is identified as an agent that modulates pancreatic activity and/or treats a pancreatic disease if the activity of the organoid is altered relative to a reference.

In another aspect, the invention provides a method of identifying an agent that modulates pancreatic activity and/or treats a pancreatic disease involving administering a candidate agent to a non-human subject transplanted with a pancreatic islet organoid or a pancreatic organoid; and measuring a pancreatic activity of the non-human subject, where the candidate agent is identified as an agent that modulates pancreatic activity and/or treats a pancreatic disease if the pancreatic activity of the non-human subject is altered relative to a reference.

In another aspect, the invention provides a method of treating a pancreatic disease in a subject involving transplanting a pancreatic islet organoid into the subject, where the pancreatic islet organoid contains an iPSC-derived beta-like cell, is vascularized, and exhibits glucose-stimulated insulin secretion (GSIS).

In another aspect, the invention provides a method of treating type 1 diabetes in a subject, involving transplanting a pancreatic islet organoid into the subject, where the pancreatic islet organoid contains an iPSC-derived beta-like cell, is vascularized, and exhibits glucose-stimulated insulin secretion (GSIS).

In another aspect, the invention provides a pancreatic islet organoid generated by culturing an induced pluripotent stem cell (iPSC)-derived beta-like cell in a 3-dimensional matrix containing gellan gum.

In another aspect, the invention provides a pancreatic organoid generated by culturing an induced pluripotent stem cell (iPSC)-derived beta-like cell and an iPSC-derived exocrine component cell in a 3-dimensional matrix containing gellan gum.

In another aspect, the invention provides a liver organoid generated by culturing an induced pluripotent stem cell (iPSC)-derived hepatocyte in a 3-dimensional matrix containing gellan gum.

In another aspect, the invention provides a heart organoid generated by culturing an induced pluripotent stem cell (iPSC)-derived cardiomyocyte in a 3-dimensional matrix containing gellan gum.

In another aspect, the invention provides an intestinal organoid generated by culturing an induced pluripotent stem cell (iPSC)-derived intestinal cell in a 3-dimensional matrix containing gellan gum.

In various embodiments of any aspect delineated herein, the method involves culturing the iPSC-derived beta-like cell with an adipose-derived stem cell and/or an endothelial cell. In various embodiments of any aspect delineated herein, the method involves culturing the iPSC-derived beta-like cell with an iPSC-derived alpha-like cell, an iPSC-derived delta-like cell, and/or an iPSC-derived duct-like cell.

In various embodiments of any aspect delineated herein, the pancreatic islet organoid contains an iPSC-derived alpha-like cell, an iPSC-derived delta-like cell, and/or an iPSC-derived duct-like cell. In various embodiments of any aspect delineated herein, the pancreatic islet organoid includes an adipose-derived stem cell and/or an endothelial cell. In various embodiments of any aspect delineated herein, the pancreatic islet organoid exhibits KCl-stimulated insulin secretion, GLP-1 stimulated insulin secretion, somatostatin secretion, and/or glucagon secretion. In various embodiments of any aspect delineated herein, the pancreatic islet organoid expresses one or more of the beta cell transcription factors Pdx1, MafA, Pax4, Pax6, NeuroD1, Nkx6-1, Gata6, and Foxa2. In certain embodiments, the pancreatic islet organoid contains an iPSC-derived beta-like cell, an iPSC-derived alpha cell, an iPSC-derived delta cell, an iPSC-derived duct cell, an adipose-derived stem cell (hADSC), and an endothelial cell, where the organoid is vascularized and exhibits glucose-stimulated insulin secretion (GSIS), KCl-stimulated insulin secretion, GLP-1 stimulated insulin secretion, somatostatin secretion, and glucagon secretion. In various embodiments of any aspect delineated herein, the pancreatic islet organoid is surrounded by an iPSC-derived exocrine component. In various embodiments, the iPSC-derived exocrine component expresses one or more of the markers PDX1, Nkx6-1, and Ptf1.

In various embodiments of any aspect delineated herein, the method involves inducing or mimicking a pancreatic disease in the organoid or non-human subject. In various embodiments of any aspect delineated herein, the disease is induced by contacting the organoid with or administering to the non-human subject one or more of the following agents: a free fatty acid (FFA), glucose, and cytokine. In various embodiments of any aspect delineated herein, the disease is mimicked by culturing the organoid with pancreatic cancer cells, stellate cells, and immune cells to create human pancreatic cancer microenvironment. In various embodiments of any aspect delineated herein, the pancreatic activity is one or more of insulin secretion, beta cell apoptosis, expression or activity of a NDUFA4, ESRRG, G6PC2, MDH1, LDHA, KCNK3, or MAFA polypeptide or polynucleotide, amylase secretion, apoptosis of an exocrine component, collagen synthesis, and stellate cell activation. In various embodiments, the non-human subject is also transplanted with a liver organoid.

In various embodiments of any aspect delineated herein, the candidate agent increases insulin secretion. In various embodiments of any aspect delineated herein, the candidate agent identified as an agent that modulates pancreatic activity is tested for the ability to treat a pancreatic disease. In various embodiments, the pancreatic disease is type 2 diabetes or pancreatic cancer.

In various embodiments of any aspect delineated herein, the organoid is an organoid according to any aspect delineated herein.

In various embodiments, the non-human organism is a mammal (e.g., a mouse).

In various embodiments of any aspect delineated herein, the pancreatic islet organoid contains an iPSC-derived alpha-like cell, an iPSC-derived delta-like cell, and/or an iPSC-derived duct-like cell.

In various embodiments of any aspect delineated herein, the pancreatic islet organoid contains an adipose-derived stem cell and/or an endothelial cell.

In various embodiments of any aspect delineated herein, a pancreatic disease is induced or mimicked in the subject. In particular embodiments, the pancreatic disease is type 1 diabetes or type 2 diabetes. In certain embodiments, the subject is a mammal (e.g., human). In various embodiments of any aspect delineated herein, the subject is administered an immunosuppressive agent.

In various embodiments of any aspect delineated herein, the liver organoid expresses one or more of the markers AFP, ALB, and Cyp3a7. In various embodiments of any aspect delineated herein, the liver organoid exhibits insulin signaling, insulin resistance by palmitic acids, and lipid accumulation.

In various embodiments of any aspect delineated herein, the heart organoid expresses one or more of the markers hMlc2a, hNkx2-5, alphaMHC and KCNQ1. In various embodiments of any aspect delineated herein, the heart organoid exhibits cardiac beating.

In various embodiments of any aspect delineated herein, the intestinal organoid expresses one or more of the markers CDX2, Muc2, and Lgr5. In various embodiments of any aspect delineated herein, the intestinal organoid exhibits budding in response to R-spondin.

In various embodiments of any aspect delineated herein, the iPSC-derived beta-like cell, iPSC-derived alpha-like cell, iPSC-derived delta-like cell, and/or iPSC-derived duct-like cell is human. In various embodiments of any aspect delineated herein, the iPSC-derived beta-like cell, iPSC-derived exocrine component cell, iPSC-derived hepatocyte, iPSC-derived cardiomyocyte, or iPSC-derived intestinal cell is human. In various embodiments, the adipose-derived stem cell is a human adipose-derived stem cell (hADSC). In various embodiments of any aspect delineated herein, the endothelial cell is a human umbilical vein endothelial cell (HUVEC).

In various embodiments of any aspect delineated herein, the pancreatic islet organoid, pancreatic organoid, liver organoid, heart organoid, or intestinal organoid, contains an adipose-derived stem cell and/or an endothelial cell. In various embodiments of any aspect delineated herein, the pancreatic islet organoid, pancreatic organoid, liver organoid, heart organoid, or intestinal organoid is vascularized.

In another aspect, the invention provides a method of generating a pancreatic islet organoid, the method comprising culturing an induced pluripotent stem cell (iPSC)-derived beta-like cell in a medium comprising Wnt4 or Wnt5a protein. In an embodiment, the induced pluripotent stem cell (iPSC)-derived beta-like cell is cultured in a 3-dimensional matrix. In an embodiment of the foregoing aspect, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein.

In another aspect the invention provides a cell culture comprising a human iPSC-derived beta-like cell and Wnt4 or Wnt5a protein. In an embodiment, the human iPSC-derived beta-like cell is in a three-dimensional matrix comprising gellan gum. In an embodiment, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein.

In another aspect, the invention provides a pancreatic islet organoid comprising an iPSC-derived beta-like cell cultured in medium comprising Wnt4 or Wnt5a protein, wherein the organoid is vascularized and exhibits glucose-stimulated insulin secretion (GSIS). In an embodiment, the organoid further exhibits KCl-stimulated insulin secretion or glucose stimulated insulin secretion. In an embodiment, the pancreatic islet organoid expresses Fltp and Esrrg genes. In an embodiment, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein.

In another aspect, the invention provides a non-human organism transplanted with the organoid defined in the above described aspects.

In another aspect, the invention provides a method of enhancing self organization of adipose-derived stem cells (ADSCs) for generating an induced pluripotent stem cell (iPSC)-derived organoid, the method comprising culturing the ADSCs in a 3-dimensional (3-D) culture matrix medium comprising a Wnt5a protein. In an embodiment of the method, the ADSCs are cultured in a 3-D culture matrix comprising gellan gum. In an embodiment, the ADSCs are cultured in the 3-D culture matrix medium comprising a Wnt5 protein and an iPSC-derived cell selected from an iPSC-derived beta-like cell, an iPSC-derived exocrine component cell, an iPSC-derived hepatocyte, an iPSC-derived cardiomyocyte, or an iPSC-derived intestinal cell. In an embodiment of the method, the iPSC-derived organoid is selected from a pancreatic islet organoid, pancreatic organoid, a liver organoid, a heart organoid, or an intestinal organoid. In an embodiment of the method, the induced pluripotent stem cell (iPSC)-derived organoid is a human induced pluripotent stem cell (hiPSC)-derived organoid. In an embodiment of the method, the Wnt5a protein is a recombinant human Wnt5a protein. In an embodiment of the method, the pancreatic islet organoid, pancreatic organoid, liver organoid, heart organoid, or intestinal organoid is derived from an iPSC-derived cell selected from an iPSC-derived beta-like cell, an iPSC-derived exocrine component cell, an iPSC-derived hepatocyte, an iPSC-derived cardiomyocyte, or an iPSC-derived intestinal cell, respectively. In an embodiment, of any of the above, the iPSC-derived cell is human. In another aspect, the invention provides a method of enhancing self organization of adipose-derived stem cells (ADSCs) for generating a pancreatic islet or pancreatic organoid, comprising culturing ADSCs in medium comprising Wnt5a protein. In an embodiment, the ADSCs are cultured in a 3-dimensional matrix comprising gellan gum. In another embodiment, the Wnt5a protein a recombinant human Wnt5a protein. In another aspect, the invention provides a pancreatic islet organoid, pancreatic organoid, a liver organoid, a heart organoid, or intestinal organoid produced by any of the above-delineated methods and embodiments thereof.

Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "AFP polypeptide" or "alpha-fetoprotein" is meant a protein or fragment thereof having at least 85% amino acid sequence identity to the sequence provided at NCBI Accession No. NP_001125.1 and having a biological activity of an AFP polypeptide. Exemplary biological activities of an AFP polypeptide include binding to copper, nickel, fatty acids, and bilirubin. The amino acid sequence provided at NCBI Accession No. NP_001125.1 is shown below (SEQ ID NO: 1):

```
  1 mkwvesifli fllnftesrt lhrneygias ildsyqctae isladlatif faqfvqeaty 61 kevskmvkda ltaiekptgd eqssgclenq lpafleelch ekeilekygh sdccsqseeg 121 rhncflahkk ptpasiplfq vpepvtscea yeedretfmn kfiyeiarrh pflyaptill 181 waarydkiip scckaenave cfqtkaatvt kelresslln qhacavmknf gtrtfqaitv 241 tklsqkftkv nfteiqklvl dvahvhehcc rgdvldclqd gekimsyics qqdtlsnkit 301 eccklttler gqciihaend ekpeglspnl nrflgdrdfn qfssgeknif lasfvheysr 361 rhpqlavsvi lrvakgyqel lekcfqtenp lecqdkgeee lqkyiqesqa lakrscglfq 421 klgeyylqna flvaytkkap qltsselmai trkmaataat ccqlsedkll acgegaadii 481 ighlcirhem tpvnpgvgqc ctssyanrrp cfsslvvdet yvppafsddk fifhkdlcqa 541 qgvalqtmkq eflinlvkqk pqiteeqlea viadfsglle kccqgqeqev cfaeegqkli 601 sktraalgv
```

By "AFP polynucleotide" is meant a polynucleotide encoding a AFP polypeptide or fragment thereof. An exemplary AFP polynucleotide sequence is provided at NCBI Ref: NM_001134.2. The sequence provided at NCBI Ref: NM_001134.2 is reproduced below (SEQ ID NO: 2):

```
   1 atattgtgct tccaccactg ccaataacaa ataactagc aaccatgaag tgggtggaat
  61 caatttttt aatttcccta ctaaatttta ctgaatccag aacactgcat agaaatgaat
 121 atggaatagc ttccatattg gattcttacc aatgtactgc agagataagt ttagctgacc
 181 tggctaccat attttttgcc cagtttgttc aagaagccac ttacaaggaa gtaagcaaaa
 241 tggtgaaaga tgcattgact gcaattgaga aacccactgg agatgaacag tcttcagggt
 301 gtttagaaaa ccagctacct gcctttctgg aagaactttg ccatgagaaa gaaattttgg
 361 agaagtacgg acattcagac tgctgcagcc aaagtgaaga gggaagacat aactgttttc
 421 ttgcacacaa aaagcccact ccagcatcga tcccactttt ccaagttcca gaacctgtca
 481 caagctgtga agcatatgaa gaagacaggg agacattcat gaacaaattc atttatgaga
 541 tagcaagaag gcatcccttc ctgtatgcac ctacaattct tctttgggct gctcgctatg
 601 acaaaataat tccatcttgc tgcaaagctg aaaatgcagt tgaatgcttc caaacaaagg
 661 cagcaacagt tacaaaagaa ttaagagaaa gcagcttgtt aaatcaacat gcatgtgcag
 721 taatgaaaaa ttttgggacc cgaactttcc aagccataac tgttactaaa ctgagtcaga
 781 agtttaccaa agttaatttt actgaaatcc agaaactagt cctggatgtg gcccatgtac
 841 atgagcactg ttgcagagga gatgtgctgg attgtctgca ggatggggaa aaaatcatgt
 901 cctacatatg ttctcaacaa gacactctgt caaacaaaat aacagaatgc tgcaaactga
 961 ccacgctgga acgtggtcaa tgtataattc atgcagaaaa tgatgaaaaa cctgaaggtc
1021 tatctccaaa tctaaacagg ttttttaggag atagagattt taaccaattt tcttcagggg
1081 aaaaaaatat cttcttggca agttttgttc atgaatattc aagaagacat cctcagcttg
1141 ctgtctcagt aattctaaga gttgctaaag gataccagga gttattggag aagtgtttcc
1201 agactgaaaa ccctcttgaa tgccaagata aggagaaga agaattacag aaatacatcc
1261 aggagagcca agcattggca aagcgaagct gcggcctctt ccagaaacta ggagaatatt
1321 acttacaaaa tgcgtttctc gttgcttaca caaagaaagc cccccagctg acctcgtcgg
1381 agctgatggc catcaccaga aaaatggcag ccacagcagc cacttgttgc caactcagtg
1441 aggacaaact attggcctgt ggcgagggag cggctgacat tattatcgga cacttatgta
1501 tcagacatga aatgactcca gtaaaccctg gtgttggcca gtgctgcact tcttcatatg
1561 ccaacaggag gccatgcttc agcagcttgg tggtggatga acatatgtc cctcctgcat
1621 tctctgatga caagttcatt ttccataagg atctgtgcca agctcagggt gtagcgctgc
1681 aaacgatgaa gcaagagttt ctcattaacc ttgtgaagca aaagccacaa ataacagagg
1741 aacaacttga ggctgtcatt gcagatttct caggcctgtt ggagaaatgc tgccaaggcc
1801 aggaacagga gtctgctttt gctgaagagg gacaaaaact gatttcaaaa actcgtgctg
1861 ctttgggagt ttaaattact tcaggggaag agaagacaaa acgagtcttt cattcggtgt
1921 gaacttttct ctttaatttt aactgattta acacttttg tgaattaatg aaatgataaa
1981 gacttttatg tgagatttcc ttatcacaga aataaatat ctccaaatgt ttcctttca
2041 aaaaaaaaa aaaaaaa
```

By "ALB polypeptide" or "albumin" is meant a protein or fragment thereof having at least 85% amino acid sequence identity to the sequence provided at NCBI Accession No. NP_000468.1 and having a biological activity of ALB polypeptide. Exemplary biological activities of ALB polypeptide include binding to fatty acids, calcium ions, sodium ions, potassium ions, hormones, and bilirubin; stabilization of extracellular fluid volume; and, transport of plasma zinc.

The amino acid sequence provided at NCBI Accession No. NP_000468.1 is shown below (SEQ ID NO: 3):

```
  1 mkwvtfisll flfssaysrg vfrrdahkse vahrfkdlge enfkalvlia faqylqqcpf
 61 edhvklvnev tefaktcvad esaencdksl htlfgdklct vatlretyge madccakqep
121 ernecflqhk ddnpnlprlv rpevdvmcta fhdneetflk kylyeiarrh pyfyapellf
181 fakrykaaft eccqaadkaa cllpkldelr degkassakq rlkcaslqkf gerafkawav
241 arlsqrfpka efaevsklvt dltkvhtecc hgdllecadd radlakyice nqdsissklk
301 eccekpllek shciaevend empadlpsla adfveskdvc knyaeakdvf lgmflyeyar
361 rhpdysvvll lrlaktyett lekccaaadp hecyakvfde fkplveepqn likqncelfe
421 qlgeykfqna llvrytkkvp qvstptlvev srnlgkvgsk cckhpeakrm pcaedylsvv
481 lnqlcvlhek tpvsdrvtkc cteslvnrrp cfsalevdet yvpkefnaet ftfhadictl
541 sekerqikkq talvelvkhk pkatkeqlka vmddfaafve kcckaddket cfaeegkklv
601 aasqaalgl
```

By "ALB polynucleotide" is meant a polynucleotide encoding a ALB polypeptide or fragment thereof. An exemplary AFP polynucleotide sequence is provided at NCBI Ref: NM_000477.5. The sequence provided at NCBI Ref: NM_000477.5 is reproduced below (SEQ ID NO: 4):

```
   1 agtatattag tgctaatttc cctccgtttg tcctagcttt tctcttctgt caacccaca
  61 cgcctttggc acaatgaagt gggtaacctt tatttccctt cttttctct ttagctcggc
 121 ttattccagg ggtgtgtttc gtcgagatgc acacaagagt gaggttgctc atcggtttaa
 181 agatttggga gaagaaaatt tcaaagcctt ggtgttgatt gcctttgctc agtatcttca
 241 gcagtgtcca tttgaagatc atgtaaaatt agtgaatgaa gtaactgaat tgcaaaaac
 301 atgtgttgct gatgagtcag ctgaaaattg tgacaaatca cttcatacc tttttggaga
 361 caaattatgc acagttgcaa ctcttcgtga aacctatggt gaaatggctg actgctgtgc
 421 aaaacaagaa cctgagagaa atgaatgctt cttgcaacac aaagatgaca cccaaacct
 481 cccccgattg gtgagaccag aggttgatgt gatgtgcact gcttttcatg acaatgaaga
 541 gacattttg aaaaaatact tatatgaaat tgccagaaga catccttact tttatgcccc
 601 ggaactcctt ttctttgcta aaaggtataa agctgctttt acagaatgtt gccaagctgc
 661 tgataaagct gcctgcctgt tgccaaagct cgatgaactt cgggatgaag ggaaggcttc
 721 gtctgccaaa cagagactca agtgtgccag tctccaaaaa tttggagaaa gagctttcaa
 781 agcatgggca gtagctcgcc tgagccagag atttcccaaa gctgagtttg cagaagtttc
 841 caagttagtg acagatctta ccaaagtcca cacggaatgc tgccatggag atctgcttga
 901 atgtgctgat gacagggcgg accttgccaa gtatatctgt gaaaatcaag attcgatctc
 961 cagtaaactg aaggaatgct gtgaaaaacc tctgttggaa aaatcccact gcattgccga
1021 agtggaaaat gatgagatgc ctgctgactt gccttcatta gctgctgatt ttgttgaaag
1081 taaggatgtt tgcaaaaact atgctgaggc aaaggatgtc ttcctgggca tgtttttgta
1141 tgaatatgca agaaggcatc ctgattactc tgtcgtgctg ctgctgagac ttgccaagac
1201 atatgaaacc actctagaga agtgctgtgc cgctgcagat cctcatgaat gctatgccaa
1261 agtgttcgat gaatttaaac ctcttgtgga agagcctcag aatttaatca aacaaaattg
1321 tgagcttttt gagcagcttg gagagtacaa attccagaat gcgctattag ttcgttacac
1381 caagaaagta ccccaagtgt caactccaac tcttgtagag gtctcaagaa acctaggaaa
```

-continued

```
1441 agtgggcagc aaatgttgta aacatcctga agcaaaaaga atgccctgtg cagaagacta 1501 tctatccgtg gtcctgaacc agttatgtgt gttgcatgag aaaacgccag taagtgacag 1561 agtcaccaaa tgctgcacag aatccttggt gaacaggcga ccatgctttt cagctctgga 1621 agtcgatgaa acatacgttc ccaaagagtt taatgctgaa acattcacct tccatgcaga 1681 tatatgcaca ctttctgaga aggagagaca aatcaagaaa caaactgcac ttgttgagct 1741 cgtgaaacac aagcccaagg caacaaaaga gcaactgaaa gctgttatgg atgatttcgc 1801 agcttttgta gagaagtgct gcaaggctga cgataaggag acctgctttg ccgaggaggg 1861 taaaaaactt gttgctgcaa gtcaagctgc cttaggctta taacatcaca tttaaaagca 1921 tctcagccta ccatgagaat aagagaaaga aaatgaagat caaaagctta ttcatctgtt 1981 tttcttttc gttggtgtaa agccaacacc ctgtctaaaa aacataaatt tctttaatca 2041 ttttgcctct tttctctgtg cttcaattaa taaaaaatgg aaagaatcta atagagtggt 2101 acagcactgt tatttttcaa agatgtgttg ctatcctgaa aattctgtag gttctgtgga 2161 agttccagtg ttctctctta ttccacttcg gtagaggatt tctagtttct tgtgggctaa 2221 ttaaataaat cattaatact cttctaaaaa aaaaaaaaaa aaaa
```

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "altered" is meant an increase or decrease. An increase is any positive change, e.g., by at least about 5%, 10%, or 20%; by at least about 25%, 50%, 75%, or even by 100%, 200%, 300% or more. A decrease is a negative change, e.g., a decrease by at least about 5%, 10%, or 20%; by at least about 25%, 50%, 75%; or even an increase by 100%, 200%, 300% or more.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "CDX2 polypeptide" is meant a protein or fragment thereof having at least 85% amino acid sequence identity to the sequence provided at NCBI Accession No. NP_001256.3 and having transcription factor activity. The amino acid sequence provided at NCBI Accession No. NP_001256.3 is shown below (SEQ ID NO: 5):

```
  1 myvsylldkd vsmypssvrh sgglnlapqn fvsppqypdy ggyhvaaaaa aaanldsaqs 61 pgpswpaayg aplredwngy apggaaaaan avahglnggs paaamgyssp adyhphhhph 121 hhphhpaaap scasgllqtl npgppgpaat aaaeqlspgg qrrnlcewmr kpaqqslgsq 181 vktrtkdkyr vvytdhqrle lekefhysry itirrkaela atlglserqv kiwfqnrrak 241 erkinkkklq qqqqqppqp pppppqppqp qpgplrsvpe plspvsslqa svsgsvpgvl 301 gptggvlnpt vtq
```

By "CDX2 polynucleotide" is meant a polynucleotide encoding a CDX2 polypeptide or fragment thereof. An exemplary CDX2 polynucleotide sequence is provided at NCBI Ref: NM_001265.4. The sequence provided at NCBI Ref: NM_001265.4 is reproduced below (SEQ ID NO: 6):

```
  1 ctccaaccat tggtgtctgt gtcattacta atagagtctt gtaaacactc gttaatcacg 61 gaaggccgcc ggcctggggc tccgcacgcc agcctgtggc gggtcttccc cgcctctgca 121 gcctagtggg aaggaggtgg gaggaaagaa ggaagaaagg gagggaggga ggaggcaggc 181 cagagggagg gaccgcctcg gaggcagaag agccgcgagg agccagcgga gcaccgcggg 241 ctggggcgca gccacccgcc gctcctcgag tcccctcgcc cctttcccct cgtgccccc
```

-continued

```
 301 ggcagcctcc agcgtcggtc cccaggcagc atggtgaggt ctgctcccgg accctcgcca 361 ccatgtacgt gagctacctc ctggacaagg acgtgagcat gtaccctagc tccgtgcgcc 421 actctggcgg cctcaacctg cgccgcaga acttcgtcag ccccccgcag tacccggact 481 acggcggtta ccacgtggcg gccgcagctg cagcggcagc gaacttggac agcgcgcagt 541 ccccggggcc atcctggccg gcagcgtatg gcgccccact ccgggaggac tggaatggct 601 acgcgcccgg aggcgccgcg gccgccgcca cgccgtggc tcacggcctc aacggtggct 661 ccccggccgc agccatgggc tacagcagcc ccgcagacta ccatccgcac caccacccgc 721 atcaccaccc gcaccacccg ccgccgcgc cttcctgcgc ttctgggctg ctgcaaacgc 781 tcaaccccgg ccctcctggg cccgccgcca ccgctgccgc cgagcagctg tctcccggcg 841 gccagcggcg gaacctgtgc gagtggatgc ggaagccggc gcagcagtcc ctcggcagcc 901 aagtgaaaac caggacgaaa gacaaatatc gagtggtgta cacggaccac cagcggctgg 961 agctggagaa ggagtttcac tacagtcgct acatcaccat ccggaggaaa gccgagctag 1021 ccgccacgct ggggctctct gagaggcagg ttaaaatctg gtttcagaac cgcagagcaa 1081 aggagaggaa aatcaacaag aagaagttgc agcagcaaca gcagcagcag ccaccacagc 1141 cgcctccgcc gccaccacag cctccccagc ctcagccagg tcctctgaga agtgtcccag 1201 agcccttgag tccggtgtct tccctgcaag cctcagtgtc tggctctgtc cctggggttc 1261 tggggccaac tgggggggtg ctaaacccca ccgtcaccca gtgacccacc gggttctgca 1321 gcggcagagc aattccaggc tgagccatga ggagcgtgga ctctgctaga ctcctcagga 1381 gagacccctc ccctcccacc cacagccata gacctacaga cctggctctc agaggaaaaa 1441 tgggagccag gagtaagaca agtgggattt ggggcctcaa gaaatatact ctcccagatt 1501 tttacttttt cccatctggc ttttttctgcc actgaggaga cagaaagcct ccgctgggct 1561 tcattccgga ctggcagaag cattgcctgg actgaccaca ccaaccaggc cttcatcctc 1621 ctccccagct cttctcttcc tagatctgca ggctgcacct ctggctagag ccgaggggag 1681 agagggactc aagggaaagg caagcttgag gccaagatgg ctgctgcctg ctcatggccc 1741 tcggaggtcc agctgggcct cctgcctccg ggcaggcaag gtttacactg cggaagccaa 1801 aggcagctaa gatagaaagc tggactgacc aaagactgca gaaccccag gtggcctgcg 1861 tcttttttct cttcccttcc cagaccagga aaggcttggc tggtgtatgc acagggtgtg 1921 gtatgagggg gtggttattg gactccaggc ctgaccaggg ggcccgaaca gggacttgtt 1981 tagagagcct gtcaccagag cttctctggg ctgaatgtat gtcagtgcta taaatgccag 2041 agccaacctg gacttcctgt cattttcaca atcttgggc tgatgaagaa gggggtgggg 2101 ggagtttgtg ttgttgttgc tgctgtttgg gttgttggtc tgtgtaacat ccaagccaga 2161 gttttttaaag ccttctggat ccatgggggg agaagtgata tggtgaaggg aagtggggag 2221 tatttgaaca cagttgaatt ttttctaaaa agaaaaagag ataaatgagc tttccagatt 2281 tcagattctg tatttatctt cagattttgt ctgcaactat ttttattttt ttaaagaaat 2341 gaaatatctt caaaaaaaaa aaaaaaaaa
```

By "CYP3A7 polypeptide" or "cytochrome P450" is meant a protein or fragment thereof having at least 85% amino acid sequence identity to the sequence provided at NCBI Accession No. NP_000756.3 and having monooxygenase activity. The amino acid sequence provided at NCBI Accession No. NP_000756.3 is shown below (SEQ ID NO: 7):

```
  1 mdlipnlave twlllavsli llylygtrth glfkklgipg ptplpflgna lsfrkgywtf
 61 dmecykkyrk vwgiydcqqp mlaitdpdmi ktvlvkecys vftnrrpfgp vgfmknaisi
121 aedeewkrir sllsptftsg klkemvpiia qygdvlvrnl rreaetgkpv tlkhvfgays
181 mdvitstsfg vsidslnnpq dpfventkkl lrfnpldpfv lsikvfpflt pilealnitv
241 fprkvisflt ksvkqikegr lketqkhrvd flqlmidsqn skdsethkal sdlelmaqsi
301 ififagyett ssvlsfiiye lathpdvqqk vqkeidtvlp nkapptydtv lqleyldmvv
361 netlrlfpva mrlervckkd veingmfipk gvvvmipsyv lhhdpkywte pekflperfs
421 kknkdnidpy iytpfgsgpr ncigmrfalv nmklalvrvl qnfsfkpcke tqiplklrfg
481 gllltekpiv lkaesrdetv sga
```

By "CYP3A7 polynucleotide" is meant a polynucleotide encoding a CYP3A7 polypeptide or fragment thereof. An exemplary AFP polynucleotide sequence is provided at NCBI Ref: NM_000765.4. The sequence provided at NCBI Ref: NM_000765.4 is reproduced below (SEQ ID NO: 8):

```
   1 aatcactgct gtgcagggca ggaaagctcc acacacacag cccagcaaac agcagcacgc
  61 tgctgaaaaa aagactcaga ggagagagat aaggaaggaa agtagtgatg gatctcatcc
 121 caaacttggc cgtggaaacc tggcttctcc tggctgtcag cctgatactc ctctatctat
 181 atggaacccg tacacatgga cttttttaaga agcttggaat tccagggccc acacctctgc
 241 cttttttggg aaatgctttg tccttccgta agggctattg gacgtttgac atggaatgtt
 301 ataaaaagta tagaaaagtc tggggtattt atgactgtca acagcctatg ctggctatca
 361 cagatcccga catgatcaaa acagtgctag tgaaagaatg ttattctgtc ttcacaaacc
 421 ggaggccttt cgggccagtg ggatttatga aaaatgccat ctctatagct gaggatgaag
 481 aatggaagag aatacgatca ttgctgtctc caacattcac cagcggaaaa ctcaaggaga
 541 tggtccctat cattgcccag tatggagatg tgttggtgag aaatctgagg cgggaagcag
 601 agacaggcaa gcctgtcacc ttgaaacacg tcttttgggc ctacagcatg gatgtgatca
 661 ctagcacatc atttggagtg agcatcgact ctctcaacaa tccacaagac cccttttgtgg
 721 aaaacaccaa gaagctttta agatttaatc cattagatcc attcgttctc tcaataaaag
 781 tctttccatt ccttacccca attcttgaag cattaaatat cactgtgttt ccaagaaaag
 841 ttataagttt tctaacaaaa tctgtaaaac agataaaaga aggtcgcctc aaagagacac
 901 aaaagcaccg agtggatttc cttcagctga tgattgactc tcagaattca aaagactctg
 961 agacccacaa agctctgtct gatctggagc tcatggccca atcaattatc tttatttttg
1021 ctggctatga accacgagc agtgttctct ccttcattat atatgaactg ccactcacc
1081 ctgatgtcca gcagaaagtg cagaaggaaa ttgatacagt tttacccaat aaggcaccac
1141 ccacctatga tactgtgcta cagttggagt atcttgacat ggtggtgaat gaaacactca
1201 gattattccc agttgctatg agacttgaga gggtctgcaa aaagatgtt gaaatcaatg
1261 ggatgtttat tccaaagggg gtggtggtga tgattccaag ctatgttctt catcatgacc
1321 caaagtactg gacagagcct gagaagttcc tccctgaaag gttcagtaaa aagaacaagg
```

```
1381 acaacataga tccttacata tacacaccct ttggaagtgg acccagaaac tgcattggca 1441 tgaggtttgc tctcgtgaac atgaaacttg ctctagtcag agtccttcag aacttctcct 1501 tcaaaccttg taaagaaaca cagatccccc tgaaattacg ctttggagga cttcttctaa 1561 cagaaaaacc cattgttcta aaggctgagt caagggatga gaccgtaagt ggagcctgat 1621 ttccctaagg acttctggtt tgctctttaa gaaagctgtg ccccagaaca ccagagacct 1681 caaattactt tacaaataga accctgaaat gaagacgggc ttcatccaat gtgctgcata 1741 aataatcagg gattctgtac gtgcattgtg ctctctcatg gtctgtatag agtgttatac 1801 ttggtaatat agaggagatg accaaatcag tgctggggaa gtagatttgg cttctctgct 1861 tctcatagga ctatctccac cacccccagt tagcaccatt aactcctcct gagctctgat 1921 aacataatta acatttctca ataatttcaa ccacaatcat taataaaaat aggaattatt 1981 ttgatggctc taacagtgac atttatatca tgtgttatat ctgtagtatt ctatagtaag 2041 ctttatatta agcaaatcaa taaaaacctc tttacaaaag taaaaaaaaa aaaaaaaa
```

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. "Differentiation" refers to the developmental process of lineage commitment.

Differentiation can be assayed by measuring an increase in one or more cell specific markers relative to their expression in a corresponding undifferentiated control cell. A "lineage" refers to a pathway of cellular development, in which precursor or "progenitor" cells undergo progressive physiological changes to become a specified cell type having a characteristic function. In some embodiments, the cell type is a beta cell. In some embodiments, the cell type is an alpha cell, delta cell, or duct cell. In some other embodiments, the cell type is a hepatocyte. In still other embodiments, the cell type is a cardiomyocyte. In some embodiments, the cell type is a intestinal cell. Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). In some embodiments, an induced pluripotent stem cell (iPSC) is differentiated into a beta-like cell, an alpha-like cell, a delta-like cell, or a duct-like cell. In some other embodiments, an induced pluripotent stem cell (iPSC) is differentiated into a hepatocyte, cardiomyocyte, or intestinal cell.

A "de-differentiated cell" is a cell in which the process of differentiation has been, at least to some degree, reversed.

De-differentiation can be assayed, for example, by identifying a reduction in the expression of one or more cell specific markers relative to their expression in a corresponding control cell. Alternatively, de-differentiation can be assayed by measuring an increase in one or more markers typically expressed in an embryonic stem cell, a pluripotent or multi-potent cell type, or expressed at an earlier stage of development. In some embodiments, the de-differentiated cell is an induced pluripotent stem cell (iPSC). In certain embodiments, the de-differentiated cell is a human induced pluripotent stem cell (iPSC).

By "disease" is meant any condition or disorder that damages or interferes with the normal function of a cell, tissue, or organ. Examples of diseases include type 1 diabetes, type 2 diabetes, and pancreatic cancer.

By "effective amount" is meant the amount of a therapeutic agent or organoid required to ameliorate the symptoms of a disease in a subject relative to an untreated subject. The effective amount of a therapeutic used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In some embodiments, the therapeutic organoid is a pancreatic islet organoid. In some other embodiments, an effective amount of a pancreatic islet organoid is administered to a subject having type 1 or type 2 diabetes.

By "ESRRG polypeptide" is meant a protein or fragment thereof having at least 85% amino acid sequence identity to the sequence provided at NCBI Accession No. NP_001230448.1 and having nuclear hormone receptor activity. The amino acid sequence provided at NCBI Accession No. NP_001230448.1 is shown below (SEQ ID NO: 9):

```
  1 msnkdrhids scssfiktep sspasltdsv nhhspggssd asgsysstmn ghqngldspp 61 lypsapilgg sgpvrklydd csstivedpq tkceymlnsm pkrlclvcgd iasgyhygva 121 sceackaffk rtiqgnieys cpatneceit krrrkscqac rfmkclkvgm lkegvrldrv 181 rggrqkykrr idaenspyln pqlvqpakkp ynkivshllv aepekiyamp dptvpdsdik 241 alttlcdlad relvviigwa khipgfstls ladqmsllqs awmeililgv vyrslsfede
```

-continued

```
301 lvyaddyimd edqsklagll dlnnailqlv kkyksmklek eefvtlkaia lansdsmhie 361 dveavqklqd vlhealqdye agqhmedprr agkmlmtlpl lrqtstkavq hfyniklegk 421 vpmhklflem leakv
```

By "ESRRG polynucleotide" is meant a polynucleotide encoding a ESRRG polypeptide or fragment thereof. An exemplary ESRRG polynucleotide sequence is provided at NCBI Ref: NM_001243519.1. The sequence provided at NCBI Ref: NM_001243519.1 is reproduced below (SEQ ID NO: 10):

```
   1 aagctccaat cggggcttta agtccttgat taggagagtg tgagagcttt ggtcccaact
  61 ggctgtgcct ataggcttgt cactaggaga acatttgtgt taattgcact gtgctctgtc
 121 aaggaaactt tgatttatag ctggggtgca caaataatgg ttgccggtcg cacatggatt
 181 cggtagaact ttgccttcct gaatcttttt ccctgcacta cgaggaagag tagacttgaa
 241 tgagacctgc ctcatcagtc atgggatcat agtgtcacag atggaaaagc aactatcagc
 301 tgaattgtac tgaactacac acttggctaa ttcatcttat tgctctacac atctaaagga
 361 aggctcattc tgttcttgga gtctagacag catcaggagt tgggctcagt gaacaaaact
 421 ttaatgtcta gagcatttat gagggtttta atgattggaa atctatcct gagaatgtgg
 481 tcaccatatg tgacagcctt gctttctatc ttgtcttcag tttctggggc ttctctgcag
 541 aatgtcaaac aaagatcgac acattgattc cagctgttcg tccttcatca agacggaacc
 601 ttccagccca gcctccctga cggacagcgt caaccaccac agccctggtg gctcttcaga
 661 cgccagtggg agctacagtt caaccatgaa tggccatcag aacggacttg actcgccacc
 721 tctctaccct tctgctccta tcctgggagg tagtgggcct gtcaggaaac tgtatgatga
 781 ctgctccagc accattgttg aagatcccca gaccaagtgt gaatacatgc tcaactcgat
 841 gcccaagaga ctgtgtttag tgtgtggtga catcgcttct gggtaccact atgggtagc
 901 atcatgtgaa gcctgcaagg cattcttcaa gaggacaatt caaggcaata tagaatacag
 961 ctgccctgcc acgaatgaat gtgaaatcac aaagcgcaga cgtaaatcct gccaggcttg
1021 ccgcttcatg aagtgtttaa aagtgggcat gctgaaagaa ggggtgcgtc ttgacagagt
1081 acgtggaggt cggcagaagt acaagcgcag gatagatgcg gagaacagcc catacctgaa
1141 ccctcagctg gttcagccag ccaaaaagcc atataacaag attgtctcac atttgttggt
1201 ggctgaaccg gagaagatct atgccatgcc tgaccctact gtccccgaca gtgacatcaa
1261 agccctcact acactgtgtg acttggccga ccgagagttg gtggttatca ttggatgggc
1321 gaagcatatt ccaggcttct ccacgctgtc cctggcggac cagatgagcc ttctgcagag
1381 tgcttggatg gaaattttga tccttggtgt cgtataccgg tctctttcgt ttgaggatga
1441 acttgtctat gcagacgatt atataatgga cgaagaccag tccaaattag caggccttct
1501 tgatctaaat aatgctatcc tgcagctggt aaagaaatac aagagcatga agctggaaaa
1561 agaagaattt gtcaccctca agctatagc tcttgctaat tcagactcca tgcacataga
1621 agatgttgaa gccgttcaga agcttcagga tgtcttacat gaagcgctgc aggattatga
1681 agctggccag cacatggaag accctcgtcg agctggcaag atgctgatga cactgccact
1741 cctgaggcag acctctacca aggccgtgca gcatttctac aacatcaaac tagaaggcaa
1801 agtcccaatg cacaaacttt ttttggaaat gttggaggcc aaggtctgac taaaagctcc
1861 ctgggccttc ccatccttca tgttgaaaaa gggaaaataa acccaagagt gatgtcgaag
1921 aaacttagag tttagttaac aacatcaaaa atcaacagac tgcactgata atttagcagc
1981 aagactatga agcagctttc agattcctcc ataggttcct gatgagtttc tttctacttt
```

-continued

```
2041 ctccatcatc ttctttcctc tttcttccca catttctctt tctctttatt ttttctcctt
2101 ttcttctttc acctccctta tttctttgct tctttcattc ctagttccca ttctcctttta
2161 ttttcttccc gtctgcctgc cttctttctt ttctttacct actctcattc ctctctttttc
2221 tcatccttcc ccttttttct aaatttgaaa tagctttagt ttaaaaaaaa atcctcccttt
2281 cccccttttcc tttcccttc tttccttttt cccttctctt ttccctttcc tttcctttcc
2341 tcttgacctt ctttccatct ttcttttttct tccttctgct gctgaacttt taaaagaggt
2401 ctctaactga agagagatgg aagccagccc tgccaaagga tggagatcca taatatggat
2461 gccagtgaac ttattgtgaa ccatactgtc cccaatgact aaggaatcaa agagagagaa
2521 ccaacgttcc taaaagtaca gtgcaacata tacaaattga ctgagtgcag tattagattt
2581 catgggagca gcctctaatt agacaactta agcaacgttg catcggctgc ttcttatcat
2641 tgcttttcca tctagatcag ttacagccat ttgattcctt aattgttttt tcaagtcttc
2701 caggtatttg ttagtttagc tactatgtaa cttttttcagg gaatagttta agctttattc
2761 attcatgcaa tactaaagag aaataagaat actgcaattt tgtgctggct ttgaacaatt
2821 acgaacaata atgaaggaca aatgaatcct gaaggaagat ttttaaaaat gtttgtttc
2881 ttcttacaaa tggagatttt tttgtaccag ctttaccact tttcagccat ttattaatat
2941 gggaattttaa cttactcaag caatagttga agggaaggtg catattatca cggatgcaat
3001 ttatgttgtg tgccagtctg gtcccaaaca tcaatttctt aacatgagct ccagtttacc
3061 taaatgttca ctgacacaaa ggatgagatt acacctacag tgactctgag tagtcacata
3121 tataagcact gcacatgaga tatagatccg tagaattgtc aggagtgcac ctctctactt
3181 gggaggtaca attgccatat gatttctagc tgccatggtg gttaggaatg tgatactgcc
3241 tgtttgcaaa gtcacagacc ttgcctcaga aggagctgtg agccagtatt catttaagag
3301 gcaataaggc aaatgccaga attaaaaaaa aaaatcatca aagacagaaa atgcctgacc
3361 aaattctaaa acctaatcca tataagttta ttcatttagg aatgttcgtt taaattaatc
3421 tgcagttttt accaagagct aagccaatat atgtgctttt caaccagtat tgtcacagca
3481 tgaaagtcaa gtcaggttcc agactgttaa gaggtgtaat ctaatgaaga aatcaattag
3541 atgccccgaa atctacagtc gctgaataac caataaacag taacctccat caaatgctat
3601 accaatggac cagtgttagt agctgctccc tgtattatgt gaacagtctt attctatgta
3661 cacagatgta attaaaattg taatcctaac aaacaaaaga aatgtagttc agcttttcaa
3721 tgtttcatgt ttgctgtgct tttctgaatt ttatgttgca ttcaaagact gttgtcttgt
3781 tcttgtggtg tttggattct tgtggtgtgt gcttttagac acagggtaga attagagaca
3841 atattggatg tacaattcct caggagacta cagtagtata ttctattcct taccagtaat
3901 aaggttcttc ctaataataa ttaagagatt gaaactccaa acaagtattc attatgaaca
3961 gatacacatc aaaatcataa taatattttc aaaacaagga ataatttctc taatggttta
4021 ttatagaata ccaatgtata gcttagaaat aaaactttga atatttcaag aatatagata
4081 agtctaatttt ttaaatgctg tatatatggc tttcactcaa tcatctctca gatgttgtta
4141 ttaactcgct ctgtgttgtt gcaaaacttt ttggtgcaga ttcgtttcca aaactattgc
4201 tactttgtgt gctttaaaca aaataccttg ggttgatgaa acatcaaccc agtgctagga
4261 atactgtgta tctatcatta gctatatggg actatattgt agattgtggt ttctcagtag
4321 agaagtgact gtagtgtgat tctagataaa tcatcattag caattcattc agatggtcaa
4381 taacttgaaa tttatagctg tgataggagt tcagaaattg gcacatccct ttaaaaataa
```

```
4441 caacagaaaa tacaactcct gggaaaaaag gtgctgattc tataagatta tttatatatg 4501 taagtgttta aaaagattat tttccagaaa gtttgtgcag ggtttaagtt gctactattc 4561 aactacacta tatataaata aaatatatac aatatataca ttgttttcac tgtatcacat 4621 taaagtactt gggcttcaga agtaagagcc aaccaactga aaacctgaga tggagatatg 4681 ttcaaagaat gagatacaat tttttagttt tcagtttaag taactctcag cattacaaaa 4741 gagtaagtat ctcacaaata ggaaataaaa ctaaaacgtg gatttaaaaa gaactgcacg 4801 ggctttaggg taaatgctca tcttaaacct cactagaggg aagtcttctc aagtttcaag 4861 caagaccatt tacttaatgt gaagttttgg aaagttataa aggtgtatgt tttagccata 4921 tgattttaat tttaattttg cttcttttag gttcgttctt atttaaagca atatgattgt 4981 gtgactcctt gtagttacac ttgtgtttca atcagatcag attgttgtat ttattccact 5041 attttgcatt taaatgataa cataaaagat ataaaaaatt taaaactgct atttttctta 5101 tagaagagaa aatgggtgtt ggtgattgta ttttaattat ttaagcgtct ctgtttacct 5161 gcctaggaaa acatttatg gcagtcttat gtgcaaagat cgtaaaagga caaaaaattt 5221 aaactgctta taataatcca ggagttgcat tatagccagt agtaaaaata ataataataa 5281 taataaaacc atgtctatag ctgtagatgg gcttcacatc tgtaaagcaa tcaattgtat 5341 attttgtga tgtgtaccat actgtgtgct ccagcaaatg tccatttgtg taaatgtatt 5401 tattttatat tgtatatatt gttaaatgca aaaaggagat atgattctgt aactccaatc 5461 agttcagatg tgtaactcaa attattatgc ctttcaggat gatggtagag caatattaaa 5521 caagcttcca cttttgactg ctaaaaaaaa aaaaaaaa
```

As used herein, "endocrine" refers to secretion of an agent (e.g., a hormone) into a bloodstream. "Exocrine" refers to secretion of an agent into an epithelial surface by way of a duct.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "FOXA2 polypeptide" is meant a protein or fragment thereof having at least 85% amino acid sequence identity to the sequence provided at NCBI Accession No. NP_068556.2 and having transcription factor activity. The amino acid sequence provided at NCBI Accession No. NP_068556.2 is shown below (SEQ ID NO: 11):

```
  1 mhsassmlga vkmeghepsd wssyyaepeg yssysnmnag lgmngmntym smsaaamgsg 61 sgnmsagsmn mssyvgagms pslagmspga gamagmggsa gaagvagmgp hlspslsplg 121 gqaagamggl apyanmnsms pmygqaglsr ardpktyrrs ythakppysy islitmaiqq 181 spnkmltlse iyqwimdlfp fyrqnqqrwq nsirhslsfn dcflkvprsp dkpgkgsfwt 241 lhpdsgnmfe ngcylrrqkr fkcekqlalk eaagaagsgk kaaagaqasq aqlgeaagpa 301 setpagtesp hssaspcqeh krgglgelkg tpaaalsppe papspgqqqq aaahllgpph 361 hpglppeahl kpehhyafnh pfsinnlmss eqqhhhshhh hqphkmdlka yeqvmhypgy 421 gspmpgslam gpvtnktgld asplaadtsy yqgvysrpim nss
```

By "FOXA2 polynucleotide" is meant a polynucleotide encoding a FOXA2 polypeptide or fragment thereof. An exemplary FOXA2 polynucleotide sequence is provided at NCBI Ref: NM_021784.4. The sequence provided at NCBI Ref: NM_021784.4 is reproduced below (SEQ ID NO: 12):

```
  1 cccgcccact tccaactacc gcctccggcc tgcccaggga gagagaggga gtggagccca 61 gggagaggga gcgcgagaga gggagggagg aggggacggt gctttggctg acttttttt 121 aaaagagggt gggggtgggg ggtgattgct ggtcgtttgt tgtggctgtt aaattttaaa
```

-continued

```
 181 ctgccatgca ctcggcttcc agtatgctgg gagcggtgaa gatggaaggg cacgagccgt
 241 ccgactggag cagctactat gcagagcccg agggctactc ctccgtgagc aacatgaacg
 301 ccggcctggg gatgaacggc atgaacacgt acatgagcat gtcggcggcc gccatgggca
 361 gcggctcggg caacatgagc gcgggctcca tgaacatgtc gtcgtacgtg ggcgctggca
 421 tgagcccgtc cctggcgggg atgtccccg gcgcgggcgc catggcgggc atgggcggct
 481 cggccggggc ggccggcgtg gcgggcatgg ggccgcactt gagtcccagc ctgagcccgc
 541 tcgggggggca ggcggccggg gccatgggcg gcctggcccc ctacgccaac atgaactcca
 601 tgagccccat gtacgggcag gcgggcctga ccgcgcccg cgaccccaag acctacaggc
 661 gcagctacac gcacgcaaag ccgccctact cgtacatctc gctcatcacc atggccatcc
 721 agcagagccc caacaagatg ctgacgctga gcgagatcta ccagtggatc atggacctct
 781 tccccttcta ccggcagaac cagcagcgct ggcagaactc catccgccac tcgctctcct
 841 tcaacgactg tttcctgaag gtgccccgct cgcccgacaa gccggcaag ggctccttct
 901 ggaccctgca ccctgactcg gcaacatgt tcgagaacgg ctgctacctg cgccgccaga
 961 agcgcttcaa gtgcgagaag cagctggcgc tgaaggaggc cgcaggcgcc gccggcagcg
1021 gcaagaaggc ggccgccgga gcccaggcct cacaggctca actcggggag gccgccgggc
1081 cggcctccga gactccggcg gcaccgagt cgcctcactc gagcgcctcc ccgtgccagg
1141 agcacaagcg agggggcctg ggagagctga aggggacgcc ggctgcggcg ctgagccccc
1201 cagagccggc gccctctccc gggcagcagc agcaggccgc ggcccacctg ctgggcccgc
1261 cccaccaccc gggcctgccg cctgaggccc acctgaagcc ggaacaccac tacgccttca
1321 accaccgtt ctccatcaac aacctcatgt cctcggagca gcagcaccac cacagccacc
1381 accaccacca accccacaaa atggacctca aggcctacga acaggtgatg cactaccccg
1441 gctacggttc ccccatgcct ggcagcttgg ccatgggccc ggtcacgaac aaaacgggcc
1501 tggacgcctc gccctggcc gcagatacct cctactacca gggggtgtac tcccggccca
1561 ttatgaactc ctcttaagaa gacgacggct tcaggcccgg ctaactctgg cacccccggat
1621 cgaggacaag tgagagagca agtgggggtc gagactttgg ggagacggtg ttgcagagac
1681 gcaagggaga agaaatccat aacacccccca ccccaacacc cccaagacag cagtcttctt
1741 caccccgctgc agccgttccg tcccaaacag agggccacac agatacccca cgttctatat
1801 aaggaggaaa acgggaaaga atataaagtt aaaaaaaagc ctccggtttc cactactgtg
1861 tagactcctg cttcttcaag cacctgcaga ttctgatttt tttgttgttg ttgttctcct
1921 ccattgctgt tgttgcaggg aagtcttact taaaaaaaaa aaaaattttt gtgagtgact
1981 cggtgtaaaa ccatgtagtt ttaacagaac cagagggttg tactattgtt taaaaacagg
2041 aaaaaaaata atgtaagggt ctgttgtaaa tgaccaagaa aagaaaaaa aaagcattcc
2101 caatcttgac acggtgaaat ccaggtctcg ggtccgatta atttatggtt tctgcgtgct
2161 ttatttatgg cttataaatg tgtattctgg ctgcaagggc cagagttcca caaatctata
2221 ttaaagtgtt atacccggtt ttatcccttg aatcttttct tccagatttt tcttttcttt
2281 acttggctta caaatatac aggcttggaa attatttcaa gaaggaggga gggataccct
2341 gtctggttgc aggttgtatt ttattttggc ccagggagtg ttgctgtttt cccaacattt
2401 tattaataaa attttcagac ataaaaaaa
```

By "GATA6 polypeptide" is meant a protein or fragment thereof having at least 85% amino acid sequence identity to the sequence provided at NCBI Accession No. NP_005248.2 and having transcription factor activity. The amino acid sequence provided at NCBI Accession No. NP_005248.2 is shown below (SEQ ID NO: 13):

```
  1 maltdggwcl pkrfgaagad asdsrafpar epstppspis sssssсsrgg ergpggasnc
 61 gtpqldteaa agpparslll ssyashpfga phgpsapgva gpggnlsswe dlllftdldq
121 aataskllws srgaklspfa peqpeemyqt laalssqgpa aydgapggfv hsaaaaaaaa
181 aaasspvyvp ttrvgsmlpg lpyhlqgsgs gpanhaggag ahpgwpqasa dsppygsggg
241 aagggaagpg gagsaaahvs arfpyspspp mangaarepg gyaaagsgga ggvsgggssl
301 aamggrepqy sslsaarpin gtyhhhhhhh hhhpspyspy vgapltpawp agpfetpvlh
361 slqsragapl pvprgpsadl ledlsesrec vncgsiqtpl wrrdgtghyl cnacglyskm
421 nglsrplikp qkrvpssrrl glscanchtt tttlwrrnae gepvcnacgl ymklhgvprp
481 lamkkegiqt rkrkpknink sktcsgnsnn sipmtptsts snsddcsknt spttqptasg
541 agapvmtgag estnpensel kysgqdglyi gvslaspaev tssvrpdswc alala
```

By "GATA6 polynucleotide" is meant a polynucleotide encoding a GATA6 polypeptide or fragment thereof. An exemplary KCNK3 polynucleotide sequence is provided at NCBI Ref: NM_005257.5. The sequence provided at NCBI Ref: NM_005257.5 is reproduced below (SEQ ID NO: 14):

```
   1 agttccgacc cacagcctgg cacccttcgg cgagcgctgt tgtttaggg ctcggtgagt
  61 ccaatcagga gcccaggctg cagtttccg gcagagcagt aagaggcgcc tcctctctcc
 121 tttttattca ccagcagcgc ggcgcagacc ccggactcgc gctcgcccgc tggcgccctc
 181 ggcttctctc cgcgcctggg agcaccctcc gccgcggccg ttctccatgc gcagcgcccg
 241 cccgaggagc tagacgtcag cttggagcgg cgccggaccg tggatggcct tgactgacgg
 301 cggctggtgc ttgccgaagc gcttcggggc gcgggtgcg gacgccagcg actccagagc
 361 ctttccagcg cgggagccct ccacgccgcc ttcccccatc tcttcctcgt cctcctcctg
 421 ctcccggggc ggagagcggg gccccggcgg cgccagcaac tgcgggacgc ctcagctcga
 481 cacggaggcg gcggccggac ccccggcccg ctcgctgctg ctcagttcct acgcttcgca
 541 tcccttcggg gctccccacg gaccttcggc gcctggggtc gcgggccccg ggggcaacct
 601 gtcgagctgg gaggacttgc tgctgttcac tgacctcgac caagccgcga ccgccagcaa
 661 gctgctgtgg tccagccgcg gcgccaagct gagccccttc gcacccgagc agccggagga
 721 gatgtaccag accctcgccg ctctctccag ccagggtccg gccgcctacg acggcgcgcc
 781 cggcggcttc gtgcactctg cggccgcggc ggcagcagcc gcggcggcgg ccagctcccc
 841 ggtctacgtg cccaccaccc gcgtgggttc catgctgccc ggcctaccgt accacctgca
 901 ggggtcgggc agtgggccag ccaaccacgg gggcggcgcg ggcgcgcacc ccggctggcc
 961 tcaggcctcg gccgacagcc ctccatacgg cagcggaggc ggcgcggctg gcggcggggc
1021 cgcggggcct ggcggcgctg gctcagccgc ggcgcacgtc tcggcgcgct tcccctactc
1081 tcccagcccg cccatggcca acggcgccgc gcgggagccg ggaggctacg cggcggcggg
1141 cagtgggggc gcgggaggcg tgagcggcgg cggcagtagc ctggcggcca tgggcggccg
1201 cgagccccag tacagctcgc tgtcggccgc gcggccgctg aacgggacgt accaccacca
1261 ccaccaccac caccaccacc atccgagccc ctactcgccc tacgtggggg cgccactgac
```

-continued

```
1321 gcctgcctgg cccgccggac ccttcgagac cccggtgctg cacagcctgc agagccgcgc
1381 cggagcccccg ctcccggtgc cccggggtcc cagtgcagac ctgctggagg acctgtccga
1441 gagccgcgag tgcgtgaact gcggctccat ccagacgccg ctgtggcggc gggacggcac
1501 cggccactac ctgtgcaacg cctgcgggct ctacagcaag atgaacgcc tcagccggcc
1561 cctcatcaag ccgcagaagc gcgtgccttc atcacggcgg cttggattgt cctgtgccaa
1621 ctgtcacacc acaactacca ccttatggcg cagaaacgcc gagggtgaac ccgtgtgcaa
1681 tgcttgtgga ctctacatga aactccatgg ggtgcccaga ccacttgcta tgaaaaaaga
1741 gggaattcaa accaggaaac gaaaacctaa gaacataaat aaatcaaaga cttgctctgg
1801 taatagcaat aattccattc ccatgactcc aacttccacc tcttctaact cagatgattg
1861 cagcaaaaat acttccccca caacacaacc tacagcctca ggggcgggtg ccccggtgat
1921 gactggtgcg ggagagagca ccaatcccga gaacagcgag ctcaagtatt cgggtcaaga
1981 tgggctctac ataggcgtca gtctcgcctc gccggccgaa gtcacgtcct ccgtgcgacc
2041 ggattcctgg tgcgccctgg ccctggcctg agcccacgcc gccaggaggc agggagggct
2101 ccgccgcggg cctcactcca ctcgtgtctg cttttgtgca gcggtccaga cagtggcgac
2161 tgcgctgaca gaacgtgatt ctcgtgcctt tattttgaaa gagatgtttt cccaagagg
2221 cttgctgaaa gagtgagaga agatggaagg gaagggccag tgcaactggg cgcttgggcc
2281 actccagcca gcccgcctcc ggggcggacc ctgctccact tccagaagcc aggactagga
2341 cctgggcctt gcctgctatg gaatattgag agagattttt taaaaagat tttgcatttt
2401 gtccaaaatc atgtgcttct tctgatcaat tttggttgtt ccagaatttc ttcatacctt
2461 ttccacatcc agatttcatg tgcgttcatg gagaagatca cttgaggcca tttggtacac
2521 atctctggag gctgagtcgg ttcatgaggt ctcttatcaa aaatattact cagtttgcaa
2581 gactgcattg taactttaac atacactgtg actgacgttt ctcaaagttc atattgtgtg
2641 gctgatctga agtcagtcgg aatttgtaaa cagggtagca acaagatat ttttcttcca
2701 tgtatacaat aatttttta aaagtgcaa tttgcgttgc agcaatcagt gttaaatcat
2761 ttgcataaga tttaacagca tttttataa tgaatgtaaa catttaact taatggtact
2821 taaaataatt taaagaaaa atgttaactt agacattctt atgcttcttt tacaactaca
2881 tcccatttta tatttccaat tgttaaagaa aaatatttca gaacaaatc ttctctcagg
2941 aaaattgcct ttctctattt gttaagaatt tttatacaag aacaccaata tacccccttt
3001 attttactgt ggaatatgtg ctggaaaaat tgcaacaaca ctttactacc taacggatag
3061 catttgtaaa tactctaggt atctgtaaac actctgatga agtctgtata gtgtgactaa
3121 cccacaggca ggttggttta cattaatttt ttttttgaa tgggatgtcc tatggaaacc
3181 tatttcacca gagttttaaa aataaaaagg gtattgttttt gtcttctgta cagtgagttc
3241 cttccctttt caaagctttc tttttatgct gtatgtgact atagatattc atataaaaca
3301 agtgcacgtg aagtttgcaa aatgctttaa ggccttcctt tcaaagcata gtccttttgg
3361 agccgttttg tacctttat accttggctt atttgaagtt gacacatggg gttagttact
3421 actctccatg tgcattgggg acagttttta taagtgggaa ggactcagta ttattatatt
3481 tgagatgata agcattttgt ttgggaacaa tgcttaaaaa tattccagaa agttcagatt
3541 ttttttcttt gtgaatgaaa tatattctgg cccacgaaca gggcgatttc ctttcagttt
3601 tttccttttg caacgtgcct tgaagtctca agctcacct gaggttgcag acgttacccc
```

```
3661 caacagaaga taggtagaaa tgattccagt ggcctctttg tatttcttc attgttgagt 3721 agatttcagg aaatcaggag gtgtttcaca atacagaatg atggccttta actgtgaaaa 3781 aaaaa
```

By "gellan gum" is meant a polysaccharide having a straight chain with a repeating unit that has any one of the following molecular structures:

Gellan Gum—High Acyl Form

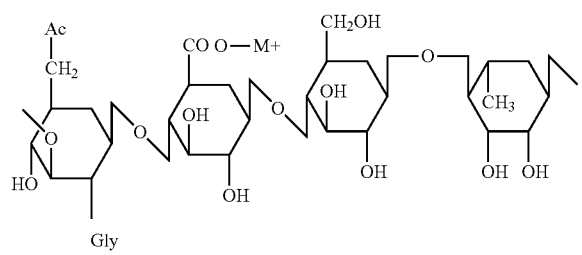

Gellan Gum—Low Acyl Form

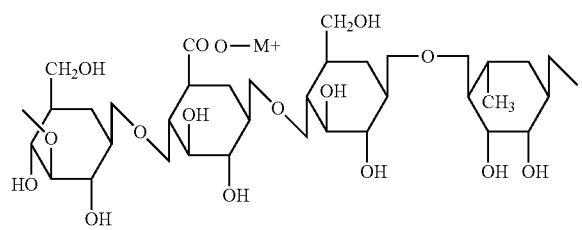

In the foregoing structures, "Ac" refers to an acetate group and "Gly" refers to a glycerate group and "M+" is a monovalent cation. In some embodiments, the gellan gum is KELCOGEL® gellan gum.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "immunosuppressive agent" or "immunosuppressant" is meant an agent that inhibits or prevents an immune reaction, such as rejection, of a transplanted organ or organoid in a subject. Examples of immunosuppressants include, but are not limited to, basilizimab, antithymocyte globulin, alemtuzumab, prednisone, azathioprine, mycophenolate, cyclosporine, sirolimus, methotrexate, interferon, and tacrolimus.

By "induced pluripotent stem cell" or "iPSC" is meant a differentiated somatic cell that acquires pluripotency by the exogenous expression of one or more transcription factors in the cell. An "iPSC-derived cell" is a cell derived from an induced pluripotent stem cell. An "iPSC-derived beta-like cell," "iPSC-derived alpha-like cell," "iPSC-derived delta-like cell," or "iPSC-derived duct-like cell" is a cell derived from an induced pluripotent stem cell and has characteristics of a beta cell, alpha cell, delta cell, or duct cell, respectively.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "KCNK3 polypeptide" is meant a protein or fragment thereof having at least 85% amino acid sequence identity to the sequence provided at NCBI Accession No. NP_002237.1 and having potassium channel activity. The amino acid sequence provided at NCBI Accession No. NP_002237.1 is shown below (SEQ ID NO: 15):

```
  1 mkrqnvrtla livctftyll vgaavfdale sepelierqr lelrqqelra rynlsqggye
 61 elervvlrlk phkagvqwrf agsfyfaitv ittigyghaa pstdggkvfc mfyallgipl
121 tlvmfqslge rintlvryll hrakkglgmr radvsmanmv ligffscist lcigaaafsh
181 yehwtffqay yycfitltti gfgdyvalqk dgalgtqpqy vafsfvyilt gltvigafln
241 lvvlrfmtmn aedekrdaeh ralltrngqa gggggggsah ttdtasstaa aggggfrnvy
301 aevlhfqsmc sclwyksrek lqysipmiip rdlstsdtcv eqshsspggg grysdtpsrr
361 cicsgaprsa issystglhs lstfrglmkr rssv
```

By "KCNK3 polynucleotide" is meant a polynucleotide encoding a KCNK3 polypeptide or fragment thereof. An exemplary KCNK3 polynucleotide sequence is provided at NCBI Ref: NM_002246.2. The sequence provided at NCBI Ref: NM_002246.2 is reproduced below (SEQ ID NO: 16):

```
   1 ggcggcggcg gcggcggcgg ccccgggcgc tgagcgggtg cccggcgcgg agagcggcga
  61 gcgcagccat gccccaggcc gcctccgggg cagcagcagc ggcggccggg gccgaggcgc
 121 gggccggggg cgccgggggg ccggcggcgg cccgggcggg acgatgaagc ggcagaacgt
 181 gcgcacgctg gcgctcatcg tgtgcacctt cacctacctg ctggtgggcg ccgcggtctt
 241 cgacgcgctg gagtcggagc ccgagctgat cgagcggcag cggctggagc tgcggcagca
 301 ggagctgcgg gcgcgctaca acctcagcca gggcggctac gaggagctgg agcgcgtcgt
 361 gctgcgcctc aagccgcaca aggccggcgt gcagtggcgc ttcgccggct ccttctactt
 421 cgccatcacc gtcatcacca ccatcggcta cgggcacgcg gcacccagca cggatggcgg
 481 caaggtgttc tgcatgttct acgcgctgct gggcatcccg ctcacgctcg tcatgttcca
 541 gagcctgggc gagcgcatca acaccttggt gaggtacctg ctgcaccgcg ccaagaaggg
 601 gctgggcatg cggcgcgccg acgtgtccat ggccaacatg gtgctcatcg gcttcttctc
 661 gtgcatcagc acgctgtgca tcggcgccgc cgccttctcc cactacgagc actggacctt
 721 cttccaggcc tactactact gcttcatcac cctcaccacc atcggcttcg gcgactacgt
 781 ggcgctgcag aaggaccagg ccctgcagac gcagccgcag tacgtggcct tcagcttcgt
 841 ctacatcctt acgggcctca cggtcatcgg cgccttcctc aacctcgtgg tgctgcgctt
 901 catgaccatg aacgccgagg acgagaagcg cgacgccgag caccgcgcgc tgctcacgcg
 961 caacgggcag gcgggcggcg gcggaggggg tggcagcgcg cacactacgg acaccgcctc
1021 atccacggcg gcagcgggcg gcggcggctt ccgcaacgtc tacgcggagg tgctgcactt
1081 ccagtccatg tgctcgtgcc tgtggtacaa gagccgcgag aagctgcagt actccatccc
1141 catgatcatc ccgcgggacc tctccacgtc cgacacgtgc gtggagcaga gccactcgtc
1201 gccgggaggg ggcggccgct acagcgacac gccctcgcga cgctgcctgt gcagcgggc
1261 gccacgctcc gccatcagct cggtgtccac gggtctgcac agcctgtcca ccttccgcgg
1321 cctcatgaag cgcaggagct ccgtgtgact gccccgaggg gcctggagca cctggggcg
1381 cgggcggggg acccctgctg ggaggccagg agactgcccc tgctgccttc tgcccagtgg
1441 gaccccgcac aacatccctc accactctcc cccagcaccc ccatctccga ctgtgcctgc
1501 ttgcaccagc cggcaggagg ccgggctctg aggaccctg gggcccccat cggagccctg
1561 caaattccga gaaatgtgaa acttggtggg gtcaggagg aaaggcagaa gctgggagcc
1621 tcccttccct ttgaaaatct aagaagctcc cagtcctcag agaccctgct ggtacccaga
1681 cccccacctt cggaggggac ttcatgttcc gtgtacgttt gcatctctat ttatacctct
```

-continued

```
1741 gtcctgctag gtctcccacc ttcccttggt tccaaaagcc agggtgtcta tgtccaagtc 1801 acccctactc agccccactc cccttcctca tccccagctg tgtctcccaa cctcccttcg 1861 tgttgttttg catggctttg cagttatgga gaaagtggaa acccagcagt ccctaaagct 1921 ggtccccaga aagcaggaca gaaagaagga gggacaggca ggcagcagga ggggcgagct 1981 gggaggcagg aggcagcggc ctgtcagtct gcagaatggt cgcactggag gttcaagcta 2041 actggcctcc agccacattc tcatagcagg taggacttca gccttccaga cactgccctt 2101 agaatctgga acagaagact tcagactcac cataattgct gataattacc cactcttaaa 2161 tttgtcgagt gattttttagc ctctgaaaac tctatgctgg ccactgattc ctttgagtct 2221 cacaaaaccc tacttaggtc atcagggcag gagttctcac tcccatttta cagatgagaa 2281 tactgaggcc tggacaggtg aagtgaccag agagcaaaag gcaaaggggt ggggctggg 2341 tgcagtggct cacacctgta ttcccaacac ttttggaggc tgaggttgga ggattgcttg 2401 agcccaggaa tttgagacca gcctaggtga catagtgaga ccccatctct acaaaaaata 2461 aaaaattaac caggtgtggt ggcacgtgcc tgggagtccc agcgacttgg gaggctgagg 2521 tgggaggatt gtttgagcct gggaggtcga ggctgtagtg agccctgatt gcaccactgt 2581 actccagcct gggtgacagg gcaagaccct gtctcaaaaa aaaaaaaaaa aatggcaaag 2641 ggagacaaga gcccagcctg cttgttgcta gccaaagtgt tctttccttc agcttggcc 2701 tgctcttaaa agcaaagctc ctgcagtgta catcctggca ttgtgtggct acctgggttt 2761 taaaccagaa tcagaagtcc cggatcagag ggcactgctg aggttcagcc tcttctcttc 2821 ttggccagga ggcagcagct ctgaatgggc ccctgaggct gcacaggggc ctttgtcact 2881 ggggcgcatg cttacaaaca gtgcagttct tgggaccgag gtaagcaggg ctgggtctca 2941 tggcagaaag gccaggatct ggggctctag gaatttggga attgggcaga gtggccaaga 3001 aagctggcag gcatatccta tgggacatca cacctggcac cattgtcatt gttggtgcct 3061 gtgtcccaag tagctagtga taagctgagg ctgcagcaag aaacacccctt cccaggtggg 3121 ggagtttgga ccagaggtgc cctctgccca ccacacctgc aacccagaag cccagatgga 3181 acgcagctga cgaaggtgat gcttgaggct cacttttggg gccccacagc tggagccggt 3241 ataatgactg gacaacatc aagggggtgga tgagggggcct ctcctcccgc aacactgcct 3301 tcccatgctg ttcccctgcc agctccttaa cactgccgac caaggccagc cctggcattc 3361 agggaaattg gagggcagca cccgtagggt ggccagcctc aggccccacc ccagctgtgt 3421 cctctagtct ctggggaccc ctgggggggaa gaagtctacc ctgcttgtga gtcccgtctc 3481 agtgtggagg aactggctgc acgtgggacc tgaaggtgcc ctctgtgttt atgttggggg 3541 tggggggggca gtgctggctg cctctgtcct gtgtgtgacc ctgccctcga agggtcctgt 3601 cctgtcagtc ccgagggagc cacaaccaaa gctgcggaga gaaggtgggg aagggtgcag 3661 aatgccgtg gggcacagcg tggcagactg ttcagtctct gctgggtctt tcctagggac 3721 ctggaaggcc agtgttgctt cccccctcact ccctttcact gcaggcagcc tctctgcttc 3781 cccaatgcct tatgcctggg cacactgcca cagaatatgc aatatgtgtg ggtgaccatg 3841 ccctcacgac cacaccccca ccccgggcag ccccggact ccaaaggtcg tggctgccac 3901 agcctccctc agctcttcct gcctatctgt cttcacactg agaatggcgc ccaataaatg 3961 ctatccacgg agaccagg
```

By "KCNQ1 polypeptide" is meant a protein or fragment thereof having at least 85% amino acid sequence identity to the sequence provided at NCBI Accession No. NP_000209.2 (isoform 1) or NP_861463.1 (isoform 2) and having potassium channel activity. The amino acid sequence provided at NCBI Accession No. NP_000209.2 is shown below (SEQ ID NO: 17):

```
  1 maaassppra erkrwgwgrl pgarrgsagl akkcpfslel aeggpaggal yapiapgapg
 61 pappaspaap aappvasdlg prppvsldpr vsiystrrpv larthvqgry ynflerptgw
121 kcfvyhfavf livlvclifs vlstieqyaa latgtlfwme ivlvvffgte yvvrlwsagc
181 rskyvglwgr lrfarkpisi idlivvvasm vvlcvgskgq vfatsairgi rflqilrmlh
241 vdrqggtwrl lgsvvfihrq elittlyigf lglifssyfv ylaekdavne sgrvefgsya
301 dalwwgvvtv ttigygdkvp qtwvgktias cfsvfaisff alpagilgsg falkvqqkqr
361 qkhfnrqipa aasliqtawr cyaaenpdss twkiyirkap rshtllspsp kpkksvvvkk
421 kkfkldkdng vtpgekmltv phitcdppee rrldhfsvdg ydssvrkspt llevsmphfm
481 rtnsfaedld legetlltpi thisqlrehh ratikvirrm qyfvakkkfq qarkpydvrd
541 viegysqghl nlmvrikelq rrldqsigkp slfisyseks kdrgsntiga rlnrvedkvt
601 qldqrlalit dmlhqllslh ggstpgsggp preggahitq pcgsggsvdp elflpsntlp
661 tyeqltvprr gpdegs
```

By "KCNQ1 polynucleotide" is meant a polynucleotide encoding a KCNQ1 polypeptide or fragment thereof. An exemplary KCNQ1 polynucleotide sequence is provided at NCBI Ref: NM_000218.2. The sequence provided at NCBI Ref: NM_000218.2 is reproduced below (SEQ ID NO: 18):

```
   1 gcggcggggc tggcagcagt ggctgcccgc actgcgcccg ggcgctcgcc ttcgctgcag
  61 ctcccggtgc cgccgctcgg gccggccccc cggcaggccc tcctcgttat ggccgcggcc
 121 tcctccccgc ccagggccga aggaagcgc tgggggttggg gccgcctgcc aggcgcccgg
 181 cggggcagcg cgggcctggc caagaagtgc cccttctcgc tggagctggc ggagggcggc
 241 ccggcgggcg cgcgctcta cgcgcccatc gcgcccggcg ccccaggtcc cgcgccccct
 301 gcgtccccgg ccgcgcccgc cgcgccccca gttgcctccg accttggccc gcggccgccg
 361 gtgagcctag acccgcgcgt ctccatctac agcacgcgcc gcccggtgtt ggcgcgcacc
 421 cacgtccagg gccgcgtcta caacttcctc gagcgtccca ccggctggaa atgcttcgtt
 481 taccacttcg ccgtcttcct catcgtcctg gtctgcctca tcttcagcgt gctgtccacc
 541 atcgagcagt atgccgccct ggccacgggg actctcttct ggatggagat cgtgctggtg
 601 gtgttcttcg gacggagta cgtggtccgc ctctggtccg ccggctgccg cagcaagtac
 661 gtgggcctct gggggcggct gcgctttgcc cggaagccca tttccatcat cgacctcatc
 721 gtggtcgtgg cctccatggt ggtcctctgc gtgggctcca aggggcaggt gtttgccacg
 781 tcggccatca ggggcatccg cttcctgcag atcctgagga tgctacacgt cgaccgccag
 841 ggaggcacct ggaggctcct gggctccgtg gtcttcatcc accgccagga gctgataacc
 901 accctgtaca tcggcttcct gggcctcatc ttctcctcgt actttgtgta cctggctgag
 961 aaggacgcgg tgaacgagtc aggccgcgtg gagttcggca gctacgcaga tgcgctgtgg
1021 tgggggtgg tcacagtcac caccatcggc tatggggaca aggtgcccca gacgtgggtc
1081 gggaagacca tcgcctcctg cttctctgtc tttgccatct ccttctttgc gctcccagcg
1141 gggattcttg gctcggggtt tgccctgaag gtgcagcaga agcagaggca gaagcacttc
```

```
1201 aaccggcaga tcccggcggc agcctcactc attcagaccg catggaggtg ctatgctgcc 1261 gagaaccccg actcctccac ctggaagatc tacatccgga aggccccccg gagccacact 1321 ctgctgtcac ccagccccaa acccaagaag tctgtggtgg taaagaaaaa aaagttcaag 1381 ctggacaaag acaatggggt gactcctgga gagaagatgc tcacagtccc ccatatcacg 1441 tgcgaccccc cagaagagcg gcggctggac cacttctctg tcgacggcta tgacagttct 1501 gtaaggaaga gcccaacact gctggaagtg agcatgcccc atttcatgag aaccaacagc 1561 ttcgccgagg acctggacct ggaagggag actctgctga cacccatcac ccacatctca 1621 cagctgcggg aacaccatcg ggccaccatt aaggtcattc gacgcatgca gtactttgtg 1681 gccaagaaga aattccagca agcgcggaag ccttacgatg tgcgggacgt cattgagcag 1741 tactcgcagg ccacctcaa cctcatggtg cgcatcaagg agctgcagag gaggctggac 1801 cagtccattg ggaagccctc actgttcatc tccgtctcag aaaagagcaa ggatcgcggc 1861 agcaacacga tcggcgcccg cctgaaccga gtagaagaca aggtgacgca gctggaccag 1921 aggctggcac tcatcaccga catgcttcac cagctgctct ccttgcacgg tggcagcacc 1981 cccggcagcg gcggccccc cagagagggc ggggcccaca tcacccagcc ctgcggcagt 2041 ggcggctccg tcgaccctga gctcttcctg cccagcaaca ccctgcccac ctacgagcag 2101 ctgaccgtgc ccaggagggg ccccgatgag gggtcctgag gaggggatgg ggctggggga 2161 tgggcctgag tgagagggga ggccaagagt ggccccacct ggccctctct gaaggaggcc 2221 acctcctaaa aggcccagag agaagagccc cactctcaga ggccccaata ccccatggac 2281 catgctgtct ggcacagcct gcacttgggg gctcagcaag gccacctctt cctggccggt 2341 gtggggccc cgtctcaggt ctgagttgtt accccaagcg ccctggcccc cacatggtga 2401 tgttgacatc actggcatgg tggttgggac ccagtggcag ggcacagggc ctggcccatg 2461 tatggccagg aagtagcaca ggctgagtgc aggcccaccc tgcttggccc aggggcttc 2521 ctgaggggag acagagcaac ccctggaccc cagcctcaaa tccaggaccc tgccaggcac 2581 aggcagggca ggaccagccc acgctgacta cagggccgcc ggcaataaaa gcccaggagc 2641 ccatttggag ggcctgggcc tggctccctc actctcagga aatgctgacc catgggcagg 2701 agactgtgga gactgctcct gagcccccag cttccagcag gagggacagt ctcaccattt 2761 ccccagggca cgtggttgag tggggggaac gcccacttcc ctgggttaga ctgccagctc 2821 ttcctagctg gagaggagcc ctgcctctcc gcccctgagc ccactgtgcg tggggctccc 2881 gcctccaacc cctcgcccag tcccagcagc cagccaaaca cacagaaggg gactgccacc 2941 tccccttgcc agctgctgag ccgcagagaa gtgacggttc ctacacagga cagggttcc 3001 ttctgggcat tacatcgcat agaaatcaat aatttgtggt gatttggatc tgtgttttaa 3061 tgagtttcac agtgtgattt tgattattaa ttgtgcaagc ttttcctaat aaacgtggag 3121 aatcacaggc tgggctgggc actgctctca ccttggttcc tggggcatcc atggggtctc 3181 tcacagacag gaccctgca gttcccctgg aagcagtgcc caggtggctg tggaatagga 3241 acgctaaaaa aaaaaaaaa aa
```

By "LGR5 polypeptide" is meant a protein or fragment thereof having at least 85% amino acid sequence identity to the sequence provided at NCBI Accession No. NP_003658.1 (isoform 1), NP_001264155.1 (isoform 2), or NP_001264156.1 (isoform 3) and having transmembrane signaling receptor activity or G-protein coupled receptor activity. The amino acid sequence provided at NCBI Accession No. NP_003658.1 is shown below (SEQ ID NO: 19):

```
  1 mdtsrlgvll slpvllqlat ggssprsgvl lrgcpthchc epdgrmllry dcsdlglsel
 61 psnlsvftsy ldlsmnnisq llpnplpslr fleelrlagn altyipkgaf tglyslkvlm
121 lqnnqlrhvp tealqnlrsl qslrldanhi syvppscfsg lhslrhlwld dnalteipvq
181 afrslsalqa mtlalnkihh ipdyafgnls slvvlhlhnn rihslgkkcf dglhsletld
241 lnynnldefp tairtlsnlk elgfhsnnir sipekafvgn pslitihfyd npiqfvgrsa
301 fghlpelrtl tlngasqite fpdltgtanl esltltgaqi sslpqtvcnq lpnlqvldls
361 ynlledlpsf svcqklqkid lrhneiyeik vdtfqqllsl rslnlawnki aiihpnafst
421 lpslikldls snllssfpit glhglthlkl tgnhalqsli ssenfpelkv iempyayqcc
481 afgvcenayk isnqwnkgdn ssmddlhkkd agmfqaqder dledflldfe edlkalhsvq
541 cspspgpfkp cehlldgwli rigvwtiavl altcnalvts tvfrsplyis piklligvia
601 avnmltgvss avlagvdaft fgsfarhgaw wengvgchvi gflsifases svflltlaal
661 ergfsvkysa kfetkapfss lkviillcal laltmaavpl lggskygasp lclplpfgep
721 stmgymvali llnslcflmm tiaytklycn ldkgdleniw dcsmvkhial llftncilnc
781 pvaflsfssl inltfispev ikfillvvvp lpaclnplly ilfnphfked lvslrkqtyv
841 wtrskhpslm sinsddvekq scdstqalvt ftsssitydl ppssvpspay pvteschlss
901 vafvpcl
```

By "LGR5 polynucleotide" is meant a polynucleotide encoding a LGR5 polypeptide or fragment thereof. An exemplary LGR5 polynucleotide sequence is provided at NCBI Ref: NM_003667.3. The sequence provided at NCBI Ref: NM_003667.3 is reproduced below (SEQ ID NO: 20):

```
   1 aaaaaacgag cgtgcaagca gagatgctgc tccacaccgc tcaggccgcg agcagcagca
  61 aggcgcaccg ccactgtcgc cgctgcagcc agggctgctc cgaaggccgg cgtggcggca
 121 accggcacct ctgtccccgc cgcgcttctc ctcgccgccc acgccgtggg gtcaggaacg
 181 cggcgtctgg cgctgcagac gcccgctgag ttgcagaagc ccacggagcg gcgcccggcg
 241 cgccacggcc cgtagcagtc cggtgctgct ctccgcccgc gtccggctcg tggccccta
 301 cttcgggcac catggacacc tcccggctcg gtgtgctcct gtccttgcct gtgctgctgc
 361 agctggcgac cggggggcagc tctcccaggt ctggtgtgtt gctgagggc tgccccacac
 421 actgtcattg cgagcccgac ggcaggatgt tgctcagggt ggactgctcc gacctggggc
 481 tctcggagct gccttccaac ctcagcgtct tcacctccta cctagacctc agtatgaaca
 541 acatcagtca gctgctcccg aatcccctgc ccagtctccg cttcctggag gagttacgtc
 601 ttgcgggaaa cgctctgaca tacattccca agggagcatt cactggcctt acagtctta
 661 aagttcttat gctgcagaat aatcagctaa gacacgtacc cacagaagct ctgcagaatt
 721 tgcgaagcct tcaatccctg cgtctggatg ctaaccacat cagctatgtg ccccaagct
 781 gtttcagtgg cctgcattcc ctgaggcacc tgtggctgga tgacaatgcg ttaacagaaa
 841 tccccgtcca ggcttttaga agtttatcgg cattgcaagc catgaccttg ccctgaaca
 901 aaatacacca cataccagac tatgcctttg gaaacctctc cagcttggta gttctacatc
 961 tccataacaa tagaatccac tccctgggaa agaaatgctt tgatgggctc cacagcctag
1021 agactttaga tttaaattac aataaccttg atgaattccc cactgcaatt aggacactct
1081 ccaaccttaa agaactagga tttcatagca acaatatcag gtcgatacct gagaaagcat
1141 ttgtaggcaa cccttctctt attacaatac atttctatga caatcccatc cagtttgttg
```

-continued

```
1201 ggagatctgc ttttcaacat ttacctgaac taagaacact gactctgaat ggtgcctcac 1261 aaataactga atttcctgat ttaactggaa ctgcaaacct ggagagtctg actttaactg 1321 gagcacagat ctcatctctt cctcaaaccg tctgcaatca gttacctaat ctccaagtgc 1381 tagatctgtc ttacaaccta ttagaagatt tacccagttt ttcagtctgc caaaagcttc 1441 agaaaattga cctaagacat aatgaaatct acgaaattaa agttgacact ttccagcagt 1501 tgcttagcct ccgatcgctg aatttggctt ggaacaaaat tgctattatt cacccccaatg 1561 cattttccac tttgccatcc ctaataaagc tggacctatc gtccaacctc ctgtcgtctt 1621 ttcctataac tgggttacat ggtttaactc acttaaaatt aacaggaaat catgccttac 1681 agagcttgat atcatctgaa aactttccag aactcaaggt tatagaaatg ccttatgctt 1741 accagtgctg tgcatttgga gtgtgtgaga atgcctataa gatttctaat caatggaata 1801 aaggtgacaa cagcagtatg gacgaccttc ataagaaaga tgctggaatg tttcaggctc 1861 aagatgaacg tgaccttgaa gatttcctgc ttgactttga ggaagacctg aaagcccttc 1921 attcagtgca gtgttcacct tccccaggcc ccttcaaacc ctgtgaacac ctgcttgatg 1981 gctggctgat cagaattgga gtgtggacca tagcagttct ggcacttact tgtaatgctt 2041 tggtgacttc aacagttttc agatcccctc tgtacatttc ccccattaaa ctgttaattg 2101 gggtcatcgc agcagtgaac atgctcacgg gagtctccag tgccgtgctg gctggtgtgg 2161 atgcgttcac ttttggcagc tttgcacgac atggtgcctg gggggagaat ggggttggtt 2221 gccatgtcat tggttttttg tccattttg cttcagaatc atctgttttc ctgcttactc 2281 tggcagccct ggagcgtggg ttctctgtga atattctgc aaaatttgaa acgaaagctc 2341 cattttctag cctgaaagta atcatttgc tctgtgccct gctggccttg accatggccg 2401 cagttcccct gctgggtggc agcaagtatg gcgcctcccc tctctgcctg cctttgcctt 2461 ttggggagcc cagcaccatg ggctacatgg tcgctctcat cttgctcaat tccctttgct 2521 tcctcatgat gaccattgcc tacaccaagc tctactgcaa tttggacaag ggagacctgg 2581 agaatatttg ggactgctct atggtaaaac acattgccct gttgctcttc accaactgca 2641 tcctaaactg ccctgtggct ttcttgtcct tctcctcttt aataaacctt acatttatca 2701 gtcctgaagt aattaagttt atccttctgg tggtagtccc acttcctgca tgtctcaatc 2761 cccttctcta catcttgttc aatcctcact ttaaggagga tctggtgagc ctgagaaagc 2821 aaacctacgt ctggacaaga tcaaaacacc caagcttgat gtcaattaac tctgatgatg 2881 tcgaaaaaca gtcctgtgac tcaactcaag ccttggtaac cttaccagc tccagcatca 2941 cttatgacct gcctcccagt tccgtgccat caccagctta tccagtgact gagagctgcc 3001 atctttcctc tgtggcattt gtcccatgtc tctaattaat atgtgaagga aaatgttttc 3061 aaaggttgag aacctgaaaa tgtgagattg agtatatcag agcagtaatt aataagaaga 3121 gctgaggtga aactcggttt aaaaaccaaa aagaatctc tcagttagta agaaaaggct 3181 gaaaacctct tgatacttga gagtgaatat aagtctaaat gctgctttgt ataatttgtt 3241 cagctaaggg atagatcgat cacactattt aagtgagccc agatcaaaaa agcagattga 3301 aattttcttt agaaaagatt ctccatgatt tgaattgcat tctctttaaa ctcaccaatg 3361 taatcatttt gggaggaggg agaacccact tgctttccaa atgggtttat ttaaacccac 3421 aaactcaaga ggttgttggg ggaattagga aaataagggt tttcaatgac ctacattgct 3481 aggtagaggc tgtgatccat gggatttcat tctaatgacc atgtgaagat gtttgagtcc 3541 tcctttgcct ttcctcagaa agaatccttc taaggcacaa atcccttaga tggataatgt 3601 aaggtattgt taactcactc atattgagat cattttaga gataccaggt tttatgtatc
```

```
3661 agcactagat ggttccaccc tcatgggata aaactgctta caagtatttt gaaagaaaaa 3721 ctgaccaaaa ttcttaaatt gttactaagg caatcatgca caggtgacgt atgtcttatc 3781 tgatttgttt ttaactcctt ggtgcccaaa gctcagaagg gaattccact gccagcaatg 3841 aacatacctg gaaaagaaag taagcaatct gggatttttt ttctgggtta gtaaagaatt 3901 tttgcaataa gttttatcag ttgattcaaa ctgatgtgca tcttaatgat caaatgtgca 3961 cattacataa attaagtcca ctgatacaac ttcttacaca tgtatctcta gtagctctgg 4021 caaacccaat atctgacacc actttggact caagagactc agtaacgtat tatcctgttt 4081 atttagcttg gttttagctg tgttctctct ggataaccca cttgatgtta ggaacattac 4141 ttctctgctt attccatatt aatactgtgt taggtatttt aagaagcaag ttattaaata 4201 agaaaagtca aagtattaat tcttaccttc tattatccta tattagcttc aatacatcca 4261 aaccaaatgg ctgttaggta gatttatttt tatataagca tgtttatttt gatcagatgt 4321 tttaacttgg atttgaaaaa atacatttat gagatgtttt ataagatgtg taaatataga 4381 actgtattta ttactatagt aaaggttcag taacattaag gaccatgata atgataataa 4441 accttgtaca gtggcatatt cttgattta tattgtgttt ctctgcccat tttctttaaa 4501 ttcattaact gtatatatgt aaatatatag tacttgtaaa tagattccaa atttgctttt 4561 ctattgggta aaaaataaat ttgtaataaa atgtgtgact atgaaacaaa aaaaaaaaaa 4621 aaaaa
```

By "LDHA polypeptide" or "lactate dehydrogenase A polypeptide" is meant a protein or fragment thereof having at least 85% amino acid sequence identity to the sequence provided at NCBI Accession No. NP_005557.1 (isoform 1), NP_001128711.1 (isoform 2), NP_001158886.1 (isoform 3), NP_001158887.1 (isoform 4), or NP_001158888.1 (isoform 5) and having dehydrogenase activity. The amino acid sequence provided at NCBI Accession No. NP_005557.1 is shown below (SEQ ID NO: 21):

```
  1 matlkdqliy nllkeeqtpq nkitvvgvga vgmacaisil mkdladelal vdviedklkg 61 emmdlqhgsl flrtpkivsg kdynvtansk lviitagarq qegesrinlv qrnvnifkfi 121 ipnvvkyspn ckllivsnpv diltyvawki sgfpknrvig sgcnldsarf rylmgerlgv 181 hplschgwvl gehgdssvpv wsgmnvagvs lktlhpdlgt dkdkeqwkev hkqvvesaye 241 viklkgytsw aiglsvadla esimknlrrv hpvstmikgl ygikddvfls vpcilgqngi 301 sdlvkvtlts eeearlkksa dtlwgiqkel qf
```

By "LDHA polynucleotide" or "lactate dehydrogenase A polynucleotide" is meant a polynucleotide encoding a LDHA polypeptide or fragment thereof. An exemplary LDHA polynucleotide sequence is provided at NCBI Ref: NM_005566.3. The sequence provided at NCBI Ref: NM_005566.3 is reproduced below (SEQ ID NO: 22):

```
  1 gtctgccggt cggttgtctg gctgcgcgcg ccacccgggc ctctccagtg ccccgcctgg 61 ctcggcatcc accccagcc cgactcacac gtgggttccc gcacgtccgc cggccccccc 121 cgctgacgtc agcatagctg ttccacttaa ggcccctccc gcgcccagct cagagtgctg 181 cagccgctgc cgccgattcc ggatctcatt gccacgcgcc cccgacgacc gcccgacgtg 241 cattcccgat tcctttggt tccaagtcca atatggcaac tctaaaggat cagctgattt 301 ataatcttct aaaggaagaa cagaccccc agaataagat tacagttgtt ggggttggtg 361 ctgttggcat ggcctgtgcc atcagtatct taatgaagga cttggcagat gaacttgctc
```

```
 421 ttgttgatgt catcgaagac aaattgaagg gagagatgat ggatctccaa catggcagcc 481 ttttccttag aacaccaaag attgtctctg gcaaagacta taatgtaact gcaaactcca 541 agctggtcat tatcacggct ggggcacgtc agcaagaggg agaaagccgt cttaatttgg 601 tccagcgtaa cgtgaacatc tttaaattca tcattcctaa tgttgtaaaa tacagcccga 661 actgcaagtt gcttattgtt tcaaatccag tggatatctt gacctacgtg gcttggaaga 721 taagtggttt tcccaaaaac cgtgttattg aagcggttg caatctggat tcagcccgat 781 tccgttacct aatgggggaa aggctgggag ttcacccatt aagctgtcat gggtgggtcc 841 ttggggaaca tggagattcc agtgtgcctg tatggagtgg aatgaatgtt gctggtgtct 901 ctctgaagac tctgcaccca gatttaggga ctgataaaga taaggaacag tggaaagagg 961 ttcacaagca ggtggttgag agtgcttatg aggtgatcaa actcaaaggc tacacatcct 1021 gggctattgg actctctgta gcagatttgg cagagagtat aatgaagaat cttaggcggg 1081 tgcacccagt ttccaccatg attaagggtc tttacggaat aaaggatgat gtcttcctta 1141 gtgttccttg cattttggga cagaatggaa tctcagacct tgtgaaggtg actctgactt 1201 ctgaggaaga ggcccgtttg aagaagagtg cagatacact ttgggggatc caaaaggagc 1261 tgcaattta aagtcttctg atgtcatatc atttcactgt ctaggctaca acaggattct 1321 aggtggaggt tgtgcatgtt gtcctttta tctgatctgt gattaaagca gtaatatttt 1381 aagatggact gggaaaaaca tcaactcctg aagttagaaa taagaatggt ttgtaaaatc 1441 cacagctata tcctgatgct ggatggtatt aatcttgtgt agtcttcaac tggttagtgt 1501 gaaatagttc tgccacctct gacgcaccac tgccaatgct gtacgtactg catttgcccc 1561 ttgagccagg tggatgttta ccgtgtgtta tataacttcc tggctccttc actgaacatg 1621 cctagtccaa cattttttcc cagtgagtca catcctggga tccagtgtat aaatccaata 1681 tcatgtcttg tgcataattc ttccaaagga tcttattttg tgaactatat cagtagtgta 1741 cattaccata taatgtaaaa agatctacat acaaacaatg caaccaacta tccaagtgtt 1801 ataccaacta aaaccccaa taaaccttga acagtgacta ctttggttaa ttcattatat 1861 taagatataa agtcataaag ctgctagtta ttatattaat ttggaaatat taggctattc 1921 ttgggcaacc ctgcaacgat ttttctaac agggatatta ttgactaata gcagaggatg 1981 taatagtcaa ctgagttgta ttggtaccac ttccattgta agtcccaaag tattatatat 2041 ttgataataa tgctaatcat aattggaaag taacattcta tatgtaaatg taaaatttat 2101 ttgccaactg aatataggca atgatagtgt gtcactatag gaacacaga tttttgagat 2161 cttgtcctct ggaagctggt aacaattaaa aacaatctta aggcagggaa aaaaaaaaa 2221 aaaaaa
```

By "MAFA polypeptide" is meant a protein or fragment thereof having at least 85% amino acid sequence identity to the sequence provided at NCBI Accession No. NP_963883.2 and having transcription factor activity. The amino acid sequence provided at NCBI Accession No. NP_963883.2 is shown below (SEQ ID NO: 23):

```
  1 maaelamgae lpssplaiey vndfdlmkfe vkkeppeaer fchrlppgsl sstplstpcs 61 svpsspsfca pspgtgqqqq aqqqqqssqa qqapqppsqq pqavqqtsqk paledlywms 121 qyqhhlnpea lnltpedave aliqsqhhqa hhqahhpaaa aayeafrqpq faqqqqaddm 181 qaqhhhqahh aahhhhaahh hhhhhhhqq aqhqqqaqhh vrleerfsdd qlvsmsvrel 241 nrqlrqfske evirlkqkrr tlknrqyaqs crfkrvqqrh ilesekcqlq sqveqlklev 301 qrlakerdly kekyeklaqr qqpqsaqqaq fprepsppqa qpqqakqtad ffl
```

By "MAFA polynucleotide" is meant a polynucleotide encoding a MAFA polypeptide or fragment thereof. An exemplary MAFA polynucleotide sequence is provided at NCBI Ref: NM_201589.3. The sequence provided at NCBI Ref: NM_201589.3 is reproduced below (SEQ ID NO: 24):

```
   1  gcgcggccgg gcgcgggccc cgggcgatgg ccgcggagct ggcgatgggc gccgagctgc
  61  ccagcagccc gctggccatc gagtacgtca acgacttcga cctgatgaag ttcgaggtga
 121  agaaggagcc tcccgaggcc gagcgcttct gccaccgcct gccgccaggc tcgctgtcct
 181  cgacgccgct cagcacgccc tgctcctccg tgccctcctc gcccagcttc tgcgcgccca
 241  gcccgggcac cggcggcggc ggcggcgcgg ggggcggcgg cggctcgtct caggccgggg
 301  gcgccccgg gccgccgagc gggggccccg cgccgtcgg gggcacctcg gggaagccgg
 361  cgctggagga tctgtactgg atgagcggct accagcatca cctcaacccc gaggcgctca
 421  acctgacgcc cgaggacgcg gtggaggcgc tcatcggcag cggccaccac ggcgcgcacc
 481  acggcgcgca ccacccggcg ccgccgcag cctacgaggc tttccgcggc ccgggcttcg
 541  cgggcggcgg cggagcggac gacatgggcg ccggccacca ccacggcgcg caccacgccg
 601  cccaccatca ccacgccgc caccaccacc accaccacca ccaccaccat ggcggcgcgg
 661  gacacggcg tggcgcgggc caccacgtgc gcctggagga gcgcttctcc gacgaccagc
 721  tggtgtccat gtcggtgcgc gagctgaacc ggcagctccg cggcttcagc aaggaggagg
 781  tcatccggct caagcagaag cggcgcacgc tcaagaaccg cggctacgcg cagtcctgcc
 841  gcttcaagcg ggtgcagcag cggcacattc tggagagcga gaagtgccaa ctccagagcc
 901  aggtggagca gctgaagctg gaggtggggc gcctggccaa agagcgggac ctgtacaagg
 961  agaaatacga gaagctggcg gccgggcg gccccgggag cgcgggcggg gccggtttcc
1021  cgcgggagcc ttcgccgccg caggccggtc ccggcgggc caagggcacg gccgacttct
1081  tcctgtaggc gccgacccc gagcccgcgc cgccgtcgcc ggggacaagt tcgcgcaggc
1141  ctctcggggc ctcggctcgg actccgcggt acaggacgtg gacaccaggc ccggcccggc
1201  cgtgctggcc ccggtgccaa gtctgcgggc gcggggctgg aggccccttc gctcccggtc
1261  cccgttcgcg cgcgtcggcc cgggtcgccg tcctgaggtt gagcggagaa cggtgatttc
1321  taaggaaact tgagccaggt ctaacttctt tccaagcgtc cgcttgtaca tacgttgaac
1381  gtggttctcc gttcccacct tcgccctgcc agcctagagg gaccgcgctg ccgtcccttc
1441  ccgggtggcc cctgcctgcc cccgccctcc ttcgttctct tctcagcctc cctttccttg
1501  ccttttttaa cttcccctcc ccgttttaaa atcggtctta ttttcgaagt atttataatt
1561  attatgcttg gtgattagaa aagaaaacct tggaggaagc cccttctttc cccagccggg
1621  gtccgccctc agtcgcgagt cacagcatga gtcgctcgcc aggaggggcc cggcccctgc
1681  ctgccccctc cccgcttgcc cccgaccctg ctaccggcgt tccttggagg tcgaagccag
1741  ggacgtcacc cgtgctgtgt ccaggcctgc tgtcctacta tgctcaaccg ggggtggggg
1801  gaggggggtg agtcctgtgc tcagtcgggt ggggctggc ccggatcccg agctgctgtc
1861  tctctatgca ccagaacata tctgtaactc ctggggaaat acatcttgtt ttaaccttca
1921  agagaagtga aagaaaaaag taatgcacag tatttctagc agaaaatttt ttttttaag
1981  aggaggcttg gccagagcc ttctggcatg gggcgggtgg agaaagtgtt tttattttaa
2041  tttaaattgt gtttcgtttt gtttgtggaa tctttcttta atgcttcgtc gctctttgga
2101  ctagccggga gagagggcga ggaggcgggt gctccaggcc ctgtaggctg gccaggcgc
2161  ctgggggatc tgcccgtttt cggaggccct caggggccat cagtgggatt ccagccgctc
```

-continued
```
2221  cacacccctc ccctgagcac tcggagtgga aggcgcgccg actcgttgaa agttttgttg 2281  tgtagttggt tttcgttgag ttcttttttc atttgctacg aaactgagaa aagaaaaaa 2341  atacacaaaa taaatctgtt cagatccaag tca
```

As used herein, a "marker" is meant any protein or polynucleotide having an alteration in expression level or activity that is associated with a disease or disorder or that is associated with a particular cell type. In some embodiments, a marker for a beta cell is Pdx1, MafA, Pax4, Pax6, NeuroD1, Nkx6-1, Gata6, or Foxa2. In some embodiments, a marker for a hepatocyte is AFP, ALB, or Cyp3a7. In some other embodiments, a marker for a cardiomyocyte is hMlc2a, hNkx2-5, alphaMHC or KCNQ1. In still other embodiments, a marker for a small intestine cell is CDX2, Muc2, or Lgr5.

By "alphaMHC polypeptide" or "myosin heavy chain (MHC) alpha polypeptide" is meant a protein or fragment thereof having at least 85% amino acid sequence identity to the sequence provided at NCBI Accession No. NP_002462.2 and having actin binding activity. The amino acid sequence provided at NCBI Accession No. NP_002462.2 is shown below (SEQ ID NO: 25):

```
   1  mtdaqmadfg aaaqylrkse kerleaqtrp fdirtecfvp ddkeefvkak ilsreggkvi
  61  aetengktvt vkedqvlqqn ppkfdkiedm amltflhepa vlfnlkerya awmiytysgl
 121  fcvtvnpykw lpvynaevva ayrgkkrsea pphifsisdn ayqymltdre nqsilitges
 181  gagktvntkr viqyfasiaa igdrgkkdna nankgtledq iiqanpalea fgnaktvrnd
 241  nssrfgkfir ihfgatgkla sadietylle ksrvifqlka ernyhifyqi lsnkkpelld
 301  mllvtnnpyd yafvsqgevs vasiddseel matdsafdvl gftseekagv ykltgaimhy
 361  gnmkfkqkqr eeqaepdgte dadksaylmg lnsadllkgl chprvkvgne yvtkggsvqq
 421  vyysigalak avyekmfnwm vtrinatlet kqprqyfigv ldiagfeifd fnsfeqlcin
 481  ftneklqqff nhhmfvleqe eykkegiewt fidfgmdlqa cidliekpmg imsileeecm
 541  fpkatdmtfk aklydnhlgk snnfqkprni kgkqeahfsl ihyagtvdyn ilgwleknkd
 601  plnetvvaly qksslklmat lfssyatadt gdsgkskggk kkgssfqtvs alhrenlnkl
 661  mtnlrtthph fvrciipner kapgvmdnpl vmhqlrcngv legiricrkg fpnrilygdf
 721  rqryrilnpv aipegqfids rkgtekllss ldidhnqykf ghtkvffkag llglleemrd
 781  erlsriitrm qaqargqlmr iefkkiverr dallviqwni rafmgvknwp wmklyfkikp
 841  llksaeteke matmkeefgr iketleksea rrkeleekmv sllqekndlq lqvqaeqdnl
 901  ndaeercdql iknkiqleak vkemnerled eeemnaelta kkrkledecs elkkdiddle
 961  ltlakvekek hatenkvknl teemagldei iakltkekka lqeahqqald dlqveedkvn
1021  slskskvkle qqvddlegsl eqekkvrmdl erakrklegd lkltqesimd lendklqlee
1081  klkkkefdin qqnskiedeq vlalqlqkkl kenqarieel eeeleaerta rakveklrsd
1141  lsreleeise rleeaggats vqiemnkkre aefqkmrrdl eeatlqheat aaalrkkhad
1201  svaelgeqid nlqrvkqkle keksefklel ddvtsnmeqi ikakanlekv srtledqane
1261  yrvkleeaqr slndfttqra klqtengela rqleekeali sqltrgklsy tqqmedlkrq
1321  leeegkakna lahalqsarh dcdllreqye eeteakaelq rvlskansev aqwrtkyetd
1381  aiqrteelee akkklaqrlq daeeaveavn akcsslektk hrlqneiedl mvdversnaa
1441  aaaldkkqrn fdkilaewkq kyeesqsele ssqkearsls telfklknay eeslehletf
1501  krenknlqee isdlteqlge ggknvhelek vrkqlevekl elqsaleeae asleheegki
1561  lraqlefnqi kaeierklae kdeemeqakr nhqrvvdslq tsldaetrsr nevlrvkkkm
1621  egdlnemeiq lshanrmaae aqkqvkslqs llkdtqiqld davranddlk eniaiverrn
1681  nllqaeleel ravveqters rklaeqelie tservqllhs qntslinqkk kmesdltqlq
```

-continued

```
1741  seveeavqec rnaeekakka itdaammaee lkkeqdtsah lermkknmeq tikdlqhrld 1801  eaeqialkgg kkqlqklear vrelegelea eqkrnaesvk gmrkserrik eltyqteedk 1861  knllrlqdlv dklqlkvkay krqaeeaeeq antnlskfrk vqheldeaee radiaesqvn 1921  klraksrdig akqkmhdee
```

By "alphaMHC polynucleotide" is meant a polynucleotide encoding a alphaMHC polypeptide or fragment thereof. An exemplary alphaMHC polynucleotide sequence is provided at NCBI Ref: NM_002471.3. The sequence provided at NCBI Ref: NM_002471.3 is reproduced below (SEQ ID NO: 26):

```
   1  agatagagag actcctgcgg cccagattct tcaggattct ccgtgaaggg ataaccaggg 61  gaagcaccaa gatgaccgat gcccagatgg ctgactttgg ggcagcggcc cagtacctcc 121  gcaagtcaga gaaggagcgt ctagaggccc agacccggcc ctttgacatt cgcactgagt 181  gcttcgtgcc cgatgacaag gaagagtttg tcaaagccaa gattttgtcc cgggagggag 241  gcaaggtcat tgctgaaacc gagaatggga agacggtgac tgtgaaggag gaccaggtgt 301  tgcagcagaa cccacccaag ttcgacaaga ttgaggacat ggccatgctg accttcctgc 361  acgagcccgc ggtgcttttc aacctcaagg agcgctacgc ggcctggatg atatatacct 421  actcgggcct cttctgtgtc actgtcaacc cctacaagtg gctgccggtg tacaatgccg 481  aggtggtggc cgcctaccgg ggcaagaaga ggagtgaggc cccgcccac atcttctcca 541  tctccgacaa cgcctatcag tacatgctga cagatcggga gaaccagtcc atcctcatca 601  cgggagaatc cggggcgggg aagactgtga acaccaagcg tgtcatccag tactttgcca 661  gcattgcagc cataggtgac cgtggcaaga aggacaatgc caatgcgaac aagggcaccc 721  tggaggacca gatcatccag gccaaccccg ctctggaggc cttcggcaat gccaagactg 781  tccggaacga caactcctcc cgctttggga aattcattag gatccacttt ggggccactg 841  gaaagctggc ttctgcagac atagagacct acctgctgga gaagtccgg gtgatcttcc 901  agctgaaagc tgagagaaac taccacatct tctaccagat tctgtccaac aagaagccgg 961  agttgctgga catgctgctg gtcaccaaca atccctacga ctacgccttc gtgtctcagg 1021  gagaggtgtc cgtggcctcc attgatgact ccgaggagct catggccacc gatagtgcct 1081  ttgacgtgct gggcttcact tcagaggaga agctggcgt ctacaagctg acgggagcca 1141  tcatgcacta cgggaacatg aagttcaagc agaagcagcg ggaggagcag gcggagccag 1201  acggcaccga agatgctgac aagtcggcct acctcatggg gctgaactca gctgacctgc 1261  tcaagggcct gtgccaccct cgggtgaaag tgggcaacga gtatgtcacc aagggcaga 1321  gcgtgcagca ggtgtactac tccatcgggg ctctggccaa ggcagtgtat gagaagatgt 1381  tcaactggat ggtgacgcgc atcaacgcca ccctggagac caagcagcca cgccagtact 1441  tcataggagt cctggacatc gctggcttcg agatcttcga cttcaacagc tttgagcagc 1501  tctgcatcaa cttcaccaac gagaagctgc agcagttctt caaccaccac atgttcgtgc 1561  tggagcagga ggagtacaag aaggagggca ttgagtggac attcattgac tttggcatgg 1621  acctgcaggc ctgcattgac ctcatcgaga gcccatggg catcatgtcc atcctggagg 1681  aggagtgcat gttccccaag gccactgaca tgaccttcaa ggccaagctg tacgacaacc 1741  acctgggcaa gtccaacaat ttccagaagc acgcaacat caaggggaag caggaagccc 1801  acttctccct gatccactac gccggcactg tggactacaa catcctgggc tggctggaaa 1861  aaaacaagga tcctctcaac gagactgttg tggccctgta ccagaagtcc tccctcaagc 1921  tcatggccac tctcttctcc tcctacgcaa ctgccgatac tggggacagt ggtaaaagca
```

-continued

```
1981  aaggaggcaa gaaaaagggc tcatccttcc agacggtgtc ggctctccac cgggaaaatc 2041  tcaacaagct aatgaccaac ctgaggacca cccatcctca ctttgtgcgt tgcatcatcc 2101  ccaatgagcg gaaggctcca ggggtgatgg acaaccccct ggtcatgcac cagctgcgct 2161  gcaatggcgt gctggagggc atccgcatct gcaggaaggg cttccccaac cgcatcctct 2221  acggggactt ccggcagagg tatcgcatcc tgaacccagt ggccatccct gagggacagt 2281  tcattgatag caggaagggg acagagaagc tgctcagctc tctggacatt gatcacaacc 2341  agtacaagtt tggccacacc aaggtgttct tcaaggcagg gctgcttggg ctgctggagg 2401  agatgcggga tgagaggctg agccgcatca tcacgcgcat gcaggcccaa gcccgggggcc 2461  agctcatgcg cattgagttc aagaagatag tggaacgcag ggatgccctg ctggtaatcc 2521  agtggaacat tcgggccttc atgggggtca agaattggcc ctggatgaag ctctacttca 2581  agatcaagcc gctgctgaag agcgcagaga cggagaagga gatggccacc atgaaggaag 2641  agttcgggcg catcaaagag acgctggaga agtccgaggc tcgccgcaag gagctggagg 2701  agaagatggt gtccctgctg caggagaaga atgacctgca gctccaagtg caggcggaac 2761  aagacaacct caatgatgct gaggagcgct gcgaccagct gatcaaaaac aagattcagc 2821  tggaggccaa agtaaaggag atgaatgaga ggctggagga tgaggaggag atgaacgcgg 2881  agctcactgc caagaagcgc aagctggaag acgagtgctc agagctcaag aaggacattg 2941  atgacctgga gctgacactg gccaaggtgg agaaggagaa gcatgcaaca gagaacaagg 3001  tgaagaacct aacagaggag atggctgggc tggatgaaat catcgctaag ctgaccaagg 3061  agaagaaagc tctacaagag gcccatcagc aggccctgga tgaccttcag gttgaggaag 3121  acaaggtcaa cagcctgtcc aagtctaagg tcaagctgga gcagcaggtg gatgatctgg 3181  agggatccct agagcaagag aagaaggtgc gcatggacct ggagcgagca aagcggaaac 3241  tggagggcga cctgaagctg acccaggaga gcatcatgga cctggaaaat gataaactgc 3301  agctggaaga aaagcttaag aagaaggagt ttgacattaa tcagcagaac agtaagattg 3361  aggatgagca ggtgctggcc cttcaactac agaagaaact gaaggaaaac caggcacgca 3421  tcgaggagct ggaggaggag ctggaggccg agcgcaccgc cagggctaag gtggagaagc 3481  tgcgctcaga cctgtctcgg gagctggagg agatcagcga gcggctggaa gaggccggcg 3541  gggccacgtc cgtgcagatc gagatgaaca agaagcgcga ggccgagttc cagaagatgc 3601  ggcgggacct ggaggaggcc acgctgcagc acgaggccac tgccgcggcc ctgcgcaaga 3661  agcacgccga cagcgtggcc gagctgggcg agcagatcga caacctgcag cgggtgaagc 3721  agaagctgga gaaggagaag agcgagttca gctggagct ggatgacgtc acctccaaca 3781  tggagcagat catcaaggcc aaggcaaacc tggagaaagt gtctcggacg ctggaggacc 3841  aggccaatga gtaccgcgtg aagctagaag aggcccaacg ctccctcaat gatttcacca 3901  cccagcgagc caagctgcag accgagaatg agagttggc ccggcagcta gaggaaaagg 3961  aggcgctaat ctcgcagctg acccggggga agctctctta tacccagcaa atggaggacc 4021  tcaaaaggca gctggaggag gagggcaagg cgaagaacgc cctggcccat gcactgcagt 4081  cggcccggca tgactgcgac ctgctgcggg agcagtacga ggaggagaca gaggccaagg 4141  ccgagctgca gcgcgtcctg tccaaggcca actcggaggt ggcccagtgg aggaccaagt 4201  atgagacgga cgccattcag cggactgagg agctcgaaga ggccaaaaag aagctggccc
```

-continued

```
4261  agcggctgca ggatgccgag gaggccgtgg aggctgttaa tgccaagtgc tcctcactgg
4321  agaagaccaa gcaccggcta cagaatgaga tagaggactt gatggtggac gtagagcgct
4381  ccaatgctgc tgctgcagcc ctggacaaga agcagagaaa ctttgacaag atcctggccg
4441  agtggaagca gaagtatgag gagtcgcagt ctgagctgga gtcctcacag aaggaggctc
4501  gctccctcag cacagagctc ttcaagctca agaacgccta cgaggagtcc ctggagcacc
4561  tagagacctt caagcgggag aacaagaacc ttcaggagga aatctcggac cttactgagc
4621  agctaggaga aggaggaaag aatgtgcatg agctggagaa ggtccgcaaa cagctggagg
4681  tggagaagct ggagctgcag tcagccctgg aggaggcaga ggcctccctg gagcacgagg
4741  agggcaagat cctccgggcc cagctagagt tcaaccagat caaggcagag atcgagcgga
4801  agctggcaga gaaggacgag gagatggaac aggccaagcg caaccaccag cgggtggtgg
4861  actcgctgca gacctccctg gatgcagaga cacgcagccg caacgaggtc ctgagggtga
4921  agaagaagat ggaaggagac ctcaatgaga tggagatcca gctcagccac gccaaccgca
4981  tggctgccga ggcccagaag caagtcaaga gcctccagag cttgctgaag gacacccaga
5041  tccagctgga cgatgcggtc cgtgccaacg acgacctgaa ggagaacatc gccatcgtgg
5101  agcggcgcaa caacctgctg caggctgagc tggaggagct gcgtgccgtg gtggagcaga
5161  cagagcggtc ccggaagctg gcggagcagg agctgattga ccagcgag cgggtgcagc
5221  tgctgcattc ccagaacacc agcctcatca accagaagaa gaagatggag tcggatctga
5281  cccagctcca gtcggaagtg gaggaggcag tgcaggagtg cagaaacgcc gaggagaagg
5341  ccaagaaggc catcacggat gccgccatga tggcagagga gctgaagaag gagcaggaca
5401  ccagcgccca cctggagcgc atgaagaaga acatggagca gaccattaag gacctgcagc
5461  accggctgga cgaggccgag cagatcgccc tcaagggagg caagaagcag ctgcagaagc
5521  tggaagcgcg ggtgcgggag ctggagggtg agctggaggc cgagcagaag cgcaacgcag
5581  agtcggtgaa gggcatgagg aagagcgagc ggcgcatcaa ggagctcacc taccagacag
5641  aggaagacaa aaagaacctg ctgcggctac aggacctggt ggacaagctg caactgaagg
5701  tcaaggccta caagcgccag gccgaggagg cggaggagca agccaacacc aacctgtcca
5761  agttccgcaa ggtgcagcat gagctggatg aggcagagga gcgggcggac atcgctgagt
5821  cccaggtcaa caagcttcga gccaagagcc gtgacattgg tgccaagcaa aaaatgcacg
5881  atgaggagtg acactgcctc gggaacctca ctcttgccaa cctgtaataa atatgagtgc
5941  c
```

By "MLC2A polypeptide" or "human MLSC2A (hMLC2A) polypeptide" is meant a protein or fragment thereof having at least 85% amino acid sequence identity to the sequence provided at NCBI Accession No. NP_067046.1 and having calcium binding activity. The amino acid sequence provided at NCBI Accession No. NP_067046.1 is shown below (SEQ ID NO: 27):

```
  1  masrkagtrg kvaatkqaqr gssnvfsmfe qaqiqefkea fscidqnrdg iickadlret
 61  ysqlgkvsvp eeeldamlqe gkgpinftvf ltlfgeklng tdpeeailsa frmfdpsgkg
121  vvnkdefkql lltqadkfsp aeveqmfalt pmdlagnidy kslcyiithg dekee
```

By "MLC2A polynucleotide" is meant a polynucleotide encoding a MLC2A polypeptide or fragment thereof. An exemplary MLC2A polynucleotide sequence is provided at NCBI Ref: NM_021223.2. The sequence provided at NCBI Ref: NM_021223.2 is reproduced below (SEQ ID NO: 28):

```
  1  tctgcagaga gaatggccag caggaaggcg gggacccggg gcaaggtggc agccaccaag
 61  caggcccaac gtggttcttc caacgtcttt tccatgtttg aacaagccca gatacaggag
121  ttcaaagaag ccttcagctg tatcgaccag aatcgtgatg catcatctg  caaggcagac
181  ctgagggaga cctactccca gctggggaag gtgagtgtcc cagaggagga gctggacgcc
241  atgctgcaag agggcaaggg ccccatcaac ttcaccgtct cctcacgct  ctttggggag
301  aagctcaatg ggacagaccc cgaggaagcc atcctgagtg ccttccgcat gtttgaccc
361  agcggcaaag gggtggtgaa caaggatgag ttcaagcagc ttctcctgac ccaggcagac
421  aagttctctc cagctgaggt ggagcagatg ttcgccctga cacccatgga cctggcgggg
481  aacatcgact acaagtcact gtgctacatc atcacccatg gagacgagaa agaggaatga
541  ggggcagggc caggcccacg gggggcacc  tcaataaact ctgttgcaaa attggaaaaa
601  aaaaaaaaaa aaaaaaaa
```

By "MUC2 polypeptide" is meant a protein or fragment thereof having at least 85% amino acid sequence identity to the sequence provided at NCBI Accession No. NP_002448.3 and having and having a biological activity of a MUC2 polypeptide. Exemplary biological activities of a MUC2 polypeptide include polymerization into a gel and coating of epithelia of the intestines and other mucus membrane-containing organs. The amino acid sequence provided at NCBI Accession No. NP_002448.3 is shown below (SEQ ID NO: 29):

```
   1  mglplarlaa vclalslagg selqtegrtr nhghnvcstw gnfhyktfdg dvfrfpgpcd
  61  ynfasdcrgs ykefavhlkr gpgqaeapag vesilltikd dtiyltrhla vlngavvstp
 121  hyspglliek sdaytkvysr agltlmwnre dalmleldtk frnhtcglcg dynglqsyse
 181  flsdgvlfsp lefgnmqkin qpdvvcedpe eevapascse hraecerllt aeafadcqdl
 241  vplepylrac qqdrcrcpgg dtcvcstvae fsrqcshagg rpgnwrtatl cpktcpgnlv
 301  ylesgspcmd tcshlevssl ceehrmdgcf cpegtvyddi gdsgcvpvsq chcrlhghly
 361  tpgqeitndc eqcvcnagrw vckdlpcpgt caleggshit tfdgktytfh gdcyyvlakg
 421  dhndsyallg elapcgstdk qtclktvvll adkkknvvvf ksdgsvllne lqvnlphvta
 481  sfsvfrpssy himvsmaigv rlqvqlapvm qlfvtldqas qgqvqglcgn fnglegddfk
 541  tasglveatg agfantwkaq stchdkldwl ddpcslnies anyaehwcsl lkktetpfgr
 601  chsavdpaey ykrckydtcn cqnnedclca alssyaract akgvmlwgwr ehvcnkdvgs
 661  cpnsqvflyn lttcqqtcrs lseadshcle gfapvdgcgc pdhtfldekg rcvplakcsc
 721  yhrglyleag dvvvrqeerc vcrdgrlhcr girligqsct apkihmdcsn ltalatskpr
 781  alscqtlaag yyhtecvsgc vcpdglmddg rggcvvekec pcvhnndlys sgakikvdcn
 841  tctckrgrwv ctqavchgtc siygsghyit fdgkyydfdg hcsyvavqdy cgqnsslgsf
 901  siitenvpcg ttgvtcskai kifmgrtelk ledkhrvviq rdeghhvayt trevgqylvv
 961  esstgiiviw dkrttvfikl apsykgtvcg lcgnfdhrsn ndfttrdhmv vsseldfgns
1021  wkeaptcpdv stnpepcsln phrrswaekq csilkssvfs ichskvdpkp fyeacvhdsc
1081  scdtggdcec fcsavasyaq ectkegacvf wrtpdlcpif cdyynpphec ewhyepcgnr
1141  sfetcrting ihsnisysyl egcyprcpkd rpiyeedlkk cvtadkcgcy vedthyppga
1201  svpteetcks cvctnssqvv crpeegkiln qtqdgafcyw eicgpngtve khfnicsitt
1261  rpstlttftt itlpttpttf tttttttpt   sstvlsttpk lcclwsdwin edhpssgsdd
1321  gdretfdgvc gapediecrs vkdphlsleq lgqkvqcdvs vgfickenedq fgngpfglcy
1381  dykirvnccw pmdkcittps pptttpsppp tstttlpptt tpsppttttt tpppttttsp
1441  pittttttppp tttspppist tttppptttp spptttpspp tttspptttt tttpppttt
```

-continued

```
1501  sppttttpitp pastttlppt  ttpsppttttt ttppptttps  ppttttpitpp tsttttlpptt
1561  tpsppptttt  tppptttpsp  pttttpsppt  ittttpppttt tpsppttttt  tppptttpsp
1621  ptttpitppt  stttlppttt  psppptttttt pppttttpspp tttttpsppit ttttppptt
1681  psspitttps  pptttmttps  ptttpsspit  tttttpssttt psppttmtt   psptttpspp
1741  tttmttlppt  ttssplttp   lppsitppt   spfsttttptt pcvplcnwtg  wldsgkpnfh
1801  kpggdtelig  dvcgpgwaan  iscratmypd  vpigqlgqtv  vcdvsvglic  knedqkpggv
1861  ipmafclnye  invqccecvt  qpttmttttt  enptpttttp  ittttvtpt   ptptgtqtpt
1921  ttpittttv   tptptptgtq  tptttpittt  ttvtptptpt  gtqtptttpi  ttttvtptp
1981  tptgtqtptt  tpittttvt   ptptptgtqt  ptttpitttt  tvtptptptg  tqtptttpit
2041  ttttvtptpt  ptgtqtpttt  pittttvtp   tptptgtqtp  tttpittttt  vtptptptgt
2101  qtptttpitt  ttvtptptp   tgtqtpttp   itttvtpt    ptptgtqtpt  ttpittttv
2161  tptptptgtq  tptttpittt  tvtptptpt   gtqtptttpi  ttttvtptp   tptgtqtptt
2221  tpittttvt   ptptgtqt    ptttpittt   tvtptptptg  tqtptttpit  ttttvtptpt
2281  ptgtqtpttt  pittttvtp   tptptgtqtp  tttpittttt  vtptptgt    qtptttpitt
2341  tttvtptpt   tgtqtptttp  itttvtpt    ptptgtqtpt  ttpittttv   tptptgtq
2401  tptttpittt  tvtptptpt   gtqtptttpi  ttttvtptp   tptgtqtptt  tpittttvt
2461  ptptptgtqt  ptttpitttt  tvtptptg    tqtptttpit  tttvtptpt   ptgtqtpttt
2521  pittttvtp   tptgtqtp    tttpittttt  vtptptgt    qtptttpitt  tttvtptpt
2581  tgtqtptttp  ittttvtpt   ptptgtqtpt  tpittttv    tptptgtq    tptttpittt
2641  ttvtptptpt  gtqtptttpi  ttttvtptp   tptgtqtptt  tpittttvt   ptptgtqt
2701  ptttpittt   tvtptptg    tqtptttpit  tttvtptpt   ptgtqtpttt  pittttvtp
2761  tptptgtqtp  tttpittttt  vtptptgt    qtptttpitt  tttvtptp    tgtqtpttp
2821  itttvtpt    ptptgtqtpt  ttpittttv   tptptgtq    tptttpittt  tvtptptpt
2881  gtqtptttpi  ttttvtptp   tptgtqtpt   tpittttvt   ptptgtqt    ptttpittt
2941  tvtptptg    tqtptttpit  tttvtptpt   ptgtqtpttt  pittttvtp   tptptgtqtp
3001  tttpittttt  vtptptgt    qtptttpitt  tttvtptp    tgtqtpttp   itttvtpt
3061  ptptgtqtpt  tpittttv    tptptgtq    tptttpittt  tvtptptpt   gtqtptttpi
3121  ttttvtptp   tptgtqtptt  tpittttvt   ptptgtqt    ptttpittt   tvtptptg
3181  tqtptttpit  tttvtptpt   ptgtqtpttt  pittttvtp   tptptgtqtp  tttpittttt
3241  vtptptgt    qtptttpitt  tttvtptp    tgtqtpttp   itttvtpt    ptptgtqtpt
3301  ttpittttv   tptptgtq    tptttpittt  tvtptptpt   gtqtptttpi  ttttvtptp
3361  tptgtqtptt  tpittttvt   ptptgtqt    ptttpittt   tvtptptg    tqtptttpit
3421  tttvtptpt   ptgtqtpttt  pittttvtp   tptptgtqtp  tttpittttt  vtptptgt
3481  qtptttpitt  tttvtptp    tgtqtpttp   itttvtpt    ptptgtqtpt  tpittttv
3541  tptptgtq    tptttpittt  tvtptptpt   gtqtptttpi  ttttvtptp   tptgtqtptt
3601  tpittttvt   ptptgtqt    ptttpittt   tvtptptg    tqtptttpit  tttvtptpt
3661  ptgtqtpttt  pittttvtp   tptptgtqtp  tttpittttt  vtptptgt    qtptttpitt
3721  tttvtptp    tgtqtpttp   itttvtpt    ptptgtqtpt  tpittttv    tptptgtq
3781  tptttpittt  tvtptptpt   gtqtptttpi  ttttvtptp   tptgtqtptt  tpittttvt
3841  ptptgtqt    ptttpittt   tvtptptg    tqtptttpit  tttvtptpt   ptgtqtpttt
3901  pittttvtp   tptptgtqtp  tttpittttt  vtptptgt    qtptttpitt  tttvtptp
```

-continued

```
3961    tgtqtptttp ittttttvtpt ptptgtqtpt ttpittttttv tptptptgtq tptttpittt
4021    ttvtptptpt gtqtptttpi tttttvtptp tptgtqtptt tpittttttvt ptptptgtqt
4081    ptttpitttt tvtptptptg tqtptttpit tttttvtptpt ptgtqtpttt pittttttvtp
4141    tptptgtqtp tttpitttttt vtptptptgt qtptttpitt tttvtptptp tgtqtgppth
4201    tstapiaelt tsnpppesst pqtsrstssp ltesttllst lppaiemtst appstptapt
4261    ttsgghtlsp ppstttsppg tptrgtttgs ssaptpstvq ttttsawtpt ptplstpsii
4321    rttglrpyps svliccvlnd tyyapgeevy ngtygdtcyf vncslsctle fynwscpstp
4381    sptptpskst ptpskpsstp skptpgtkpp ecpdfdpprq enetwwlcdc fmatckynnt
4441    veivkvecep ppmptcsngl qpvrvedpdg ccwhwecdcy ctgwgdphyv tfdglyysyq
4501    gnctyvlvee ispsvdnfgv yidnyhcdpn dkvscprtli vrhetqevli ktvhmmpmqv
4561    qvqvnrqava lpykkyglev yqsginyvvd ipelgvlvsy nglsfsvrlp yhrfgnntkg
4621    qcgtctntts ddcilpsgei vsnceaaadq wlvndpskph cphsssttkr pavtvpgggk
4681    ttphkdctps plcqlikdsl faqchalvpp qhyydacvfd scfmpgssle caslqayaal
4741    caqqnicldw rnhthgaclv ecpshreyqa cgpaeeeptck ssssqqnntv lvegcfcpeg
4801    tmnyapgfdv cvktcgcvgp dnvprefgeh fefdckncvc leggsgiicq pkrcsqkpvt
4861    hcvedgtyla tevnpadtcc nitvckcnts lckekpsvcp lgfevkskmv pgrccpfywc
4921    eskgvcvhgn aeyqpgspvy sskcqdcvct dkvdnntlln viacthvpcn tscspgfelm
4981    eapgecckkc eqthciikrp dnqhvilkpg dfksdpknnc tffscvkihn qlissysnit
5041    cpnfdasici pgsitfmpng ccktctprne trvpcstvpv ttevsyagct ktvlmnhcsg
5101    scgtfvmysa kaqaldhscs cckeektsqr evvlscpngg slthtythie scqcqdtvcg
5161    lptgtsrrar rsprhlgsg
```

By "MUC2 polynucleotide" is meant a polynucleotide encoding a MUC2 polypeptide or fragment thereof. An exemplary MUC2 polynucleotide sequence is provided at NCBI Ref: NM_002457.3. The sequence provided at NCBI Ref: NM_002457.3 is reproduced below (SEQ ID NO: 30):

```
  1    caacccacac cgcccctgcc agccaccatg gggctgccac tagcccgcct ggcggctgtg
 61    tgcctggccc tgtctttggc aggggggctcg gagctccaga cagagggcag aacccgaaac
121    cacggccaca acgtctgcag cacctggggc aacttccact acaagacctt cgacggggac
181    gtcttccgct tccccggccc ctgcgactac aacttcgcct ccgactgccg aggctcctac
241    aaggaatttg ctgtgcacct gaagcgggt ccgggccagg ctgaggcccc cgccgggtg
301    gagtccatcc tgctgaccat caaggatgac accatctacc tcacccgcca cctggctgtg
361    cttaacgggg ccgtggtcag caccccgcac tacagcccg ggctgctcat tgagaagagc
421    gatgcctaca ccaaagtcta ctcccgcgcc ggcctcaccc tcatgtggaa ccgggaggat
481    gcactcatgc tggagctgga cactaagttc cggaaccaca cctgtggcct ctgcggggac
541    tacaacggcc tgcagagcta ttcagaattc ctctctgacg gcgtgctctt cagtcccctg
601    gagtttggga acatgcagaa gatcaaccag cccgatgtgg tgtgtgagga tcccgaggag
661    gaggtggccc ccgcatcctg ctccgagcac cgcgccgagt gtgagaggct gctgaccgcc
721    gaggccttcg cggactgtca ggacctggtg ccgctggagc cgtatctgcg cgcctgccag
781    caggaccgct gccggtgccc gggcggtgac acctgcgtct gcagcaccgt ggccgagttc
841    tcccgccagt gctcccacgc cggcggccgg cccgggaact ggaggaccgc cacgctctgc
```

-continued

```
 901 cccaagacct gccccgggaa cctggtgtac ctggagagcg gctcgccctg catggacacc
 961 tgctcacacc tggaggtgag cagcctgtgc gaggagcacc gcatggacgg ctgtttctgc
1021 ccagaaggca ccgtatatga cgacatcggg gacagtggct gcgttcctgt gagccagtgc
1081 cactgcaggc tgcacggaca cctgtacaca ccgggccagg agatcaccaa tgactgcgag
1141 cagtgtgtct gtaacgctgg ccgctgggtg tgcaaagacc tgccctgccc cggcacctgt
1201 gccctggaag gcggctccca catcaccacc ttcgatggga agacgtacac cttccacggg
1261 gactgctact atgtcctggc caagggtgac cacaacgatt cctacgctct cctgggcgag
1321 ctggccccct gtggctccac agacaagcag acctgcctga gacggtggt gctgctggct
1381 gacaagaaga gaatgtggt ggtcttcaag tccgatggca gtgtactgct caacgagctg
1441 caggtgaacc tgccccacgt gaccgcgagc ttctctgtct ccgcccgtc ttcctaccac
1501 atcatggtga gcatggccat tggcgtccgg ctgcaggtgc agctggcccc agtcatgcaa
1561 ctctttgtga cactggacca ggcctcccag gggcaggtgc agggcctctg cgggaacttc
1621 aacggcctgg aaggtgacga cttcaagacg gccagcgggc tggtggaggc cacggggggcc
1681 ggctttgcca cacctggaa ggcacagtca acctgccatg acaagctgga ctggttggac
1741 gatccctgct ccctgaacat cgagagcgcc aactacgccg agcactggtg ctccctcctg
1801 aagaagacag agaccccctt tggcaggtgc cactcggctg tggaccctgc tgagtattac
1861 aagaggtgca aatatgacac gtgtaactgt cagaacaatg gaggactgcct gtgcgccgcc
1921 ctgtcctcct acgcgcgcgc ctgcaccgcc aagggcgtca tgctgtgggg ctggcgggag
1981 catgtctgca caaggatgt gggctcctgc cccaactcgc aggtcttcct gtacaacctg
2041 accacctgcc agcagacctg ccgctcccct ccgaggccg acagccactg tctcgagggc
2101 tttgcgcctg tggacggctg cggctgccct gaccacacct tcctggacga aagggccgc
2161 tgcgtacccc tggccaagtg ctcctgttac caccgcgtc tctacctgga ggcgggggac
2221 gtggtcgtca ggcaggaaga acgatgtgtg tgccgggatg gcggctgca ctgtaggcag
2281 atccggctga tcggccagag ctgcacggcc ccaaagatcc acatggactg cagcaacctg
2341 actgcactgg ccacctcgaa gccccgagcc ctcagctgcc agacgctggc cgccggctat
2401 taccacacag agtgtgtcag tggctgtgtg tgccccgacg ggctgatgga tgacggccgg
2461 ggtggctgcg tggtggagaa ggaatgccct tgcgtccata caacgacct gtattcttcc
2521 ggcgccaaga tcaaggtgga ctgcaatacc tgcacctgca agagaggacg ctgggtgtgc
2581 acccaggctg tgtgccatgg cacctgctcc atttacggga gtggccacta catcaccttt
2641 gacgggaagt actacgactt tgacggacac tgctcctacg tggctgttca ggactactgc
2701 ggccagaact cctcactggg ctcattcagc atcatcaccg agaacgtccc ctgtggcact
2761 acgggcgtca cctgctccaa ggccatcaag atcttcatgg ggaggacgga gctgaagttg
2821 gaagacaagc accgtgtggt gatccagcgt gatgagggtc accacgtggc ctacaccacg
2881 cgggaggtgg gccagtacct ggtggtggag tccagcacgg gcatcatcgt catctgggac
2941 aagaggacca ccgtgttcat caagctggct ccctcctaca gggcaccgt gtgtggcctg
3001 tgtgggaact ttaccaccg ctccaacaac gacttcacca cgcgggacca catggtggtg
3061 agcagcgagc tggacttcgg aacagctgg aaggaggccc ccacctgccc agatgtgagc
3121 accaaccccg agccctgcag cctgaacccg caccgccgct cctgggccga aagcagtgc
3181 agcatcctca aaagcagcgt gttcagcatc tgccacagca aggtggaccc caagcccttc
3241 tacgaggcct gtgtgcacga ctcgtgctcc tgtgacacgg gtgggggactg tgagtgcttc
```

-continued

```
3301  tgctctgccg tggcctccta cgcccaggag tgtaccaaag aggggggcctg cgtgttctgg
3361  aggacgccgg acctgtgccc catattctgc gactactaca ccctccgca tgagtgtgag
3421  tggcactatg agccatgtgg gaaccggagc ttcgagacct gcaggaccat caatggcatc
3481  cactccaaca tctccgtgtc ctacctggag ggctgctacc cccggtgccc caaggacagg
3541  cccatctatg aggaggatct gaagaagtgt gtcactgcag acaagtgtgg ctgctatgtc
3601  gaggcacccc actacccacc tggagcatcg gttcccaccg aggagacctg caagtcctgc
3661  gtgtgtacca actcctccca agtcgtctgc aggccggagg aaggaaagat tcttaaccag
3721  acccaggatg cgccttctg ctactgggag atctgtggcc ccaacggac ggtggagaag
3781  cacttcaaca tctgttccat tacgacacgc ccgtccaccc tgaccaccct caccaccatc
3841  accctcccca ccccccac caccttcacc actaccacca ccaccaccac cccgacctcc
3901  agcacagttt tatcaacaac tccgaagctg tgctgcctct ggtctgactg gatcaatgag
3961  gaccacccca gcagtggcag cgacgacggt gaccgagaaa catttgatgg ggtctgcggg
4021  gcccctgagg acatcgagtg caggtcggtc aaggatcccc acctcagctt ggagcagcta
4081  ggccagaagg tgcagtgtga tgtctctgtt gggttcattt gcaagaatga agaccagttt
4141  ggaaatggac catttggact gtgttacgac tacaagatac gtgtcaattg ttgctggccc
4201  atggataagt gtatcaccac tcccagccct ccaactacca ctcccagccc tccaccaacc
4261  agcacgacca cccttccacc aaccaccacc cccagccctc caaccaccac cacaaccacc
4321  cctccaccaa ccaccacccc cagccctcca ataaccacca cgaccacccc tccaccaacc
4381  accactccca gccctccaat aagcaccaca ccacccctc caccaaccac cactcccagc
4441  cctccaacca ccactccag ccctccaacc accactccca gccctccaac aaccaccaca
4501  accaccctc caccaaccac cactcccagc cctccaacga ctacgcccat cactccacca
4561  gccagcacta ccacccttcc accaaccacc actcccagcc tccaacaac caccacaacc
4621  acccctccac caaccaccac tcccagtcct ccaacgacta cgcccatcac tccaccaacc
4681  agcactacta cccttccacc aaccaccact cccagccctc caccaaccac cacaaccacc
4741  cctccaccaa ccaccactcc cagccctcca caaccacca ctcccagtcc tccaacaatc
4801  accacaacca cccctccacc aaccaccact cccagccctc caacaacgac cacaaccacc
4861  cctccaccaa ccaccactcc cagccctcca cgactacac ccatcactcc accaaccagc
4921  actaccaccc ttccaccaac caccactccc agccctccac caaccaccac aaccacccct
4981  ccaccaacca ccactcccag ccctccaaca accaccactc cagccctccc aataaccacc
5041  acaaccaccc ctccaccaac caccactccc agctctccaa taaccaccac tcccagccct
5101  ccaacaacca ccatgaccac cccttcacca accaccaccc ccagctctcc aataaccacc
5161  acaaccaccc cttcctcaac taccactccc agccctccac caaccaccat gaccaccct
5221  tcaccaacca ccactcccag ccctccaaca accaccatga ccacccttcc accaaccacc
5281  acttccagcc ctctaacaac tactcctcta cctccatcaa taactcctcc tacatttttca
5341  ccattctcaa cgacaacccc tactacccca tgcgtgcctc tctgcaattg gactggctgg
5401  ctggattctg gaaaacccaa cttttcacaaa ccaggtggag acacagaatt gattggagac
5461  gtctgtggac caggctgggc agctaacatc tcttgcagag ccaccatgta tcctgatgtt
5521  cccattggac agcttggaca aacagtggtg tgtgatgtct ctgtggggct gatatgcaaa
5581  aatgaagacc aaaagccagg tggggtcatc cctatggcct tctgcctcaa ctacgagatc
5641  aacgttcagt gctgtgagtg tgtcacccaa cccaccacca tgacaaccac caccacagag
5701  aacccaactc cgccaaccac gacacccatc accaccacca ctacggtgac cccaaccccca
```

```
5761  acacccaccg gcacacagac cccaaccacg acacccatca ccaccaccac tacggtgacc
5821  ccaaccccaa cacccaccgg cacacagacc ccaaccacga cacccatcac caccaccact
5881  acggtgaccc aaccccaac acccaccggc acacagaccc caaccacgac acccatcacc
5941  accaccacta cggtgacccc aaccccaaca cccaccggca cacagacccc aaccacgaca
6001  cccatcacca ccaccactac ggtgacccca accccaacac ccaccggcac acagacccca
6061  accacgacac ccatcaccac caccactacg gtgaccccaa ccccaacacc caccggcaca
6121  cagacccaa ccacgacacc catcaccacc accactacgg tgaccccaac cccaacaccc
6181  accggcacac agacccaac cacgacaccc atcaccacca ccactacggt gaccccaacc
6241  ccaacaccca ccggcacaca gaccccaacc acgacaccca tcaccaccac cactacggtg
6301  accccaaccc caacacccac cggcacacag accccaacca cgacacccat caccaccacc
6361  actacggtga ccccaacccc aacacccacc ggcacacaga ccccaaccac gacacccatc
6421  accaccacca ctacggtgac cccaaccca cacccaccg gcacacagac cccaaccacg
6481  acacccatca ccaccaccac tacggtgacc ccaaccccaa cacccaccgg cacacagacc
6541  ccaaccacga cacccatcac caccaccact acggtgaccc aaccccaac acccaccggc
6601  acacagaccc caaccacgac acccatcacc accaccacta cggtgacccc aaccccaaca
6661  cccaccggca cacagacccc aaccacgaca cccatcacca ccaccactac ggtgacccca
6721  accccaacac ccaccggcac acagacccca accacgacac ccatcaccac caccactacg
6781  gtgaccccaa ccccaacacc caccggcaca cagacccaa ccacgacacc catcaccacc
6841  accactacgg tgaccccaac cccaacaccc accggcacac agacccaac cacgacaccc
6901  atcaccacca ccactacggt gaccccaacc ccaacaccca ccggcacaca gaccccaacc
6961  acgacaccca tcaccaccac cactacggtg accccaaccc caacacccac cggcacacag
7021  accccaacca cgacacccat caccaccacc actacggtga ccccaacccc aacacccacc
7081  ggcacacaga ccccaaccac gacacccatc accaccacca ctacggtgac cccaacccca
7141  cacccaccg gcacacagac cccaaccacg acacccatca ccaccaccac tacggtgacc
7201  ccaaccccaa cacccaccgg cacacagacc ccaaccacga cacccatcac caccaccact
7261  acggtgaccc aaccccaac acccaccggc acacagaccc caaccacgac acccatcacc
7321  accaccacta cggtgacccc aaccccaaca cccaccggca cacagacccc aaccacgaca
7381  cccatcacca ccaccactac ggtgacccca accccaacac ccaccggcac acagacccca
7441  accacgacac ccatcaccac caccactacg gtgaccccaa ccccaacacc caccggcaca
7501  cagacccaa ccacgacacc catcaccacc accactacgg tgaccccaac cccaacaccc
7561  accggcacac agacccaac cacgacaccc atcaccacca ccactacggt gaccccaacc
7621  ccaacaccca ccggcacaca gaccccaacc acgacaccca tcaccaccac cactacggtg
7681  accccaaccc caacacccac cggcacacag accccaacca cgacacccat caccaccacc
7741  actacggtga ccccaacccc aacacccacc ggcacacaga ccccaaccac gacacccatc
7801  accaccacca ctacggtgac cccaaccca cacccaccg gcacacagac cccaaccacg
7861  acacccatca ccaccaccac tacggtgacc ccaaccccaa cacccaccgg cacacagacc
7921  ccaaccacga cacccatcac caccaccact acggtgaccc aaccccaac acccaccggc
7981  acacagaccc caaccacgac acccatcacc accaccacta cggtgacccc aaccccaaca
8041  cccaccggca cacagacccc aaccacgaca cccatcacca ccaccactac ggtgacccca
8101  accccaacac ccaccggcac acagacccca accacgacac ccatcaccac caccactacg
```

-continued

```
 8161 gtgaccccaa ccccaacacc caccggcaca cagaccccaa ccacgacacc catcaccacc
 8221 accactacgg tgaccccaac cccaacaccc accggcacac agaccccaac cacgacaccc
 8281 atcaccacca ccactacggt gaccccaacc ccaacaccca ccggcacaca gaccccaacc
 8341 acgacaccca tcaccaccac cactacggtg accccaaccc caacaccacc cggcacacag
 8401 accccaacca cgacacccat caccaccacc actacggtga ccccaacccc aacacccacc
 8461 ggcacacaga ccccaaccac gacacccatc accaccacca ctacggtgac cccaaccccca
 8521 acacccaccg gcacacagac cccaaccacg acacccatca ccaccaccac tacggtgacc
 8581 ccaaccccaa cacccaccgg cacacagacc ccaaccacga cacccatcac caccaccact
 8641 acggtgaccc caaccccaac acccaccggc acacagaccc caaccacgac acccatcacc
 8701 accaccacta cggtgacccc aaccccaaca cccaccggca cacagacccc aaccacgaca
 8761 cccatcacca ccaccactac ggtgacccca accccaacac ccaccggcac acagacccca
 8821 accacgacac ccatcaccac caccactacg gtgacccccaa ccccaacacc caccggcaca
 8881 cagaccccaa ccacgacacc catcaccacc accactacgg tgaccccaac cccaacaccc
 8941 accggcacac agaccccaac cacgacaccc atcaccacca ccactacggt gaccccaacc
 9001 ccaacaccca ccggcacaca gaccccaacc acgacaccca tcaccaccac cactacggtg
 9061 accccaaccc caacacccac cggcacacag accccaacca cgacacccat caccaccacc
 9121 actacggtga ccccaacccc aacacccacc ggcacacaga ccccaaccac gacacccatc
 9181 accaccacca ctacggtgac cccaaccccca acacccaccg gcacacagac cccaaccacg
 9241 acacccatca ccaccaccac tacggtgacc ccaaccccaa cacccaccgg cacacagacc
 9301 ccaaccacga cacccatcac caccaccact acggtgaccc caaccccaac acccaccggc
 9361 acacagaccc caaccacgac acccatcacc accaccacta cggtgacccc aaccccaaca
 9421 cccaccggca cacagacccc aaccacgaca cccatcacca ccaccactac ggtgacccca
 9481 accccaacac ccaccggcac acagacccca accacgacac ccatcaccac caccactacg
 9541 gtgacccccaa ccccaacacc caccggcaca cagaccccaa ccacgacacc catcaccacc
 9601 accactacgg tgaccccaac cccaacaccc accggcacac agaccccaac cacgacaccc
 9661 atcaccacca ccactacggt gaccccaacc ccaacaccca ccggcacaca gaccccaacc
 9721 acgacaccca tcaccaccac cactacggtg accccaaccc caacaccacc cggcacacag
 9781 accccaacca cgacacccat caccaccacc actacggtga ccccaacccc aacacccacc
 9841 ggcacacaga ccccaaccac gacacccatc accaccacca ctacggtgac cccaaccccca
 9901 acacccaccg gcacacagac cccaaccacg acacccatca ccaccaccac tacggtgacc
 9961 ccaaccccaa cacccaccgg cacacagacc ccaaccacga cacccatcac caccaccact
10021 acggtgaccc caaccccaac acccaccggc acacagaccc caaccacgac acccatcacc
10081 accaccacta cggtgacccc aaccccaaca cccaccggca cacagacccc aaccacgaca
10141 cccatcacca ccaccactac ggtgacccca accccaacac ccaccggcac acagacccca
10201 accacgacac ccatcaccac caccactacg gtgacccccaa ccccaacacc caccggcaca
10261 cagaccccaa ccacgacacc catcaccacc accactacgg tgaccccaac cccaacaccc
10321 accggcacac agaccccaac cacgacaccc atcaccacca ccactacggt gaccccaacc
10381 ccaacaccca ccggcacaca gaccccaacc acgacaccca tcaccaccac cactacggtg
10441 accccaaccc caacacccac cggcacacag accccaacca cgacacccat caccaccacc
10501 actacggtga ccccaacccc aacacccacc ggcacacaga ccccaaccac gacacccatc
10561 accaccacca ctacggtgac cccaaccccca acacccaccg gcacacagac cccaaccacg
```

```
10621  acacccatca ccaccaccac tacggtgacc ccaaccccaa cacccaccgg cacacagacc
10681  ccaaccacga cacccatcac caccaccact acggtgaccc caaccccaac acccaccggc
10741  acacagaccc caaccacgac acccatcacc accaccacta cggtgacccc aaccccaaca
10801  cccaccggca cacagacccc aaccacgaca cccatcacca ccaccactac ggtgacccca
10861  accccaacac ccaccggcac acagacccca accacgacac ccatcaccac caccactacg
10921  gtgaccccaa ccccaacacc caccggcaca cagacccaa ccacgacacc catcaccacc
10981  accactacgg tgacccaac cccaacaccc accggcacac agacccaac cacgacaccc
11041  atcaccacca ccactacggt gaccccaacc ccaacaccca ccggcacaca gaccccaacc
11101  acgacaccca tcaccaccac cactacggtg accccaaccc caacacccac cggcacacag
11161  accccaacca cgacacccat caccaccacc actacggtga ccccaacccc aacacccacc
11221  ggcacacaga ccccaaccac gacacccatc accaccacca ctacggtgac cccaaccca
11281  acacccaccg gcacacagac cccaaccacg acacccatca ccaccaccac tacggtgacc
11341  ccaaccccaa cacccaccgg cacacagacc caaccacga cacccatcac caccaccact
11401  acggtgaccc caaccccaac acccaccggc acacagaccc caaccacgac acccatcacc
11461  accaccacta cggtgacccc aaccccaaca cccaccggca cacagaccc aaccacgaca
11521  cccatcacca ccaccactac ggtgacccca accccaacac ccaccggcac acagacccca
11581  accacgacac ccatcaccac caccactacg gtgacccaa ccccaacacc caccggcaca
11641  cagaccccaa ccacgacacc catcaccacc accactacgg tgaccccaac cccaacaccc
11701  accggcacac agacccaac cacgaccc atcaccacca ccactacggt gaccccaacc
11761  ccaacaccca ccggcacaca gaccccaacc acgacaccca tcaccaccac cactacggtg
11821  accccaaccc caacacccac cggcacacag accccaacca cgacacccat caccaccacc
11881  actacggtga ccccaacccc aacacccacc ggcacacaga ccccaaccac gacacccatc
11941  accaccacca ctacggtgac cccaacccca cacccaccg gcacacagac cccaaccacg
12001  acacccatca ccaccaccac tacggtgacc ccaaccccaa cacccaccgg cacacagacc
12061  ccaaccacga cacccatcac caccaccact acggtgaccc caaccccaac acccaccggc
12121  acacagaccc caaccacgac acccatcacc accaccacta cggtgacccc aaccccaaca
12181  cccaccggca cacagacccc aaccacgaca cccatcacca ccaccactac ggtgacccca
12241  accccaacac ccaccggcac acagacccca accacgacac ccatcaccac caccactacg
12301  gtgaccccaa ccccaacacc caccggcaca cagacccaa ccacgacacc catcaccacc
12361  accactacgg tgacccaac cccaacaccc accggcacac agacccaac cacgacaccc
12421  atcaccacca ccactacggt gaccccaacc ccaacaccca ccggcacaca gaccccaacc
12481  acgacaccca tcaccaccac cactacggtg accccaaccc caacacccac cggcacacag
12541  accccaacca cgacacccat caccaccacc actacggtga ccccaacccc aacacccacc
12601  ggcacacaga cccggccccc cacccacaca agcacagcac cgattgctga gttgaccaca
12661  tccaatcctc cgcctgagtc ctcaacccct cagacctctc ggtccacctc ttccctctc
12721  acggagtcaa ccacccttct gagtacccta ccacctgcca ttgagatgac cagcacggcc
12781  ccaccctcca cacccacggc acccacgacc acgagcggag gccacacact gtctccaccg
12841  cccagcacca ccacgtcccc tccaggcacc cccactcgcg gtaccacgac tgggtcatct
12901  tcagccccca cccccagcac tgtgcagacg accaccacca gtgcctggac ccccacgccg
12961  accccactct ccacacccag catcatcagg accacaggcc tgaggcccta cccttcctct
```

-continued

```
13021  gtgcttatct gctgtgtcct gaacgacacc tactacgcac caggtgagga ggtgtacaac
13081  ggcacatacg gagacacctg ttatttcgtc aactgctcac tgagctgtac gttggagttc
13141  tataactggt cctgcccatc cacgccctcc ccaacaccca cgccctccaa gtcgacgccc
13201  acgccttcca agccatcgtc cacgccctcc aagccgacgc ccggcaccaa gccccccgag
13261  tgcccagact tgatcctcc cagacaggag aacgagactt ggtggctgtg cgactgcttc
13321  atggccacgt gcaagtacaa caacacggtg gagatcgtga aggtggagtg tgagccgccg
13381  cccatgccca cctgctccaa cggcctccaa cccgtgcgcg tcgaggaccc cgacggctgc
13441  tgctggcact gggagtgcga ctgctactgc acgggctggg gcgacccgca ctatgtcacc
13501  ttcgacggac tctactacag ctaccagggc aactgcacct acgtgctggt ggaggagatc
13561  agcccctccg tggacaactt cggagtttac atcgacaact accactgcga tcccaacgac
13621  aaggtgtcct gccccgcac cctcatcgtg cgccacgaga cccaggaggt gctgatcaag
13681  accgtgcata tgatgcccat gcaggtgcag gtgcaggtga acaggcaggg ggtggcactg
13741  ccctacaaga agtacgggct ggaggtgtac cagtctggca tcaactacgt ggtggacatc
13801  cccgagctgg gtgtcctcgt ctcctacaat ggcctgtcct tctccgtcag gctgccctac
13861  caccggtttg gcaacaacac caagggccag tgtggcacct gcaccaacac cacctccgac
13921  gactgcattc tgcccagcgg ggagatcgtc tccaactgtg aggctgcggc tgaccagtgg
13981  ctggtgaacg acccctccaa gccacactgc cccacagca gctccacgac caagcgcccg
14041  gccgtcactg tgcccggggg cggtaaaacg accccacaca aggactgcac cccatctccc
14101  ctctgccagc tcatcaagga cagcctgttt gcccagtgcc acgcactggt gccccccgcag
14161  cactactacg atgcctgcgt gttcgacagc tgcttcatgc cgggctcgag cctggagtgc
14221  gccagtctgc aggcctacgc agccctctgt gcccagcaga acatctgcct cgactggcgg
14281  aaccacacgc atggggcctg cttggtggag tgcccatctc acagggagta ccaggcctgt
14341  ggccctgcag aagagcccac gtgcaaatcc agctcctccc agcagaacaa cacagtcctg
14401  gtggaaggct gcttctgtcc tgagggcacc atgaactacg ctcctggctt tgatgtctgc
14461  gtgaagacct gcggctgtgt gggacctgac aatgtgccca gagagtttgg ggagcacttc
14521  gagttcgact gcaagaactg tgtctgcctg gagggtggaa gtggcatcat ctgccaaccc
14581  aagaggtgca gccagaagcc cgttacccac tgcgtggaag acggcaccta cctcgccacg
14641  gaggtcaacc ctgccgacac ctgctgcaac attaccgtct gcaagtgcaa caccagcctg
14701  tgcaaagaga agccctccgt gtgcccgctg ggattcgaag tgaagagcaa gatggtgcct
14761  ggaaggtgct gtccttctcta ctggtgtgag tccaaggggg tgtgtgttca cgggaatgct
14821  gagtaccagc ccggttctcc agtttattcc tccaagtgcc aggactgcgt gtgcacggac
14881  aaggtggaca caacaccct gctcaacgtc atcgcctgca cccacgtgcc ctgcaacacc
14941  tcctgcagcc ctggcttcga actcatggag gccccgggg agtgctgtaa gaagtgtgaa
15001  cagacgcact gtatcatcaa acggcccgac aaccagcacg tcatcctgaa gcccggggac
15061  ttcaagagcg acccgaagaa caactgcaca ttcttcagct gcgtgaagat ccacaaccag
15121  ctcatctcgt ccgtctccaa catcacctgc cccaactttg atgccagcat ttgcatcccg
15181  ggctccatca cattcatgcc caatggatgc tgcaagacct gcacccctcg caatgagacc
15241  agggtgccct gctccaccgt ccccgtcacc acggaggttt cgtacgccgg ctgcaccaag
15301  accgtcctca tgaatcattg ctccgggtcc tgcgggacat tgtcatgta ctcggccaag
15361  gcccaggccc tggaccacag ctgctcctgc tgcaaagagg agaaaaccag ccagcgtgag
15421  gtggtcctga gctgccccaa tggcggctcg ctgacacaca cctacacccca catcgagagc
```

-continued

```
15481  tgccagtgcc aggacaccgt ctgcgggctc cccaccggca cctcccgccg ggcccggcgc 15541  tcccctaggc atctggggag cgggtgagcg gggtgggcac agccccttc actgccctcg 15601  acagctttac ctcccccgga ccctctgagc ctcctaagct cggcttcctc tcttcagata 15661  tttattgtct gagtctttgt tcagtccttg ctttccaata ataaactcag ggggacatgc
```

By "NKX2-5 polypeptide" or "human NKX2-5 (hNKX2-5) polypeptide" is meant a protein or fragment thereof having at least 85% amino acid sequence identity to the sequence provided at NCBI Accession No. NP_004378.1 (isoform 1), NP_001159647.1 (isoform 2), or NP_001159648.1 (isoform 3) and having transcription factor activity. The amino acid sequence provided at NCBI Accession No. NP_004378.1 is shown below (SEQ ID NO: 31):

```
  1  mfpspaltpt pfsvkdilnl eqqqrslaaa gelsarleat lapsscmlaa fkpeayagpe 61  aaapglpelr aelgrapspa kcasafpaap afypraysdp dpakdpraek kelcalqkav 121  elekteadna erprarrrrk prvlfsqaqv yelerrfkqq rylsaperdq lasvlkltst 181  qvkiwfqnrr ykckrqrqdq tlelvglppp pppparriav pvlvrdgkpc lgdsapyapa 241  ygvglnpygy naypaypgyg gaacspgysc taaypagpsp aqpataaann nfvnfgvgdl 301  navqspgipq snsgvstlhg iraw
```

By "NKX2-5 polynucleotide" is meant a polynucleotide encoding a NKX2-5 polypeptide or fragment thereof. An exemplary NKX2-5 polynucleotide sequence is provided at NCBI Ref: NM_004387.3. The sequence provided at NCBI Ref: NM_004387.3 is reproduced below (SEQ ID NO: 32):

```
   1  gctcctgtca tcgaggcccc tggcccaatg gcaggctgag tcccctcct ctggcctggt 61  cccgcctctc ctgcccttg tgctcagcgc tacctgctgc ccggacacat ccagagctgg 121  ccgacgggtg cgcggcggg cggcggcacc atgcagggaa gctgccaggg gccgtgggca 181  gcgccgcttt ctgccgccca cctggcgctg tgagactggc gctgccacca tgttccccag 241  ccctgctctc acgcccacgc ccttctcagt caaagacatc ctaaacctgg aacagcagca 301  gcgcagcctg gctgccgccg gagagctctc tgcccgcctg gaggcgaccc tggcgccctc 361  ctcctgcatg ctggccgcct tcaagccaga ggcctacgct gggcccgagg cggctgcgcc 421  gggcctccca gagctgcgcg cagagctggg ccgcgcgcct tcaccggcca agtgtgcgtc 481  tgcctttccc gccgcccccg ccttctatcc acgtgcctac agcgaccccg acccagccaa 541  ggaccctaga gccgaaaaga aagagctgtg cgcgctgcag aaggcggtgg agctggagaa 601  gacagaggcg gacaacgcgg agcggccccg ggcgcgacgg cggaggaagc cgcgcgtgct 661  cttctcgcag gcgcaggtct atgagctgga gcggcgcttc aagcagcagc ggtacctgtc 721  ggcccccgaa cgcgaccagc tggccagcgt gctgaaactc acgtccacgc aggtcaagat 781  ctggttccag aaccggcgct acaagtgcaa gcggcagcgg caggaccaga ctctggagct 841  ggtggggctg ccccgcgcc cgccgccgcc tgcccgcagg atcgcggtgc cagtgctggt 901  gcgcgatggc aagccatgcc tagggggactc ggcgcctac gcgcctgcct acggcgtggg 961  cctcaatccc tacggttata acgcctaccc cgcctatccg ggttacggcg gcgcggcctg 1021  cagccctggc tacagctgca ctgccgctta ccccgccggg ccttccccag cgcagccggc 1081  cactgccgcc gccaacaaca acttcgtgaa cttcggcgtc ggggacttga atgcggttca
```

```
-continued 1141   gagccccggg attccgcaga gcaactcggg agtgtccacg ctgcatggta tccgagcctg 1201   gtagggaagg gacccgcgtg gcgcgaccct gaccgatccc acctcaacag ctccctgact 1261   ctcggggga  gaagggctc  ccaacatgac cctgagtccc ctggattttg cattcactcc 1321   tgcggagacc taggaacttt ttctgtccca cgcgcgtttg ttcttgcgca cgggagagtt 1381   tgtggcggcg attatgcagc gtgcaatgag tgatcctgca gcctggtgtc ttagctgtcc 1441   ccccaggagt gccctccgag agtccatggg cacccccggt tggaactggg actgagctcg 1501   ggcacgcagg gcctgagatc tggccgccca ttccgcgagc cagggccggg cgcccgggcc 1561   tttgctatct cgccgtcgcc cgcccacgca cccacccgta tttatgtttt tacctattgc 1621   tgtaagaaat gacgatcccc ttcccattaa agagagtgcg ttgaccccg
```

By "NEUROD1 polypeptide" is meant a protein or fragment thereof having at least 85% amino acid sequence identity to the sequence provided at NCBI Accession No. NP_002491.2 and having transcription factor activity. The amino acid sequence provided at NCBI Accession No. NP_002491.2 is shown below (SEQ ID NO: 33):

```
  1   mtksysesgl mgepqpqgpp swtdeclssq deeheadkke ddleamnaee dslrnggeee 61   dededleeee eeeeedddqk pkrrgpkkkk mtkarlerfk lrrmkanare rnrmhglnaa 121   ldnlrkvvpc ysktqklski etlrlaknyi walseilrsg kspdlvsfvq tickglsqpt 181   tnlvagclql nprtflpeqn qdmpphlpta sasfpvhpys yqspglpspp ygtmdsshvf 241   hvkppphays aalepffesp ltdctspsfd gplspplsin gnfsfkheps aefeknyaft 301   mhypaatlag aqshgsifsg taaprceipi dnimsfdshs hhervmsaql naifhd
```

By "NEUROD1 polynucleotide" is meant a polynucleotide encoding a NEUROD1 polypeptide or fragment thereof. An exemplary NEUROD1 polynucleotide sequence is provided at NCBI Ref: NM_002500.4. The sequence provided at NCBI Ref: NM_002500.4 is reproduced below (SEQ ID NO: 34):

```
  1   ggggaggagg ggagaacggg gagcgcacag cctggacgcg tgcgcaggcg tcaggcgcat 61   agacctgcta gcccctcagc tagcggcccc gcccgcgctt agcatcacta actgggctat 121   ataacctgag cgcccgcgcg gccacgacac gaggaattcg cccacgcagg aggcgcggcg 181   tccggaggcc ccagggttat gagactatca ctgctcagga cctactaaca acaaaggaaa 241   tcgaaacatg accaaatcgt acagcgagag tgggctgatg ggcgagcctc agccccaagg 301   tcctccaagc tggacagacg agtgtctcag ttctcaggac gaggagcacg aggcagacaa 361   gaaggaggac gacctcgaag ccatgaacgc agaggaggac tcactgagga cgggggaga 421   ggaggaggac gaagatgagg acctggaaga ggaggaagaa gaggaagagg aggatgacga 481   tcaaaagccc aagagacgcg gccccaaaaa gaagaagatg actaaggctc gcctggagcg 541   ttttaaattg agacgcatga aggctaacgc ccgggagcgg aaccgcatgc acggactgaa 601   cgcggcgcta gacaacctgc gcaaggtggt gccttgctat tctaagacgc agaagctgtc 661   caaaatcgag actctgcgct tggccaagaa ctacatctgg gctctgtcgg agatcctgcg 721   ctcaggcaaa agcccagacc tggtctcctt cgttcagacg ctttgcaagg cttatcccg 781   acccaccacc aacctggttg cgggctgcct gcaactcaat cctcggactt ttctgcctga 841   gcagaaccag gacatgcccc cccacctgcc gacggccagc gcttccttcc ctgtacaccc
```

-continued

```
 901 ctactcctac cagtcgcctg ggctgcccag tccgccttac ggtaccatgg acagctccca 961 tgtcttccac gttaagcctc cgccgcacgc ctacagcgca gcgctggagc ccttctttga 1021 aagccctctg actgattgca ccagcccttc ctttgatgga cccctcagcc cgccgctcag 1081 catcaatggc aacttctctt tcaaacacga accgtccgcc gagtttgaga aaaattatgc 1141 ctttaccatg cactatcctg cagcgacact ggcagggggcc caaagccacg gatcaatctt 1201 ctcaggcacc gctgcccctc gctgcgagat ccccatagac aatattatgt ccttcgatag 1261 ccattcacat catgagcgag tcatgagtgc ccagctcaat gccatatttc atgattagag 1321 gcacgccagt ttcaccattt ccgggaaacg aacccactgt gcttacagtg actgtcgtgt 1381 ttacaaaagg cagccctttg ggtactactg ctgcaaagtg caaatactcc aagcttcaag 1441 tgatatatgt atttattgtc attactgcct ttggaagaaa caggggatca agttcctgt 1501 tcaccttatg tattattttc tatagctctt ctatttaaaa aataaaaaaa tacagtaaag 1561 tttaaaaaat acaccacgaa tttggtgtgg ctgtattcag atcgtattaa ttatctgatc 1621 gggataacaa atcacaagc ataattagg atctatgcaa tttttaaact agtaatgggc 1681 caattaaaat atatataaat atatattttt caaccagcat tttactactt gttacctttc 1741 ccatgctgaa ttattttgtt gtgattttgt acagaatttt taatgacttt ttataatgtg 1801 gatttcctat tttaaaacca tgcagcttca tcaattttta tacatatcag aaaagtagaa 1861 ttatatctaa tttatacaaa ataatttaac taatttaaac cagcagaaaa gtgcttagaa 1921 agttattgtg ttgccttagc acttctttcc tctccaattg taaaaaaaaa aaaaaaaaaa 1981 aaaaaaaaaa aaaaattgca caatttgagc aattcatttc actttaaagt ctttccgtct 2041 ccctaaaata aaaaccagaa tcataatttt caagagaaga aaaattaag agatacattc 2101 cctatcaaaa catatcaatt caacacatta cttgcacaag cttgtatata catattataa 2161 ataaatgcca acatacccctt ctttaaatca aaagctgctt gactatcaca tacaatttgc 2221 actgttactt tttagtcttt tactcctttg cattccatga ttttacagag aatctgaagc 2281 tattgatgtt tccagaaaat ataaatgcat gattttatac atagtcacaa aaatggtggt 2341 ttgtcatata ttcatgtaat aaatctgagc ctaaatctaa tcaggttgtt aatgttggga 2401 tttatatcta tagtagtcaa ttagtacagt agcttaaata aattcaaacc atttaattca 2461 taattagaac aatagctatt gcatgtaaaa tgcagtccag ataagtgct gtttgagatg 2521 tgatgctggt accactggaa tcgatctgta ctgtaatttt gtttgtaatc ctgtatatta 2581 tggtgtaatg cacaatttag aaaacattca tccagttgca ataaatagt attgaaagtg 2641 agagcaattg ttgcatttct tcttaaaggg attctgtttt tattttttggg gaaagtagtt 2701 gcttttttgc tgagttaaaa aatactaaac actatatgta gaataaaaga aagaaaaaa 2761 gtttaccttg gcatatgctc ttgtctgttt atcttgcaca gggagtcacc agttctatgt 2821 agataatgaa aagacctaac tgatatttca ttatttggaa tatgggactg gacggcagta 2881 caaacagtgt gtttttttct ttgtttttaag tggcttagcc tttaggtttt ttatttccat 2941 ttttaaaaat gattgttaca tgttttcttc tatttctttt tttaaaggt ggattttaat 3001 aa
```

By "NKX6-1 polypeptide" is meant a protein or fragment thereof having at least 85% amino acid sequence identity to the sequence provided at NCBI Accession No. NP_006159.2 and having transcription factor activity. The amino acid sequence provided at NCBI Accession No. NP_006159.2 is shown below (SEQ ID NO: 35):

```
  1  mlavgamegt rqsafllssp plaalhsmae mktplypaay pplpagppss ssssssssssp
 61  spplgthnpg glkppatggl sslgsppqql saatphgind ilsrpsmpva sgaalpsasp
121  sgsssssss asassasaaa aaaaaaaaaa sspagllagl prfsslsppp pppglyfsps
181  aaavaavgry pkplaelpgr tpifwpgvmq sppwrdarla ctphqgsill dkdgkrkhtr
241  ptfsgqqifa lektfeqtky lagperarla yslgmtesqv kvwfqnrrtk wrkkhaaema
301  takkkqdset erlkgasene eedddynkpl dpnsddekit qllkkhksss ggggglllha
361  sepesss
```

By "NKX6-1 polynucleotide" is meant a polynucleotide encoding a NKX6-1 polypeptide or fragment thereof. An exemplary NKX6-1 polynucleotide sequence is provided at NCBI Ref: NM_006168.2. The sequence provided at NCBI Ref: NM_006168.2 is reproduced below (SEQ ID NO: 36):

```
   1  cgtgggatgt tagcggtggg ggcaatggag ggcacccggc agagcgcatt cctgctcagc
  61  agccctcccc tggccgccct gcacagcatg gccgagatga agaccccgct gtaccctgcc
 121  gcgtatcccc cgctgcctgc cggccccccc tcctcctcgt cctcgtcgtc gtcctcctcg
 181  tcgccctccc cgcctctggg cacccacaac ccaggcggcc tgaagccccc ggccacgggg
 241  gggctctcat ccctcggcag ccccccgcag cagctctcgg ccgccacccc acacggcatc
 301  aacgatatcc tgagccggcc ctccatgccc gtggcctcgg gggccgccct gccctccgcc
 361  tcgccctccg gttcctcctc ctcctcttcc tcgtccgcct ctgcctcctc cgcctctgcc
 421  gccgccgcgg ctgctgccgc ggccgcagcc gccgcctcat ccccggcggg gctgctggcc
 481  ggactgccac gctttagcag cctgagcccg ccgccgccgc cgcccgggct ctacttcagc
 541  cccagcgccg cggccgtggc cgccgtgggc cggtacccca gccgctggc tgagctgcct
 601  ggccggacgc ccatcttctg gccggagtg atgcagagcc cgccctggag ggacgcacgc
 661  ctggcctgta cccctcatca aggatccatt ttgttggaca aagacgggaa gagaaaacac
 721  acgagaccca cttttccgg acagcagatc ttcgccctgg agaagacttt cgaacaaaca
 781  aaatacttgg cggggcccga gagggctcgt ttggcctatt cgttggggat gacagagagt
 841  caggtcaagg tctggttcca gaaccgccgg accaagtgga ggaagaagca cgctgccgag
 901  atggccacgg ccaagaagaa gcaggactcg gagacagagc gcctcaaggg ggcctcggag
 961  aacgaggaag aggacgacga ctacaataag cctctggatc ccaactcgga cgacgagaaa
1021  atcacgcagc tgttgaagaa gcacaagtcc agcagcggcg gcggcggcgg cctcctactg
1081  cacgcgtccg agccggagag ctcatcctga acgccg
```

By "NDUFA4 polypeptide" is meant a protein or fragment thereof having at least 85% amino acid sequence identity to the sequence provided at NCBI Accession No. NP_002480.1 and having NADH dehydrogenase activity and oxidoreductase activity. The amino acid sequence provided at NCBI Accession No. NP_002480.1 is shown below (SEQ ID NO: 37):

```
  1  maaelamgae  lpssplaiey  vndfdlmkfe  vkkeppeaer  fchrlppgsl  sstplstpcs 61  svpsspsfca  pspgtggggg  aggggssqa   ggapgppsgg  pgavggtsgk  paledlywms 121  gyqhhlnpea  lnltpedave  aligsghhga  hhgahhpaaa  aayeafrgpg  faggggaddm 181  gaghhhgahh  aahhhhaahh  hhhhhhhhgg  aghgggaghh  vrleerfsdd  qlvsmsvrel 241  nrqlrgfske  evirlkqkrr  tlknrgyaqs  crfkrvqqrh  ilesekcqlq  sqveqlklev 301  grlakerdly  kekyeklagr  ggpgsaggag  fprepsppqa  gpggakgtad  ffl
```

By "NDUFA4 polynucleotide" is meant a polynucleotide encoding a NDUFA4 polypeptide or fragment thereof. An exemplary NDUFA4 polynucleotide sequence is provided at NCBI Ref: NM_002489.3. The sequence provided at NCBI Ref: NM_002489.3 is reproduced below (SEQ ID NO: 38):

```
   1  gggtccttca  ggtaggaggt  cctgggtgac  tttggaagtc  cgtagtgtct  cattgcagat 61  aattttagc   ttagggcctg  gtggctaggt  cggttctctc  ctttccagtc  ggagacctct 121  gccgcaaaca  tgctccgcca  gatcatcggt  caggccaaga  agcatccgag  cttgatcccc 181  ctctttgtat  ttattggaac  tggagctact  ggagcaacac  tgtatctctt  gcgtctggca 241  ttgttcaatc  cagatgtttg  ttgggacaga  ataacccag   agccctggaa  caaactgggt 301  cccaatgatc  aatacaagtt  ctactcagtg  aatgtggatt  acagcaagct  gaagaaggaa 361  cgtccagatt  tctaaatgaa  atgtttcact  ataacgctgc  tttagaatga  aggtcttcca 421  gaagccacat  ccgcacaatt  ttccacttaa  ccaggaaata  tttctcctct  aaatgcatga 481  aatcatgttg  gagatctcta  ttgtaatctc  tattggagat  tacaatgatt  aaatcaataa 541  ataactgaaa  cttgatatgt  gtcactttt   tatgctgaaa  gtatgctctg  aactttagag 601  tataggaaat  taactattag  aatttaaaga  atttcttgaa  tttctgtagt  ttgaaaatac 661  gactttaagc  tgctttagta  aaacacttcc  attttgtgta  tagactgttg  gtaacttcac 721  tagagcatac  ataacaactg  gaactggaaa  ttatacaaaa  gtaaattggg  aaggatactc 781  cagcatctga  cactggcaaa  atgaaaacct  ttgagtttct  cttactggct  gttgaagtgt 841  gtgcagtttt  taacaatggt  ttttacttgg  catctctttg  ttgtgattt   caaggttata 901  agttgctttg  gtcctaggat  tgaagttgaa  atctgagttt  atcagtgcta  accatggtgc 961  tagtagtcaa  gagatcttga  gaattttggc  tgctgagtct  tggtgcaggg  tgcaggtttt 1021  cttttctttt  ttctttttt   tttttttgag  atagtctctg  tcacccaggc  tggagtgcag 1081  tggtacaaac  atggatcact  gcagcctcta  cctcccgggc  ttaagtgatc  ctcctgcctc 1141  agcccctaag  tagccgggac  tacaggtatg  tgccaccatg  cccagttaat  ttttgtaatt 1201  ttttagag   acagggtttt  gccatgttgc  ccaggctggt  ctcaaactct  tgagctcaag 1261  cgatccattc  tcctcagcct  cccagggtgc  tgggattaca  ggcgtgagcc  attgcgctta 1321  gccatggtgc  aggttttcaa  aggccaggaa  gtatattcat  aatttaaga   tggggaatat 1381  agcaagtttt  cacataggtg  tgtgtaagtc  atcacatcat  agaaacttga  ggaattcagt 1441  gacattaatt  ttggattttc  atacgtaagt  atacaattaa  atgtttacag  ggtagtagaa 1501  gcacatttta  aatgtcagga  actgaactaa  gtatttgaat  tacgtggatt  atctcaaaaa 1561  ttttgaaatt  gttaaacgag  ttgaattact  tgaattcatt  ctgttagtca  aatggtggat 1621  atttacaccc  atgtagtttt  gaatttagag  tgtgtagagt  gttttcagtt  accagactcc 1681  atgctttac   ctcctatgtg  tcaggtataa  tttgaacctc  taagaacagg  gtttctcaac 1741  cttgccactg  ttgactattt  ctgaaagaca  gtttggttta  gcagaccatc  ccatgcgctt
```

```
-continued
1801  tagcttgttt agtagctaac ttgggctctg ccactacaga caaaaagcac tctttccctc 1861  caattcccac aggctatgag aagaatggag acattaccaa atgtccattg gtgggcaaaa 1921  ttgcttcatt cctacctctg ttgagaatta ctctagatcc tttggcacaa attacctcaa 1981  agtttaaaat tgtgtaaaca aacagtgtgt catgtaattg aaaaacatta agcaactcca 2041  aataaatgct acattaag
```

As used herein, "obtaining" as in "obtaining an agent" includes synthesizing, purchasing, or otherwise acquiring the agent.

By "organ" is meant a collection of cells that perform a biological function. In one embodiment, an organ includes, but is not limited to, bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, skin, bone, and cartilage. The biological function of an organ can be assayed using standard methods known to the skilled artisan.

By "organoid" is meant an in vitro generated body that mimics organ structure and function. "Organoid" and "mini organ" are used interchangeably herein. A "pancreatic islet organoid" is an in vitro generated cell cluster that mimics structure and function of a pancreatic islet. Exemplary functions of a pancreatic islet include, without limitation, glucose-stimulated insulin secretion (GSIS), potassium chloride (KCl)-stimulated insulin secretion, GLP-1 stimulated insulin secretion, somatostatin secretion, or glucagon secretion. "Pancreatic islet organoid" and "mini pancreatic islet" are used interchangeably herein. A "pancreatic organoid" is an in vitro generated body that mimics structure and function of a pancreas. Exemplary functions of a pancreas include, without limitation, endocrine secretion of hormones, such as glucose and glucagon, that regulate glucose metabolism and blood glucose concentration, and exocrine secretion of digestive enzymes that help break down carbohydrates, proteins, and lipids. "Pancreatic organoid" and "mini pancreas" are used interchangeably herein.

By "PAX4 polypeptide" is meant a protein or fragment thereof having at least 85% amino acid sequence identity to the sequence provided at NCBI Accession No. NP_006184.2 and having transcription factor activity. The amino acid sequence provided at NCBI Accession No. NP_006184.2 is shown below (SEQ ID NO: 39):

```
  1  mnqlgglfvn grplpldtrq qivrlavsgm rpcdisrilk vsngcvskil gryyrtgvle 61  pkgiggskpr latppvvari aqlkgecpal faweiqrqlc aeglctqdkt psvssinrvl 121  ralqedqglp ctrlrspavl apavltphsg setprgthpg tghrnrtifs psqaealeke 181  fqrggypdsv argklatats lpedtvrvwf snrrakwrrq eklkwemqlp gasqgltvpr 241  vapgiisagq spgsvptaal paleplgpsc yqlcwatape rclsdtppka clkpcwghlp 301  pqpnsldsgl lclpcpsshc hlaslsgsqa llwpgcplly gle
```

By "PAX4 polynucleotide" is meant a polynucleotide encoding a PAX4 polypeptide or fragment thereof. An exemplary PAX4 polynucleotide sequence is provided at NCBI Ref: NM_006193.2. The sequence provided at NCBI Ref: NM_006193.2 is reproduced below (SEQ ID NO: 40):

```
  1  caaagactca cccgtgagcc agctctcaaa gaaagcagct tgcgttgaca gcctgggggc 61  agcaaggatg cagtctccca ggagaggatg cactcggtgg tgggaagcca ggctggaggg 121  gcctgagtga ccctctccac aggcgggcag ggcagtggga gaggtggtgt gtggatacct 181  ctgtctcacg cccagggatc agcagcatga accagcttgg ggggctcttt gtgaatggcc 241  ggcccctgcc tctggatacc cggcagcaga ttgtgcggct agcagtcagt ggaatgcggc 301  cctgtgacat ctcacggatc cttaaggtat ctaatgctg tgtgagcaag atcctagggc 361  gttactaccg cacaggtgtc ttggagccaa agggcattgg gggaagcaag ccacggctgg 421  ctacacccc tgtggtggct cgaattgccc agctgaaggg tgagtgtcca gccctctttg 481  cctgggaaat ccaacgccag ctttgtgctg aagggctttg cacccaggac aagactccca 541  gtgtctcctc catcaaccga gtcctgcggg cattacagga ggaccaggga ctaccgtgca 601  cacggctcag gtcaccagct gttttggctc cagctgtcct cactccccat agtggctctg 661  agactcccg gggtacccac ccagggaccg gccaccggaa tcggactatc ttctccccaa
```

```
 721   gccaagcaga ggcactggag aaagagttcc agcgtgggca gtatcctgat tcagtggccc
 781   gtggaaagct ggctactgcc acctctctgc ctgaggacac ggtgagggtc tggttttcca
 841   acagaagagc caaatggcgt cggcaagaga agctcaagtg ggaaatgcag ctgccaggtg
 901   cttcccaggg gctgactgta ccaaggggttg ccccaggaat catctctgca cagcagtccc
 961   ctggcagtgt gcccacagca gccctgcctg ccctggaacc actgggtccc tcctgctatc
1021   agctgtgctg ggcaacagca ccagaaaggt gtctgagtga cacccacct aaagcctgtc
1081   tcaagccctg ctggggccac ttgcccccac agccgaattc cctggactca ggactgcttt
1141   gccttccttg cccttcctcc cactgtcacc tggccagtct tagtggctct caggccctgc
1201   tctggcctgg ctgcccacta ctgtatggct tggaatgagg caggagtggg aaggagatgg
1261   catagagaag atctaatacc atcctgccca ttgtccttac cgtcctgccc atacagactg
1321   tggctccttc ctccttcctg tgattgctcc ctcctgtgtg gacgttgcct ggccctgcct
1381   cgatgcctct ctggcgcatc acctgattgg aggggctggt aaagcaacac ccacccactt
1441   ctcacactag ccttaagagg cctccactca gcagtaataa aagctgtttt tattagcagt
1501   agttctgttg tccatcatgt tttccctatg agcacccta tgcccactct aatattcaac
1561   aattatagac aatttgccct atcatttatt tacatctatg tatctaccat ctaatctatg
1621   catgtatgta ggcaatacat gtatctaaac aatgtatttg tcaatgcatc aatttaccta
1681   ctctatgtat gcatctatat gtgtattatg tatgcgtgca tgcgtgcgcg cacacacaca
1741   cacacacaca cacactgaca ttatatcatg gcattttatt cctaaatctt ccagcatgca
1801   tccccaaaaa acaagaaact tgtcttacat aatcacaata atatatccac atctaagaaa
1861   atttactgta acttcttaat ctaagaaaat tatgtatttt tgtcatatgt attttgtcat
1921   atgtattttg tatttgcata tgtattttgt atttgcatat gtattttgt catagcagca
1981   aacagagtga aatgccattt ttcatattct
```

By "PAX6 polypeptide" is meant a protein or fragment thereof having at least 85% amino acid sequence identity to the sequence provided at NCBI Accession No. NP_001297090.1 and having transcription factor activity. The amino acid sequence provided at NCBI Accession No. NP_001297090.1 is shown below (SEQ ID NO: 41):

```
  1   mgadgmydkl rmlngqtgsw gtrpgwypgt svpgqptqdg cqqqegggen tnsissnged
 61   sdeaqmrlql krklqrnrts ftqeqieale keferthypd vfarerlaak idlpeariqv
121   wfsnrrakwr reeklrnqrr qasntpship isssfstsvy qpipqpttpv ssftsgsmlg
181   rtdtaltnty salppmpsft mannlpmqpp vpsqtssysc mlptspsvng rsydtytpph
241   mqthmnsqpm gtsgttstgl ispgvsvpvq vpgsepdmsq ywprlq
```

By "PAX6 polynucleotide" is meant a polynucleotide encoding a PAX6 polypeptide or fragment thereof. An exemplary PAX6 polynucleotide sequence is provided at NCBI Ref: NM_001310161.1. The sequence provided at NCBI Ref: NM_001310161.1 is reproduced below (SEQ ID NO: 42):

```
  1   cttttcaatt agccttccat gcatgatccg gagcgacttc cgcctatttc cagaaattaa
 61   gctcaaactt gacgtgcagc tagttttatt ttaaagacaa atgtcagaga ggctcatcat
121   attttccccc ctcttctata tttggagctt atttattgct aagaagctca ggctcctggc
181   gtcaatttat cagtaggctc caaggagaag agaggagagg agaggagagc tgaacaggga
241   gccacgtctt ttcctgggag ggctgctatc taagtcgggg ctgcaggtca cagcggagtg
```

-continued

```
 301   aatcagctcg gtggtgtctt tgtcaacggg cggccactgc cggactccac ccggcagaag
 361   attgtagagc tagctcacag cggggcccgg ccgtgcgaca tttcccgaat tctgcagacc
 421   catgcagatg caaaagtcca agtgctggac aatcaaaacg tgtccaacgg atgtgtgagt
 481   aaaattctgg gcaggtatta cgagactggc tccatcagac ccagggcaat cggtggtagt
 541   aaaccgagag tagcgactcc agaagttgta agcaaaatag cccagtataa gcgggagtgc
 601   ccgtccatct ttgcttggga aatccgagac agattactgt ccgaggggt ctgtaccaac
 661   gataacatac caagcgtgtc atcaataaac agagttcttc gcaacctggc tagcgaaaag
 721   caacagatgg gcgcagacgg catgtatgat aaactaagga tgttgaacgg gcagaccgga
 781   agctggggca cccgccctgg ttggtatccg gggacttcgg tgccagggca acctacgcaa
 841   gatggctgcc agcaacagga aggaggggga gagaatacca actccatcag ttccaacgga
 901   gaagattcag atgaggctca aatgcgactt cagctgaagc ggaagctgca agaaataga
 961   acatcctta cccaagagca aattgaggcc ctggagaaag agtttgagag aacccattat
1021   ccagatgtgt tgcccgaga aagactagca gccaaaatag atctacctga agcaagaata
1081   caggtatggt tttctaatcg aagggccaaa tggagaagag aagaaaaact gaggaatcag
1141   agaagacagg ccagcaacac acctagtcat attcctatca gcagtagttt cagcaccagt
1201   gtctaccaac caattccaca accaccaca ccggtttcct ccttcacatc tggctccatg
1261   ttgggccgaa cagacacagc cctcacaaac acctacagcg ctctgccgcc tatgcccagc
1321   ttcaccatgg caataaccct gcctatgcaa cccccagtcc ccagccagac ctcctcatac
1381   tcctgcatgc tgcccaccag cccttcggtg aatgggcgga gttatgatac ctacaccccc
1441   ccacatatgc agacacacat gaacagtcag ccaatgggca cctcgggcac cacttcaaca
1501   ggactcattt ccctggtgt gtcagttcca gttcaagttc ccggaagtga acctgatatg
1561   tctcaatact ggccaagatt acagtaaaaa aaaaaaaaa aaaaaaagg aaaggaaata
1621   ttgtgttaat tcagtcagtg actatgggga cacaacagtt gagctttcag gaaagaaaga
1681   aaaatggctg ttagagccgc ttcagttcta caattgtgtc ctgtattgta ccactgggga
1741   aggaatggac ttgaaacaag gacctttgta tacagaaggc acgatatcag ttggaacaaa
1801   tcttcatttt ggtatccaaa cttttattca ttttggtgta ttatttgtaa atgggcattt
1861   gtatgttata atgaaaaaaa gaacaatgta gactggatgg atgtttgatc tgtgttggtc
1921   atgaagttgt ttttttttt tttaaaaaga aaaccatgat caacaagctt tgccacgaat
1981   ttaagagttt tatcaagata tatcgaatac ttctacccat ctgttcatag tttatggact
2041   gatgttccaa gtttgtatca ttcctttgca tataattaaa cctggaacaa catgcactag
2101   atttatgtca gaaatatctg ttggttttcc aaaggttgtt aacagatgaa gttatgtgc
2161   aaaaagggt aagatataaa ttcaaggaag aaaaaagtt gatagctaaa aggtagagtg
2221   tgtcttcgat ataatccaat ttgttttatg tcaaatgta agtatttgtc ttccctagaa
2281   atcctcagaa tgatttctat aataaagtta atttcattta tatttgacaa gaatatagat
2341   gttttataca cattttcatg caatcatacg tttctttttt ggccagcaaa agttaattgt
2401   tcttagatat agttgtatta ctgttcacgg tccaatcatt ttgtgcatct agagttcatt
2461   cctaatcaat taaaagtgct tgcaagagtt ttaaacttaa gtgttttgaa gttgttcaca
2521   actacatatc aaaattaacc attgttgatt gtaaaaaacc atgccaaagc ctttgtattt
2581   cctttattat acagttttct ttttaacctt atagtgtggt gttacaaatt ttatttccat
2641   gttagatcaa cattctaaac caatggttac tttcacacac actctgtttt acatcctgat
```

```
-continued
2701  gatccttaaa aaataatcct tatagatacc ataaatcaaa aacgtgttag aaaaaaattc
2761  cacttacagc agggtgtaga tctgtgccca tttatacccca caacatatat acaaaatggt
2821  aacatttccc agttagccat ttaattctaa agctcaaagt ctagaaataa tttaaaaatg
2881  caacaagcga ttagctagga attgtttttt gaattaggac tggcattttc aatctgggca
2941  gatttccatt gtcagcctat ttcaacaatg atttcactga agtatattca aaagtagatt
3001  tcttaaagga gactttctga aagctgttgc cttttttcaaa taggccctct cccttttctg
3061  tctccctccc ctttgcacaa gaggcatcat ttcccattga accactacag ctgttcccat
3121  ttgaatcttg cttttctgtgc ggttgtggat ggttggaggg tggagggggg atgttgcatg
3181  tcaaggaata atgagcacag acacatcaac agacaacaac aaagcagact gtgactggcc
3241  ggtgggaatt aaaggccttc agtcattggc agcttaagcc aaacattccc aaatctatga
3301  agcagggccc attgttggtc agttgttatt tgcaatgaag cacagttctg atcatgttta
3361  aagtggaggc acgcagggca ggagtgcttg agcccaagca aaggatggaa aaaaataagc
3421  ctttgttggg taaaaaagga ctgtctgaga ctttcatttg ttctgtgcaa catataagtc
3481  aatacagata agtcttcctc tgcaaacttc actaaaaagc ctggggggttc tggcagtcta
3541  gattaaaatg cttgcacatg cagaaacctc tggggacaaa gacacacttc cactgaatta
3601  tactctgctt taaaaaaatc cccaaaagca aatgatcaga aatgtagaaa ttaatggaag
3661  gatttaaaca tgaccttctc gttcaatatc tactgttttt tagttaagga attacttgtg
3721  aacagataat tgagattcat tgctccggca tgaaatatac taataatttt attccaccag
3781  agttgctgca catttggaga caccttccta agttgcagtt tttgtatgtg tgcatgtagt
3841  tttgttcagt gtcagcctgc actgcacagc agcacatttc tgcaggggag tgagcacaca
3901  tacgcactgt tggtacaatt gccggtgcag acatttctac ctcctgacat tttgcagcct
3961  acattccctg agggctgtgt gctgagggaa ctgtcagaga agggctatgt gggagtgcat
4021  gccacagctg ctggctggct tacttcttcc ttctcgctgg ctgtaatttc caccacggtc
4081  aggcagccag ttccggccca cggttctgtt gtgtagacag cagagacttt ggagacccgg
4141  atgtcgcacg ccaggtgcaa gaggtgggaa tgggagaaaa ggagtgacgt gggagcggag
4201  ggtctgtatg tgtgcacttg ggcacgtata tgtgtgctct gaaggtcagg attgccaggg
4261  caaagtagca cagtctggta tagtctgaag aagcggctgc tcagctgcag aagccctctg
4321  gtccggcagg atgggaacgg ctgccttgcc ttctgcccac accctaggga catgagctgt
4381  ccttccaaac agagctccag gcactctctt ggggacagca tggcaggctc tgtgtggtag
4441  cagtgcctgg gagttggcct tttactcatt gttgaaataa ttttttgttta ttatttattt
4501  aacgatacat atatttatat atttatcaat ggggtatctg cagggatgtt ttgacaccat
4561  cttccaggat ggagattatt tgtgaagact tcagtagaat cccaggacta aacgtctaaa
4621  tttttctcc aaacttgact gacttgggaa accaggtga atagaataag agctgaatgt
4681  tttaagtaat aaacgttcaa actgctctaa gtaaaaaaat gcattttact gcaatgaatt
4741  tctagaatat ttttccccca aagctatgcc tcctaaccct aaatggtga acaactggtt
4801  tcttgctaca gctcactgcc atttcttctt actatcatca ctaggtttcc taagattcac
4861  tcatacagta ttatttgaag attcagcttt gttctgtgaa tgtcatctta ggattgtgtc
4921  tatattcttt tgcttatttc ttttttactct gggcctctca tactagtaag attttaaaaa
4981  gccttttctt ctctgtatgt ttggctcacc aaggcgaaat atatattctt ctctttttca
5041  tttctcaaga ataaacctca tctgcttttt tgttttttctg tgttttggct tggtactgaa
5101  tgactcaact gctcggtttt aaagttcaaa gtgtaagtac ttagggttag tactgcttat
```

-continued

```
5161  ttcaataatg ttgacggtga ctatctttgg aaagcagtaa catgctgtct tagaaatgac 5221  attaataatg ggcttaaaca aatgaatagg ggggtccccc cactctcctt ttgtatgcct 5281  atgtgtgtct gatttgttaa aagatggaca gggaattgat tgcagagtgt cgcttccttc 5341  taaagtagtt ttattttgtc tactgttagt atttaaagat cctggaggtg gacataagga 5401  ataaatggaa gagaaaagta gatattgtat ggtggctact aaaaggaaat tcaaaaagtc 5461  ttagaacccg agcacctgag caaactgcag tagtcaaaat atttatctca tgttaaagaa 5521  aggcaaatct agtgtaagaa atgagtacca tagggtttt  tgaagttcat atactagaaa 5581  cacttaaaag atatcatttc agatattacg tttggcattg ttcttaagta tttatatctt 5641  tgagtcaagc tgataattaa aaaaaatctg ttaatggagt gtatatttca taatgtatca 5701  aaatggtgtc tatacctaag gtagcattat tgaagagaga tatgtttatg tagtaagtta 5761  ttaacataat gagtaacaaa taatgtttcc agaagaaagg aaaacacatt ttcagagtgc 5821  gtttttatca gaggaagaca aaaatacaca cccctctcca gtagcttatt tttacaaagc 5881  cggcccagtg aattagaaaa acaaagcact tggatatgat ttttggaaag cccaggtaca 5941  cttattattc aaaatgcact tttactgagt ttgaaaagtt tcttttatat ttaaaataag 6001  ggttcaaata tgcatattca attttatag  tagttatcta tttgcaaagc atatattaac 6061  tagtaattgg ctgttaattt tatagacatg gtagccaggg aagtatatca atgacctatt 6121  aagtattttg acaagcaatt tacatatctg atgacctcgt atctcttttt cagcaagtca 6181  aatgctatgt aattgttcca ttgtgtgttg tataaaatga atcaacacgg taagaaaaag 6241  gttagagtta ttaaaataat aaactgacta aaatactcat ttgaatttat tcagaatgtt 6301  cataatgctt tcaaaggaca tagcagagct tttgtggagt atccgcacaa cattatttat 6361  tatctatgga ctaaatcaat tttttgaagt tgctttaaaa tttaaaagca cctttgctta 6421  atataaagcc ctttaatttt aactgacaga tcaattctga aactttattt tgaaaagaaa 6481  atggggaaga atctgtgtct ttagaattaa aagaaatgaa aaaaataaac ccgacattct 6541  aaaaaaatag aataagaaac ctgattttta gtactaatga aatagcgggt gacaaaatag 6601  ttgtcttttt gattttgatc acaaaaaata aactggtagt gacaggatat gatggagaga 6661  tttgacatcc tggcaaatca ctgtcattga ttcaattatt ctaattctga ataaaagctg 6721  tatacagtaa aa
```

By "PDX1 polypeptide" is meant a protein or fragment thereof having at least 85% amino acid sequence identity to the sequence provided at NCBI Accession No. NP_000200.1 and having transcription factor activity. The amino acid sequence provided at NCBI Accession No. NP_000200.1 is shown below (SEQ ID NO: 43):

```
  1  mngeeqyyaa tqlykdpcaf qrgpapefsa sppaclymgr qpppppphpf pgalgaleqg 61  sppdispyev ppladdpava hlhhhlpaql alphppagpf pegaepgvle epnrvqlpfp 121  wmkstkahaw kgqwaggaya aepeenkrtr taytraqlle lekeflfnky isrprrvela 181  vmlnlterhi kiwfqnrrmk wkkeedkkrg ggtavggggv aepeqdcavt sgeellalpp 241  ppppggavpp aapvaaregr lppglsaspq pssvaprrpq epr
```

By "PDX1 polynucleotide" is meant a polynucleotide encoding a PDX1 polypeptide or fragment thereof. An exemplary PDX1 polynucleotide sequence is provided at NCBI Ref: NM_000209.3. The sequence provided at NCBI Ref: NM_000209.3 is reproduced below (SEQ ID NO: 44):

```
   1  gggtggcgcc gggagtggga acgccacaca gtgccaaatc cccggctcca gctcccgact
  61  cccggctccc ggctcccggc tcccggtgcc caatcccggg ccgcagccat gaacggcgag
 121  gagcagtact acgcggccac gcagctttac aaggacccat gcgcgttcca gcgaggcccg
 181  gcgccggagt tcagcgccag ccccccctgcg tgcctgtaca tgggccgcca gccccgccg
 241  ccgccgccgc acccgttccc tggcgccctg ggcgcgctgg agcagggcag ccccccggac
 301  atctcccgt acgaggtgcc ccccctcgcc gacgaccccg cggtggcgca ccttcaccac
 361  cacctcccgg ctcagctcgc gctcccccac ccgcccgccg ggccttccc ggagggagcc
 421  gagccgggcg tcctggagga gcccaaccgc gtccagctgc ctttcccatg gatgaagtct
 481  accaaagctc acgcgtggaa aggccagtgg gcaggcggcg cctacgctgc ggagccggag
 541  gagaacaagc ggacgcgcac ggcctacacg cgcgcacagc tgctagagct ggagaaggag
 601  ttcctattca acaagtacat ctcacggccg cgccgggtgg agctggctgt catgttgaac
 661  ttgaccgaga gacacatcaa gatctggttc caaaaccgcc gcatgaagtg gaaaaaggag
 721  gaggacaaga agcgcggcgg cgggacagct gtcggggtg gcggggtcgc ggagcctgag
 781  caggactgcg ccgtgacctc cggcgaggag cttctggcgc tgccgccgcc gccgccccc
 841  ggaggtgctg tgccgcccgc tgccccgtt gccgcccgag agggccgcct gccgcctggc
 901  cttagcgcgt cgccacagcc ctccagcgtc gcgcctcggc ggccgcagga accacgatga
 961  gaggcaggag ctgctcctgg ctgaggggct tcaaccactc gccgaggagg agcagagggc
1021  ctaggaggac cccgggcgtg gaccacccgc cctggcagtt gaatggggcg gcaattgcgg
1081  ggcccacctt agaccgaagg ggaaaacccg ctctctcagg cgcatgtgcc agttgggggcc
1141  ccgcgggtag atgccggcag gccttccgga agaaaaagag ccattggttt ttgtagtatt
1201  ggggccctct tttagtgata ctggattggc gttgtttgtg gctgttgcgc acatccctgc
1261  cctcctacag cactccacct tgggacctgt ttagagaagc cggctcttca aagacaatgg
1321  aaactgtacc atacacattg gaaggctccc taacacacac agcggggaag ctgggccgag
1381  taccttaatc tgccataaag ccattcttac tcgggcgacc ctttaagtt tagaaataat
1441  tgaaaggaaa tgtttgagtt ttcaaagatc ccgtgaaatt gatgccagtg gaatacagtg
1501  agtcctcctc ttcctcctcc tcctcttccc cctcccctc ctcctcctcc tcttcttttc
1561  cctcctcttc ctcttcctcc tgctctcctt tcctcccct cctctttcc ctcctcttcc
1621  tcttcctcct gctctccttt cctcccctc ctctttctcc tcctcctcct cttcttcccc
1681  ctcctctccc tcctcctctt cttcccccct ctctcccctcc tcctcttctt ctccctcctc
1741  ttcctcttcc tcctcttcca cgtgctctcc tttcctcccc ctcctcttgc tccccttctt
1801  cccgtcctc ttcctcctcc tcctcttctt ctccctcctc ttcctcctcc tctttcttcc
1861  tgacctcttt cttttctcctc ctcctccttc tacctcccct tctcatccct cctcttcctc
1921  ttctctagct gcacacttca ctactgcaca tcttataact tgcaccccct tcttctgagg
1981  aagagaacat cttgcaaggc agggcgagca gcggcagggc tggcttagga gcagtgcaag
2041  agtccctgtg ctccagttcc acactgctgg cagggaaggc aagggggac gggcctggat
2101  ctgggggtga gggagaaaga tggacccctg ggtgaccact aaaccaaaga tattcggaac
2161  tttctattta ggatgtggac gtaattcctg ttccgaggta gaggctgtgc tgaagacaag
2221  cacagtggcc tggtgcgcct tggaaaccaa caactattca cgagccagta tgaccttcac
2281  atctttagaa attatgaaaa cgtatgtgat tggagggttt ggaaaaccag ttatcttatt
2341  taacatttta aaaattacct aacagttatt tacaaacagg tctgtgcatc ccaggtctgt
2401  cttcttttca aggtctgggc cttgtgctcg ggttatgttt gtgggaaatg cttaataaat
```

```
2461  actgataata tgggaagaga tgaaaactga ttctcctcac tttgtttcaa acctttctgg 2521  cagtgggatg attcgaattc acttttaaaa ttaaattagc gtgttttgtt ttg
```

By "PTF1 polypeptide" is meant a protein or fragment thereof having at least 85% amino acid sequence identity to the sequence provided at NCBI Accession No. NP_835455.1 and having transcription factor activity. The amino acid sequence provided at NCBI Accession No. NP_835455.1 is shown below (SEQ ID NO: 45):

```
  1  mdavllehfp ggldafpssy fdeddfftdq ssrdpledgd elladeqaev eflshqlhey 61  cyrdgaclll qpappaapla lappssgglg epddgggggy ccetgappgg fpyspgspps 121  claypcagaa vlspgarlrg lsgaaaaaar rrrrvrseae lqqlrqaanv rerrrmqsin 181  dafeglrshi ptlpyekrls kvdtlrlaig yinflselvq adlplrggga ggcggpgggg 241  rlggdspgsq aqkviichrg trspspsdpd yglpplaghs lswtdekqlk eqniirtakv 301  wtpedprkln skssfnnien eppfefvs
```

By "PTF1 polynucleotide" is meant a polynucleotide encoding a PTF1 polypeptide or fragment thereof. An exemplary PTF1 polynucleotide sequence is provided at NCBI Ref: NM_178161.2. The sequence provided at NCBI Ref: NM_178161.2 is reproduced below (SEQ ID NO: 46):

```
   1  atggacgcgg tgttgctgga gcacttcccc gggggcctag acgcctttcc ttcttcgtac 61  ttcgacgagg acgacttctt caccgaccag tcttcacggg acccctgga ggacggcgat 121  gagctgctgg cggacgagca ggccgaggtg gagttcctta gccaccagct ccacgagtac 181  tgctaccgcg acggggcgtg cctgctgctg cagcccgcgc cccggccgc cccgctagcg 241  ctcgccccgc cgtcctcggg gggcctcggt gagccagacg acggcggcgg cggcggctac 301  tgctgcgaga cgggggcgcc cccaggcggc ttcccctact cgcccggctc gccgccctcg 361  tgcctggcct acccgtgcgc cggggcggca gtactgtctc ccggggcgcg gctgcgcggc 421  ctgagcggag cggcggctgc ggcggcgcgg cgccggcggc gggtgcgctc cgaggcggag 481  ctgcagcagc tgcggcaggc ggccaacgtg cgcgagcggc ggcgcatgca gtccatcaac 541  gacgccttcg aggggctgcg ctcgcacatc cccacgctgc cctacgagaa gcgcctctcc 601  aaggtggaca cgctgcgcct ggccatcggc tacatcaact tcctcagcga gctcgtgcag 661  gccgacctgc ccttgcgcgg cggtggcgcg ggcggctgcg ggggccggg cggcggcggg 721  cgcctgggcg gggacagccc gggcagccag gcccagaagg tcatcatctg ccatcggggc 781  acccggtccc cctccccag cgaccctgat tatggcctcc ctcccctagc aggacactct 841  ctctcatgga ctgatgaaaa acaactcaag gaacaaaata ttatccgaac agccaaagtc 901  tggaccccag aggacccag aaaactcaac agcaaatctt ccttcaacaa catagaaaac 961  gaaccaccat ttgagtttgt gtcctgagaa gtcccagact cggctgaaga tctgattatg 1021  tctctgtgca tattgtacat gtaaatatct ataatgtaaa tgtaatttaa gaatcaaatt 1081  tttcgaatgg caatcaactg tttattattt atctatttat tatcctgttg agttgatgaa 1141  atagatgatt tcttttaaa tatataattt ataacttga tcctgatttt ctgaaaatat 1201  gcaatagcct atgattttcc tgaactctgt gttgttggga gaactctggc cagaaaacgt 1261  cctgcttatt tattgccaga tatggtttat ttctaagcgt tgtcaataaa tgctatttac 1321  accttttcct gaaaaaaaa
```

By "Wnt3a polynucleotide" is meant a polynucleotide encoding a Wnt3a polypeptide or a fragment thereof, or a polynucleotide having at least 85% sequence identity to the human Wnt3a polynucleotide sequence. An exemplary human Wnt3a polynucleotide sequence is provided at NCBI GenBank Accession No. AB060284.1. The polynucleotide sequence provided at NCBI GenBank Accession No. AB060284.1 is reproduced below (SEQ ID NO: 47):

```
   1   cggcgatggc cccactcgga tacttcttac tcctctgcag cctgaagcag gctctgggca
  61   gctacccgat ctggtggtcg ctggctgttg ggccacagta ttcctccctg ggctcgcagc
 121   ccatcctgtg tgccagcatc ccgggcctgg tccccaagca gctccgcttc tgcaggaact
 181   acgtggagat catgccagc gtggccgagg gcatcaagat tggcatccag gagtgccagc
 241   accagttccg cggccgccgg tggaactgca ccaccgtcca cgacagcctg gccatcttcg
 301   ggcccgtgct ggacaaagct accagggagt cggcctttgt ccacgccatt gcctcagccg
 361   gtgtggcctt tgcagtgaca cgctcatgtg cagaaggcac ggccgccatc tgtggctgca
 421   gcagccgcca ccagggctca ccaggcaagg gctggaagtg gggtggctgt agcgaggaca
 481   tcgagtttgg tgggatggtg tctcgggagt tcgccgacgc ccgggagaac cggccagatg
 541   cccgctcagc catgaaccgc cacaacaacg aggctgggcg ccaggccatc gccagccaca
 601   tgcacctcaa gtgcaagtgc cacgggctgt cggcagctg cgaggtgaag acatgctggt
 661   ggtcgcaacc cgacttccgc gccatcggtg acttcctcaa ggacaagtac gacagcgcct
 721   cggagatggt ggtggagaag caccgggagt cccgcggctg ggtggagacc ctgcggccgc
 781   gctacaccta cttcaaggtg cccacggagc gcgacctggt ctactacgag gcctcgccca
 841   acttctgcga gcccaaccct gagacgggct ccttcggcac gcgcgaccgc acctgcaacg
 901   tcagctcgca cggcatcgac ggctgcgacc tgctgtgctg cggccgcggc cacaacgcgc
 961   gagcggagcg gcgccgggag aagtgccgct gcgtgttcca ctggtgctgc tacgtcagct
1021   gccaggagtg cacgcgcgtc tacgacgtgc acacctgcaa gtaggcaccg gccgcggctc
1081   cccctggacg gggcgggccc tgcctgaggg tgggcttttc cctgggtgga gcaggactcc
1141   cacctaaacg gggcagtact cctccctggg ggcgggactc ctccctgggg gtggggctcc
1201   tacctggggg cagaactcct acctgaaggc agggctcctc cctggagcta gtgtctcctc
1261   tctggtggct gggctgctcc tgaatgaggc ggagctccag gatggggagg ggctctgcgt
1321   tggcttctcc ctggggacgg ggctccctg dacagaggcg gggctacaga ttgggcgggg
1381   cttctcttgg gtgggacagg gcttctcctg cggggcgag gcccctccca gtaagggcgt
1441   ggctctgggt gggcgggca ctaggtaggc ttctacctgc aggcggggct cctcctgaag
1501   gaggcggggc tctaggatgg ggcacggctc tggggtaggc tgctccctga gggcg
```

By "Wnt3a polypeptide" is meant a Wnt3a polypeptide or a fragment thereof, or a polypeptide having at least 85% sequence identity to the human Wnt3a polypeptide sequence. An exemplary human Wnt3a polypeptide sequence is provided at NCBI GenBank: AAI03924.1. The sequence provided at GenBank: AAI03924.1 is reproduced below (SEQ ID NO: 48):

```
  1  maplgyflll cslkqalgsy piwwslavgp qysslgsqpi lcasipglvp kqlrfcrnyv
 61  eimpsvaegi kigiqecqhq frgrrwnctt vhdslaifgp vldkatresa fvhaiasagv
121  afavtrscae gtaaicgcss rhqgspgkgw kwggcsedie fggmvsrefa darenrpdar
181  samnrhnnea grqaiashmh lkckchglsg scevktcwws qpdfraigdf lkdkydsase
```

-continued

```
241  mvvekhresr gwvetlrpry tyfkvpterd lvyyeaspnf cepnpetgsf gtrdrtcnvs 301  shgidgcdll ccgrghnara errrekcrcv fhwccyvscq ectrvydvht cknpgsragn 361  sahqpphpqp pvrfhpplrr agkvp
```

By "Wnt4 polynucleotide" is meant a polynucleotide encoding Wnt4 polypeptide or a fragment thereof, or a polynucleotide having at least 85% sequence identity to the human Wnt4 polynucleotide sequence. An exemplary human Wnt4 polynucleotide sequence is provided at NCBI GenBank Accession No. AY009398.1. Accession number NCBI Ref NG 008974.1 is a reference standard Wnt4a polynucleotide sequence. The polynucleotide sequence provided at NCBI GenBank Accession No. AY009398.1 is reproduced below (SEQ ID NO: 49):

```
   1  atgagtcccc gctcgtgcct gcgttcgctg cgcctcctcg tcttcgccgt cttctcagcc 61  gccgcgagca actggctgta cctggccaag ctgtcgtcgg tggggagcat ctcagaggag 121  gagacgtgcg agaaactcaa gggcctgatc cagaggcagg tgcagatgtg caagcggaac 181  ctggaagtca tggactcggt gcgccgcggt gcccagctgg ccattgagga gtgccagtac 241  cagttccgga accggcgctg gaactgctcc acactcgact ccttgcccgt cttcggcaag 301  gtggtgacgc aagggattcg ggaggcggcc ttggtgtacg ccatctcttc ggcaggtgtg 361  gcctttgcag tgacgcgggc gtgcagcagt ggggagctgg agaagtgcgg ctgtgacagg 421  acagtgcatg gggtcagccc acagggcttc cagtggtcag gatgctctga caacatcgcc 481  tacggtgtgg ccttctcaca gtcgtttgtg gatgtgcggg agagaagcaa gggggcctcg 541  tccagcagag ccctcatgaa cctccacaac aatgaggccg gcaggaaggc catcctgaca 601  cacatgcggg tggaatgcaa gtgccacggg gtgtcaggct cctgtgaggt aaagacgtgc 661  tggcgagccg tgccgccctt ccgccaggtg ggtcacgcac tgaaggagaa gtttgatggt 721  gccactgagg tggagccacg ccgcgtgggc tcctccaggg cactggtgcc acgcaacgca 781  cagttcaagc cgcacacaga tgaggacttg gtgtacttgg agcctagccc cgacttctgt 841  gagcaggaca tgcgcagcgg cgtgctgggc acgagggggcc gcacatgcaa caagacgtcc 901  aaggccatcg acggctgtga gctgctgtgc tgtggccgcg gcttccacac ggcgcaggtg 961  gagctggctg aacgctgcag ctgcaaattc cactggtgct gcttcgtcaa gtgccggcag 1021  tgccagcggc tcgtggagtt gcacacgtgc cgatga
```

By "Wnt4 polypeptide" is meant a Wnt4 polypeptide or a fragment thereof, or a polypeptide having at least 85% sequence identity to the human Wnt4 polypeptide sequence. An exemplary human Wnt4 polypeptide sequence is provided at NCBI GenBank Accession No.: AAG38658.1. The sequence provided at GenBank Accession No.: AAG38658.1 is reproduced below (SEQ ID NO: 50):

```
  1  msprsclrsl rllvfavfsa aasnwlylak lssvgsisee etceklkgli qrqvqmckrn 61  levmdsvrrg aqlaieecqy qfrnrrwncs tldslpvfgk vvtqgireaa lvyaissagv 121  afavtracss gelekcgcdr tvhgvspqgf qwsgcsdnia ygvafsqsfv dvrerskgas 181  ssralmnlhn neagrkailt hmrveckchg vsgscevktc wravppfrqv ghalkekfdg 241  ateveprrvg ssralvprna qfkphtdedl vylepspdfc eqdmrsgvlg trgrtcnkts 301  kaidgcellc cgrgfhtaqv elaercsckf hwccfvkcrq cqrlvelhtc r
```

By "Wnt5a polynucleotide" is meant a polynucleotide encoding Wnt5a polypeptide or a fragment thereof, or a polynucleotide having at least 85% sequence identity to the human Wnt5a polynucleotide sequence. An exemplary polynucleotide sequence coding for human Wnt5a is provided at NCBI Ref: GenBank NM_003392, a reference standard sequence. Nucleotides 658-1800 of the Wnt5a genomic sequence having 6194 nucleotides codes for a human Wnt5a polypeptide. The polynucleotide sequence of the human Wnt5a coding sequence provided at bases 658-1800 of NCBI Ref: GenBank NM_003392 is reproduced below (SEQ ID NO: 51):

```
 658  atg
 661  aagaagtcca ttggaatatt aagcccagga gttgctttgg ggatggctgg aagtgcaatg
 721  tcttccaagt tcttcctagt ggctttggcc atattttct ccttcgccca ggttgtaatt
 781  gaagccaatt cttggtggtc gctaggtatg aataaccctg ttcagatgtc agaagtatat
 841  attataggag cacagcctct ctgcagccaa ctggcaggac tttctcaagg acagaagaaa
 901  ctgtgccact tgtatcagga ccacatgcag tacatcggag aaggcgcgaa gacaggcatc
 961  aaagaatgcc agtatcaatt ccgacatcga aggtggaact gcagcactgt ggataacacc
1021  tctgtttttg gcagggtgat gcagataggc agccgcgaga cggccttcac atacgcggtg
1081  agcgcagcag gggtggtgaa cgccatgagc cgggcgtgcc gcgagggcga gctgtccacc
1141  tgcggctgca gccgcgccgc gcgccccaag gacctgccgc gggactggct ctggggcggc
1201  tgcggcgaca acatcgacta tggctaccgc tttgccaagg agttcgtgga cgcccgcgag
1261  cgggagcgca tccacgccaa gggctcctac gagagtgctc gcatcctcat gaacctgcac
1321  aacaacgagg ccggccgcag gacggtgtac aacctggctg atgtggcctg caagtgccat
1381  ggggtgtccg gctcatgtag cctgaagaca tgctggctgc agctggcaga cttccgcaag
1441  gtgggtgatg ccctgaagga agtacgac agcgcggcgg ccatgcggct caacagccgg
1501  ggcaagttgg tacaggtcaa cagccgcttc aactcgccca ccacacaaga cctggtctac
1561  atcgacccca gccctgacta ctgcgtgcgc aatgagagca ccggctcgct gggcacgcag
1621  ggccgcctgt gcaacaagac gtcggagggc atggatggct gcgagctcat gtgctgcggc
1681  cgtggctacg accagttcaa gaccgtgcag acggagcgct gccactgcaa gttccactgg
1741  tgctgctacg tcaagtgcaa gaagtgcacg gagatcgtgg accagtttgt gtgcaagtag
```

By "Wnt5a polypeptide" is meant a Wnt5a polypeptide or a fragment thereof, or a polypeptide having at least 85% sequence identity to the human Wnt5a polypeptide sequence. An exemplary human Wnt5a (isoform 1) polypeptide sequence is provided at UniProtKB Identifier: P41221-1. The sequence provided at UniProtKB Identifier: P41221-1 is reproduced below (SEQ ID NO: 52):

```
  1  mkksigilsp gvalgmagsa msskfflval aiffsfaqvv ieanswwslg
 51  mnnpvqmsev yiigaqplcs qlaglsqgqk klchlyqdhm qyigegaktg
101  ikecqyqfrh rrwncstvdn tsvfgrvmqi gsretaftya vsaagvvnam
151  sracregels tcgcsraarp kdlprdwlwg gcgdnidygy rfakefvdar
201  ererihakgs yesarilmnl hnneagrrtv ynladvackc hgvsgscslk
251  tcwlqladfr kvgdalkeky dsaaamrlns rgklvqvnsr fnspttqdlv
301  yidpspdycv rnestgslgt ggrlcnktse gmdgcelmcc grgydqfktv
351  qterchckfh wccyvkckkc teivdqfvck
```

By "progenitor cell" is meant a cell that a multipotent stem cell that is capable of generating (e.g., by differentiation or division) an endothelial cell. A progenitor cell that is capable of generating an endothelial cell may express this capability when grown under appropriate in vitro or in vivo conditions, such as those described herein.

By "progeny" is meant a cell derived from a multipotent stem cell of the invention. Progeny include without limitation progenitor cells, differentiated cells, and terminally differentiated cells.

By "derived from" is meant the process of obtaining a progeny cell.

By "reduces" is meant a negative alteration of at least 10%, 25%, 50%, 75%, or 100%.

By "reference" or "control" is meant a standard condition. For example, an untreated cell, tissue, or organ that is used as a reference.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

A "somatic" cell refers to a cell that is obtained from a tissue of a subject. Such subjects are at a post-natal stage of development (e.g., adult, infant, child). In contrast, an "embryonic cell" or "embryonic stem cell" is derived from an embryo at a pre-natal stage of development.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 μg/ml denatured salmon sperm DNA (ssDNA). In yet another embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "self renewal" as used herein refers to the process by which a stem cell divides to generate one (asymmetric division) or two (symmetric division) daughter cells with development potentials that are indistinguishable from those of the mother cell. Self renewal involves both proliferation and the maintenance of an undifferentiated state.

The term "stem cell" is meant a pluripotent cell or multipotent stem cell having the capacity to self-renew and to differentiate into multiple cell lineages.

By "subject" is meant a mammal, including, but not limited to, a human or non-human mammal, such as a bovine, equine, canine, ovine, rodent, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "tissue" is meant a collection of cells having a similar morphology and function.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "vascularized" is meant having a blood vessel. In some embodiments, the pancreatic islet organoid or pancreatic organoid is vascularized.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2 compares the appearance of human iPSC-derived pancreatic progenitors (PPs. Day 15-day 19), human umbilical vein endothelial cells (HUVEC), and hADSCs cultured on plates (2D) with those cultured in the 3 dimensional matrigel (Matrigel®) system for 24 hours in PP cell differentiation media, endothelial cell growth media, and hADSC growth media, respectively. FIG. 2D shows transcriptional changes occurring in hADSCs during 48 hours of culture in Matrigel, depicted as a heatmap. Statistically different changes in gene expression were determined by RNA-Seq analyses of cells after the indicated time in Matrigel. Biological pathways altered during culture in Matrigel were identified using DAVID software. FIG. 2E is a schematic describing the generation of human islet-like organoids by culturing in Matrigel. FIG. 2F is an image of human islet-like organoids in a single well of a 24 well plate. FIG. 2G is a set of images of a human islet-like organoid generated by co-culturing hiPSC-derived pancreatic progenitors, HUVECs, and hADSCs for 1-5 days in Matrigel. GFP is used to indicate human insulin expression (green, $1^{st}$ panel), mCherry to label HUVEC cells (red, $2^{nd}$ panel), brightfield image ($3^{rd}$ panel), and an overlay of GFP and mCherry images ($4^{th}$ panel).

FIG. 3A is a schematic showing the generation of a stably-expressed insulin reporter in the rat beta cell line INS-1 cells, where luciferase expression is under the control of the proinsulin promoter. FIG. 3B is a plot showing luciferase activity induced in the INS-1 reporter cells in response to treatment with 3 mM glucose (G3), 20 mM glucose (G20), 20 mM glucose (G20) plus 100 nM Exendin-4 (Ex-4), or 20 mM potassium chloride (KCl). FIG. 3C is an image showing a single mouse islet in one well of a 96-well plate. The mouse islet cells were infected with the proinsulin-luciferase lentivirus reporter construct 2 days before assaying. FIG. 3D is a set of plots showing the luciferase activity from individual mouse islets infected with the proinsulin luciferase reporter in response to 3 mM glucose (G3 mM) and 20 mM glucose (G20 mM) (left), and the average of the individual assays (right). FIG. 3E is an image showing a single human islet in one well of a 96-well plate. The human islet cells were infected with the proinsulin-luciferase lentivirus reporter construct 2 days before assaying. FIG. 3F is a set of plots showing the luciferase activity from individual human islets infected with the proinsulin luciferase reporter in response to 3 mM glucose (G3 mM) and 20 mM glucose (G20 mM) (left), and the average of the individual assays (right). FIGS. 3D and 3F show that glucose-stimulated insulin secretion (GSIS) can be measured from single mouse and human islets, respectively, after the infection with the lentiviral luciferase reporter.

FIGS. 4A-4I are plots, images, graphs and a schematic showing generation of functional, vascularized human pancreatic islets in a dish. FIG. 4A is a schematic showing a scheme for the generation of functional, vascularized human pancreatic islets in Gellan gum. FIG. 4B shows human islet-like mini organs. Top panels show insulin positive cells (green fluorescent protein expression driven by the insulin promoter (left)) and phase contrast images (left) of islet-like organoids grown in 3D Gellan gum suspensions (bottom panel). Electron microscopy images reveal insulin granules in the β-like cells and lipid droplets in the hADSCs. FIG. 4C shows that human islet-like-mini organs generated by methods described herein are morphologically identical to human islets. FIG. 4D and FIG. 4E show relative expression of genes associated with (β cell determination (FIG. 4D), and mitochondrial function (FIG. 4E), as measured by qPCR. Islet-like cell clusters (derived from pancreatic progenitors cultured in gellan gum, day 35) and islet-like organoids (derived from pancreatic progenitors co-cultured with HUVECs and hADSCs in gellan gum) were FACS stored into insulin expressing (GFP positive) and non-expressing (GFP negative) cells prior to analysis, and compared with gene expression in human islets. FIG. 4F shows glucose-stimulated insulin secretion, measured by the fold change in c-peptide secretion 30 minutes after exposure to 20 mM glucose, in selected islet-like organoid preparations prepared in 3D gellan gum cultures and human islets. FIG. 4G shows that human islet-like mini organs generated by the methods described herein can develop functional vascularization. Human islet-like organoids were transferred to matrigel and grown in the presence of endothelial growth media. Cells expressing insulin are visualized as green fluorescence. Top panels are fluorescent images of cells showing HUVEC cell outgrowth 24 and 48 hours after stimulation by endothelial cell growth medium (ECM). The bottom panel is a schematic summarizing the experiment and the finding. FIG. 4H shows a graph illustrating that human islet-like mini organs generated by the methods described herein can regulate blood glucose in a known mouse model of type 1 diabetes, NODSCID. In this mouse model, the SCID (Severe Combined Immune Deficiency) mutation has been transferred onto a diabetes-susceptible Non-Obese Diabetic (NOD) background. The multiple immunological defects in this mouse model provide a system for reconstituting the animal with human hematopoietic cells. The graph in FIG. 4H shows the blood glucose levels in NODSCID mice treated with streptozotocin (STZ) (180 mg/kg) to induce type 1 diabetes after transplantation into the kidney capsule of hiPSC-derived human islet-like organoids (n=1000), (dotted line with squares); human islets (n=1000), (dashed line); or mock treatment (solid line with white circles). FIG. 4I shows a bar graph illustrating that human islet-like mini organs ("human islets organoids") generated by the methods described herein are able to secrete insulin postprandially. The graph of FIG. 4I shows the serum levels of human c-peptide (pmol/L) in NODSCID mice 4 weeks after the transplantations described in FIG. 4H under random fed (left bar), 8 hour fasted (middle bar), and refed (right bar) conditions. Human c-peptide levels provide a measure of insulin secretion from the transplants that is distinct from endogenous murine insulin.

FIGS. 5A-5E are diagrams and plots showing the generation of functional islet-like organoids in 3D gellan gum cultures. FIG. 5A is a schematic describing the generation of hiPSCs stably incorporating dual reporters for insulin expression (GFP) and insulin secretion (luciferase). FIG. 5B is a bar graph showing the increased expression of human insulin during the differentiation of hiPSCs incorporating the dual reporters. FIG. 5C is a bar graph comparing the glucose stimulated insulin secretion (GSIS) from human islet-like organoids generated using the methods described herein with human islets. GSIS, as measured using secreted luciferase, in single islet-like organoids or human islets in response to 3 mM and 20 mM glucose. Arrows indicate functional organoids capable of increasing insulin secretion in response to a glucose challenge. FIG. 5D is a bar graph comparing the insulin secretion of independent batches of islet-like organoids, prepared as described herein, to mouse islets as a negative control. Insulin secretion was measured in response to 3 mM glucose (G3 mM), 20 mM glucose (G20 mM), 20 mM glucose (G20 mM) and Exendin-4 (Ex4), or 20 mM potassium chloride (KCl 20 mM) after 133 days in culture. Response was measured as secreted luciferase activity from pooled organoids (100 organoids/sample). FIG. 5E shows intracellular luciferase activity as a measure of intracellular insulin (100 organoids/sample).

FIGS. 6A-6H are schematics and images showing generation of functional human mini-organs in a dish. FIG. 6A is a schematic showing generation of functional human mini organs including human islets, pancreas, liver, heart, and intestine. FIGS. 6B-6C show the generation of a human heart organoid. FIG. 6B (top) provides a schematic illustrating the protocol for differentiation of a human pluripotent stem cell (hPSC) into a cardiomyocyte (when cultured in 2D) or into a mini heart (when co-cultured with hADSCs and HUVECs in 3D). FIG. 6B (bottom left) provides a plot showing relative expression of cardiomyocyte-specific genes human MLC2a (hMLC2a), human Nkx2-5 (hNkx2-5), alpha myosin heavy chain (alphaMHC), and KCNQ1 before (day 0) and at day 18 of the differentiation protocol, with and without the PPARδ agonist GW501516. At the bottom right of FIG. 6B is a videomicrograph showing beating of the hiPSC-derived cardiomyocytes. FIG. 6C shows an image of a human mini heart-like organoid generated by culturing the hiPSC-derived cardiomyocytes with hADSC and HUVEC, as described in the schematic above. FIGS. 6D-6F show generation of a human liver organoid. FIG. 6D (top) provides a schematic illustrating the protocol for differentiation of a human pluripotent stem cell (hPSC) into hepatocytes. FIG. 6D (bottom left) provides a plot showing relative expression of hepatocyte-specific genes AFP, ALB, and Cyp3a7, during the differentiation of 6 independent preparations. At the bottom right of FIG. 6D is a micrograph showing hiPSC-derived hepatocytes. FIG. 6E is a set of micrographs showing hiPSC-derived hepatocytes. Top panels show expression of Cyp7a1 (Cyp7a1-GFP reporter, left) and SREBP1c (SREBP1c-GFP reporter, right) in hiPSC-derived hepatocytes indicating functional maturation. The bottom panels show hiPSC-derived hepatocytes cultured with (right) or without (left) phosphatidic acid (PA) overnight. Higher magnification images shown in the bottom left reveal the accumulation of lipid droplets in the hepatocytes treated with phosphatidic acid. FIG. 6F shows a human mini liver-like organoid generated by culturing the hiPSC-derived hepatocytes with hADSCs and HUVECs in the gellan gum 3D culture system. FIG. 6G (top) provides a schematic illustrating the protocol for differentiation of human pluripotent stem cells (hPSCs) into intestinal organoids when co-cultured with hADSCs and HUVECs in the gellan gum 3D culture system. The lower images shows budding of the human intestinal organoid cultures, consistent with crypt-like structures and indicating functional organoids. FIG. 6H (top) provides a schematic illustrating the protocol for differentiation of human pluripotent stem cells (hPSCs) into a mini pancreas when co-cultured with hADSCs and HUVECs in the gellan gum 3D culture system. The middle panels show images of insulin positive β cells, marked by the expression of green fluorescent protein driven by the insulin promoter, and the equivalent light microscopy image of pancreatic organoids. Exocrine cells are the remaining unlabeled cells. The bottom panels show an image of a single pancreatic organoid in a 96 well plate.

FIGS. 8A and 8B are schematics showing platforms for drug screening and the subsequent evaluation of potential candidates for human type 2 diabetes and pancreatic cancer. FIG. 8A shows a scheme for screening potential drugs for use in human type 2 diabetes or human pancreatic cancer tumorigenesis in a dish. Organoid cultures are exposed to appropriate stress (e.g. high levels of free fatty acids (FFAs), high glucose levels, or relevant cytokines) to induce disease-like phenotypes prior to screening drug libraries for compounds that reverse or diminish disease indications. FIG. 8B shows approaches to evaluate potential drug candidates for type 2 diabetes and human pancreatic cancer tumorigenesis/ metastasis in mice. Mice transplanted with individual (e.g. pancreas) or combinations of human organoids (e.g., pancreas and liver) are exposed to appropriate disease-inducing stressors (e.g. high fat/high cholesterol (HF/HC) diet) prior to treatment with potential disease altering drug candidates.

FIG. 10A is a schematic describing the protocol to generate islet-like organoids by culturing in 3D in gellan gum. FIG. 10B is a series of images recording the growth and differentiation of hPSCs into pancreatic lineages in 3D Gellan gum cultures, as described herein. Insulin expression is indicated by the green fluorescence seen at day 21. FIG. 10C is a heatmap representation of changes in gene expression during the differentiation of hiPSCs into islet-like organoids. FIG. 10D is a set of bar graphs reporting the changes in relative expression of the pluripotency marker Nanog, the endocrine hormones insulin, somatostatin, and glucagon, and the β cell lineage marker Nkx6-1 in hiPSCs and two stem cell lines (HuES8 and H1ES) during differentiation as described in the methods herein. Gene expression was measured by qPCR.

FIG. 11A is a heatmap depiction of gene expression changes in hADSCs during the spontaneous self-organization that occurs in 3D culture. Genes that are induced in the WNT5a pathway are listed. FIG. 11B is a graph showing the relative levels of several individual WNT proteins in hADSC 3D culture over time, identifying the WNT5a protein as the predominant protein expressed.

FIGS. 12A-12H show a set of bar graphs and images illustrating the role of WNT proteins in the metabolic maturation of iPSC-derived islet organoids. FIG. 12A shows bar graphs comparing the expression of Fltp and Esrrg genes in iPSC-derived islet organoids (day 21, generated without co-culture with hADSCs or HUVECs) after treatment with PBS, WNT3a (500 ng/ml), WNT4 (100 ng/ml), or WNT5a (400 ng/ml) for 5 days. FIG. 12B is a bar graph showing the induction of Esrrg gene expression in hiPSC-derived islet organoids, generated in the absence of supporting hADSC or HUVECs, in response to increasing doses of WNT4 (0, 10, 25, 50, 100, 200 ng/ml) and WNT5a (0, 25, 50, 100, 200, 400 ng/ml). FIG. 12C is a bar graph showing the induction of mitochondrial genes involved in oxidative phosphorylation (Cox7a2, Ndufa1, Ndufa7), lactate dehydrogenase (Ldha) and Fltp (a Wnt/planar cell polarity (PCP) effector and reporter gene) in hiPSC-derived islet organoids, generated in the absence of supporting hADSC or HUVECs, in response to increasing doses of WNT4 (0, 10, 25, 50, 100, 200 ng/ml) and WNT5a (0, 25, 50, 100, 200, 400 ng/ml). FIG. 12D shows fluorescent images showing mitochondrial (Mitotracker; Mito-Red) and insulin (Insulin-GFP) levels in hiPSC-derived islet organoids (day 27) after 8 days treatment with PBS or WNT4 (100 ng/ml). FIG. 12E shows fluorescent images of FACS analysis of hiPSC-derived islet organoids (day 27) after 8 days treatment with PBS or WNT4 (100 ng/ml).

FIGS. 12F, 12G, and 12H show a set of bar graphs illustrating the results of FACS analyses of hiPSC-derived islet organoids (day 27) after 8 days treatment with PBS, WNT4 (100 ng/ml), WNT5a (400 ng/ml), control fibroblast conditioned media (50%), or WNT5a secreting fibroblast conditioned media (50%). The WNT proteins used were recombinant human (rh) proteins.

FIG. 13 shows a bar graph demonstrating a role for WNT4 in the functional maturation of hiPSC-derived islet organoids. Human iPSC (hiPSC)-derived islet organoids (day 22) were treated with PBS (Vehicle, "Veh") or WNT4 (100 ng/ml) for 12 days, and the secretion of human c-peptide was measured in response to low glucose (3 mM, "G3 mM"), high glucose (20 mM, "G20 mM"), or high KCl levels (20 mM, "KCL20 mM").

DETAILED DESCRIPTION OF THE INVENTION

The invention features compositions and methods that are useful for generating scalable, functional, vascularized organoids in vitro, particularly human pancreatic or pancreatic islet organoids. The invention is based, at least in part, on the discovery that culturing iPSC-derived beta-like cells with human adipose-derived stem cells (hADSC) and human umbilical vein endothelial cells (Huvec) in a three-dimensional matrix containing gellan gum generated functional pancreatic and pancreatic islet organoids.

The organoids generated were vascularized and exhibited functional properties, such as glucose-stimulated insulin secretion (GSIS). Islet transplantation is known as the best therapy for curing insulin deficient diabetes such as type 1 and late stage of type 2 diabetes. Recent studies have shown the possibility of generating glucose responsive insulin producing beta-like cells from human Pluripotent Stem Cells (PSCs), however the generation of functional, vascularized pancreatic islets from PSCs capable of secreting insulin, glucagon and somatostatin in response to nutrients has not been previously achieved.

Studies described herein demonstrate that using the self-organizing function of human adipose-derived stem cells (hADSC), HUVEC, and human iPSC-derived beta-like cells allows for the in vitro generation of glucose-responsive insulin secreting islet-like organoids with the ability to form functional vasculature. Studies herein further demonstrate the successful scaling of islet-like organoids production through the use of Gellan gum based 3D culture systems. Using a *Gaussia* luciferase reporter to measure insulin secretion, the functional heterogeneity in hiPSC-derived islet-like organoids was characterized. Without intending to be bound by theory, results herein suggest that the novel human islet-like organoids may offer a therapeutic treatment for diabetes, as well as offer a platform for drug screening, genome editing, and the modeling of organogenesis and pathogenesis of diabetes.

Pancreas

Figure 9:
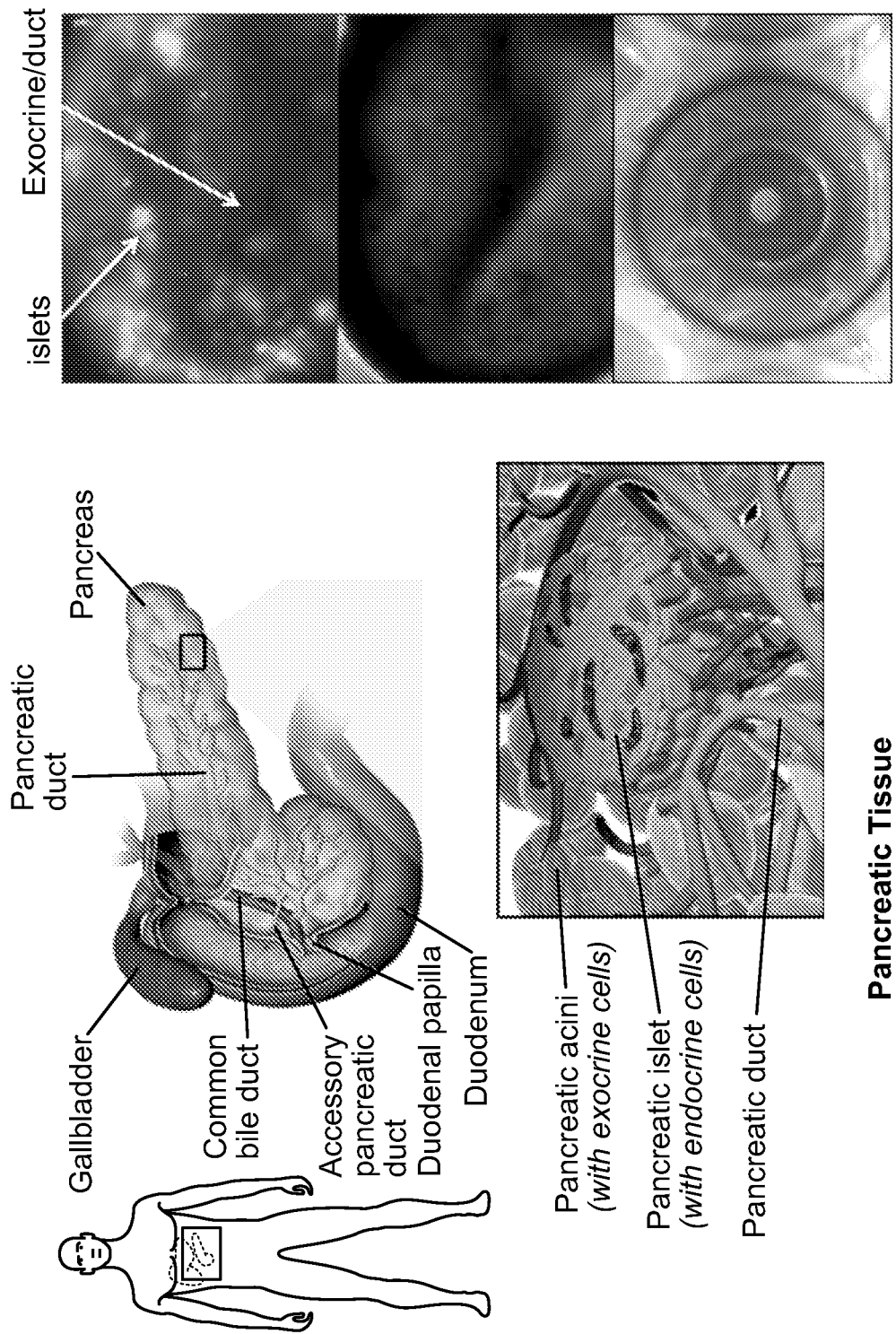
FIG. 9 is a set of schematics and images showing a structure of a pancreas and pancreatic tissue and images of a pancreatic islet-like organoid and pancreatic organoid generated herein. The schematics on the left of FIG. 9 depict the anatomy and structure of a pancreas (top) and pancreatic islets (bottom). The image on the top-right corner of FIG. 9 shows an iPSC-derived pancreatic organoid with pancreatic islets (as marked by green fluorescent protein expression driven by the insulin promoter) and an exocrine/duct component as indicated. The image in the middle-right of FIG. 9 shows the corresponding light microscopy image of the fluorescent image above. The image on the bottom-right corner of FIG. 9 shows a single pancreatic islet organoid.

In some aspects, the invention provides a pancreatic organoid or a pancreatic islet organoid. The pancreas is an organ that lies in the abdomen and has endocrine and exocrine functions. FIG. 9 provides schematics showing the structure of the pancreas. The portion of the pancreas having an endocrine role are cell clusters called "pancreatic islets" (also known as islets of Langerhans). Pancreatic endocrine secretions include hormones that regulate glucose metabolism and blood glucose concentration. Four main cell types are present in the islets: alpha cells which secrete glucagon (a hormone that increases blood glucose concentration); beta cells which secrete insulin (a hormone that decreases blood glucose concentration); delta cells, which secrete somatostatin (a hormone that regulates alpha and beta cells), and gamma cells which secrete pancreatic polypeptide.

The portion of the pancreas that has an exocrine role is referred to as the exocrine component. The exocrine pancreatic secretions contain digestive enzymes that pass into the small intestine and help break down carbohydrates, proteins, and lipids. The exocrine component has ducts arranged in clusters called pancreatic acini. Pancreatic exocrine secretions are secreted into the lumen of the acinus, which accumulate and drain into the pancreatic duct and duodenum.

Pancreatic islet organoids and pancreatic organoids of the invention mimic the structure of a pancreatic islet and a pancreas, respectively. In some embodiments, the pancreatic islet organoid or pancreatic organoid of the invention contains any one or more of the following cells: an iPSC-derived beta-like cell, an iPSC-derived alpha-like cell, an iPSC derived delta-like cell, and an iPSC-derived duct-like cell. In some embodiments, the pancreatic organoid of the invention contains an iPSC-derived exocrine component. In some embodiments, the iPSC is a human iPSC (hiPSC). Human embryonic stem cells and human induced pluripotent stem cells are commercially available (e.g., from WiCell, which provides iPS (IMR-90)-1, iPS (IMR-90)-4 and iPS (Foreskin)-1). Human induced pluripotent stem cells can also be generated using methods known in the art from a variety of somatic cell types (Yu, J., K. Hu, et al. (2009). "Human induced pluripotent stem cells free of vector and transgene sequences." Science 324(5928): 797-801).

Pancreatic islet organoids and pancreatic organoids of the invention also exhibit function(s) of a pancreatic islet and a pancreas. In certain embodiments, the pancreatic islet organoid or pancreatic organoid exhibits any one or more of the following functions: glucose-stimulated insulin secretion (GSIS), KCl-stimulated insulin secretion, GLP-1 stimulated insulin secretion, somatostatin secretion, and glucagon secretion. In some embodiments, the pancreatic islet or pancreatic organoid expresses any one or more of the transcription factors Pdx1, MafA, Pax4, Pax6, NeuroD1, Nkx6-1, Gata6, and Foxa2.

Generation of Pancreatic and Pancreatic Islet Organoids

In some other aspects, the invention features methods of generating a pancreatic or pancreatic islet organoid. Recent studies have shown that while it was possible to generate glucose responsive insulin producing beta-like cells, efforts to generate pancreatic islets which are capable of secreting insulin, glucagon and somatostatin in response to nutrients, as well as efforts to obtain vascularization from stem cells, have not succeeded. Described herein are results demonstrating that using the self-organizing function of human Adipose-derived stem cells (hADSC), human umbilical vein endothelial cells (HUVEC), and human iPSC-derived beta-like cells, glucose responsive insulin secreting islet-like organoids capable of functional vascularization are successfully generated in vitro. Further, islet-like organoid generation methods were successfully scaled up using gellan gum based 3D culture systems. The functional heterogeneity in hiPSC-derived human islet-like organoids was also investigated using a *Gaussia* luciferase reporter to measure insulin secretion.

Generation of functional human organs provides new therapeutic strategies in drug-screening, disease modeling and inhibiting or preventing end point organ failure. Efficient stepwise differentiation methods from human embryonic stem cells (hESC) and human induced pluripotent stem cells (hiPSC) to insulin producing β-like cells were demonstrated previously. D'Amour et al and Kroon E et al reported the efficient differentiation of hESCs into insulin producing cells which, after 4 to 5 months in vivo maturation, are able to secrete insulin in response to glucose (D'Amour et al., 2006, Nature biotechnology 24, 1392-1401; Kroon et al., 2008, Nature biotechnology 26, 443-452). Recently, Rezania et al. and Pagliuca et al. reported differentiation methods that induced formation of mature human beta-like cells in vitro in that they expressed terminal β-cells marker, MAFA and Nkx6-1 and exhibited partial functionality (e.g., insulin secretion) (Rezania et al., 2014, Nature Biotechnology November; 32(11):1121-33; Pagliuca et al., 2014, Cell 159, 428-439). However, in contrast to cadaveric human islets, those beta-like cells required in vivo functional maturation for a few months, and lacked the functionality provided by the other pancreatic islet cell types, such as glycemic control by α-cells (glucagon secrete) and δ-cells (somatostatin secretion). Further, the beta-like cells lacked both a mesenchyme and vascularized endothelial cells, which human islets naturally have. These crucial differences between hPSCs derived beta-like cells and human islets may compromise the ability of hPSCs based therapies to treat insulin dependent diabetes (such as type 1 or late stage type 2 diabetes).

Previously, it was identified that a metabolic transition occurs during the neonatal to adult maturation of β-cells in which the orphan nuclear receptor Estrogen-related receptor γ (ERRγ) regulates an increase in oxidative metabolism required for fully functional β cells. Consistent with this result, human iPSC-derived β like cells expressing insulin, MAFA, and Nkx6-1 can be metabolically matured through the overexpression of ERRγ to increase their oxidative metabolism and thereby enhance their glucose stimulated insulin secretion (GSIS) functionality. These results indicated that in addition to the expression of lineage determination factors such as PDX1, MAFA, Nkx6-1, and insulin, further cellular signaling which mature the β-cells' metabolism is required to generate fully functional β-cells.

During early pancreas organogenesis, newly specified pancreatic cells originate from the foregut endodermal sheet and form a pancreatic bud, a condensed tissue mass that is soon vascularized. A similar progression has been observed in liver organogenesis as well. Such large-scale morphogenetic changes depend on the exquisite orchestration of signals between endodermal epithelial, mesenchymal, and endothelial progenitors before blood perfusion. Takebe et al, successfully generated hepatic organ buds by culturing hepatic endoderm cells with endothelial and mesenchymal linages which rapidly vascularized and functional matured in vivo (Takebe et al., 2013, Nature 499, 481-484).

Previous work did not reveal the possibility of generating in vitro other organoid tissue types, such as pancreas organoids, which were mature, functional, and vascularized. Further, previous work showed a lack of scalability because the organoids were generated using MATRIGEL® matrix, which is not efficient to use for scaled-up production.

Described herein are studies demonstrating successful large-scale generation of human islet-like organoids which are capable of secreting insulin and which are vascularized, as seen in human islets. It is demonstrated herein that (1) human adipose derived stem cells (hADSCs) have a self-organizing capacity; (2) late stage pancreatic progenitors are capable of forming an islet-like cluster when co-cultured with HUVECs and hADSCs with comparable efficiency to beta-like cells; (3) human islet-like organoids had improved expression of lineage determination factors as well as metabolic regulatory genes including ERRγ; (4) islet insulin secretion assays, measured using a *Gaussia* Luciferase proinsulin system, revealed that human islet-like organoids contain functional cells capable of secreting insulin in response to glucose; (5) human islet-like organoids exhibited vascularization; (6) human islet-like organoids derived from hiPSC by the method described herein recaptured human islet organogenesis and pathogenesis of type 1 and type 2 diabetes in a dish; (7) human islet-like organoids derived from hiPSC by the method described herein offered a new replaceable resource for human islet transplantation to treat type 1 and type 2 diabetes; and (8) human islet-like organoids transplanted into an STZ-induced NODSCID mouse model of type 1 diabetes ameliorated type 1 diabetes in the recipient animals. (FIGS. 4H and 4I).

Figure 11A:
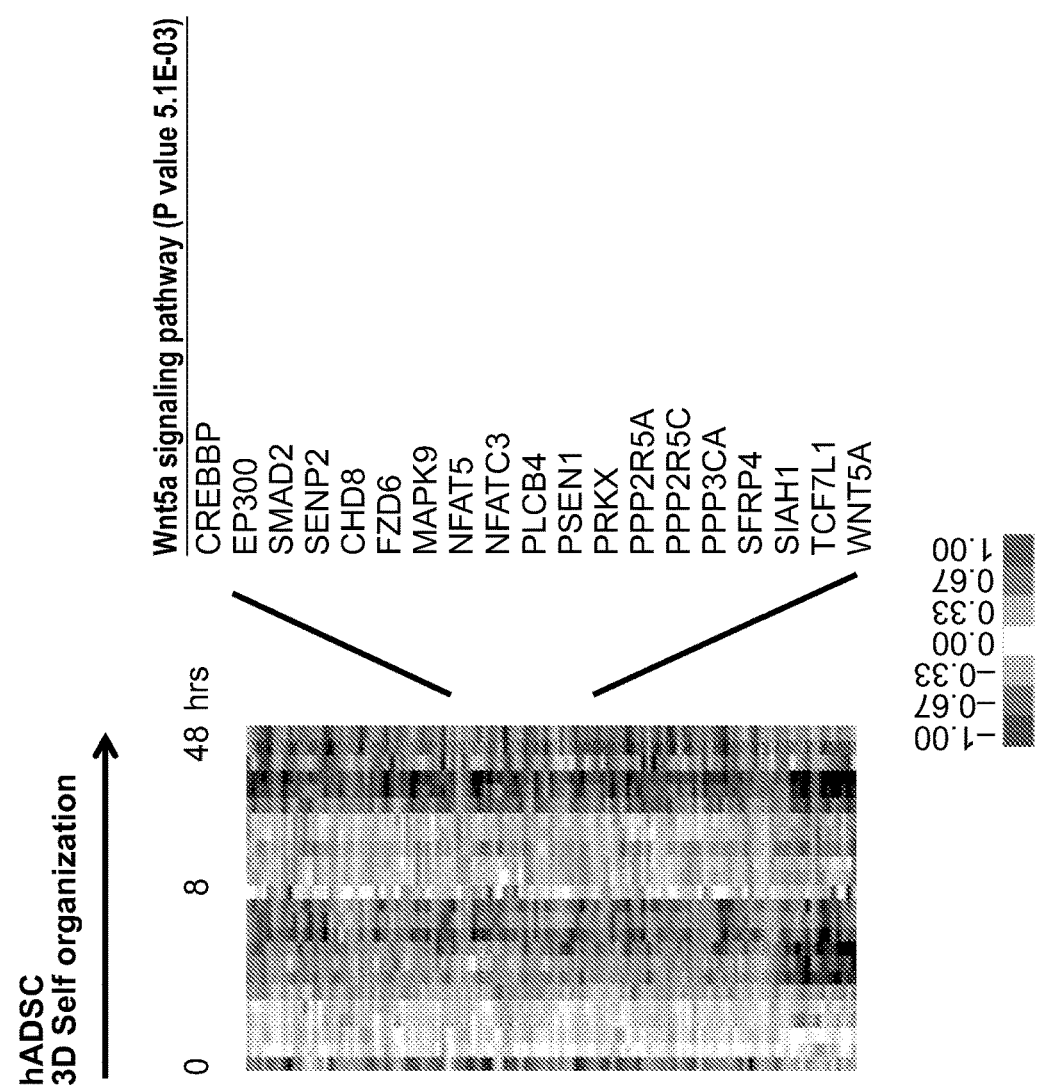
FIGS. 11A and 11B show a heatmap and graph illustrating the role of WNT proteins in the hADSCs in 3D culture.
Figure 11B:
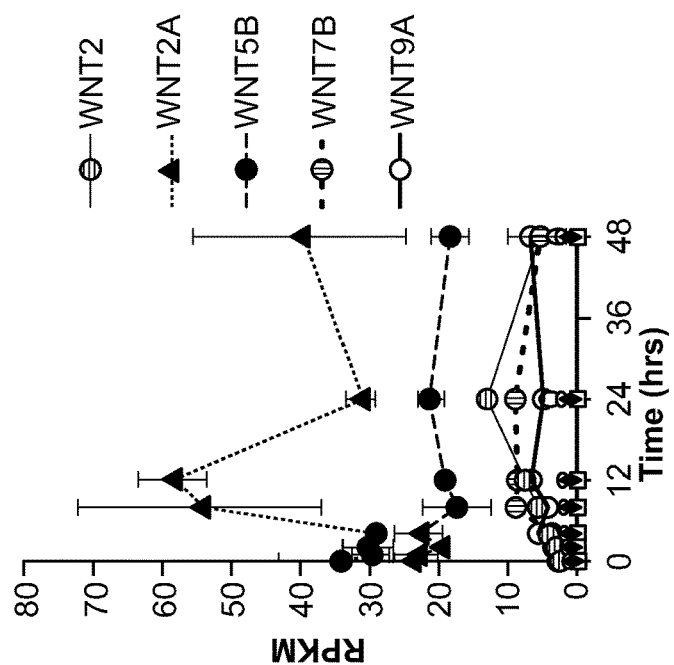

Also described herein are studies in which the role of certain Wnt (also "WNT" herein) proteins was assessed in developing human islet-like organoids which are capable of secreting insulin and which are vascularized, as seen in human islets. The WNT gene family consists of structurally related genes that encode secreted signaling proteins, which have been implicated in oncogenesis and in several developmental processes, including regulation of cell fate and patterning during embryogenesis. Wnt proteins comprise a major family of signaling molecules that orchestrate and influence a variety of cell biological and developmental processes. Wnt proteins undergo a complex set of posttranslational modifications involving several highly specialized processing enzymes. Upon release from the cell, the Wnt proteins interact with a number of molecules in the extracellular environment, such as glycans, protein-binding partners (e.g., WIF, Sfrp) and cell surface receptors. (Willert, K. et al., 2012, Cold Spring Harbor, Perspectives in Biology, 2012). It is demonstrated herein that (1) Wnt5a is the predominant Wnt protein that induces the self-organization of hADSCs (FIGS. 11A and 11B); (2) Wnt5a, as well as Wnt4, activate the ERRγ-mitochondrial metabolic pathway (FIGS. 12A-12H); (3) Wnt4 is sufficient to induce in vitro functional maturation of hiPSC-derived islet-like organoids in the absence of additional cell types such as hADSC and HUVECs (FIG. 13).

Methods of Treatment

Islet transplantation is a therapy for treating insulin deficient diabetes such as type 1 and late stage type 2 diabetes. Thus, in another aspect, the present invention provides methods of treating a pancreatic disease such as type 1 or type 2 diabetes comprising administering a pancreatic or pancreatic islet organoid of the invention to a subject (e.g., a mammal such as a human) by transplantation. One embodiment is a method of treating a subject suffering from or susceptible to a pancreatic disease (e.g., type 1 diabetes) or disorder or symptom thereof. The method includes the step of transplanting a pancreatic or pancreatic islet organoid of the invention to the mammal sufficient to treat the disease or disorder or symptom thereof, under conditions such that the disease or disorder is treated.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration (in particular, transplantation) of an effective amount of a pancreatic or pancreatic islet organoid to a subject (e.g., animal, human) in need thereof, including a mammal, particularly a human. The administration of the pancreatic or pancreatic islet organoid may be by any suitable means that results in an amount of the organoid that, combined with other components, is effective in ameliorating, reducing, or stabilizing a pancreatic disease such as type 1 or type 2 diabetes.

In some aspects, the subject is further administered an immunosuppressant. The immunosuppressant can be administered to the subject before, during, or after the subject is administered (e.g., transplanted) with the organoid. The immunosuppressive agent can be an agent that inhibits or prevents rejection (e.g., acute rejection) of the transplanted organoid upon transplantation, or an agent that maintains immunosuppression after the transplantation. Immunosuppressants include, but are not limited to, basilizimab, antithymocyte globulin, alemtuzumab, prednisone, azathioprine, mycophenolate, cyclosporine, sirolimus, and tacrolimus.

In some embodiments, at least about 100,000, at least about 200,000, at least about 300,000, at least about 400,000, at least about 500,000, at least about 600,000, at least about 700,000, at least about 800,000, at least about 900,000 or at least about 1 million pancreatic islet organoids are transplanted into the subject. In some embodiments, islets of the subject are removed prior to transplanting the organoids of the invention. In some other embodiments, pancreatic islet organoids are transplanted into a subject by injection into the upper abdomen of the subjects. In some embodiments, the pancreatic islet organoids are injected into the liver. The pancreatic islet organoids can be injected into the subject using a catheter. In some other embodiments, the pancreatic organoid or pancreatic islet organoid is administered to the subject by surgery. In another embodiment, pancreatic islet organoids are transplanted onto the omentum. For omentum transplantation, a layering technique can be used in which the islet organoid (or cells thereof) are combined with autologous plasma and are laparoscopically layered onto the omentum. A solution (20 ml) containing recombinant thrombin (1000 U/ml) is next layered over the islet organoid, followed by another layer of autologous plasma to produce a biodegradable biologic scaffold that can survive and function in the patient for at least a year (See, e.g., Baidal, D. et al., 2017, *N. Engl. J. Med.,* 376:19). In another embodiment, hydrogel biomaterials that mitigate an immune response by the recipient can be used for islet organoid transplantation. (See, e.g., Vegas, A. et al., 2016, *Nature Biotechnology,* 34:345-352).

To further reduce an immune reaction to the transplanted organoid in the subject, the organoid can be encapsulated in a hydrogel and then transplanted in the subject. Such methods of transplantation are further described in Vegas et al., Nature Medicine 2016, doi:10.1038/nm.4030; Vegas et al., Nature Biotechnology 2016, doi:10.1038/nbt.3462. In some embodiments, the hydrogel contains an alginate or alginate derivative (e.g., triazole-thiomorpholine dioxide). Various modifications of alginate hydrogels that substantially reduce inflammatory or fibrotic effects of alginate hydrogels have also been identified (Vegas et al., Nature Biotechnology 2016, doi:10.1038/nbt.3462). Thus, in some other embodiments, the hydrogel contains a chemical modification that reduces an inflammatory effect of the transplanted organoid in the subject.

Screening Assays

Pancreatic islet organoids and pancreatic organoids of the invention can be useful for modeling diseases of the pancreas in vitro or in vivo. Such pancreas disease models can be used to identify drugs that are useful for treatment of a pancreatic disease. Thus, in some aspects, the invention provides methods for identifying modulators, i.e., candidate or test compounds or agents (e.g., proteins, peptides, peptidomimetics, peptoids, polynucleotides, small molecules or other drugs) that are useful for the treatment of a pancreatic disease, particularly type 2 diabetes and/or pancreatic cancer. In one embodiment, the agent modulates an activity of an organoid of the invention.

The test agents of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. (1994) et al., J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Chemical compounds to be used as test agents (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Combinations of substituents and variables in compounds envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis- or trans- or E- or Z-double bond isomeric forms. All such isomeric forms of such compounds are expressly included in the present invention.

Test agents of the invention can also be peptides (e.g., growth factors, cytokines, receptor ligands) or polynucleotides encoding such peptides.

Screening methods of the invention identify agents that increase or decrease a biological activity of pancreatic islet organoids and pancreatic organoids of the invention. In some embodiments, a pancreatic disease, such as type 2 diabetes or pancreatic cancer, is induced or mimicked in the pancreatic islet organoid or pancreatic organoid. Type 2 diabetes in the pancreatic islet or pancreatic organoid can be induced, for example, by contacting the organoid with free fatty acids (FFAs), glucose, and cytokines (in particular, high levels of glucose and/or high levels of FFAs). In one embodiment, a pancreatic organoid is co-cultured with pancreatic cancer cells, stellate cells and immune cells to create a human pancreatic cancer microenvironment in vitro.

In some embodiments, the organoid is contacted with a candidate agent, and an effect of the candidate agent on a biological activity, function, or event is assayed. In some embodiments, the candidate agent is a drug approved by the Food and Drug Administration (FDA). For example, biological activities of a pancreatic islet organoid or pancreatic organoid assayed in the screening methods of the invention include insulin secretion (e.g., glucose-stimulated insulin secretion (GSIS)), beta cell apoptosis, LDHA activity, K(ATP) channel activity, mitochondrial function, level or activity of NDUFA4, ESRRG, KCNK3, or MAFA polypeptide or polynucleotide, cell death, cell growth, and metastasis. In some embodiments, the agent increases GSIS.

In some other embodiments, an organoid of the invention (e.g., pancreatic islet organoid or pancreatic organoid) is transplanted into a host to model pancreatic disease, such as type 2 diabetes or pancreatic cancer, in vivo. Methods of transplanting an organ or organoid are known in the art. The host can be any non-human mammal, such as a rat or mouse.

To reduce an immune reaction to the transplanted organoid in the host after, the organoid can be encapsulated in a hydrogel and then transplanted in the host. Such methods of transplantation are further described in Vegas et al., Nature Medicine 2016, doi:10.1038/nm.4030; Vegas et al., Nature Biotechnology 2016, doi:10.1038/nbt.3462. In some embodiments, the hydrogel contains an alginate or alginate derivative (e.g., triazole-thiomorpholine dioxide). Various modifications of alginate hydrogels that substantially reduce inflammatory or fibrotic effects of alginate hydrogels have also been identified (Vegas et al., Nature Biotechnology 2016, doi:10.1038/nbt.3462). Thus, in some other embodiments, the hydrogel contains a chemical modification that reduces an inflammatory effect of the transplanted organoid in the host.

In some embodiments, a pancreatic organoid and liver organoid are co-transplanted in the host. The liver is a major target organ for metastasis of pancreatic cancer. In mice in vivo endothelial cells in the mini pancreas and in the mini liver are connected to each other and create a pancreas-liver vasculature network for pancreatic cancer metastasis. Therefore, a host co-transplanted with a pancreatic organoid and liver organoid can be useful for studies of human pancreatic cancer metastasis into human liver.

In some embodiments, the host transplanted with an organoid of the invention is administered an environmental stress (e.g., administered a high fat/high glucose diet or administered pancreatic cancer cells) to induce or mimic a pancreatic disease in the host. In some other embodiments, the host is transplanted with a pancreatic islet or pancreatic organoid and/or a liver organoid where a disease (e.g., type 2 diabetes or pancreatic cancer) has been induced.

In some embodiments, the host is administered with a candidate agent. In certain embodiments, the candidate agent is a drug approved by the Food and Drug Administration (FDA). In some embodiments, an effect of the candidate agent on a host phenotype (such as biological activity or function associated with the pancreas, or activities associated with a disease) is assayed. Exemplary biological activities include insulin secretion (e.g., glucose-stimulated insulin secretion (GSIS)), beta cell apoptosis, LDHA activity, K(ATP) channel activity, mitochondrial function, level or activity of NDUFA4, ESRRG, or MAFA polypeptide or polynucleotide, cell death, cell growth, and metastasis. In some embodiments, the agent increases GSIS.

In any one of the embodiments herein, the effect of the candidate agent (i.e., ability to modulate a pancreatic activity or function) is measured relative to a reference. The reference can be, for example, an untreated pancreatic islet organoid or pancreatic organoid. In some embodiments, the reference is a host transplanted with an organoid of the invention, where the host is not administered with a candidate agent.

Agents useful in the methods of the invention can also be detected by identifying an increase in expression of a desirable marker (e.g., MAFA as a beta cell fate marker). The level of expression can be measured in a number of ways, including, but not limited to: measuring the mRNA encoded by the genetic markers; measuring the amount of protein encoded by the genetic markers; or measuring the activity of the protein encoded by the genetic markers.

The level of mRNA corresponding to a marker can be determined both by in situ and by in vitro formats. The isolated mRNA can be used in hybridization or amplification assays that include, but are not limited to, Southern or Northern analyses, polymerase chain reaction analyses and probe arrays. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the markers described herein.

The level of mRNA in a sample can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1:
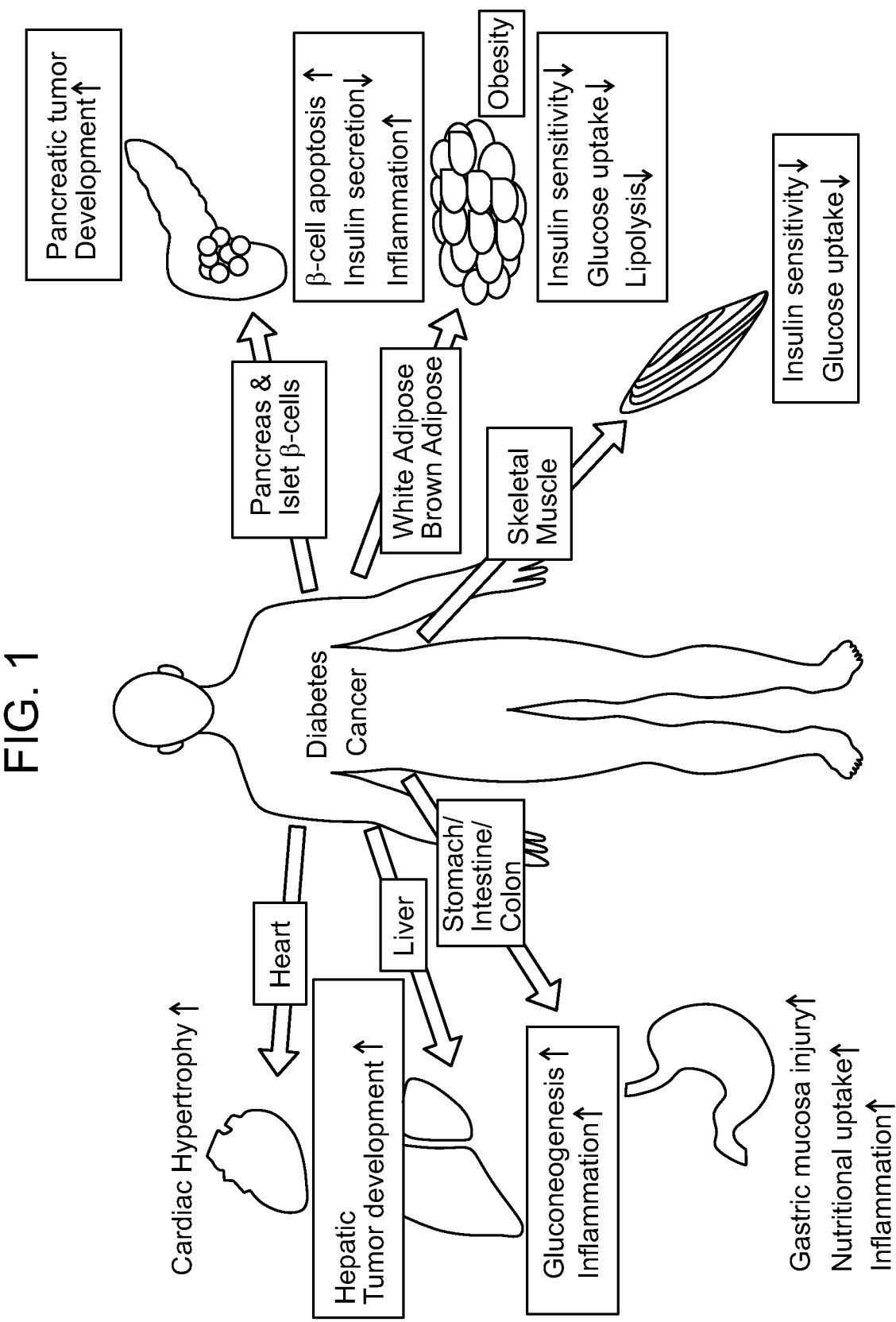
FIG. 1 is a schematic showing the various symptoms of human disease that can be modeled in a dish. Generation of functional human organs provides new therapeutic strategies in drug-screening and disease modeling. Described herein is a novel technique to generate 3D human mini-organs in a dish. Using this technique, human type 2 diabetes can be modeled in a dish to find effective drugs in genetic, patients or environmental specific diseases such as human type 2 diabetes.

Example 1: Generation and Characterization of Pancreatic and Pancreatic Islet Organoids Although an animal disease model can yield insight into the pathogenesis of diseases, drugs identified from screens using animal models often fail to be adopted in human patients. Generation of functional human organoids provides a new therapeutic strategy in drug-screening and disease modeling (FIG. 1). Described herein is a novel technique to generate 3D human "mini-organs" or organoids in a dish. Using this technique, diseases such as human type 2 diabetes can be modeled in a dish to find effective drugs in genetic, patient or environmental specific diseases such as human type 2 diabetes.

Developing Gellan Gum Based 3D Culture System for β-Like Cells Differentiation

Figure 10A:
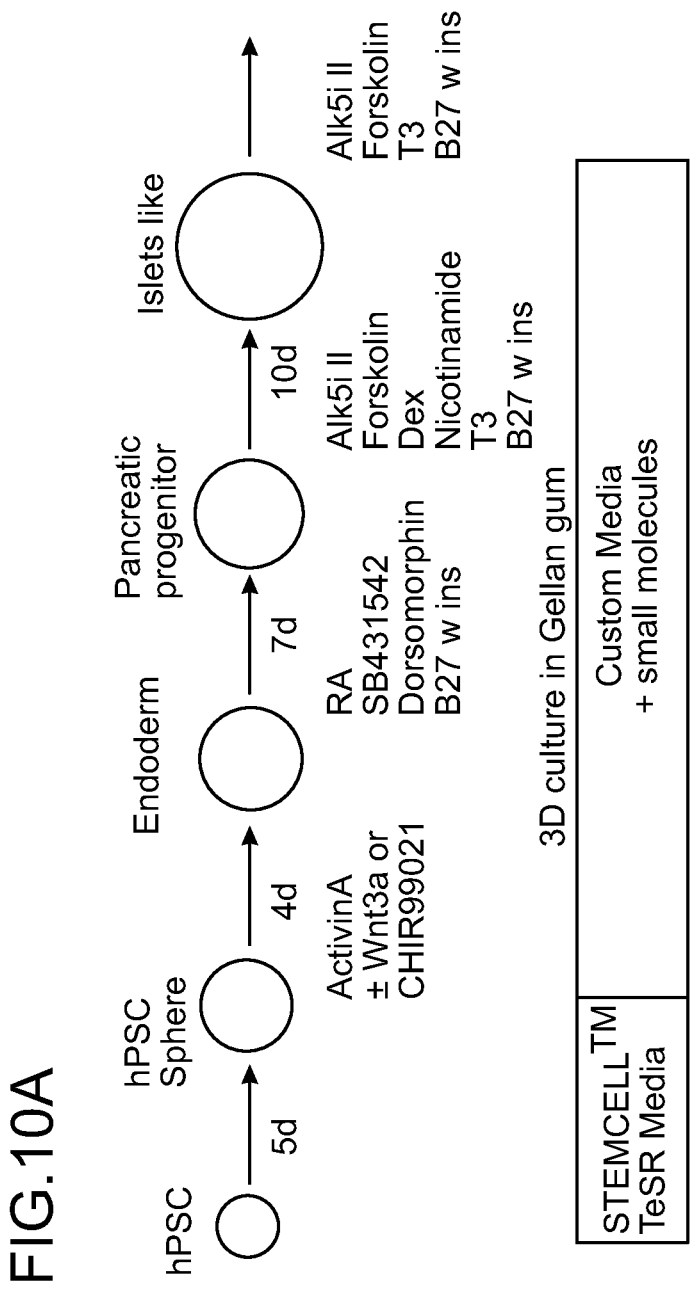
FIGS. 10A-10D is a set of schematics, images, heatmaps, and bar graphs summarizing the generation of islet-like organoids from PSCs.
Figure 10B:
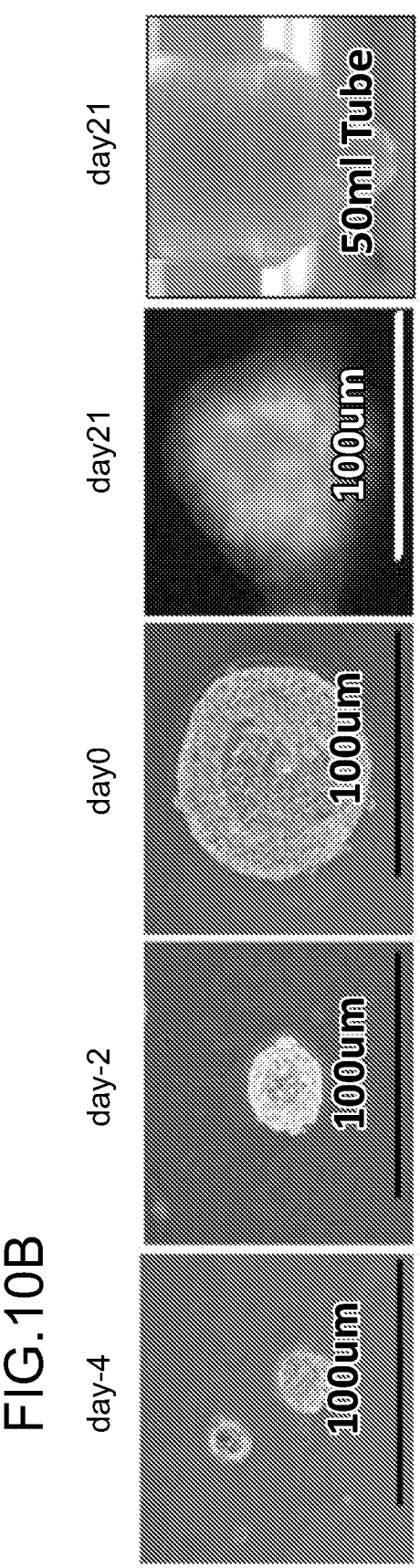
Figure 10C:
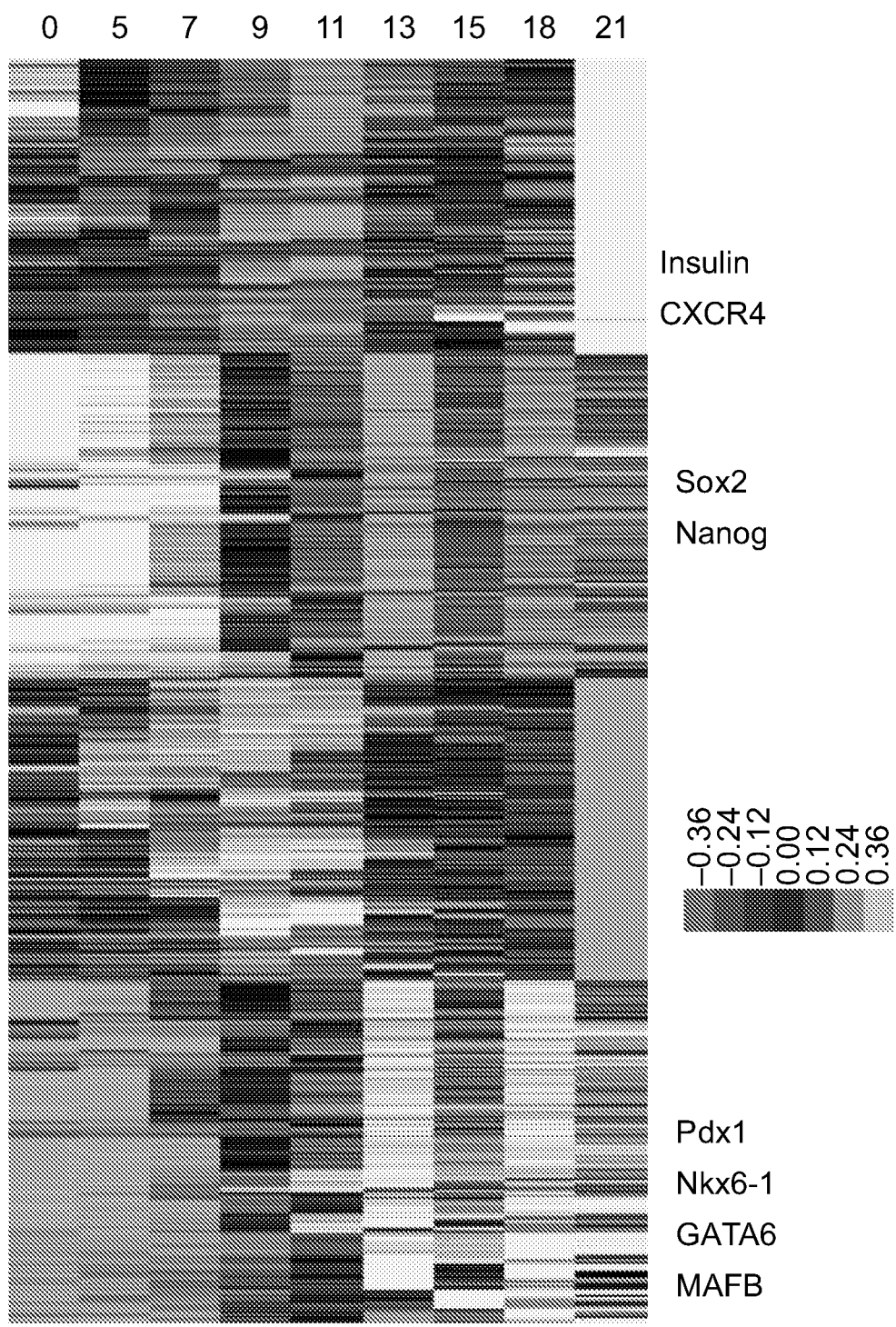
Figure 10D:
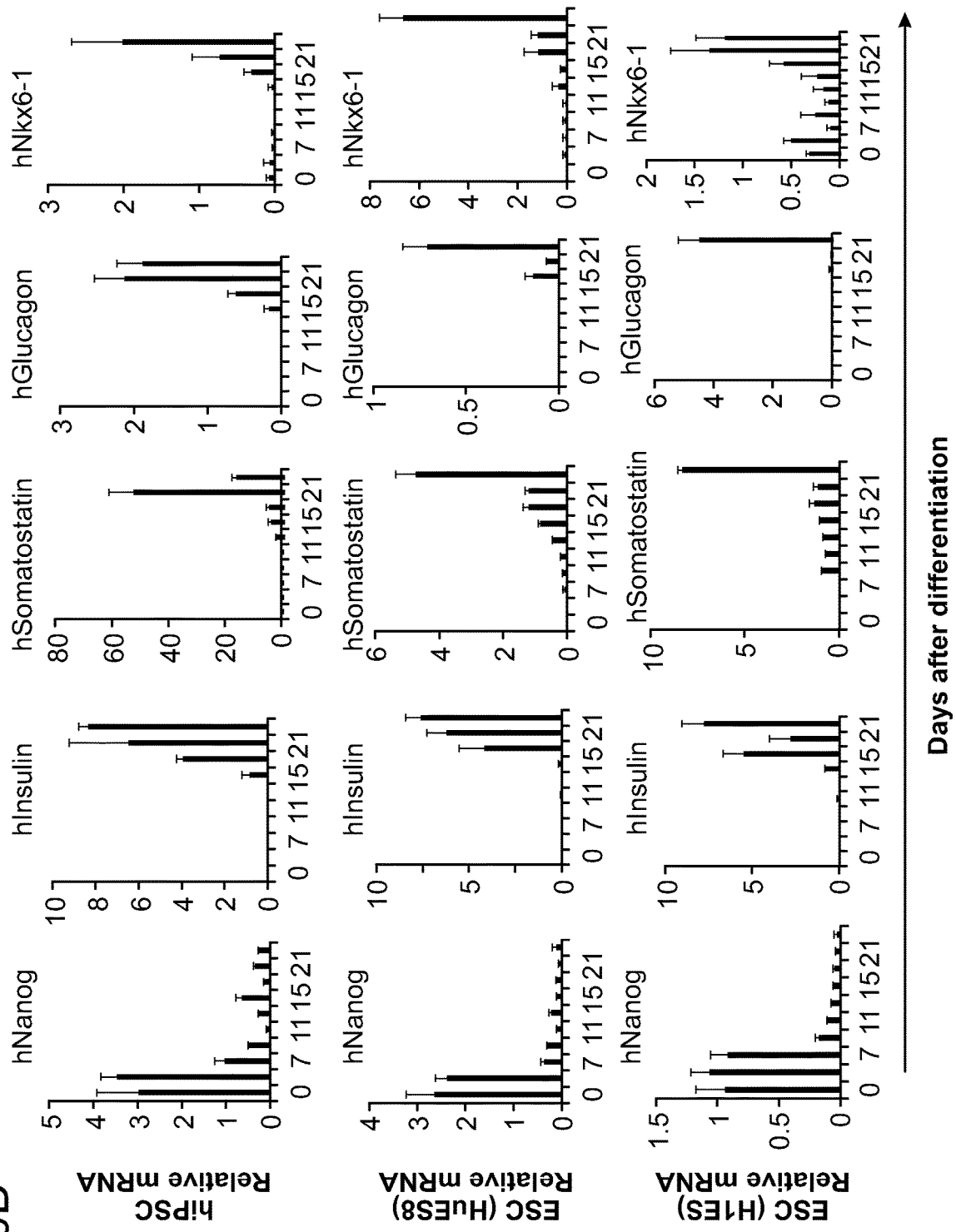

It is known that 3 dimensional (3D) culture systems contribute to facilitating self-organization and integration of cells. Therefore, MATRIGEL® matrix containing extracellular matrix components such as collagen and fibronectin is often used as the basement of a 3D culture system. However, MATRIGEL® matrix-based 3D culture systems are not ideal for large-scale human organoid generation because of their cost and difficulties in scale up. Described herein are Gellan-gum based 3D culture systems and methods for β-like cell differentiation, which are cost effective and easily scalable. Using a fully chemically-defined stepwise differentiation protocol (FIG. 10A) human pluripotent cells (hPSCs) are differentiated into insulin producing islet-like spherical cell clusters with high efficiency and reproducibility in Gellan-gum based 3D culture systems (FIG. 10B). Single dissociated pluripotent stem cells (PSCs) successfully formed into spheres within 5 days in Gellan gum containing STEMCELL™ TeSR™ media. Fifteen (15) to 21 days after differentiation in Gellan gum-containing Custom TeSR™ with defined small molecule stimulation, insulin positive GFP clusters were observed (FIG. 10B). Global transcriptome analysis by RNA-seq revealed the stepwise differentiation of hiPSCs into insulin positive cells expressing β cell lineage specific marker genes including Pdx1, Nkx6-1, GATA6 and MAFB (FIG. 10C). The differentiation of hiPSCs, as well as the human ESC lines HuES8 and H1ES, into islet-like cell clusters was further confirmed by the progressive loss of the pluripotent marker Nanog, the induction of the β cell specific marker Nkx6-1, and the progressive induction of the endocrine hormones insulin, somatostatin and glucagon, as determined by qPCR (FIG. 10D). These results demonstrate that the Gellan-gum based 3D culture systems is suitable for the generation of large-scale islet-like organoids from hPSCs.

Generation of Scalable, Human Islet-Like Organoids In Vitro

β-like cells derived from human embryonic stem cells (hESC) or human induced pluripotent stem cells (hiPSC) have limited functionality and lack the morphological and functional feature of human islets. Previous studies revealed that co-culturing hiPSC derived hepatocyte with human umbilical vein endothelial cells (HUVECs) and human bone marrow-derived mesenchymal stem cells (hMSC) generates self-organized 3D liver-bud spheres in matrigel (Takebe et al., 2013, Nature 499, 481-484). This study found that the liver "organoids" had superior expression of lineage determinant factors compared to the differentiation of isolated hepatocytes and that these organoids rapidly vascularized and functionally matured in vivo.

Figure 2A:
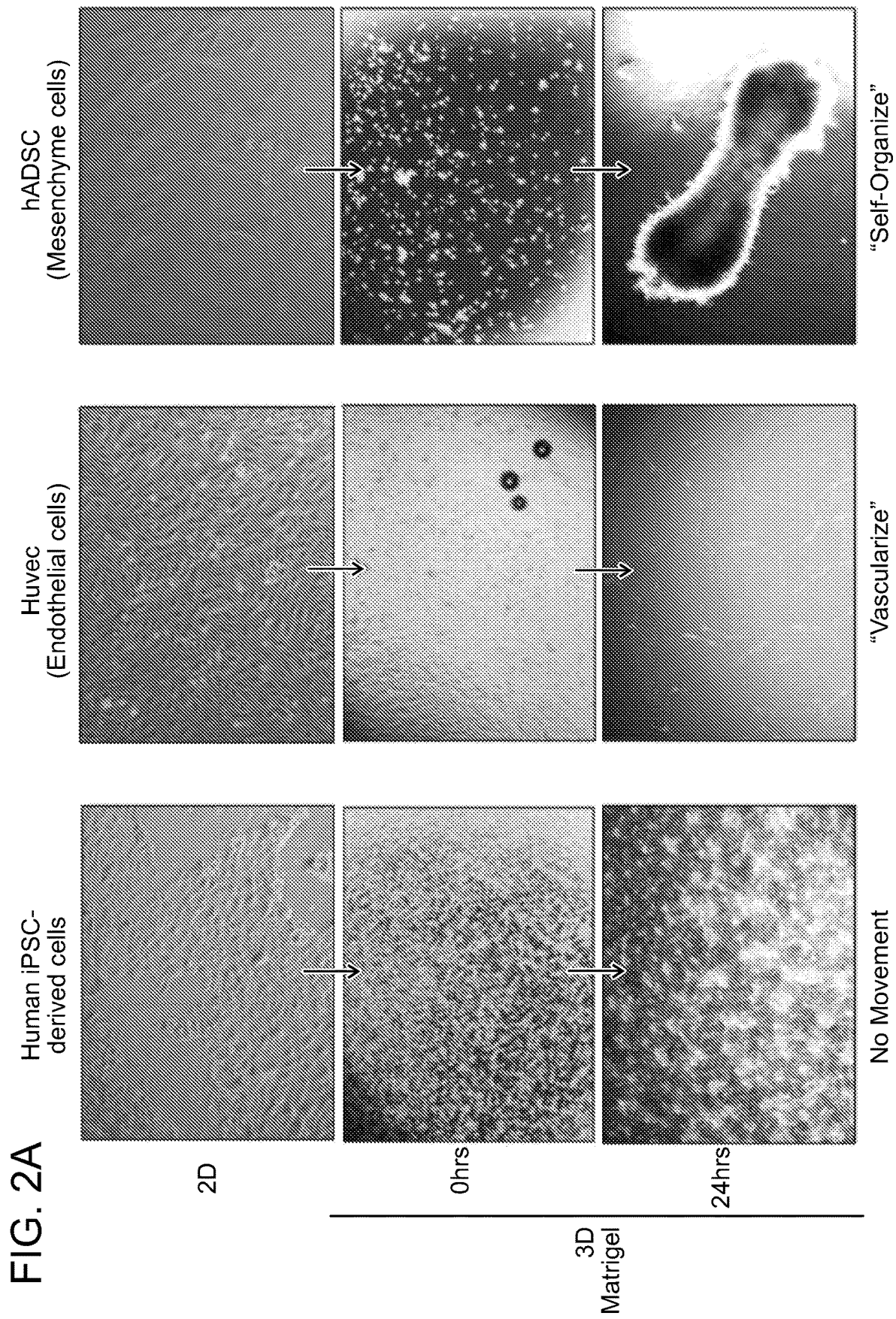
FIG. 2A is a set of micrographs showing the utility of human adipose-derived stem cells (hADSC) in organogenesis. In studies described herein, human adipose-derived stem cells were found to be a novel resource for generation of self-organized organoids (organ bud).
Figure 2B:
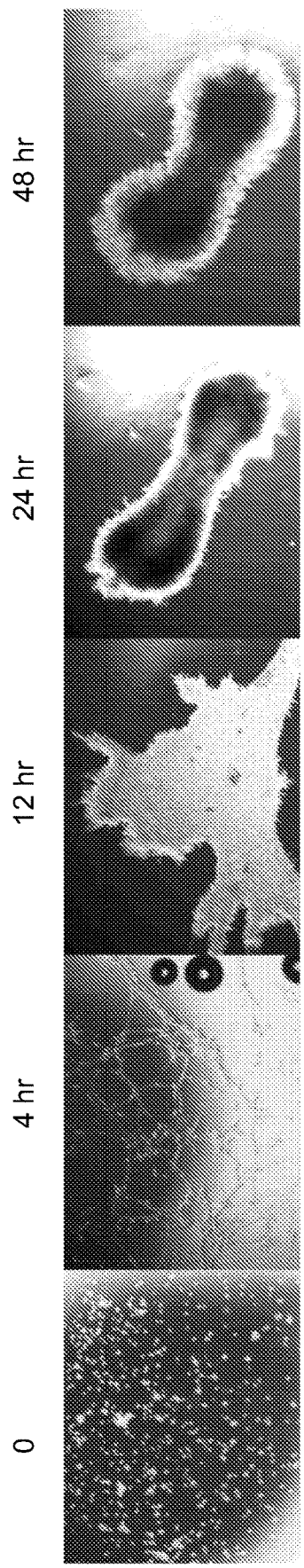
FIG. 2B is a set of micrographs demonstrating the ability of ADSCs to progressively self-organize when cultured in Matrigel.
Figure 2C:
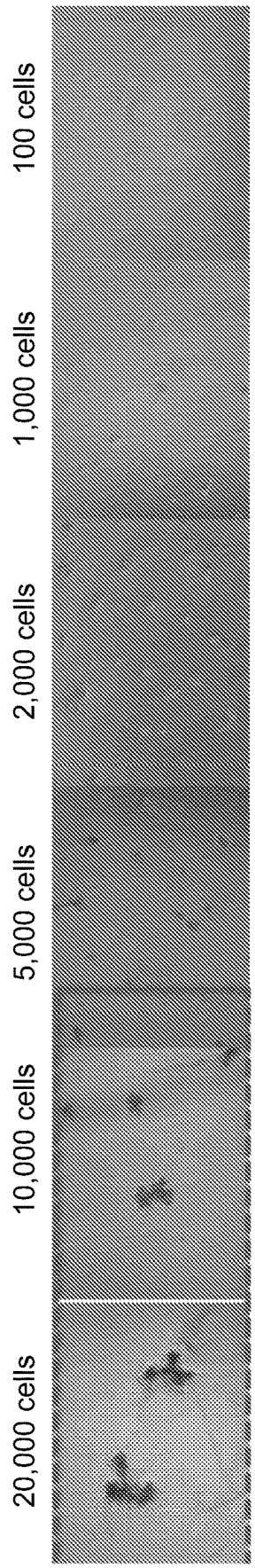
FIG. 2C is a set of images of hADSCs, seeded at the indicated density, that demonstrate the minimum number of cells required for sphere formation when grown in Matrigel.
Figure 3B:
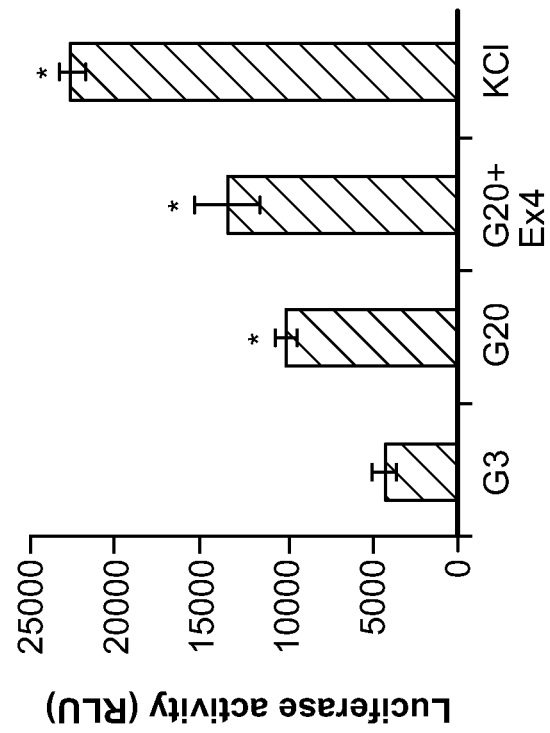
FIGS. 3A-3F are plots, images, and a schematic showing characterization of insulin secretion of INS-1 cells, mouse islets, and human islets using a proinsulin luciferase reporter system as a quantitative insulin secretion assay.
Figure 3A:
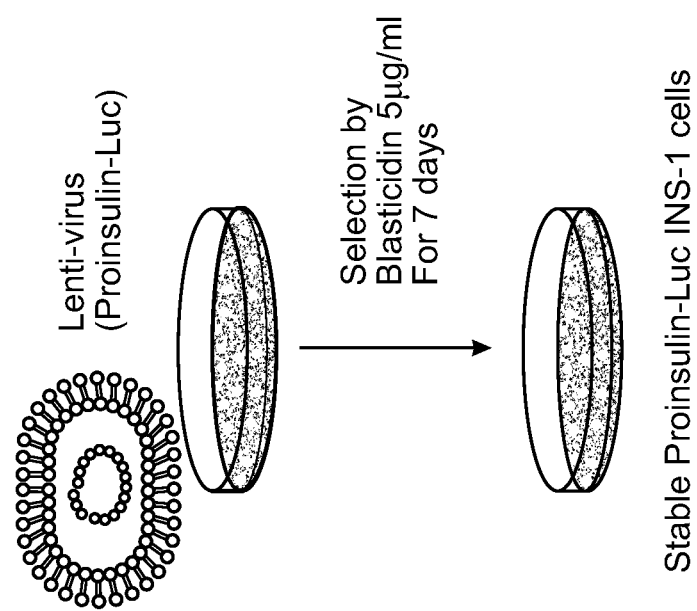
Figure 3D:
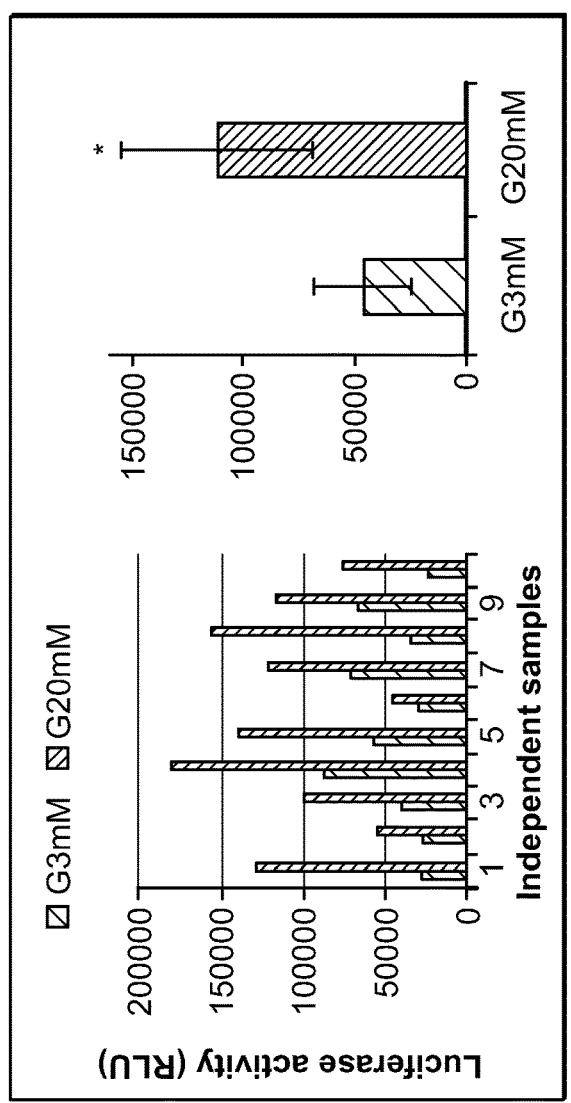
Figure 3F:
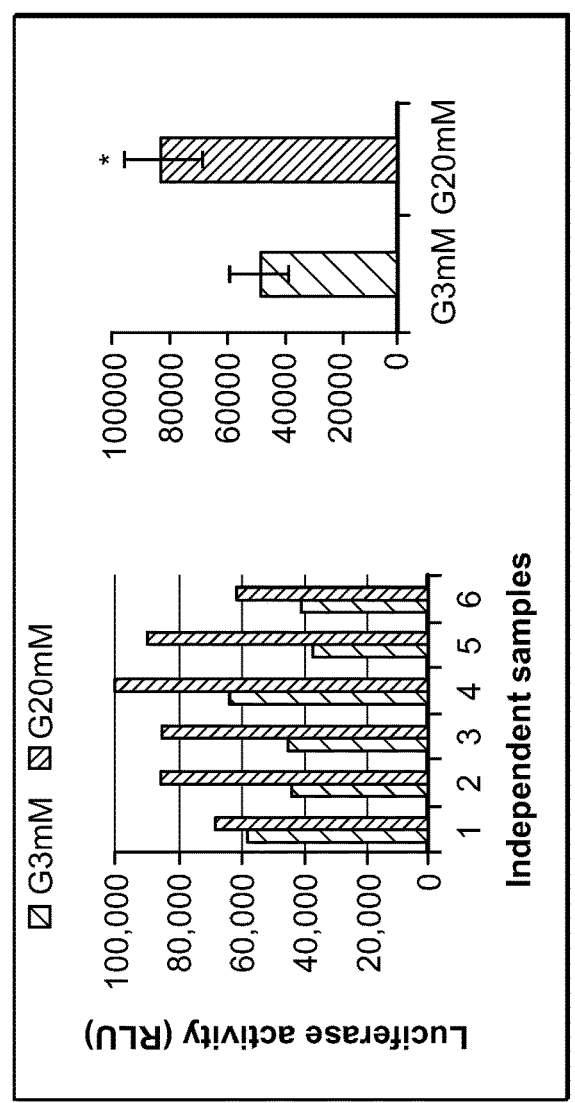
Figure 3C:
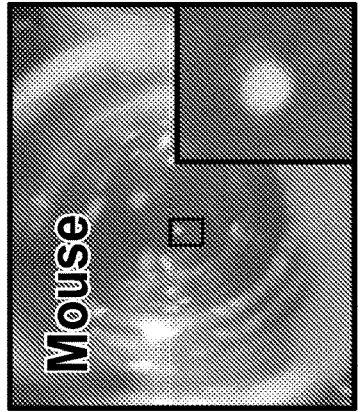
Figure 3E:
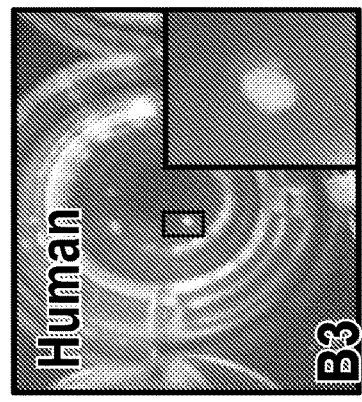

Studies herein found that hiPSC-derived pancreatic progenitor cells (hiPSC-PP) generated using a 2D differentiation protocol (Yoshihara et al, Cell Metab. 23, 622-634) did not self-organize in 3D MATRIGEL® matrix (FIG. 2A). In contrast, HUVEC cells rapidly formed a vasculature-like structure while human adipocyte-derived stem cells (hADSCs) self-organized in 3D MATRIGEL® matrix (FIG. 2A). In MATRIGEL® matrix, dispersed hADSC cells projected processes within 4 hours, formed a cloth-like wrapper within 12 hours, and adopted a sphere-like formation within 24 to 48 hours (FIG. 2B). Furthermore, a minimum cell density for self-organization was identified (i.e., ~10,000-20,000 cells in 300 µl of MATRIGEL® matrix in ~2 cm² well (FIG. 2C). RNA-seq analysis identified dynamic transcriptional changes during hADSC 3D self-organization, suggesting that the ability to self-organize under 3D culture conditions is an inherent feature of naïve hADSCs (FIG. 2D). These results identify the mesenchymal hADSC as a resource for generating self-organizing organoids.

To explore pancreatic organogenesis, hiPSC-PP ($1\times10^6$ cells) cells were co-cultured with HUVECs ($7\times10^5$ cells) and hADSCs ($1\text{-}2\times10^5$ cells) (FIG. 2E) in Matrigel matrix. This co-culture yielded macroscopically visible 3D cell clusters 48 hours after seeding (FIG. 2F). Furthermore, insulin expression, based on the expression of a GFP reporter, was detected 5 days after seeding and increased with time in culture in the human islet-like organoids. In addition, HUVECs-based endothelial cells are integrated inside the organoids as shown by fluorescence-labeled (mCherry) HUVECs (FIG. 2G).

The limitations of MATRIGEL® matrix for organoid production include high cost, difficult organoid recovery, scaling restrictions, and batch to batch variabilities.

Figure 4D:
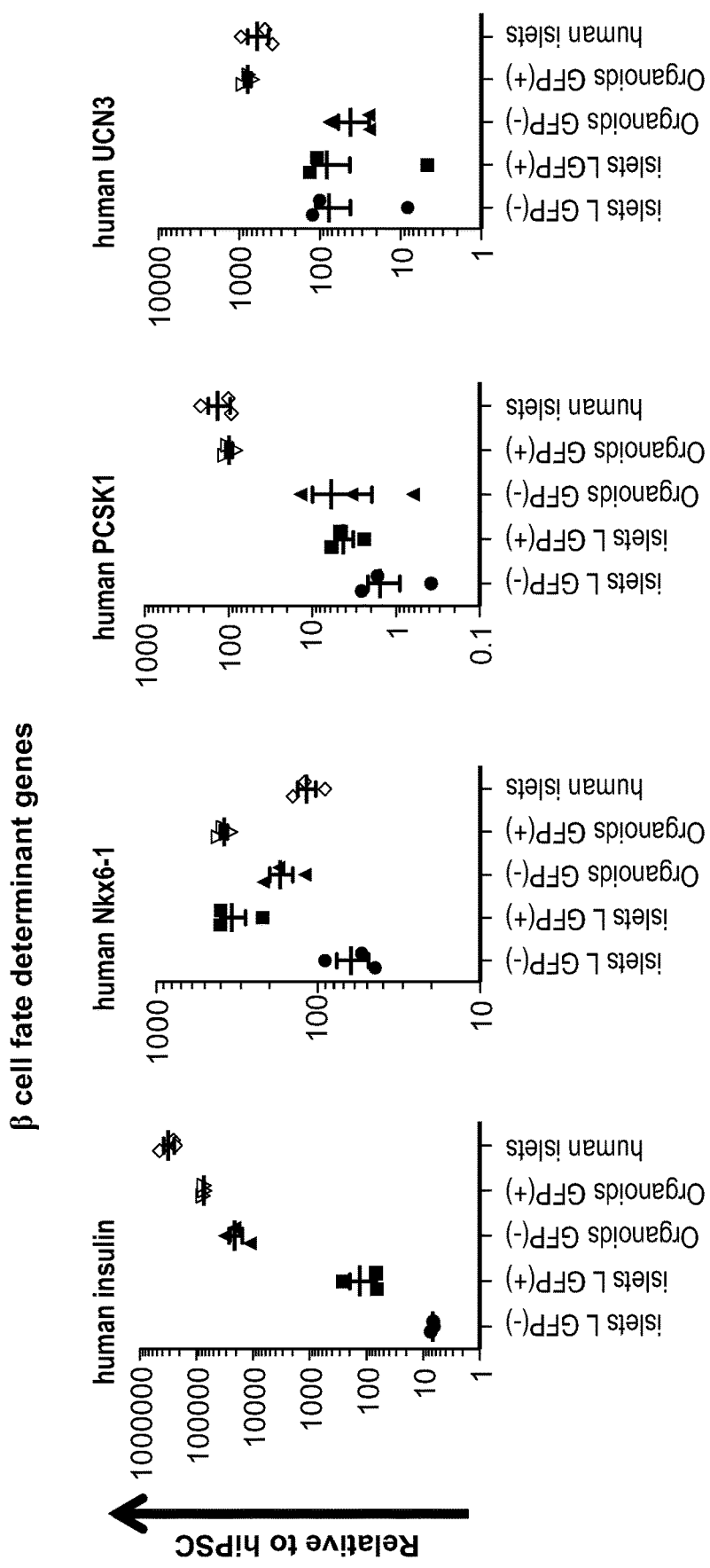
Figure 4E:
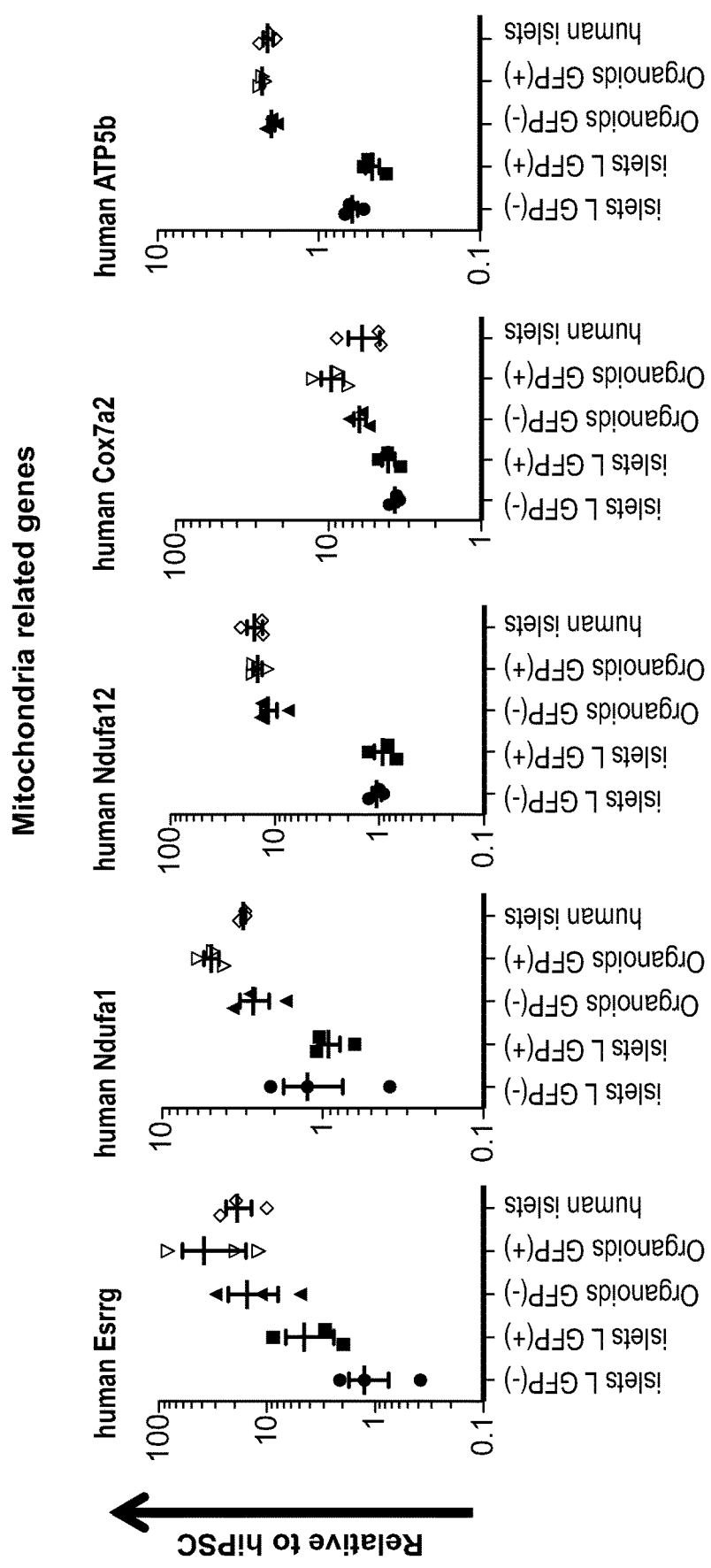
Figure 4F:
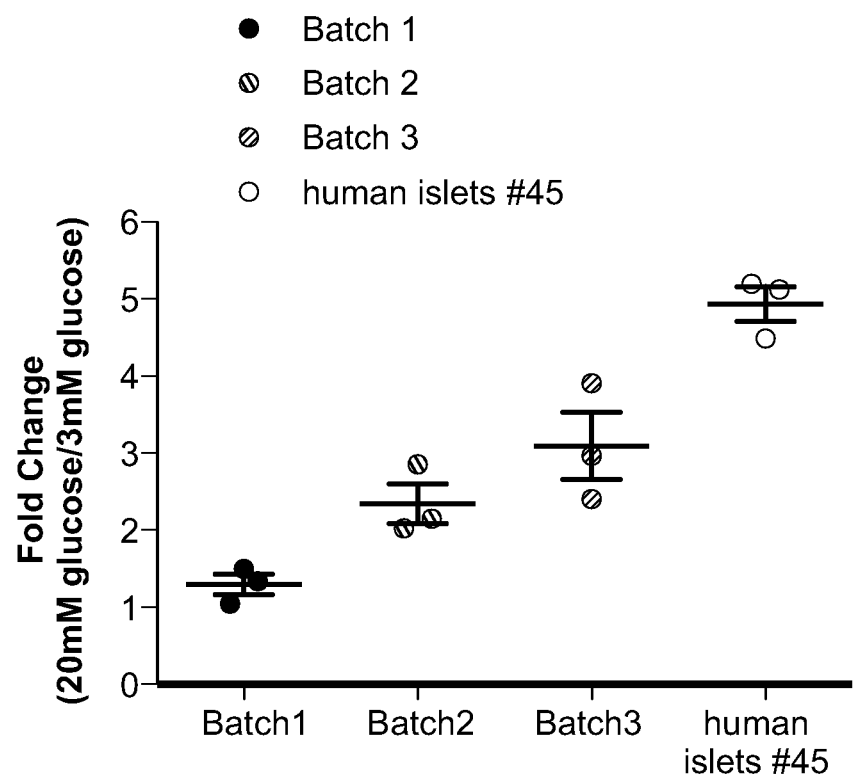
Figure 4I:
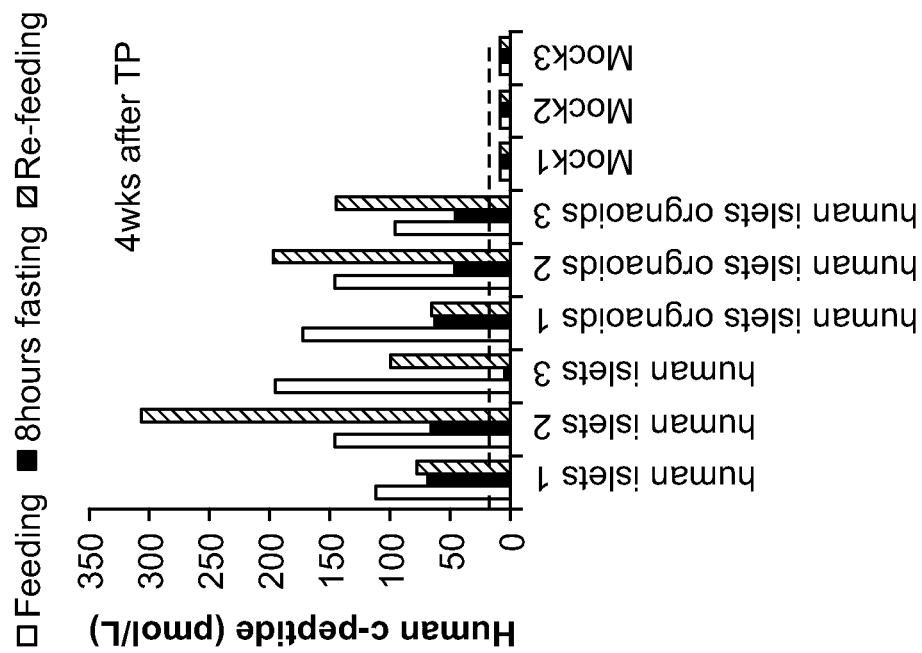
Figure 4H:
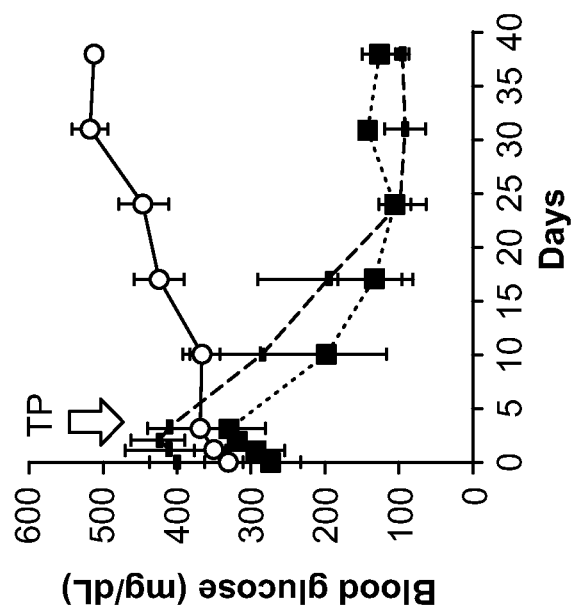

Described herein are methods to generate morphologically identical human islet-like organoids using gellan gum based 3D cultures (FIGS. 4A-4G). FIG. 4A shows a scheme for generation of functional, vascularized human pancreatic islets in as dish. Human induced pluripotent stem cells derived-pancreatic progenitors (hiPSC-PPs) ($1\times10^8$ cells) were cultivated with a stromal cell population such as human umbilical vein endothelial cells (HUVECs) (2-7×10⁶ cells) and human adipose-derived stem cells (hADSCs) (2-7×10⁶) in 50 ml of gellan gum based 3D culture media (FIG. 4B). FIG. 4B shows that hiPSC-PP rapidly formed isle-like sphere formation with HUVECs and hADSCs within 5 days after seeding into the gellan gum based 3D culture media. Human islets like mini-organs expressed human insulin GFP reporter in 5 days after seeding with gradually enhancing GFP intensity. Co-culturing hiPSC-PP, hADSCs, and HUVECs according to this method, generated human islet-like organoids with high reproducibility that were morphologically similar to human islets (FIG. 4C). In addition, the generated human islet-like organoids contained insulin granules in β-like cells (FIG. 4B). Genes expression analyses revealed increased expression of β cell fate determinant genes (Insulin, Nkx6-1, PCSK1 and UCN3) and mitochondrial related metabolic genes (Esrrg, Ndufa1, Ndufa 12, Cox7a2. Atp5b) in the insulin expressing cell population (GFP enriched (GFP+)) in islet-like organoids compared to those prepared without hADSC and HUVEC co-culture (FIGS. 4D & 4E). Glucose-stimulated human c-peptide secretion assay revealed that islet-like organoids generated by this method are able to secrete human c-peptide in response to high (20 mM) glucose (FIG. 4F).

An in vitro functional vascularization test was then performed. FIG. 4G shows in vitro functional vascularization tests performed. Islet-like mini organs generated in gellan gum were transferred to MATRIGEL® matrix and cultured in endothelial growth media (EGM). Green fluorescence indicates expression of insulin genes. Within 24 hours to 48 hours after stimulation by EGM, the outgrowth of HUVEC cells was observed, indicating that human islet-like organoids generated by the method described herein possessed the ability to form vascular structures.

Establishment of Single Islet Insulin Secretion Assay Using Proinsulin-NanoLuc *Gaussia* Luciferase Assay System It was previously published that a reporter construct, in which the *Gaussia* luciferase is placed within the c-peptide portion of proinsulin accurately measures insulin secretion without affecting β-cell function (Burns et al., 2015, Cell metabolism 21, 126-137). Using a lentiviral system, INS-1 cells stably expressing this *Gaussia* luciferase were generated (FIGS. 3A-3F). Luciferase secretion from INS-1 cells stably expressing Proinsulin-NanoLuc increased with high-glucose (20 mM), high glucose with Exendin-4 (G20 mM+Ex4), and the depolarizing agent, potassium chloride (FIGS. 3A-3B), confirming the utility of this reporter system. Next, the usefulness of this reporter to measure insulin secretion in mouse or human islets transiently infected with the Proinsulin-NanoLuc reporter was evaluated. Luciferase secretion in response to 20 mM high glucose was detected in both transiently infected mouse and human islets were detected (FIGS. 3C-3F). Importantly, the assay sensitivity was sufficient that insulin secretion could be qualified at the level of single islets. These results indicate that the Proinsulin-NanoLuc luciferase reporter based insulin secretion assay is applicable to not only the rat beta cell line INS-1 cells, but also to primary mouse and human primary β cells.

Figure 5B:
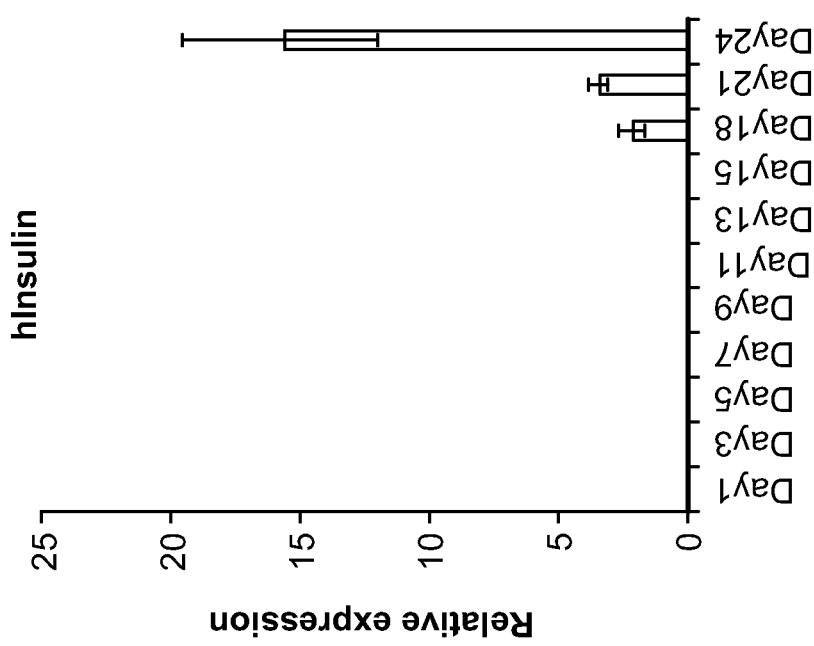
Figure 5A:
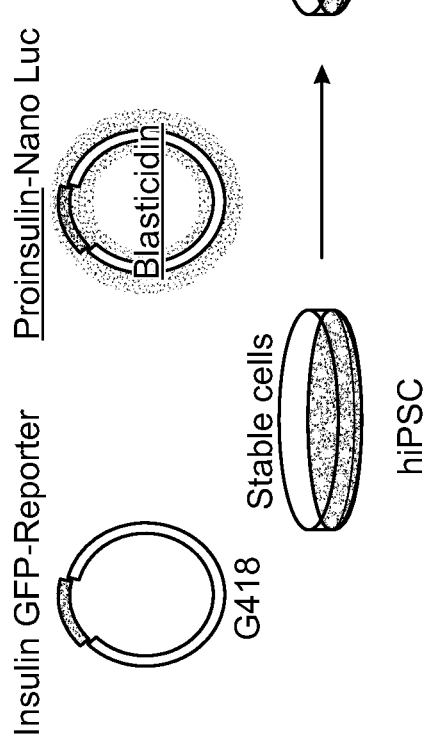

Establishment of hiPSC and hESC Cells Incorporating Dual Lineage and Functional Reporters Human iPSCs and hESCs stably expressing reporters for βcell lineage (human insulin reporter) and β cell function (proinsulin-NanoLuc reporter) were generated, hiPSC$^{hINS-GFP/Sec-Luc}$ and hESC$^{hINS-GFP/Sec-Luc}$, respectively (FIG. 5A). First, a neomycin resistant construct of human insulin GFP reporter was generated by inserting human insulin promoter sequence of pGreenZeo lenti-reporter (SR10028PA-1, System Bioscience) into pGreenFire Lenti-Reporter plasmid (TR019PA-1, System Bioscience) (named as hINS-GFP-EF1a-Neo). hINS-GFP-EF1a-Neo lenti virus was infected into hiPSC and hESC by spin fection (800 g, 1 hour, 37 degree) followed by a media changed to fresh STEMCELL™ TeSR™ media. Three (3) days after the first infection, the cells were treated with 100 μg/ml G418 in STEMCELL™ TeSR™ media for 7 days. Selected hiPSC and hESC cells stably expressing hINS-GFP-EF1a-Neo were subsequently infected with the Proinsulin-NanoLuc (Addgene, Plasmid #62057) lenti-virus by spin fection (800 g, 1 hour, 37 degree) followed by a media change to fresh STEMCELL™ TeSR™ media. Three (3) days after the second infection, the cells were treated with 5 μg/ml blasticysin and 100 μg/ml G418 in STEMCELL™ TeSR™ media for 7 days. Subsequently, cells were maintained in STEMCELL™ TeSR™ media (FIG. 5A). The generated stable cell lines incorporating the dual reporters maintained self-renewal and pluripotency capabilities, as well as the capacity to differentiate into insulin producing β like cells (FIG. 5B).

Pooled Human Islet-Like Organoid Cultures Display Consistent Insulin Secretion Despite Variable Functionality Seen in Individual Organoids.

Recent studies have reported the generation of insulin producing β-like cells from hESC and hiPSC capable of secreting insulin in response to glucose (Pagliuca et al. 2014, Cell 159, 428-439; Rezania et al., 2014, Nature Biotechnology November; 32(11):1121-33; Russ et al., 2015, EMBO Journal 34, 1759-1772). However, fully functional human islet-like clusters able to appropriately secrete insulin in response to nutritional signals including glucose, amino acids, fatty acids and incretins such as GLP-1 have yet to be demonstrated. To date efforts have focused on the independent generation of insulin producing β-like cells, glucagon producing a-like cells, and somatostatin producing δ-like cells from hPSC. However, these approaches lack the supporting cells important for regulation, such as mesenchymal cells, adipose cells, and vasculature cells. Since the 3D structure of islets naturally enhances their function, these missing cellular components may compromise the functionality of islet-like cells clusters. In addition, organogenesis of pancreatic islets involves clonal expansion of β-cells, suggesting that these cells may have multiple functions in islet-like organoids. To test this idea, single organoid proinsulin secretion assays were performed. Human islet-like organoids generated by methods described herein are morphologically identical with human islet (FIG. 4C). However, significant variability was seen in the glucose-stimulated insulin secretion (GSIS) capabilities of individual human islet-like organoids compared to human islets, as measured by proinsulin luciferase secretion assay (FIG. 5C) Consistent GSIS functionality was demonstrated in pooled organoids (10 to 100 organoids for assay) (FIG. 5D). Furthermore, pooled human islet like organoids demonstrate enhanced GSIS when co-stimulation with GLP-1, as well as robust KCl-stimulated insulin secretion (FIG. 5D).

In vitro cultured iPSC-derived human pancreatic islet-like organoids generated herein retained their ability to respond to glucose, GLP1 and KCl after extended time (133 days) in culture (FIG. 5D).

Example 2: Generation and Characterization of Human Organoids

Figure 6A:
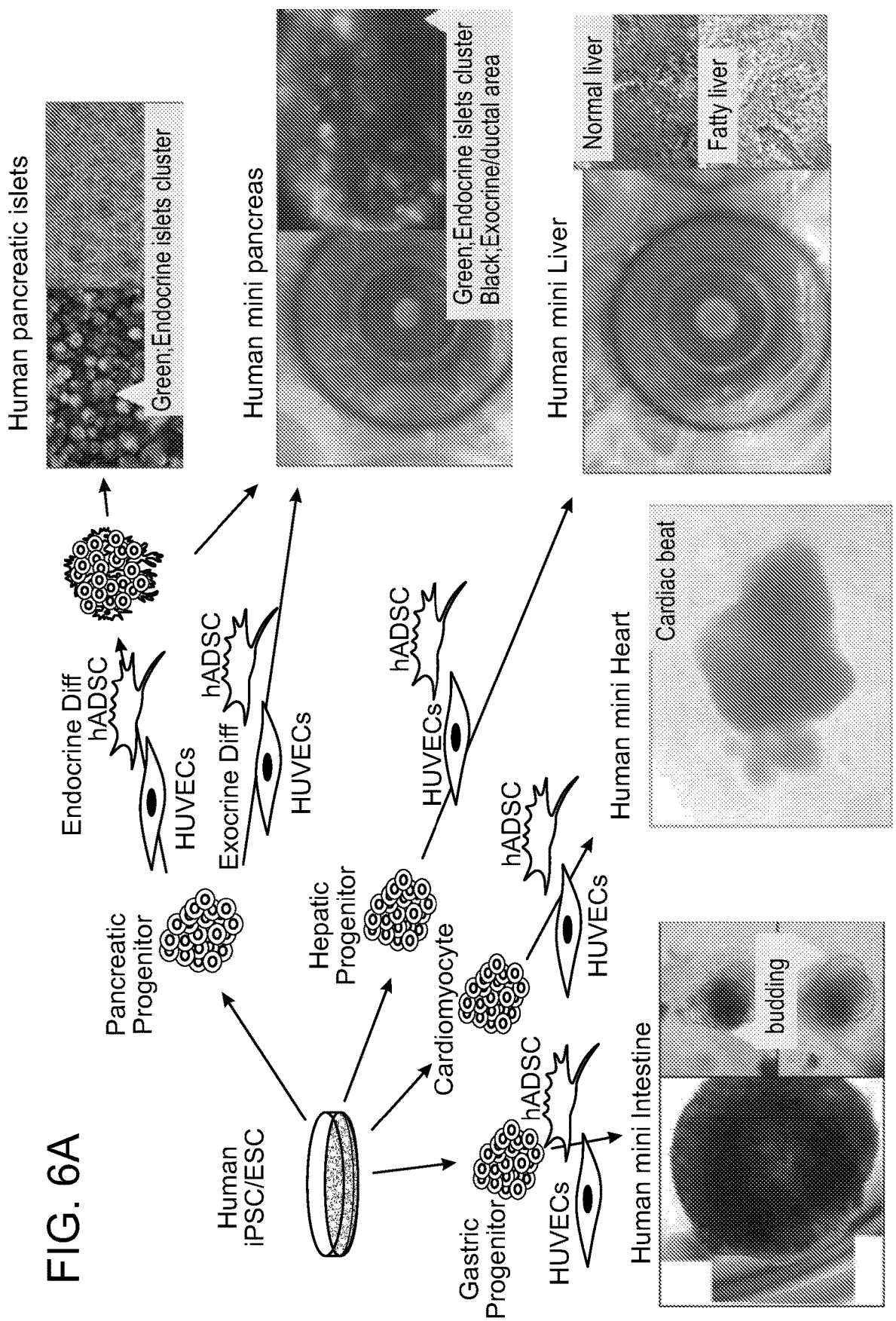

Functional human mini organs, including human islets, pancreas, liver, heart, and intestine, can be generated using the methods described herein (FIG. 6A). FIG. 9 shows a structure of a human pancreas and human pancreatic islets within the pancreas. Using the methods herein, human pancreatic islets mini organs or organoids were generated in about 30 days. The pancreatic islets generated contained human induced pluripotent stem cell (hiPSC)-derived beta cells, alpha cells, delta cells, duct cells, as well as endothelial cells and hADSCs. The pancreatic islet organoids generated express key beta cells transcription factors such as Insulin, Nkx6-1, PCSK1, and UCN3, as well as key mitochondrial metabolic genes including Esrrg, Ndufa 1, Ndufa 12, Cox7a2 and Atp5b (FIGS. 4D-4E). The pancreatic islet organoids exhibited at least partial GSIS, KCl-stimulated insulin secretion, GLP-1 stimulated insulin secretion, vascularization, somatostatin secretion, and glucagon secretion (FIGS. 4G, 5D).

Figure 6E:
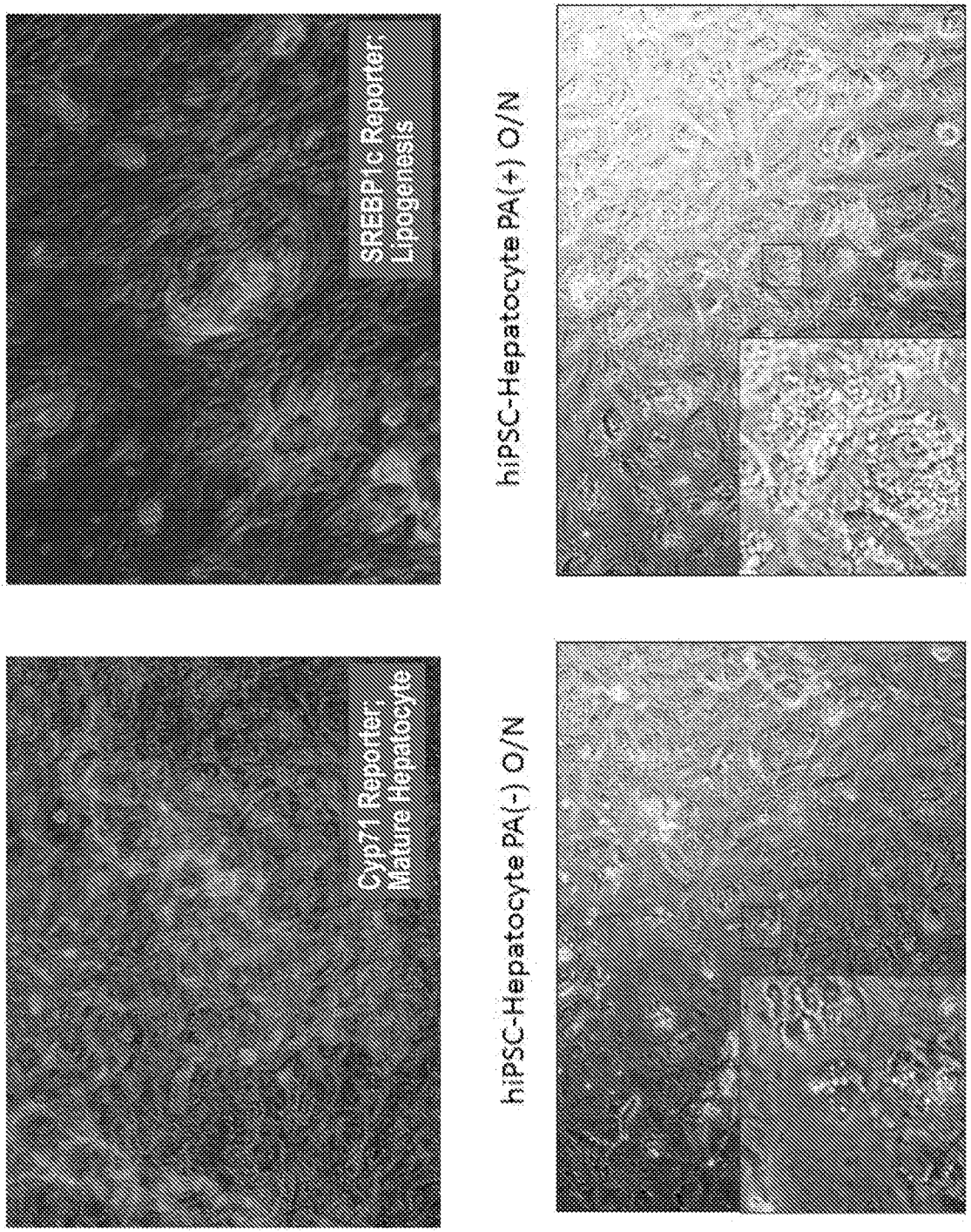
Figure 6G:
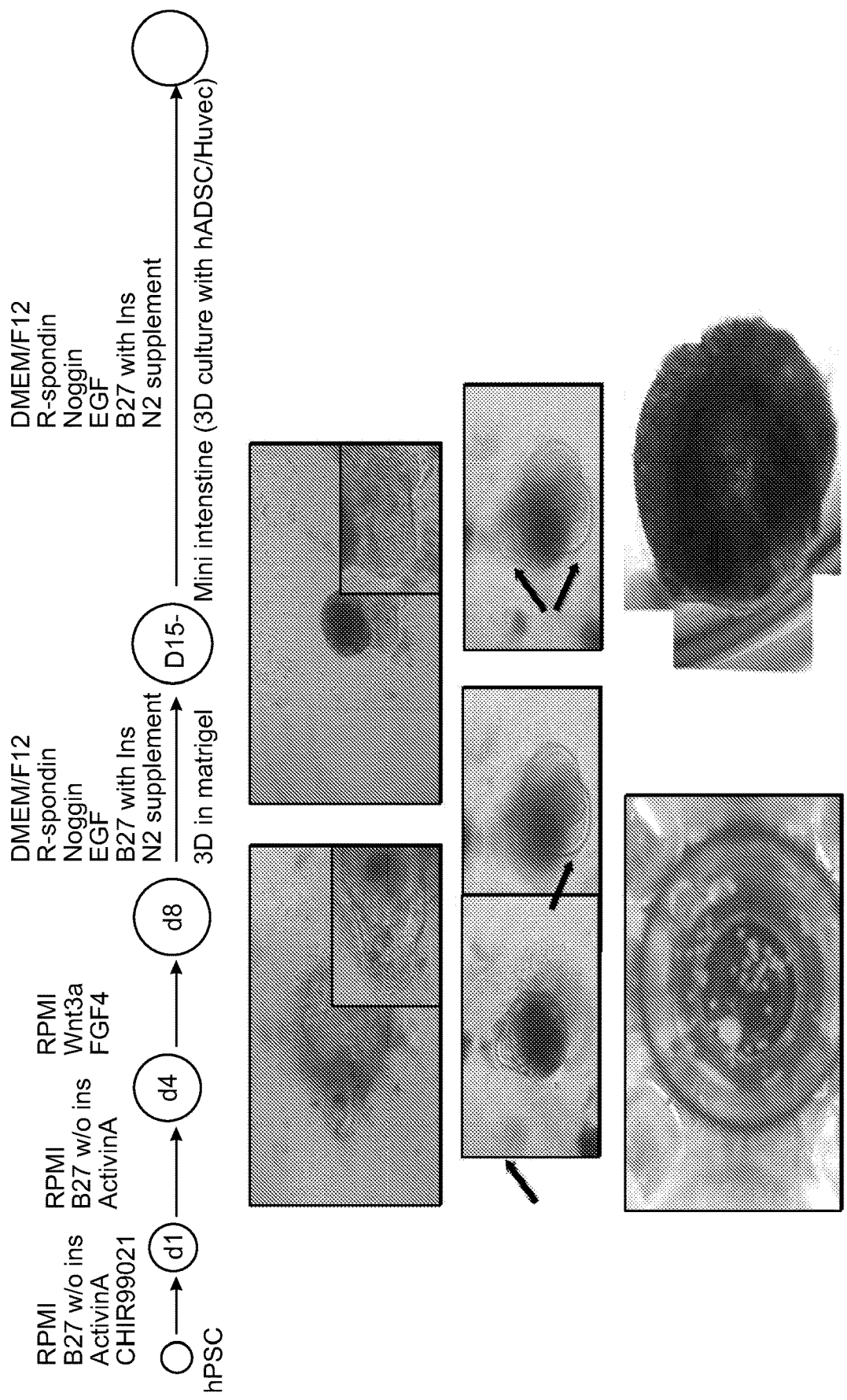
Figure 6H:
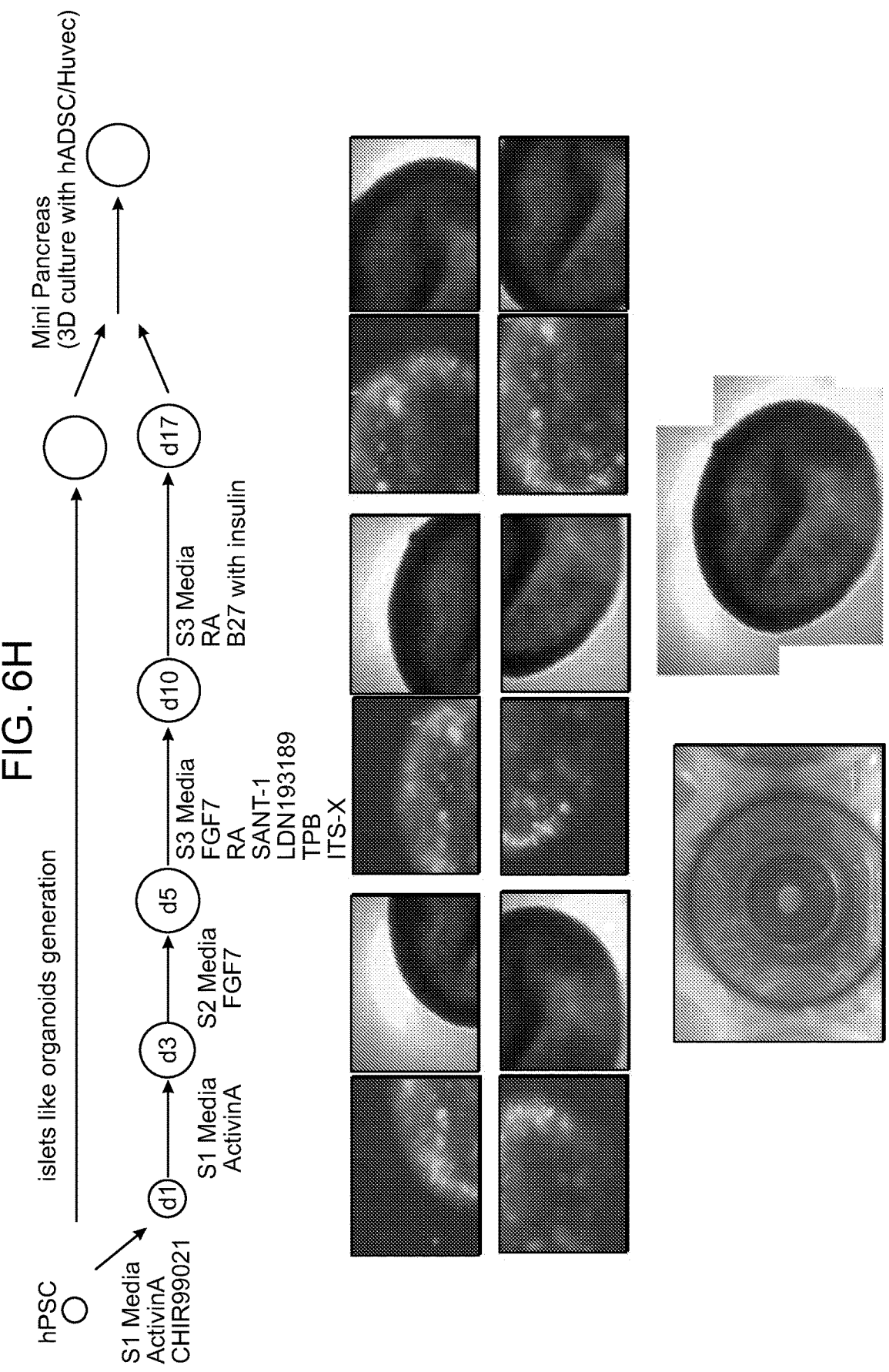

A human mini pancreas or human pancreatic organoid was generated in about 30 days (FIG. 6H). The human pancreatic organoid contained hiPSC-derived islets clustered within the interior of the organoid and a hiPSC-derived exocrine component surrounding the islets (FIG. 6H). The pancreatic organoid also contained endothelial cells and hADSC. Function of the human pancreatic organoid was demonstrated using an amylase secretion test, among other tests.

A human mini liver was generated in about 15 days (FIGS. 6D-6F). The human mini liver contained hiPSC derived hepatocytes, endothelial cells, and hADSCs. Analysis of functional characteristics of the human mini liver revealed that the mini liver expressed AFP, ALB, and Cyp3a7 (FIG. 6D), as well as the mature hepatocyte marker Cyp7a1 and lipogenesis marker SREBP1c (FIG. 6E). The human mini liver also exhibited insulin signaling, insulin resistance by palmitic acids, and lipid accumulation. The human mini liver is further tested for gluconeogenesis and metabolic function for drug metabolism.

A human mini heart was generated in about 15 days (FIGS. 6B-6C). The human mini heart contained hiPSC derived cardiomyocytes, endothelial cells, and hADSCs. The human mini heart expressed key cardiomyocyte genes such as hMlc2a, hNkx2-5, alpha MHC and KCNQ1 (FIG. 6B), and was seen to beat in cultures.

A human mini intestine was generated in about 30 days (FIG. 6G). The human mini intestine contained hiPSC derived intestinal cells, endothelial cells, and hADSCs. The human mini intestine expressed small intestine markers CDX2, Muc2, and Lgr5, and exhibited budding of intestinal organoids in response to R-Spondin.

Example 3: Transplantation of Functional Pancreatic Islet Organoids Rescued Type 1 Diabetic Mice Expression of specific functional islets marker such as MAFA, UCN3 and mitochondrial oxidative genes such as ERRγ (Esrrg), Ndufa 1, Ndufa 12, Cox7a2 and Atp5b in hiPSC-derived human islet-like organoids was observed. Notably, these islet-like organoids recapture both human islets development as well as the pathogenesis of diabetes in a dish. Transplantation of these functional islet-like organoids rescue type 1 diabetic mice with long survival, rapid vascularization, and reduced immune rejection.

Example 4: Drug Screening and Disease Modeling in Human Islet-Like Organoids

Figure 7:
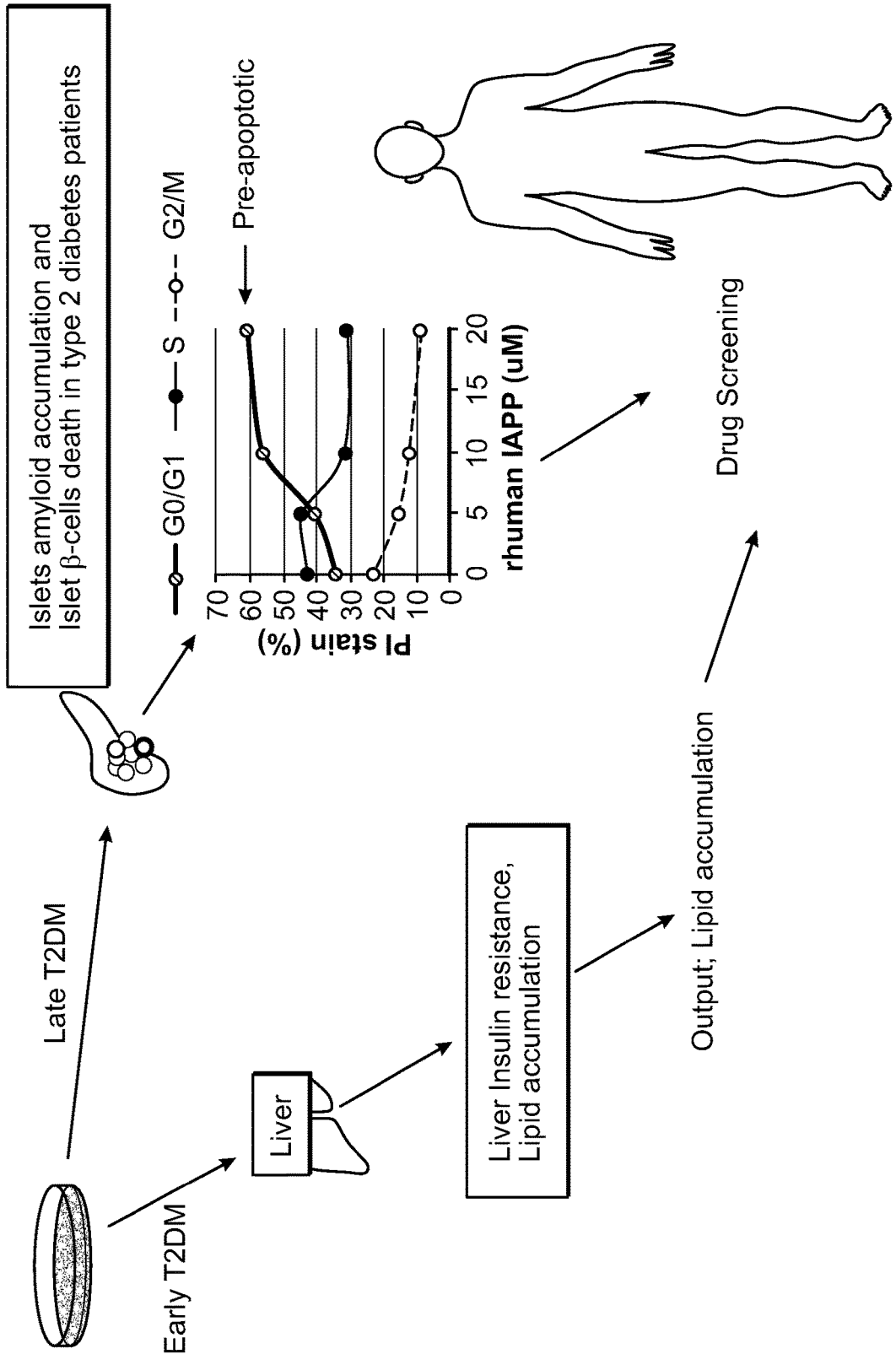
FIG. 7 is a schematic showing modeling of human Type 2 diabetes in a dish. Generation of functional human organs such as a liver, pancreas, and islets provides new therapeutic strategies in drug-screening and modeling of human type 2 diabetes. For example, hepatic organoids with accumulated lipids can be used to study early insulin resistance phenotypes, while human islet-like organoids can be used to study β cell death seen in late stage type 2 diabetes. Inserted graph shows the response of islet-like organoids to increasing concentrations of human amyloid polypeptide (hIAPP). The increase in propidium iodide (PI) staining in G0/G1 stage cells indicates that hIAPP induces apoptosis in islet-like organoids.

Generation of functional human organs according to methods described herein provides new strategies for drug-screening and disease modeling. Specifically, functional organoids can be used as models of type 2 diabetes for drug screening (FIG. 7). Human islet-like organoids responded to amyloid polypeptide (hIAPP) toxicity, an inducer of β cell loss in type 2 diabetic patients and islet dysfunction after transplantation in hyperglycemic patients, hIAPP dose-dependently induced G0/G1 arrest in 24 hours in human islet-like organoids (FIG. 7).

FIG. 8A provides a schematic showing experimental approaches to model type 2 diabetes and potentially screen for drugs using pancreatic islet and/or pancreatic organoids generated by the methods herein. In an exemplary assay, 3D mini organs are exposed to stressors that induce type 2 diabetes, such as high levels of free fatty acids (FFAs) and/or, glucose and selected cytokines. The stressed 3D mini organs are then treated with various drugs. In some embodiments, the drug is approved by the Food and Drug Administration (FDA).

As output, the following are assayed in human pancreatic islet organoids: insulin secretion, beta cell apoptosis (PI stain), lactate dehydrogenase A (LDHA) expression via a luciferase reporter, and changes in expression of marker genes including NDUFA4 (Mitochondrial oxidative phosphorylation), ESRRG (Mitochondrial function), KCNK3 (Katp channel activity) and MAFA (beta cell fate marker). For the human pancreas organoid, amylase secretion and apoptosis of exocrine cells (PI stain) are assayed. For the liver organoid, lipid accumulation is assayed using oil red O or histology. In the case of heart organoid, heart beat and heart size (hypertrophy) are measured. The intestine organoid is analyzed by measuring lipid accumulation using oil red O or histology.

FIG. 8A also shows modeling of human pancreatic cancer tumorigenesis and metastasis in a dish and the potential to screen for drugs that target those diseases. In an exemplary assay, a 3D mini human pancreas is co-cultured with pancreatic cancer cells, stellate cells, and immune cells to create human pancreatic cancer microenvironment in a dish. Various drugs (e.g., FDA-approved drugs) are then screened to find compounds which effectively suppress pancreatic cancer growth or metastasis in a mini human pancreas microenvironment. As output, the following are measured for the pancreas organoid: apoptosis of exocrine cells (PI stain), collagen synthesis (Trichrome stain) and stellate cells activation (GFAP-reporter). Potential candidate drugs identified in these assays are tested in pancreatic cancer tumorigenesis and metastasis mouse models. Genes expression and morphology as well as the degree of cell death, cell growth, and metastasis are investigated.

FIG. 8B provides a schematic showing modeling of human Type 2 diabetes in mice. In an exemplary assay, human islet organoids and/or human liver organoids are transplanted into mice. The mice are then administered various stressors that induce type 2 diabetes, such as a high fat diet (HFD) or cytokines injection. The potential candidate drugs identified in this assay are further tested in human type 2 diabetic mouse model. Genes expression and morphology as well as the degree of diabetes are investigated.

FIG. 8B also shows modeling of human pancreatic cancer tumorigenesis and metastasis in mice. In an exemplary assay, human pancreas organoids and/or human liver organoids are transplanted into mice. Mice transplanted with a mini pancreas are used to study human pancreatic cancer growth in human pancreas microenvironment. In another exemplary assay, a mini pancreas and mini liver are co-transplanted in mice. The liver is a major site for metastasis of pancreatic cancer. In vivo, endothelial cells in the mini pancreas and in the mini liver create a pancreas-liver vasculature network for pancreatic cancer metastasis. Thus, mice co-transplanted with a mini pancreas and mini liver are used to study the metastasis of human pancreatic cancer into the human liver.

An ultimate goal of the generation of functional organ-like clusters from pluripotent stem cells (PSC) is to gain insight into the mechanisms underlying human diseases. Although great advances have been made in terms of developing disease models in animals, many of these models fail to faithfully recapture the human condition. In the case of pancreatic islets, their development, cytoarchitecture, and physiology in rodents and human are notably different.

Results herein were obtained using the following materials and methods.

3D Kelcogel® (3DKG) Culture Media

Kelcogel® F low acyl gellan gum (GG-LA) obtained from Modernist Pantry is suspended in pure water 0.3% (w/v) and dissolved by stirring at 90° C. or by microwave. The aqueous solution is sterilized at 121° C. for 20 minutes in an autoclave. The solution is added to TeSR™ (Ludwid et al., Nature methods 3, 637-646) or custom TeSR™ media (800 ml DMEM/F12, 13.28 g BSA. 10 ml Glutamax, 560 mg $NaHCO_3$, 330 mg thiamine, 100 mg reduced glutathione, 3300 mg Vitamin C, 14 µg Selenium, 10 ml NEAA, 2 ml Trace element B, 1 ml Trace Element C, 7 µl β-ME, 2 ml DLC, 2 ml GABA, 2 ml LiCl, 129.7 µg pipecolic acid, Insulin 2 mg up to 1000 ml) at final concentration of 0.015%. Methylcellulose (MC) stock solution is added to a final concentration of 0.3% (R&D systems) (e.g., 0.3% Kelcogel® stock: Kelcogel® F low acyl GG-LA 300 mg+MilliQ water 100 ml; 3DKG Stem TeSR™ Base Media: STEMCELL™ TeSR™ 95 ml+0.3% Kelcogel® stock 5 ml+MC stock solution 300 ul; 3DKG Custom TeSR™ Base Media: custom TeSR™ media 95 ml+0.3% Kelcogel® stock 5 ml+MC stock solution 300 ul; 1% final concentration of Penicillin/streptozocin is added for 3DKG media).

Preparation of Human Pancreatic Endocrine Progenitors and β-Like Cells In Vitro

Pancreatic endocrine cells (hiPSC-PEs) were prepared from human iPSC using differentiation methods as previously described. Briefly, human induced pluripotent stem cells (hiPSC) derived from HUVECs were obtained from the Stem Cell Core (Salk Institute). Cells were maintained on MATRIGEL® (BD)-coated dishes in complete STEM-CELL™ TeSR™ media at 37 degree in a humidified 5% $CO_2$ incubator. For pancreatic differentiation, hiPSC were infected with a human insulin reporter lentivirus (pGreen-Zero lenti reporter human insulin, System Biosciences) by Spinfection (800 g, 1 hour). Methods 1: Media was changed to 100 ng/ml human Activin (R&D Systems), 25 ng/ml recombinant human Wnt3a (R&D Systems) in custom TeSR™ media (800 ml DMEM/F12, 13.28 g BSA, 10 ml Glutamax, 560 mg $NaHCO_3$, 330 mg thiamine, 100 mg reduced glutathione, 3300 mg Vitamin C, 14 µg Selenium, 10 ml NEAA, 2 ml Trace Element B, 1 ml Trace Element C, 7 µl β-ME, 2 ml DLC, 2 ml GABA, 2 ml LiCl, 129.7 µg PA, Insulin 2 mg up to 1000 ml) for 2 days and then 100 ng/ml human Activin in differentiation media for another 2 days (Stage 1, Pancreatic Endoderm). Subsequently, media was replaced with custom TeSR™ media with 1 uM dorsomorphin (Calbiochem), 2 µM Retinoic Acid (Sigma), 10 µM SB431542 and 1% of B27 supplement for 7 days (Stage 2). Media was then replaced with custom TeSR™ media with 10 uM forskolin (Sigma), 10 µM dexamethasone (Stemgent), 10 µM TGFβ RI Kinase inhibitor II/Alk5 inhibitor II (Calbiochem or Enzo), 10 µM Nicotinamide (Sigma), 1 µM 3,3',5-Triiodo-L-thyronine sodium salt (T3) and 1% of B27 supplement for 4-5 days (day15-day21, Pancreatic endocrine progenitors). Media was replaced every day (stage 1) or every other day (stage 2 & stage 3).

Methods 2: Media was changed to 100 ng/ml human Activin (R&D Systems), 25 ng/ml recombinant human Wnt3a (R&D Systems) or 3 µM CHIR99021 (Axon or Selleckchem) in differentiation media (S1) for 1 day and then 100 ng/ml human Activin in differentiation media (S1) for another 2 days (Stage 1, Pancreatic Endoderm). Subsequently, media was replaced with differentiation media (S2) with 50 ng/ml FGF7 (R&D Systems) for 2 days and then differentiation media (S3) with 50 ng/ml FGF7, 0.25 µM SANT-1 (Sigma), Retinoic Acid (Sigma), 100 nM LDN193189 and 100 nM α-Amyloid Precursor Protein Modulator TPB for 3 days. Subsequently, media was replaced with differentiation media (S4) with 0.25 µM SANT-1, 50 nM Retinoic Acid, 10 µM Alk5 inhibitor II, 1 µM T3 for 3 days. Subsequently, media was replaced with differentiation media (S5) with 100 nM LDN193189, 100 nM Gamma Secretase inhibitor XX GSiXX (Millipore), 10 µM Alk5 inhibitor II, 1 µM T3 for 7 days. Subsequently, media was replaced with differentiation media (S5) with 10 µM Trolox (Calbiochem), 2 µM R428 (Selleckchem), 1 mM N-acetyl cysteine, 10 µM Alk5 inhibitor II, 1 µM T3 for additional 7 to 20 days.

S1 Media (MCDB131 Media, 8 mM glucose, 2.46 g/L $NaHCO_3$, 2% Fatty acid free BSA, 0.25 mM L-Ascorbic acid 0.002% Insulin-Transferrin-Selenium ITS-X (GIBCO), 2 mM Glutamax, 1% Penicillin-Streptomycin), S2 Media (MCDB131 Media, 8 mM glucose, 1.23 g/L $NaHCO_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin), S3 Media (MCDB131 Media, 8 mM glucose, 1.23 g/L $NaHCO_3$, 2% Fatty acid free BSA, 0.25 mM L-Ascorbic acid, 0.5% Insulin-Transferrin-Selenium ITS-X (GIBCO), 2 mM Glutamax, 1% Penicillin-Streptomycin), S4 Media (MCDB131 Media, 8 mM glucose, 1.23 g/L $NaHCO_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin, 10 µg/ml Heparin, 10 µM Zinc Sulfate), S5 Media (MCDB131 Media or BLAR Media, 20 mM glucose, 1.754 g/L $NaHCO_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin). For 3 dimensional culture, hiPSC or hESC were cultured in 3DKG Stem TeSR™ Base Media with 10 µM Y-27632 for 5 to 7 days and then Media were replaced each Differentiation media with 0.015% Kelcogel and 0.3% Methylcellulose.

Generation of Three-Dimensional Pancreatic Islet Bud In Vitro: Islet-Like Organoids in Matrigel Through Co-Culture with hADSCs and HUVECs Primary HUVECs and human Adipose-derived stem cells (hADSC) (Invitrogen or PromoCell) were cultured in 15 cm dish with EBM Medium (Ronza, cc-3121) or Mesen-ProRS™ Medium (GIBCO, 12747-010 or Preadipocyte Growth Medium Kit, C-27417), respectively, at 37 degree Celsius in a humidified 5% $CO_2$ incubator. For co-culturing experiments, pancreatic endocrine progenitors derived from human iPSC were treated with Accutase, while HUVECs and hADSC were treated with TrypLE (GIBCO, 12604-013) and cells collected into a 50 ml tube respectively. After the cells were counted, $1 \times 10^6$ cells of hiPS-PP, $7 \times 10^6$ cells of HUVEC and $1-2 \times 10^5$ cells of hADSC were co-cultured in 1 well of 24 well with 300 ul of MATRIGEL® matrix. For the purpose of scalable generation of human islets like organoids, 1×10⁶ cells of hiPS-PP (day15-day21), 7×10⁶ cells of HUVEC and 1-2×10⁵ cells of hADSC were co-cultured in 3DKG Custom TeSR® media with 10 uM forskolin (Sigma), 10 μM dexamethasone (Stemgent), 10 uM TGFβ RI Kinase inhibitor II/Alk5 inhibitor II (Calbiochem or Enzo), 10 uM Nicotinamide (Sigma), 1 uM 3,3',5-Triiodo-L-thyronine sodium salt (T3) and 1% of B27 supplement, R428 (2 μM), Zinc sulfate (10 μM) and N-Cys (1 mM). (Methods 1) or co-cultured in differentiation media (S5) with 100 nM LDN193189, 100 nM Gamma Secretase inhibitor XX GSiXX (Millipore), 10 μM Alk5 inhibitor II, 1 μM T3 for 7 days. Subsequently, media was replaced with differentiation media (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days (Methods 2). Mixed cells formed spherical, islet-like clusters within a few days. Media was changed every other day.
Generation of 3D (Three-Dimensional) Pancreatic Islet Buds In Vitro: Islet-Like Organoids in Scalable Gellan Gum Through Co-Culture with hADSCs and HUVECs Cells were prepared as described above. Briefly, 1×10⁸ cells of hiPS-PP, 2-7×10⁷ cells of HUVECs and 5-7×10⁶ cells of hADSC were co-cultured in 60-100 ml of 3DKG Custom TeSR™ with 10 μM forskolin (Sigma), 10 μM dexamethasone (Stemgent), 10 μM TGFβ RI Kinase inhibitor II/Alk5 inhibitor II (Calbiochem or Enzo), 10 μM Nicotinamide (Sigma), 1 μM 3,3',5-Triiodo-L-thyronine sodium salt (T3) and 1% of B27 supplement, R428 (2 μM), Zinc sulfate (10 μM) and N-Cys (1 mM) (Methods 1) or co-cultured in differentiation media (S5) with 100 nM LDN193189, 100 nM Gamma Secretase inhibitor XX GSiXX (Millipore), 10 μM Alk5 inhibitor II, 1 μM T3 for 7 days. Subsequently, media was replaced with differentiation media (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days (Methods 2). Mixed cells formed spherical, islet-like clusters within a few days. Media was changed every day or every other day.
Generation of 3D (Three-Dimensional) Pancreatic Islets Bud In Vitro: Islet-Like Organoids in Scalable Gellan Gum 3D Culture Methods without (w/o) Using hADSC and HUVECs Human PSCs, including iPSC or ESC, were initially cultured in matrigel-coated plates (2 dimensional (2D) cultures. Cells were then treated with Accutase (Innovative Cell Technologies, Inc., San Diego, Calif.) to generate a single cell suspension, washed with PBS and centrifuged at 1000-1300 rpm for 5 minutes to pellet cells. Cells were resuspended with 3DKG Stem TeSR™ Base Medium (Stemcell Technologies, Cambridge, Mass.) with 10 μM Y-27632 (a RHO/ROCK pathway inhibitor compound) and cultured for an additional for 5 to 7 days until PSC sphere growth reached 50-100 μm diameter. Media was then replaced with differentiation media supplemented with 0.015% Kelcogel and 0.3% Methylcellulose. The culture medium was changed to differentiation medium (S1) containing 100 ng/ml human Activin (R&D Systems), 25 ng/ml recombinant human Wnt3a (R&D Systems) or 3 μM CHIR99021, a glycogen synthase kinase GSK-3 inhibitor (Axon Medchem, Reston, Va.; or Selleckchem) for 1 day and then to differentiation medium (51) containing 100 ng/ml human Activin for another 2 days (Stage 1, Pancreatic Endoderm). Subsequently, the medium was replaced with differentiation medium (S2) containing 50 ng/ml FGF7 (R&D Systems) for 2 days, and then with differentiation medium (S3) containing 50 ng/ml FGF7, 0.25 uM SANT-1 (Sigma), 1 μM Retinoic Acid (Sigma), 100 nM LDN193189 (an ALK2 and ALK3 inhibitor, Sigma) and 100 nM α-Amyloid Precursor Protein Modulator TPB for 3 days. Subsequently, this medium was replaced with differentiation medium (S4) containing 0.25 μM SANT-1, 50 nM Retinoic Acid, 10 μM Alk5 inhibitor II, 1 μM T3 for 3 days. Subsequently, the medium was replaced with differentiation medium (S5) containing 100 nM LDN193189, 100 nM Gamma Secretase inhibitor XX GSiXX (Millipore) 10 μM Alk5 inhibitor II, 1 μM T3 for 7 days. Subsequently, the medium was replaced with differentiation medium (S5) containing 10 uM Trolox (Calbiochem), 2 μM R428 (Selleckchem), 1 mM N-acetyl cysteine, 10 μM Alk5 inhibitor II, 1 μM T3 for an additional 7 to 20 days. After confirmation of the insulin gene expression by either reporter expression or qPCR (typically on day 20-30), the medium was changed to differentiation medium (S5) containing 10 μM Trolox (Calbiochem), 2 μM R428 (Selleckchem), 1 mM N-acetyl cysteine, 10 μM Alk5 inhibitor II, 1 μM T3 and 100 ng/ml recombinant human (rh)Wnt4 (R&D Systems), 400 ng/ml rhWnt5a, or 50% Wnt5a conditioned medium for 1-20 days. Wnt5a conditioned medium was prepared by culturing an L-Wnt5a cell line (ATCC, CRL-2814) in DMEM with 10% FBS, 1% Penicillin-streptomycin for 4 days after cells had reached 70-100% confluence in T175-T225 Frasko cell culture flasks.
Generation of 3D (Three-Dimensional) Liver Bud In Vitro: Organ Buds Hepatocyte cells (hiPSC-HEs) from human iPSC were prepared using differentiation methods as previously described. Briefly, hiPSCs were maintained on MATRIGEL® (BD)-coated dishes in complete STEMCELL™ TeSR™ media at 37 degrees Celsius in a humidified 5% $CO_2$ incubator. For hepatic differentiation, hiPSC (90% confluence in 6 well) were cultured with 100 ng/ml human Activin (Sigma) and 25 ng/ml recombinant human Wnt3a (R&D systems) or 3 μM CHIR99021 and 1% B27 supplement minus Insulin in RPMI1640 media for 1 day and then 100 ng/ml human Activin and 1% B27 supplement minus Insulin in RPMI media for another 4 days (Stage 1 Hepatic-Endoderm). Subsequently, media was replaced with differentiation media with 10 ng/ml bFGF, 20 ng/ml BMP4 and 1% of B27 supplement in RPMI1640 media for 3 days (Stage 2). Media was then replaced with differentiation media with 0.1 μM Dexamethasone, 20 ng/ml OncostatinM (R&D Systems) and 10-20 ng/ml Hepatic Growth Factor (HGF, R&D Systems) and 1% of B27 supplement in Hepatocyte Culture Media (Lonza, MD, CC-3198, withdraw EGF and Gentamicin/Amphotericin-B) for 4-22 days (day15-day19, Pancreatic endocrine progenitors). Media was replaced every day (stage 1) or every other day (stage 2 & stage 3). Primary HUVECs cells and human Adipose-derived stem cells (hADSC) (InVitrogen or PromoCell) were cultured in 15 cm dish with EBM Media (Ronza, cc-3121) or MesenProRS Media (GIBCO, 12747-010 or Preadipocyte Growth Medium Kit, C-27417), respectively, at 37 degree Celsius in a humidified 5% $CO_2$ incubator. For co-culturing experiments, day 10-hepatocytes derived from human iPSC were treated with Accutase, while HUVECs and hADSC were treated with TrypLE (GIBCO, 12604-013) and cells were collected into 50 ml tube, respectively. After the cells were counted, 1×10⁶ cells of hiPS-PP, 7×10⁶ cells of HUVEC and 1-2×10⁵ cells of hADSC were co-cultured in 1 well of 24 well with 300 ul of matrigel. Liver-like organoids were formed within 1 to 2 days. Then, liver-like organoids were taken out from MATRIGEL® matrix and cultured in in 3DKG Custom TeSR™.

Generation of 3D (Three-Dimensional) Heart Bud In Vitro: Organ Buds

Cardiomyocyte cells (hiPSC-CDs) were prepared from human iPSC using differentiation methods as previously described. Briefly, hiPSCs were maintained on MATRIGEL® (BD)-coated dishes in complete Stemcell™ TeSR™ media at 37 degree Celsius in a humidified 5% $CO_2$ incubator. For hepatic differentiation, hiPSC (90% confluence in 6 well) were cultured with 100 ng/ml human Activin (R&D Systems) and 10 uM CHIR99021 and 1% B27 supplement minus Insulin in RPMI1640 media for 1 days and then 1% B27 supplement minus Insulin in RPMI media for another 2 days (Stage 1 cardiac-Mesoderm). Subsequently, media was replaced with RPMI1640 with 5 uM IWP-2 and 1% B27 supplement minus Insulin in RPMI media for 1 days (Stage 2). Media was then replaced with 1% B27 supplement minus Insulin in RPMI Media for 6 days or more (Stage 3). Cardiac contraction started around day 13. Media was replaced every day (stage 1) or every other day (stage 2 & stage 3). Primary HUVECs cells and human Adipose-derived stem cells (hADSC) (Invitrogen or PromoCell) were cultured in 15 cm dish with EBM Media (Ronza, cc-3121) or MesenProRS™ Media (GIBCO, 12747-010 or Preadipocyte Growth Medium Kit, C-27417), respectively at 37 degrees Celsius in a humidified 5% $CO_2$ incubator. For co-culturing experiments, day 13 to day 15 cardiomyocytes derived from human iPSC were treated with Dispase, while HUVECs and hADSC were treated with TrypLE (GIBCO, 12604-013) and cells collected into 50 ml tube respectively. After the cells were counted, $1 \times 10^6$ cells of hiPS-PP, $7 \times 10^6$ cells of HUVEC and $1 - 2 \times 10^5$ cells of hADSC were co-cultured in 3DKG Custom TeSR™ media. Mini heart like organs capable of contracting were formed within a few days.

Generation of 3D (Three-Dimensional) Intestine Bud In Vitro: Organ Buds

Intestinal cells (hiPSC-ITs) were prepared from human iPSC using differentiation methods as previously described. Briefly, hiPSCs were maintained on Matrigel® (BD)-coated dishes in complete Stemcell™ TeSR™ Media at 37 degrees Celsius in a humidified 5% $CO_2$ incubator. For hepatic differentiation, hiPSC (90% confluence in 6 well) were cultured with 100 ng/ml human Activin (R&D Systems), 3 uM CHIR99021, 2 mM Glutamax and 1% B27 supplement minus Insulin in RPMI1640 media for 1 day and then 100 ng/ml human Activin (R&D Systems), 2 mM Glutamax and 1% B27 supplement minus Insulin in RPMI1640 media for another 3 days (Stage 1 Forgut-Endoderm). Subsequently, media was replaced with 500 ng/ml Wnt3a, 500 ng/ml FGF4 and 1% B27 supplement in RPMI 1640 media for 4 days (Stage 2). Cells were transferred to Matrigel® matrix and then a 3D-spheroid Matrigel® dorm was made in the bottom of 24 well. Media was then replaced with 1% B27 supplement, 1% N2 supplement, 500 ng/ml R-spondin, 100 ng/ml Noggin, 50 ng/ml EGF, 2 mM Glutamax™ supplement, 10 uM HEPES in DMEM/F12 Media for 7 days or more (stage3). Intestinal-like organoid spheroids were observed within a week. Media was replaced every day (stage 1) and every other day (stage 2 & stage 3). Primary HUVECs cells and human Adipose-derived stem cells (hADSC) (Invitrogen or PromoCell) were cultured in a 15 cm dish with EBM Media (Ronza, cc-3121) or MesenProRS™ Media (GIBCO®, 12747-010 or Preadipocyte Growth Medium Kit, C-27417), respectively, at 37 degrees Celsius in a humidified 5% $CO_2$ incubator. For co-culturing experiments, intestinal progenitors (day 7) derived from human iPSC were treated with Accutase, while HUVECs and hADSC were treated with TrypLE (GIBCO®, 12604-013) and cells collected into a 50 ml tube respectively. After counting the cells, $1 \times 10^6$ cells of hiPS-PP, $7 \times 10^6$ HUVEC cells and $1-2 \times 10^5$ hADSC cells were co-cultured in 3DKG Custom TeSR™ media.

Insulin Secretion Assay (Primary Mouse and Human Pancreatic Islets and Human iPSC-Derived Cells)

Insulin release from intact islets was monitored using batch incubation methods (Yoshihara et al., 2010, Nat. Commun. 1:127). Briefly, overnight-cultured isolated pancreatic islets (RPMI-1640 supplemented with 10% (v/v) fetal bovine serum and 1% (v/v) Antibiotic-Antimycotic (Gibco)) were pre-cultured at 37° C. for 30 min (Krebs-Ringer bicarbonate buffer (KRBB) containing 129.4 mM NaCl, 3.7 mM KCl, 2.7 mM $CaCl_2$, 1.3 mM $KH_2PO_4$, 1.3 mM $MgSO_4$, 24.8 mM $NaHCO_3$ (equilibrated with 5% $CO_2$, 95% $O_2$, pH7.4), 10 mM HEPES and 0.2% (v/v) BSA (fraction V, Sigma) (KRBH) with 3 mM glucose). Pancreatic islets were then incubated in KRBH buffer (500 µl/10 islets) with 3 mM or 20 mM glucose to determine insulin secretion levels. After 30 min, islets were pelleted by centrifugation and insulin levels determined by ELISA (Rat/mouse Insulin ELISA KIT (Millipore) and Human Insulin ELISA KIT (Millipore) for mouse and human islets, respectively). For human iPSC derived cells, the cells ($1 \times 10^6$ cells/well in 24 well) were pre-cultured in 3 mM glucose KRBH buffer (500 µl/well). The cells were then incubated in KRBB (200 µl/well) with 3 mM or 20 mM glucose to determine c-peptide secretion levels as indicator of insulin secretion levels. After 30 min, the cells were pelleted by centrifugation and c-peptide levels were determined by human c-peptide ELISA KIT (Millipore).

Quantitative RT-PCR Analysis

Total RNA was extracted using TRIzol reagent (Invitrogen) and RNeasy KIT (Qiagen). Reverse transcription was performed with a SuperScript III First-Strand Synthesis System kit (Invitrogen) or PrimeScript RT reagent kit (TAKARA). Real time quantitative RT-PCR (qPCR) was performed using SYBR Green (Bio-Rad).

Lentivirus Production for Proinsulin-NanoLuc

Proinsulin-NanoLuc in pLX304 (Addgene, #62057) was obtained from Addgene. Proinsulin-NanoLuc lentivirus was produced using a second-generation viral packaging system. Briefly, 14 µg of Proinsulin-NanoLuc, 6.6 µg of PsPAX2 packaging plasmid (Addgene 12260), 5.4 µg of pMD2.G envelope plasmid (Addgene 12259) and 54 µl Lipofectamin2000 (Invitrogen) were used to transfect a T75 flask of HEK293LTV packaging cells. Twenty-four (24) hours after transfection, media was changed to fresh DMEM with 10% FBS and 1% Penicillin/Streptozocine. Forty-eight (48) hours and 96 hours after transfection, viruses were collected as day 1 and day 3, respectively and passed through 0.2 µm cellulose acetate filters (VWR). Viruses were aliquoted and frozen at −80 degrees Celsius until use.

*Gaussia* Luciferase Assay for Insulin Secretion Measurement

Mouse islets, human islets and human islets like organoids were plated in their respective growth media with 10 µg/ml Polybrene® polymer (Santacruz). Viruses were then added. After overnight culture, cells were placed in fresh growth media. Forty-eight (48) to 72 hours after infection, mouse islets, human islets and human islet-like organoids were picked up by hand and then placed into 96 wells with single islet or organoid. Then, insulin secretion assays were performed. Briefly, a single islet or organoid was pre-incubated with 3 mM glucose KRBB at 37° C. for 30 min to 1 hour. The cells were then incubated in KRBB (100 µl/well) with 3 mM for 30 min and then sequentially incubated with 20 mM glucose with or without 100 nM Exendin-4 or 3 mM glucose with 20 mM KCl (100 μl/well). To determine *Gaussia* Luciferase activity as indicator of insulin secretion levels, 10 μl of samples are used for Luciferase assay using Pierce *Gaussia* Luciferase Flash Assay Kit (Prod#16159, Thermo Scientific).

INS-1 cells were infected with the virus by spinfection (800 g, 1 hour at 37 degrees Celsius) and then changed to fresh INS-1 growth media. Seventy-two (72) hours after transfection, INS-1 cells were treated with 5 μg/ml Blasticidin (Invitrogen) for 7 days to select for Proinsulin-Nano-Luc expressing cells. For insulin secretion assay, the cells ($5\times10^4$-$1\times10^5$ cells/well in 96 well) were pre-cultured in 3 mM glucose KRBB (100 μl/well). The cells were then incubated in KRBB (100 μl/well) with 3 mM and then sequentially incubated with 20 mM glucose with or without 100 nM Exendine-4 or 3 mM glucose with 20 mM KCl (100 μl/well). To determine *Gaussia* Luciferase activity as indicator of insulin secretion levels, 10 μl of samples are used for Luciferase assay using Pierce *Gaussia* Luciferase Flash Assay Kit (Prod#16159, Thermo Scientific).

Vascularization Test In Vitro

Human islet-like organoids were embedded in 1 well of 24 well plate with 300 μl of Matrigel® matrix with EBM Media (Ronza, cc-3121). Vascularization was observed within 24-72 hours.

3D Culture of hADSCs and WNT Protein Expression hADSCs undergo changes in the expression of Wnt genes, in particular genes in the Wnt5a pathway, during the spontaneous self-organization that occurs in 3D culture. (FIG. 11A). Wnt5a was found to be the predominant protein expressed among the Wnt proteins in hADSC 3D culture over time. (FIG. 11B).

Figure 12B:
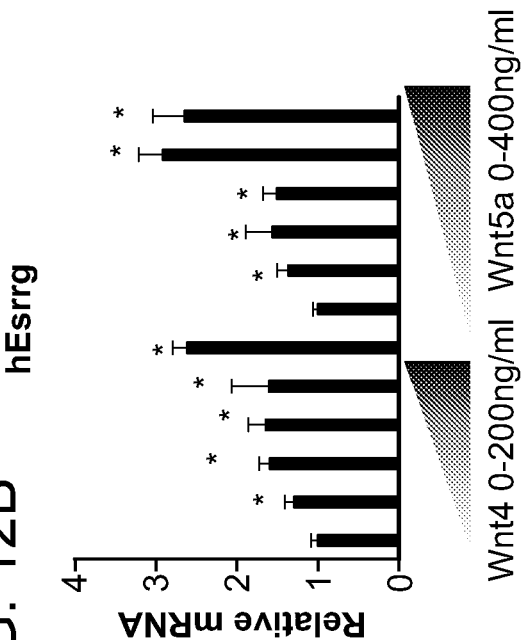
Figure 12A:
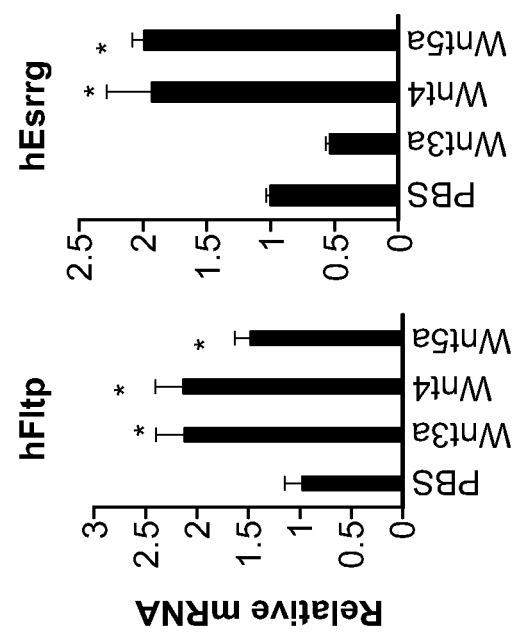
Figure 12D:
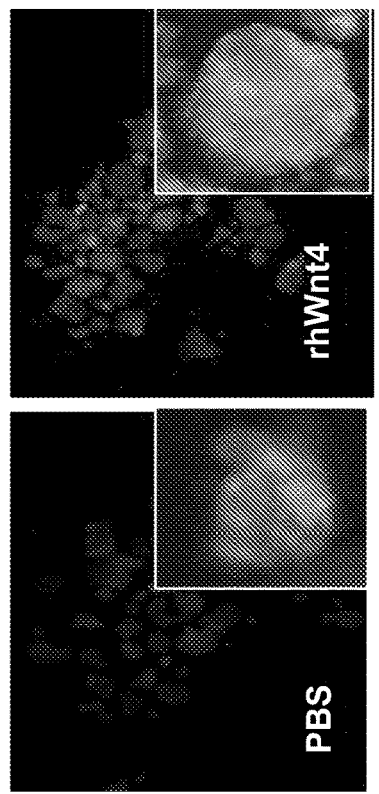
Figure 12E:
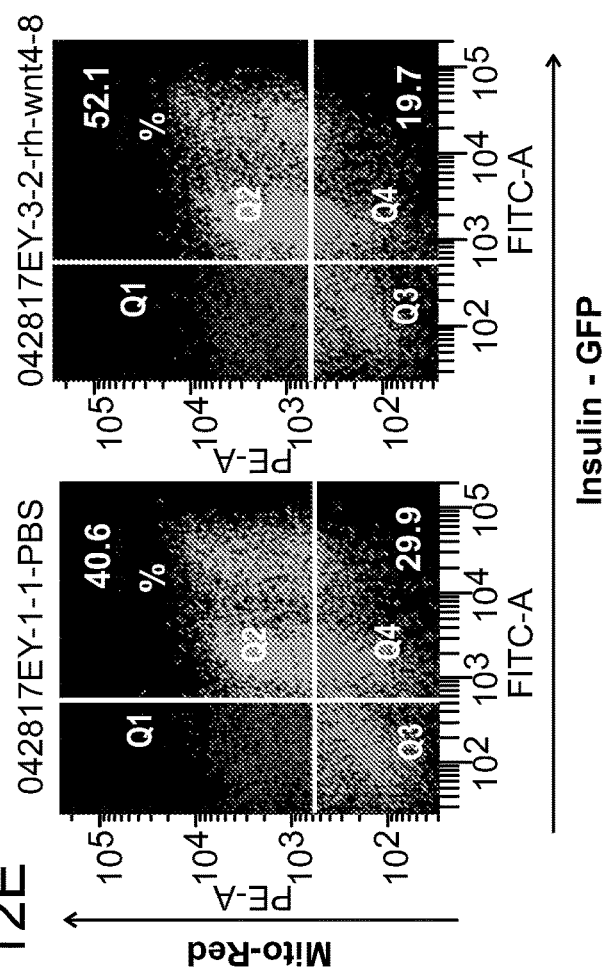
Figure 12C:
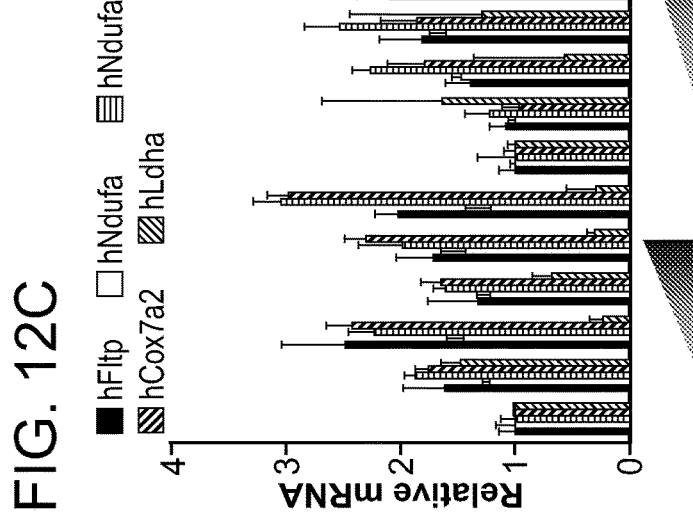

Example 5: Wnt Proteins in the Metabolic Maturation of iPSC-Derived Islet Organoids Fltp and Esrrg genes were found to be expressed in iPSC-derived islet organoids (day 21, generated without co-culture with hADSCs or HUVECs) after treatment with PBS, WNT3a (500 ng/ml), recombinant human (rh)WNT4 (100 ng/ml), or rhWNT5a (400 ng/ml) for 5 days. (FIG. 12A). As shown in FIG. 12B, Esrrg gene expression was induced in hiPSC-derived islet organoids that were generated in the absence of supporting hADSC or HUVECs, in response to increasing doses of rhWNT4 (0, 10, 25, 50, 100, 200 ng/ml) and rhWNT5a (0, 25, 50, 100, 200, 400 ng/ml). In addition, mitochondrial genes involved in oxidative phosphorylation (Cox7a2, Ndufa1, Ndufa7), lactate dehydrogenase (Ldha) and Fltp (a Wnt/planar cell polarity (PCP) effector and reporter gene) were induced in hiPSC-derived islet organoids that were generated in the absence of supporting hADSC or HUVECs, in response to increasing doses of rhWNT4 (0, 10, 25, 50, 100, 200 ng/ml) and rhWNT5a (0, 25, 50, 100, 200, 400 ng/ml), (FIG. 12C). Mitochondrial (Mitotracker; Mito-Red) and insulin (Insulin-GFP) levels were increased in hiPSC-derived islet organoids (day 27) after 8 days treatment with PBS or WNT4 (100 ng/ml). (FIG. 12D). Human iPSC-derived islet organoids (day 27) were generated after 8 days treatment with PBS or WNT4 (100 ng/ml). (FIG. 12E). Insulin production was found in hiPSC-derived islet organoids (day 27) after 8 days treatment with rhWNT4 (100 ng/ml), rhWNT5a (400 ng/ml), or WNT5a secreting fibroblast conditioned media (50%), compared with PBS and control fibroblast conditioned media (50%). (FIGS. 12F-12H). Human iPSC (hiPSC)-derived islet organoids (day 22) treated with rhWnt4 (100 ng/ml) for 12 days showed functional maturation based on their secretion of human c-peptide, as measured in response to low glucose (3 mM, "G3 mM"), high glucose (20 mM, "G20 mM"), or high KCl levels (20 mM, "KCL20 mM"), (FIG. 13).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating a pancreatic disease in a subject, the method comprising administering a pancreatic islet organoid to the subject, wherein the pancreatic islet organoid comprises an induced pluripotent stem cell (iPSC)-derived beta-like cell, an iPSC-derived alpha cell and an iPSC-derived delta cell, and wherein the pancreatic islet organoid exhibits glucose-stimulated insulin secretion (GSIS), KCl-stimulated insulin secretion, GLP-stimulated insulin secretion, somatostatin secretion, and glucagon secretion.

2. The method of claim 1, wherein the pancreatic islet organoid further comprises an adipose-derived stem cell and/or an endothelial cell.

3. The method of claim 2, wherein the adipose-derived stem cell is a human adipose-derived stem cell (hADSC) and/or the endothelial cell is a human umbilical vein endothelial cell (HUVEC).

4. The method of claim 1, wherein the pancreatic islet organoid expresses a beta cell transcription factor selected from the group consisting of: PDX1, MAFA, PAX4, PAX6, NEUROD1, NKX6-1, GATA6, and FOXA2.

5. The method of claim 1, wherein the iPSC-derived beta-like cell, alpha cell and delta cell is a human cell.

6. The method of claim 1, further wherein the pancreatic islet organoid is vascularized.

7. The method of claim 1, wherein the pancreatic islet organoid is generated by culturing an iPSC-derived beta-like cell in a 3-dimensional matrix.

8. The method of claim 7, wherein the 3-dimensional matrix comprises gellan gum and/or an extracellular matrix.

9. The method of claim 1, wherein the pancreatic islet organoid is generated in vitro.

10. The method of claim 1, wherein the pancreatic islet organoid expresses metabolic regulatory genes including ERRγ.

11. The method of claim 1, wherein the subject is further administered an immunosuppressive agent.

12. The method of claim 1, wherein the subject is human.

13. The method of claim 12, wherein at least 100,000 pancreatic islet organoids are administered to the human subject.

14. The method of claim 12, wherein the pancreatic disease is type 1 diabetes or type 2 diabetes.

15. The method of claim 14, wherein the treatment ameliorates, reduces, and/or stabilizes the type I diabetes or type II diabetes in the subject.

16. The method of claim 1, wherein the administering is by transplantation.

* * * * *

SEQUENCE LISTING

```
<160> NUMBER OF SEQ ID NOS: 52

<210> SEQ ID NO 1
<211> LENGTH: 609
<212> TYPE: PRT
<213> ORGANISM: Homo sapiens

<400> SEQUENCE: 1

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60
```

```
Lys Met Val Lys Asp Ala Leu Thr Ala Ile Glu Lys Pro Thr Gly Asp
 65                  70                  75                  80

Glu Gln Ser Ser Gly Cys Leu Glu Asn Gln Leu Pro Ala Phe Leu Glu
                 85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
            195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
            450                 455                 460

Ser Glu Asp Lys Leu Leu Ala Cys Gly Glu Gly Ala Ala Asp Ile Ile
465                 470                 475                 480
```

```
Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
            530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
            595                 600                 605

Val

<210> SEQ ID NO 2
<211> LENGTH: 2057
<212> TYPE: DNA
<213> ORGANISM: Homo sapiens

<400> SEQUENCE: 2
atattgtgct tccaccactg ccaataacaa ataactagc aaccatgaag tgggtggaat      60 caatttttt aatttccta ctaaatttta ctgaatccag aacactgcat agaaatgaat     120
atggaatagc ttccatattg gattcttacc aatgtactgc agagataagt ttagctgacc     180
tggctaccat attttttgcc cagtttgttc aagaagccac ttacaaggaa gtaagcaaaa     240
tggtgaaaga tgcattgact gcaattgaga acccactgg agatgaacag tcttcagggt     300
gtttagaaaa ccagctacct gcctttctgg aagaactttg ccatgagaaa gaaattttgg     360
agaagtacgg acattcagac tgctgcagcc aaagtgaaga gggaagacat aactgttttc     420
ttgcacacaa aaagcccact ccagcatcga tcccactttt ccaagttcca gaacctgtca     480
caagctgtga agcatatgaa gaagacaggg agacattcat gaacaaattc atttatgaga     540
tagcaagaag gcatccctcc tgtatgcac ctacaattct tctttgggct gctcgctatg     600
acaaaataat tccatcttgc tgcaaagctg aaaatgcagt tgaatgcttc caaacaaagg     660
cagcaacagt tacaaaagaa ttaagagaaa gcagcttgtt aaatcaacat gcatgtgcag     720
taatgaaaaa ttttgggacc cgaactttcc aagccataac tgttactaaa ctgagtcaga     780
agtttaccaa agttaatttt actgaaatcc agaaactagt cctggatgtg cccatgtac      840 atgagcactg ttgcagagga gatgtgctgg attgtctgca ggatggggaa aaaatcatgt     900
cctacatatg ttctcaacaa gacactctgt caaacaaaat aacagaatgc tgcaaactga     960
ccacgctgga acgtggtcaa tgtataattc atgcagaaaa tgatgaaaaa cctgaaggtc    1020
tatctccaaa tctaaacagg ttttaggag atagagattt taaccaattt tcttcagggg    1080
aaaaaaatat cttcttggca agttttgttc atgaatattc aagaagacat cctcagcttg    1140
ctgtctcagt aattctaaga gttgctaaag gataccagga gttattggag aagtgtttcc    1200
agactgaaaa ccctcttgaa tgccaagata aggagaaga agaattacag aaatacatcc    1260
aggagagcca agcattggca aagcgaagct gcggcctctt ccagaaacta ggagaatatt    1320
acttacaaaa tgcgtttctc gttgcttaca caaagaaagc cccccagctg acctcgtcgg    1380
```

```
agctgatggc catcaccaga aaaatggcag ccacagcagc cacttgttgc caactcagtg   1440
aggacaaact attggcctgt ggcgaggag cggctgacat tattatcgga cacttatgta   1500
tcagacatga aatgactcca gtaaaccctg gtgttggcca gtgctgcact tcttcatatg   1560
ccaacaggag gccatgcttc agcagcttgg tggtggatga acatatgtc cctcctgcat   1620 tctctgatga caagttcatt ttccataagg atctgtgcca agctcagggt gtagcgctgc   1680
aaacgatgaa gcaagagttt ctcattaacc ttgtgaagca aaagccacaa ataacagagg   1740
aacaacttga ggctgtcatt gcagatttct caggcctgtt ggagaaatgc tgccaaggcc   1800
aggaacagga agtctgcttt gctgaagagg gacaaaaact gatttcaaaa actcgtgctg   1860
ctttgggagt ttaaattact tcaggggaag agaagacaaa acgagtcttt cattcggtgt   1920
gaacttttct ctttaatttt aactgattta acacttttg tgaattaatg aaatgataaa   1980
gacttttatg tgagatttcc ttatcacaga aataaaatat ctccaaatgt ttcctttca   2040 aaaaaaaaaa aaaaaaa                                                  2057

<210> SEQ ID NO 3
<211> LENGTH: 609
<212> TYPE: PRT
<213> ORGANISM: Homo sapiens

<400> SEQUENCE: 3

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
```

```
            245                 250                 255
Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 4
<211> LENGTH: 2264
<212> TYPE: DNA
<213> ORGANISM: Homo sapiens

<400> SEQUENCE: 4
agtatattag tgctaatttc cctccgtttg tcctagcttt tctcttctgt caaccccaca    60
```

```
cgcctttggc acaatgaagt gggtaacctt tatttccctt cttttctctt ttagctcggc    120
ttattccagg ggtgtgtttc gtcgagatgc acacaagagt gaggttgctc atcggtttaa    180
agatttggga gaagaaaatt tcaaagcctt ggtgttgatt gcctttgctc agtatcttca    240
gcagtgtcca tttgaagatc atgtaaaatt agtgaatgaa gtaactgaat ttgcaaaaac    300
atgtgttgct gatgagtcag ctgaaaattg tgacaaatca cttcataccc ttttggaga     360 caaattatgc acagttgcaa ctcttcgtga aacctatggt gaaatggctg actgctgtgc    420
aaaacaagaa cctgagagaa atgaatgctt cttgcaacac aaagatgaca acccaaacct    480
cccccgattg gtgagaccag aggttgatgt gatgtgcact gcttttcatg acaatgaaga    540 gacattttg aaaaatact tatatgaaat tgccagaaga catccttact tttatgcccc      600
ggaactcctt ttctttgcta aaaggtataa agctgctttt acagaatgtt gccaagctgc    660
tgataaagct gcctgcctgt tgccaaagct cgatgaactt cgggatgaag ggaaggcttc    720
gtctgccaaa cagagactca agtgtgccag tctccaaaaa tttggagaaa gagctttcaa    780
agcatgggca gtagctcgcc tgagccagag atttcccaaa gctgagtttg cagaagtttc    840
caagttagtg acagatctta ccaaagtcca cacggaatgc tgccatggag atctgcttga    900
atgtgctgat gacagggcgg accttgccaa gtatatctgt gaaaatcaag attcgatctc    960
cagtaaactg aaggaatgct gtgaaaaacc tctgttggaa aaatcccact gcattgccga   1020
agtggaaaat gatgagatgc ctgctgactt gccttcatta gctgctgatt ttgttgaaag   1080
taaggatgtt tgcaaaaact atgctgaggc aaaggatgtc ttcctgggca tgttttgta    1140 tgaatatgca agaaggcatc ctgattactc tgtcgtgctg ctgctgagac ttgccaagac   1200
atatgaaacc actctagaga agtgctgtgc cgctgcagat cctcatgaat gctatgccaa   1260
agtgttcgat gaatttaaac ctcttgtgga agagcctcag aatttaatca acaaaattg    1320 tgagcttttt gagcagcttg gagagtacaa attccagaat gcgctattag ttcgttacac   1380
caagaaagta ccccaagtgt caactccaac tcttgtagag gtctcaagaa acctaggaaa   1440
agtgggcagc aaatgttgta acatcctga agcaaaaaga atgccctgtg cagaagacta    1500
tctatccgtg gtcctgaacc agttatgtgt gttgcatgag aaaacgccag taagtgacag   1560
agtcaccaaa tgctgcacag aatccttggt gaacaggcga ccatgctttt cagctctgga   1620
agtcgatgaa acatacgttc ccaaagagtt taatgctgaa acattcaccct tccatgcaga   1680 tatatgcaca ctttctgaga aggagagaca aatcaagaaa caaactgcac ttgttgagct   1740
cgtgaaacac aagcccaagg caacaaaaga gcaactgaaa gctgttatgg atgatttcgc   1800
agcttttgta gagaagtgct gcaaggctga cgataaggag acctgctttg ccgaggaggg   1860
taaaaaactt gttgctgcaa gtcaagctgc cttaggctta taacatcaca tttaaaagca   1920
tctcagccta ccatgagaat aagagaaaga aaatgaagat caaaagctta ttcatctgtt   1980 tttcttttc gttggtgtaa agccaacacc ctgtctaaaa aacataaatt tctttaatca    2040
ttttgcctct tttctctgtg cttcaattaa taaaaaatgg aaagaatcta atagagtggt   2100
acagcactgt tattttcaa agatgtgttg ctatcctgaa aattctgtag gttctgtgga    2160
agttccagtg ttctctctta ttccacttcg gtagaggatt tctagtttct tgtgggctaa   2220
ttaaataaat cattaatact cttctaaaaa aaaaaaaaaa aaaa                    2264
```

<210> SEQ ID NO 5
<211> LENGTH: 313
<212> TYPE: PRT

<213> ORGANISM: Homo sapiens

<400> SEQUENCE: 5

```
Met Tyr Val Ser Tyr Leu Leu Asp Lys Asp Val Ser Met Tyr Pro Ser
1               5                   10                  15
Ser Val Arg His Ser Gly Gly Leu Asn Leu Ala Pro Gln Asn Phe Val
            20                  25                  30
Ser Pro Pro Gln Tyr Pro Asp Tyr Gly Gly Tyr His Val Ala Ala Ala
        35                  40                  45
Ala Ala Ala Ala Ala Asn Leu Asp Ser Ala Gln Ser Pro Gly Pro Ser
    50                  55                  60
Trp Pro Ala Ala Tyr Gly Ala Pro Leu Arg Glu Asp Trp Asn Gly Tyr
65                  70                  75                  80
Ala Pro Gly Gly Ala Ala Ala Ala Asn Ala Val Ala His Gly Leu
                85                  90                  95
Asn Gly Gly Ser Pro Ala Ala Ala Met Gly Tyr Ser Ser Pro Ala Asp
            100                 105                 110
Tyr His Pro His His Pro His His Pro His His Pro Ala Ala
        115                 120                 125
Ala Pro Ser Cys Ala Ser Gly Leu Leu Gln Thr Leu Asn Pro Gly Pro
    130                 135                 140
Pro Gly Pro Ala Ala Thr Ala Ala Glu Gln Leu Ser Pro Gly Gly
145                 150                 155                 160
Gln Arg Arg Asn Leu Cys Glu Trp Met Arg Lys Pro Ala Gln Ser
                165                 170                 175
Leu Gly Ser Gln Val Lys Thr Arg Thr Lys Asp Lys Tyr Arg Val Val
            180                 185                 190
Tyr Thr Asp His Gln Arg Leu Glu Leu Glu Lys Glu Phe His Tyr Ser
        195                 200                 205
Arg Tyr Ile Thr Ile Arg Arg Lys Ala Glu Leu Ala Ala Thr Leu Gly
    210                 215                 220
Leu Ser Glu Arg Gln Val Lys Ile Trp Phe Gln Asn Arg Arg Ala Lys
225                 230                 235                 240
Glu Arg Lys Ile Asn Lys Lys Lys Leu Gln Gln Gln Gln Gln Gln
                245                 250                 255
Pro Pro Gln Pro Pro Pro Pro Pro Gln Pro Pro Gln Pro
            260                 265                 270
Gly Pro Leu Arg Ser Val Pro Glu Pro Leu Ser Pro Val Ser Ser Leu
        275                 280                 285
Gln Ala Ser Val Ser Gly Ser Val Pro Gly Val Leu Gly Pro Thr Gly
    290                 295                 300
Gly Val Leu Asn Pro Thr Val Thr Gln
305                 310
```

<210> SEQ ID NO 6
<211> LENGTH: 2370
<212> TYPE: DNA
<213> ORGANISM: Homo sapiens

<400> SEQUENCE: 6

```
ctccaaccat tggtgtctgt gtcattacta atagagtctt gtaaacactc gttaatcacg      60
gaaggccgcc ggcctggggc tccgcacgcc agcctgtggc gggtcttccc cgcctctgca     120
gcctagtggg aaggaggtgg gaggaaagaa ggaagaaagg gagggaggga ggaggcaggc     180
cagagggagg gaccgcctcg gaggcagaag agccgcgagg agccagcgga gcaccgcggg     240
```

```
ctggggcgca gccacccgcc gctcctcgag tcccctcgcc cctttccctt cgtgccccc     300 ggcagcctcc agcgtcggtc cccaggcagc atggtgaggt ctgctcccgg accctcgcca    360
ccatgtacgt gagctacctc ctggacaagg acgtgagcat gtaccctagc tccgtgcgcc    420
actctggcgg cctcaacctg cgccgcagaa cttcgtcag ccccccgcag tacccggact     480
acggcggtta ccacgtggcg gccgcagctg cagcggcagc gaacttggac agcgcgcagt    540
ccccggggcc atcctggccg gcagcgtatg gcgccccact ccgggaggac tggaatggct    600
acgcgcccgg aggcgccgcg gccgccgcca cgccgtggc tcacggcctc aacggtggct     660
ccccggccgc agccatgggc tacagcagcc ccgcagacta ccatccgcac caccaccgc     720 atcaccaccc gcaccacccg gccgccgcgc cttcctgcgc ttctgggctg ctgcaaacgc    780
tcaaccccgg ccctcctggg cccgccgcca ccgctgccgc cgagcagctg tctcccggcg    840
gccagcggcg gaacctgtgc gagtggatgc ggaagccggc gcagcagtcc ctcggcagcc    900
aagtgaaaac caggacgaaa gacaaatatc gagtggtgta cacggaccac cagcggctgg    960
agctggagaa ggagtttcac tacagtcgct acatcaccat ccggaggaaa gccgagctag   1020
ccgccacgct ggggctctct gagaggcagg ttaaaatctg gtttcagaac cgcagagcaa   1080
aggagaggaa aatcaacaag aagaagttgc agcagcaaca gcagcagcag ccaccacagc   1140
cgcctccgcc gccaccacag cctcccccagc ctcagccagg tcctctgaga agtgtcccag   1200
agcccttgag tccggtgtct tccctgcaag cctcagtgtc tggctctgtc cctggggttc   1260
tggggccaac tggggggtg ctaaaccca ccgtcaccca gtgacccacc gggttctgca    1320
gcggcagagc aattccaggc tgagccatga ggagcgtgga ctctgctaga ctcctcagga   1380
gagacccctc ccctcccacc cacagccata gacctacaga cctggctctc agaggaaaaa   1440
tgggagccag gagtaagaca agtgggattt ggggcctcaa gaaatatact ctcccagatt   1500
tttacttttt cccatctggc ttttctgcc actgaggaga cagaaagcct ccgctgggct    1560
tcattccgga ctggcagaag cattgcctgg actgaccaca ccaaccaggc cttcatcctc   1620
ctccccagct cttctcttcc tagatctgca ggctgcacct ctggctagag ccgaggggag   1680
agagggactc aagggaaagg caagcttgag gccaagatgg ctgctgcctg ctcatggccc   1740
tcggaggtcc agctgggcct cctgcctccg ggcaggcaag gtttacactg cggaagccaa   1800
aggcagctaa gatagaaagc tggactgacc aaagactgca gaaccccag gtggcctgcg    1860 tcttttttct cttcccttcc cagaccagga aaggcttggc tggtgtatgc acagggtgtg   1920
gtatgagggg gtggttattg gactccaggc ctgaccaggg ggcccgaaca gggacttgtt   1980
tagagagcct gtcaccagag cttctctggg ctgaatgtat gtcagtgcta taaatgccag   2040
agccaacctg gacttcctgt cattttcaca atcttgggc tgatgaagaa ggggtgggg     2100 ggagtttgtg ttgttgttgc tgctgttttgg gttgttggtc tgtgtaacat ccaagccaga   2160 gttttttaaag ccttctggat ccatgggggg agaagtgata tggtgaaggg aagtggggag   2220
tatttgaaca cagttgaatt ttttctaaaa agaaaaagag ataaatgagc tttccagatt    2280
tcagattctg tatttatctt cagattttgt ctgcaactat ttttatttt ttaaagaaat     2340 gaaatatctt caaaaaaaaa aaaaaaaaa                                      2370
```

<210> SEQ ID NO 7
<211> LENGTH: 503
<212> TYPE: PRT
<213> ORGANISM: Homo sapiens

```
<400> SEQUENCE: 7

Met Asp Leu Ile Pro Asn Leu Ala Val Glu Thr Trp Leu Leu Leu Ala
1               5                   10                  15

Val Ser Leu Ile Leu Leu Tyr Leu Tyr Gly Thr Arg Thr His Gly Leu
            20                  25                  30

Phe Lys Lys Leu Gly Ile Pro Gly Pro Thr Pro Leu Pro Phe Leu Gly
        35                  40                  45

Asn Ala Leu Ser Phe Arg Lys Gly Tyr Trp Thr Phe Asp Met Glu Cys
    50                  55                  60

Tyr Lys Lys Tyr Arg Lys Val Trp Gly Ile Tyr Asp Cys Gln Gln Pro
65                  70                  75                  80

Met Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Asn Ala Ile Ser Ile Ala Glu Asp Glu Glu Trp Lys Arg
        115                 120                 125

Ile Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys His Val Phe
                165                 170                 175

Gly Ala Tyr Ser Met Asp Val Ile Thr Ser Thr Ser Phe Gly Val Ser
            180                 185                 190

Ile Asp Ser Leu Asn Asn Pro Gln Asp Pro Phe Val Glu Asn Thr Lys
    195                 200                 205

Lys Leu Leu Arg Phe Asn Pro Leu Asp Pro Phe Val Leu Ser Ile Lys
    210                 215                 220

Val Phe Pro Phe Leu Thr Pro Ile Leu Glu Ala Leu Asn Ile Thr Val
225                 230                 235                 240

Phe Pro Arg Lys Val Ile Ser Phe Leu Thr Lys Ser Val Lys Gln Ile
                245                 250                 255

Lys Glu Gly Arg Leu Lys Glu Thr Gln Lys His Arg Val Asp Phe Leu
            260                 265                 270

Gln Leu Met Ile Asp Ser Gln Asn Ser Lys Asp Ser Glu Thr His Lys
        275                 280                 285

Ala Leu Ser Asp Leu Glu Leu Met Ala Gln Ser Ile Ile Phe Ile Phe
    290                 295                 300

Ala Gly Tyr Glu Thr Thr Ser Ser Val Leu Ser Phe Ile Ile Tyr Glu
305                 310                 315                 320

Leu Ala Thr His Pro Asp Val Gln Gln Lys Val Gln Lys Glu Ile Asp
                325                 330                 335

Thr Val Leu Pro Asn Lys Ala Pro Pro Thr Tyr Asp Thr Val Leu Gln
            340                 345                 350

Leu Glu Tyr Leu Asp Met Val Val Asn Glu Thr Leu Arg Leu Phe Pro
        355                 360                 365

Val Ala Met Arg Leu Glu Arg Val Cys Lys Lys Asp Val Glu Ile Asn
    370                 375                 380

Gly Met Phe Ile Pro Lys Gly Val Val Met Ile Pro Ser Tyr Val
385                 390                 395                 400

Leu His His Asp Pro Lys Tyr Trp Thr Glu Pro Glu Lys Phe Leu Pro
                405                 410                 415
```

```
Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
            435                 440                 445

Leu Val Asn Met Lys Leu Ala Leu Val Arg Val Leu Gln Asn Phe Ser
450                 455                 460

Phe Lys Pro Cys Lys Glu Thr Gln Ile Pro Leu Lys Leu Arg Phe Gly
465                 470                 475                 480

Gly Leu Leu Leu Thr Glu Lys Pro Ile Val Leu Lys Ala Glu Ser Arg
                485                 490                 495

Asp Glu Thr Val Ser Gly Ala
            500

<210> SEQ ID NO 8
<211> LENGTH: 2099
<212> TYPE: DNA
<213> ORGANISM: Homo sapiens

<400> SEQUENCE: 8
aatcactgct gtgcagggca ggaaagctcc acacacacag cccagcaaac agcagcacgc    60
tgctgaaaaa aagactcaga ggagagagat aaggaaggaa agtagtgatg gatctcatcc   120
caaacttggc cgtggaaacc tggcttctcc tggctgtcag cctgatactc tctctatctat  180 atggaacccg tacacatgga cttttttaaga agcttggaat tccagggccc acacctctgc  240
cttttttggg aaatgctttg tccttccgta agggctattg gacgtttgac atggaatgtt   300
ataaaaagta tagaaaagtc tggggtattt atgactgtca acagcctatg ctggctatca   360
cagatcccga catgatcaaa acagtgctag tgaaagaatg ttattctgtc ttcacaaacc   420
ggaggccttt cgggccagtg ggatttatga aaaatgccat ctctatagct gaggatgaag   480
aatggaagag aatacgatca ttgctgtctc aacattcac cagcggaaaa ctcaaggaga    540
tggtccctat cattgcccag tatggagatg tgttggtgag aaatctgagg cgggaagcag   600
agacaggcaa gcctgtcacc ttgaaacacg tctttggggc ctacagcatg gatgtgatca   660
ctagcacatc atttggagtg agcatcgact ctctcaacaa tccacaagac cccttttgtgg  720 aaaacaccaa gaagcttttta agatttaatc cattagatcc attcgttctc tcaataaaag   780
tctttccatt ccttacccca attcttgaag cattaaatat cactgtgttt ccaagaaaag   840
ttataagttt tctaacaaaa tctgtaaaac agataaaaga aggtcgcctc aaagagacac   900
aaaagcaccg agtggatttc cttcagctga tgattgactc tcagaattca aaagactctg   960
agacccacaa agctctgtct gatctggagc tcatggccca atcaattatc tttatttttg  1020
ctggctatga aaccacgagc agtgttctct ccttcattat atatgaactg gccactcacc  1080
ctgatgtcca gcagaaagtg cagaaggaaa ttgatacagt tttacccaat aaggcaccac  1140
ccacctatga tactgtgcta cagttggagt atcttgacat ggtggtgaat gaaacactca   1200
gattattccc agttgctatg agacttgaga gggtctgcaa aaagatgtt gaaatcaatg   1260 ggatgtttat tcccaaaggg gtggtggtga tgattccaag ctatgttctt catcatgacc  1320
caaagtactg gacagagcct gagaagttcc tccctgaaag gttcagtaaa agaacaagg   1380 acaacataga tccttacata tacacaccct ttggaagtgg acccagaaac tgcattggca  1440
tgaggtttgc tctcgtgaac atgaaacttg ctcagtcag agtccttcag aacttctcct   1500
tcaaaccttg taagaaaaca cagatccccc tgaaattacg ctttggagga cttcttctaa  1560
```

```
cagaaaaacc cattgttcta aaggctgagt caagggatga gaccgtaagt ggagcctgat    1620
ttccctaagg acttctggtt tgctctttaa gaaagctgtg ccccagaaca ccagagacct    1680
caaattactt tacaaataga accctgaaat gaagacgggc ttcatccaat gtgctgcata    1740
aataatcagg gattctgtac gtgcattgtg ctctctcatg gtctgtatag agtgttatac    1800
ttggtaatat agaggagatg accaaatcag tgctggggaa gtagatttgg cttctctgct    1860
tctcatagga ctatctccac caccccagt  tagcaccatt aactcctcct gagctctgat    1920
aacataatta acatttctca ataatttcaa ccacaatcat taataaaaat aggaattatt    1980
ttgatggctc taacagtgac atttatatca tgtgttatat ctgtagtatt ctatagtaag    2040
ctttatatta agcaaatcaa taaaaacctc tttacaaaag taaaaaaaaa aaaaaaaaa     2099
```

<210> SEQ ID NO 9
<211> LENGTH: 435
<212> TYPE: PRT
<213> ORGANISM: Homo sapiens

<400> SEQUENCE: 9

```
Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
    130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Val Gln Pro Ala Lys
        195                 200                 205

Lys Pro Tyr Asn Lys Ile Val Ser His Leu Leu Val Ala Glu Pro Glu
    210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
            260                 265                 270

Asp Gln Met Ser Leu Leu Gln Ser Ala Trp Met Glu Ile Leu Ile Leu
        275                 280                 285
```

```
Gly Val Val Tyr Arg Ser Leu Ser Phe Glu Asp Glu Leu Val Tyr Ala
        290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335

Lys Leu Glu Lys Glu Glu Phe Val Thr Leu Lys Ala Ile Ala Leu Ala
                340                 345                 350

Asn Ser Asp Ser Met His Ile Glu Asp Val Glu Ala Val Gln Lys Leu
        355                 360                 365

Gln Asp Val Leu His Glu Ala Leu Gln Asp Tyr Glu Ala Gly Gln His
        370                 375                 380

Met Glu Asp Pro Arg Arg Ala Gly Lys Met Leu Met Thr Leu Pro Leu
385                 390                 395                 400

Leu Arg Gln Thr Ser Thr Lys Ala Val Gln His Phe Tyr Asn Ile Lys
                405                 410                 415

Leu Glu Gly Lys Val Pro Met His Lys Leu Phe Leu Glu Met Leu Glu
                420                 425                 430

Ala Lys Val
        435

<210> SEQ ID NO 10
<211> LENGTH: 5559
<212> TYPE: DNA
<213> ORGANISM: Homo sapiens

<400> SEQUENCE: 10
aagctccaat cggggcttta agtccttgat taggagagtg tgagagcttt ggtcccaact      60
ggctgtgcct ataggcttgt cactaggaga acatttgtgt taattgcact gtgctctgtc     120
aaggaaactt tgatttatag ctggggtgca caaataatgg ttgccggtcg cacatggatt     180
cggtagaact ttgccttcct gaatcttttt ccctgcacta cgaggaagag tagacttgaa     240
tgagacctgc ctcatcagtc atgggatcat agtgtcacag atggaaaagc aactatcagc     300
tgaattgtac tgaactacac acttggctaa ttcatcttat tgctctacac atctaaagga     360
aggctcattc tgttcttgga gtctagacag catcaggagt tgggctcagt gaacaaaact     420
ttaatgtcta gagcatttat gagggtttta atgattggaa aatctatcct gagaatgtgg     480
tcaccatatg tgacagcctt gctttctatc ttgtcttcag tttctggggc ttctctgcag     540
aatgtcaaac aaagatcgac acattgattc cagctgttcg tccttcatca agacggaacc     600
ttccagccca gctccctga cggacagcgt caaccaccac agccctggtg gctcttcaga     660
cgccagtggg agctacagtt caaccatgaa tggccatcag aacggacttg actcgccacc     720
tctctaccct tctgctccta tcctgggagg tagtgggcct gtcaggaaac tgtatgatga     780
ctgctccagc accattgttg aagatcccca gaccaagtgt gaatacatgc tcaactcgat     840
gcccaagaga ctgtgtttag tgtgtggtga catcgcttct gggtaccact atggggtagc     900
atcatgtgaa gcctgcaagg cattcttcaa gaggacaatt caaggcaata tagaatacag     960
ctgccctgcc acgaatgaat gtgaaatcac aaagcgcaga cgtaaatcct gccaggcttg    1020
ccgcttcatg aagtgtttaa agtgggcat gctgaaagaa ggggtgcgtc ttgacagagt    1080
acgtggaggt cggcagaagt acaagcgcag gatagatgcg gagaacagcc catacctgaa    1140
ccctcagctg gttcagccag ccaaaaagcc atataacaag attgtctcac atttgttggt    1200
```

```
ggctgaaccg agaagatct atgccatgcc tgaccctact gtccccgaca gtgacatcaa      1260
agccctcact acactgtgtg acttggccga ccgagagttg gtggttatca ttggatgggc     1320
gaagcatatt ccaggcttct ccacgctgtc cctggcggac cagatgagcc ttctgcagag     1380
tgcttggatg gaaattttga tccttggtgt cgtataccgg tctctttcgt ttgaggatga     1440
acttgtctat gcagacgatt ataatggac gaagaccag tccaaattag caggccttct       1500
tgatctaaat aatgctatcc tgcagctggt aaagaaatac aagagcatga agctggaaaa     1560
agaagaattt gtcaccctca agctatagc tcttgctaat tcagactcca tgcacataga     1620
agatgttgaa gccgttcaga agcttcagga tgtcttacat gaagcgctgc aggattatga    1680
agctggccag cacatggaag accctcgtcg agctggcaag atgctgatga cactgccact    1740
cctgaggcag acctctacca aggccgtgca gcatttctac aacatcaaac tagaaggcaa    1800
agtcccaatg cacaaacttt ttttggaaat gttggaggcc aaggtctgac taaaagctcc    1860
ctgggccttc ccatccttca tgttgaaaaa gggaaaataa acccaagagt gatgtcgaag    1920
aaacttagag tttagttaac aacatcaaaa atcaacagac tgcactgata atttagcagc    1980
aagactatga agcagctttc agattcctcc ataggttcct gatgagtttc tttctacttt    2040
ctccatcatc ttcttcctc tttcttccca catttctctt tctctttatt ttttctcctt     2100
ttcttctttc acctccctta tttctttgct tctttcattc ctagttccca ttctccttta    2160
ttttcttccc gtctgcctgc cttctttctt ttctttacct actctcattc ctctcttttc    2220
tcatccttcc cctttttct aaatttgaaa tagctttagt ttaaaaaaaa atcctcccctt    2280 ccccccttttcc tttcccttttc tttccttttt ccctttcctt ttcccttttcc tttccttttcc  2340 tcttgaccct ctttccatct ttctttttct tccttctgct gctgaacttt taaaagaggt      2400
ctctaactga agagagatgg aagccagccc tgccaaagga tggagatcca taatatggat      2460
gccagtgaac ttattgtgaa ccatactgtc cccaatgact aaggaatcaa agagagagaa      2520
ccaacgttcc taaaagtaca gtgcaacata tacaaattga ctgagtgcag tattagattt      2580
catgggagca gcctctaatt agacaactta agcaacgttg catcggctgc ttcttatcat     2640
tgcttttcca tctagatcag ttacagccat ttgattcctt aattgttttt tcaagtcttc     2700
caggtatttg ttagtttagc tactatgtaa cttttttcagg gaatagttta agctttattc    2760
attcatgcaa tactaaagag aaataagaat actgcaattt tgtgctggct ttgaacaatt     2820
acgaacaata atgaaggaca aatgaatcct gaaggaagat ttttaaaaat gttttgtttc     2880
ttcttacaaa tggagatttt tttgtaccag ctttaccact tttcagccat ttattaatat     2940
gggaatttaa cttactcaag caatagttga agggaaggtg catattatca cggatgcaat     3000
ttatgttgtg tgccagtctg gtcccaaaca tcaatttctt aacatgagct ccagtttacc    3060
taaatgttca ctgacacaaa ggatgagatt acacctacag tgactctgag tagtcacata    3120
tataagcact gcacatgaga tatagatccg tagaattgtc aggagtgcac ctctctactt    3180
gggaggtaca attgccatat gatttctagc tgccatggtg gttaggaatg tgatactgcc    3240
tgtttgcaaa gtcacagacc ttgcctcaga aggagctgtg agccagtatt catttaagag    3300
gcaataaggc aaatgccaga attaaaaaaa aaaatcatca aagacagaaa atgcctgacc    3360
aaattctaaa acctaatcca tataagttta ttcatttagg aatgttcgtt taaattaatc    3420
tgcagttttt accaagagct aagccaatat atgtgctttt caaccagtat tgtcacagca    3480
tgaaagtcaa gtcaggttcc agactgttaa gaggtgtaat ctaatgaaga aatcaattag    3540
atgccccgaa atctacagtc gctgaataac caataaacag taacctccat caaatgctat    3600
```

```
accaatggac cagtgttagt agctgctccc tgtattatgt gaacagtctt attctatgta   3660
cacagatgta attaaaattg taatcctaac aaacaaaaga aatgtagttc agcttttcaa   3720
tgtttcatgt ttgctgtgct tttctgaatt ttatgttgca ttcaaagact gttgtcttgt   3780
tcttgtggtg tttggattct tgtggtgtgt gcttttagac acagggtaga attagagaca   3840
atattggatg tacaattcct caggagacta cagtagtata ttctattcct taccagtaat   3900
aaggttcttc ctaataataa ttaagagatt gaaactccaa acaagtattc attatgaaca   3960
gatacacatc aaaatcataa taatattttc aaaacaagga ataatttctc taatggttta   4020
ttatagaata ccaatgtata gcttagaaat aaaactttga atatttcaag aatatagata   4080
agtctaattt ttaaatgctg tatatatggc tttcactcaa tcatctctca gatgttgtta   4140
ttaactcgct ctgtgttgtt gcaaaacttt tggtgcaga ttcgtttcca aaactattgc    4200
tactttgtgt gctttaaaca aaataccttg ggttgatgaa acatcaaccc agtgctagga   4260
atactgtgta tctatcatta gctatatggg actatattgt agattgtggt ttctcagtag   4320
agaagtgact gtagtgtgat tctagataaa tcatcattag caattcattc agatggtcaa   4380
taacttgaaa tttatagctg tgataggagt tcagaaattg gcacatccct ttaaaaataa   4440
caacagaaaa tacaactcct gggaaaaaag gtgctgattc tataagatta tttatatatg   4500
taagtgttta aaaagattat tttccagaaa gtttgtgcag ggtttaagtt gctactattc   4560
aactacacta tatataaata aaatatatac aatatataca ttgttttcac tgtatcacat   4620
taaagtactt gggcttcaga agtaagagcc aaccaactga aaacctgaga tggagatatg   4680
ttcaaagaat gagatacaat ttttttagttt tcagtttaag taactctcag cattacaaaa   4740
gagtaagtat ctcacaaata ggaaatataaaa ctaaaacgtg gatttaaaaa gaactgcacg   4800
ggctttaggg taaatgctca tcttaaacct cactagaggg aagtcttctc aagttttcaag  4860 caagaccatt tacttaatgt gaagttttgg aaagttataa aggtgtatgt tttagccata   4920 tgatttttaat tttaattttg cttcttttag gttcgttctt atttaaagca atatgattgt   4980
gtgactcctt gtagttacac ttgtgtttca atcagatcag attgttgtat ttattccact   5040 atttttgcatt taaatgataa cataaaagat ataaaaaatt taaaactgct atttttctta   5100
tagaagagaa aatgggtgtt ggtgattgta ttttaattat ttaagcgtct ctgtttacct   5160
gcctaggaaa acattttatg gcagtcttat gtgcaaagat cgtaaaagga caaaaatttt   5220
aaactgctta taataatcca ggagttgcat tatagccagt agtaaaaata ataataataa   5280
taataaaacc atgtctatag ctgtagatgg gcttcacatc tgtaaagcaa tcaattgtat   5340 attttttgtga tgtgtaccat actgtgtgct ccagcaaatg tccatttgtg taaatgtatt   5400 tatttttatat tgtatatatt gttaaatgca aaaaggagat atgattctgt aactccaatc   5460
agttcagatg tgtaactcaa attattatgc ctttcaggat gatggtagag caatattaaa   5520
caagcttcca cttttgactg ctaaaaaaaa aaaaaaaa                            5559
```

<210> SEQ ID NO 11
<211> LENGTH: 463
<212> TYPE: PRT
<213> ORGANISM: Homo sapiens

<400> SEQUENCE: 11

Met His Ser Ala Ser Ser Met Leu Gly Ala Val Lys Met Glu Gly His
1               5                   10                  15

Glu Pro Ser Asp Trp Ser Ser Tyr Tyr Ala Glu Pro Glu Gly Tyr Ser

-continued

```
             20                  25                  30
Ser Val Ser Asn Met Asn Ala Gly Leu Gly Met Asn Gly Met Asn Thr
         35                  40                  45
Tyr Met Ser Met Ser Ala Ala Ala Met Gly Ser Gly Ser Gly Asn Met
         50                  55                  60
Ser Ala Gly Ser Met Asn Met Ser Ser Tyr Val Gly Ala Gly Met Ser
 65                  70                  75                  80
Pro Ser Leu Ala Gly Met Ser Pro Gly Ala Gly Ala Met Ala Gly Met
                 85                  90                  95
Gly Gly Ser Ala Gly Ala Ala Gly Val Ala Gly Met Gly Pro His Leu
                100                 105                 110
Ser Pro Ser Leu Ser Pro Leu Gly Gly Gln Ala Ala Gly Ala Met Gly
                115                 120                 125
Gly Leu Ala Pro Tyr Ala Asn Met Asn Ser Met Ser Pro Met Tyr Gly
                130                 135                 140
Gln Ala Gly Leu Ser Arg Ala Arg Asp Pro Lys Thr Tyr Arg Arg Ser
145                 150                 155                 160
Tyr Thr His Ala Lys Pro Pro Tyr Ser Tyr Ile Ser Leu Ile Thr Met
                165                 170                 175
Ala Ile Gln Gln Ser Pro Asn Lys Met Leu Thr Leu Ser Glu Ile Tyr
                180                 185                 190
Gln Trp Ile Met Asp Leu Phe Pro Phe Tyr Arg Gln Asn Gln Gln Arg
                195                 200                 205
Trp Gln Asn Ser Ile Arg His Ser Leu Ser Phe Asn Asp Cys Phe Leu
                210                 215                 220
Lys Val Pro Arg Ser Pro Asp Lys Pro Gly Lys Gly Ser Phe Trp Thr
225                 230                 235                 240
Leu His Pro Asp Ser Gly Asn Met Phe Glu Asn Gly Cys Tyr Leu Arg
                245                 250                 255
Arg Gln Lys Arg Phe Lys Cys Glu Lys Gln Leu Ala Leu Lys Glu Ala
                260                 265                 270
Ala Gly Ala Ala Gly Ser Gly Lys Lys Ala Ala Gly Ala Gln Ala
                275                 280                 285
Ser Gln Ala Gln Leu Gly Glu Ala Ala Gly Pro Ala Ser Glu Thr Pro
                290                 295                 300
Ala Gly Thr Glu Ser Pro His Ser Ser Ala Ser Pro Cys Gln Glu His
305                 310                 315                 320
Lys Arg Gly Gly Leu Gly Glu Leu Lys Gly Thr Pro Ala Ala Ala Leu
                325                 330                 335
Ser Pro Pro Glu Pro Ala Pro Ser Pro Gly Gln Gln Gln Ala Ala
                340                 345                 350
Ala His Leu Leu Gly Pro Pro His Pro Gly Leu Pro Pro Glu Ala
                355                 360                 365
His Leu Lys Pro Glu His His Tyr Ala Phe Asn His Pro Phe Ser Ile
                370                 375                 380
Asn Asn Leu Met Ser Ser Glu Gln Gln His His Ser His His His
385                 390                 395                 400
His Gln Pro His Lys Met Asp Leu Lys Ala Tyr Glu Gln Val Met His
                405                 410                 415
Tyr Pro Gly Tyr Gly Ser Pro Met Pro Gly Ser Leu Ala Met Gly Pro
                420                 425                 430
Val Thr Asn Lys Thr Gly Leu Asp Ala Ser Pro Leu Ala Ala Asp Thr
                435                 440                 445
```

Ser Tyr Tyr Gln Gly Val Tyr Ser Arg Pro Ile Met Asn Ser Ser
    450                 455                 460

<210> SEQ ID NO 12
<211> LENGTH: 2428
<212> TYPE: DNA
<213> ORGANISM: Homo sapiens

<400> SEQUENCE: 12

| | | | | | |
|---|---|---|---|---|---|
| cccgcccact | tccaactacc | gcctccggcc | tgcccaggga | gagagaggga | gtggagccca | 60 |
| gggagaggga | gcgcgagaga | ggggaggag | aggggacggt | gctttggctg | acttttttt | 120 |
| aaaagagggt | gggggtgggg | ggtgattgct | ggtcgtttgt | tgtggctgtt | aaattttaaa | 180 |
| ctgccatgca | ctcggcttcc | agtatgctgg | gagcggtgaa | gatggaaggg | cacgagccgt | 240 |
| ccgactggag | cagctactat | gcagagcccg | agggctactc | ctccgtgagc | aacatgaacg | 300 |
| ccggcctggg | gatgaacggc | atgaacacgt | acatgagcat | gtcggcggcc | gccatgggca | 360 |
| gcggctcggg | caacatgagc | gcgggctcca | tgaacatgtc | gtcgtacgtg | ggcgctggca | 420 |
| tgagcccgtc | cctggcgggg | atgtcccccg | gcgcgggcgc | catggcgggc | atgggcggct | 480 |
| cggccgggc | ggcggcgtg | gcgggcatgg | ggccgcactt | gagtcccagc | ctgagcccgc | 540 |
| tcggggggca | ggcggccggg | gccatgggcg | gcctggcccc | ctacgccaac | atgaactcca | 600 |
| tgagccccat | gtacgggcag | gcgggcctga | gccgcgcccg | cgaccccaag | acctacaggc | 660 |
| gcagctacac | gcacgcaaag | ccgccctact | cgtacatctc | gctcatcacc | atggccatcc | 720 |
| agcagagccc | caacaagatg | ctgacgctga | gcgagatcta | ccagtggatc | atggaccttt | 780 |
| tccccttcta | ccggcagaac | cagcagcgct | ggcagaactc | catccgccac | tcgctctcct | 840 |
| tcaacgactg | tttcctgaag | gtgccccgct | cgcccgacaa | gccggcaag | ggctccttct | 900 |
| ggaccctgca | ccctgactcg | gcaacatgt | tcgagaacgg | ctgctacctg | cgccgccaga | 960 |
| agcgcttcaa | gtgcgagaag | cagctggcgc | tgaaggaggc | cgcaggcgcc | gccggcagcg | 1020 |
| gcaagaaggc | ggccgccgga | gcccaggcct | acaggctca | actcggggag | gccgccgggc | 1080 |
| cggcctccga | gactccggcg | gcaccgagt | cgcctcactc | gagcgcctcc | ccgtgccagg | 1140 |
| agcacaagcg | agggggcctg | ggagagctga | aggggacgcc | ggctgcggcg | ctgagccccc | 1200 |
| cagagccggc | gccctctccc | gggcagcagc | agcaggccgc | ggcccacctg | ctgggccccg | 1260 |
| cccaccaccc | gggcctgccg | cctgaggccc | acctgaagcc | ggaacaccac | tacgccttca | 1320 |
| accacccgtt | ctccatcaac | aacctcatgt | cctcggagca | gcagcaccac | cacagccacc | 1380 |
| accaccacca | accccacaaa | atggacctca | aggcctacga | acaggtgatg | cactaccccg | 1440 |
| gctacggttc | ccccatgcct | ggcagcttgg | ccatgggccc | ggtcacgaac | aaaacgggcc | 1500 |
| tggacgcctc | gcccctggcc | gcagatacct | cctactacca | ggggtgtac | tcccggccca | 1560 |
| ttatgaactc | ctcttaagaa | gacgacggct | tcaggcccgg | ctaactctgg | caccccggat | 1620 |
| cgaggacaag | tgagagagca | agtggggtc | gagactttgg | ggagacggtg | ttgcagagac | 1680 |
| gcaagggaga | agaaatccat | aacaccccca | ccccaacacc | cccaagacag | cagtcttctt | 1740 |
| caccgctgc | agccgttccg | tcccaaacag | agggccacac | agatacccca | cgttctatat | 1800 |
| aaggaggaaa | acgggaaaga | atataaagtt | aaaaaaaagc | ctccggttc | cactactgtg | 1860 |
| tagactcctg | cttcttcaag | cacctgcaga | ttctgatttt | tttgttgttg | ttgttctcct | 1920 |
| ccattgctgt | tgttgcaggg | aagtcttact | taaaaaaaaa | aaaaattt | gtgagtgact | 1980 |
| cggtgtaaaa | ccatgtagtt | ttaacagaac | cagagggttg | tactattgtt | taaaaacagg | 2040 |

```
aaaaaaaata atgtaagggt ctgttgtaaa tgaccaagaa aaagaaaaaa aaagcattcc    2100
caatcttgac acggtgaaat ccaggtctcg ggtccgatta atttatggtt tctgcgtgct    2160
ttatttatgg cttataaatg tgtattctgg ctgcaagggc cagagttcca caaatctata    2220
ttaaagtgtt atacccggtt ttatcccttg aatcttttct tccagatttt tcttttcttt    2280
acttggctta caaatatac aggcttggaa attatttcaa gaaggaggga gggatacct      2340 gtctggttgc aggttgtatt ttattttggc ccagggagtg ttgctgtttt cccaacattt    2400
tattaataaa attttcagac ataaaaaa                                       2428
```

<210> SEQ ID NO 13
<211> LENGTH: 595
<212> TYPE: PRT
<213> ORGANISM: Homo sapiens

<400> SEQUENCE: 13

```
Met Ala Leu Thr Asp Gly Gly Trp Cys Leu Pro Lys Arg Phe Gly Ala
1               5                   10                  15

Ala Gly Ala Asp Ala Ser Asp Ser Arg Ala Phe Pro Ala Arg Glu Pro
            20                  25                  30

Ser Thr Pro Pro Ser Pro Ile Ser Ser Ser Ser Ser Cys Ser Arg
        35                  40                  45

Gly Gly Glu Arg Gly Pro Gly Gly Ala Ser Asn Cys Gly Thr Pro Gln
    50                  55                  60

Leu Asp Thr Glu Ala Ala Ala Gly Pro Pro Ala Arg Ser Leu Leu Leu
65                  70                  75                  80

Ser Ser Tyr Ala Ser His Pro Phe Gly Ala Pro His Gly Pro Ser Ala
                85                  90                  95

Pro Gly Val Ala Gly Pro Gly Gly Asn Leu Ser Ser Trp Glu Asp Leu
            100                 105                 110

Leu Leu Phe Thr Asp Leu Asp Gln Ala Ala Thr Ala Ser Lys Leu Leu
        115                 120                 125

Trp Ser Ser Arg Gly Ala Lys Leu Ser Pro Phe Ala Pro Glu Gln Pro
    130                 135                 140

Glu Glu Met Tyr Gln Thr Leu Ala Ala Leu Ser Ser Gln Gly Pro Ala
145                 150                 155                 160

Ala Tyr Asp Gly Ala Pro Gly Gly Phe Val His Ser Ala Ala Ala
                165                 170                 175

Ala Ala Ala Ala Ala Ala Ala Ser Ser Pro Val Tyr Val Pro Thr Thr
            180                 185                 190

Arg Val Gly Ser Met Leu Pro Gly Leu Pro Tyr His Leu Gln Gly Ser
        195                 200                 205

Gly Ser Gly Pro Ala Asn His Ala Gly Gly Ala Gly Ala His Pro Gly
    210                 215                 220

Trp Pro Gln Ala Ser Ala Asp Ser Pro Pro Tyr Gly Ser Gly Gly Gly
225                 230                 235                 240

Ala Ala Gly Gly Gly Ala Ala Gly Pro Gly Gly Ala Gly Ser Ala Ala
                245                 250                 255

Ala His Val Ser Ala Arg Phe Pro Tyr Ser Pro Ser Pro Pro Met Ala
            260                 265                 270

Asn Gly Ala Ala Arg Glu Pro Gly Gly Tyr Ala Ala Ala Gly Ser Gly
        275                 280                 285

Gly Ala Gly Gly Val Ser Gly Gly Gly Ser Ser Leu Ala Ala Met Gly
    290                 295                 300
```

Gly Arg Glu Pro Gln Tyr Ser Ser Leu Ser Ala Ala Arg Pro Leu Asn
305                 310                 315                 320

Gly Thr Tyr His His His His His His His His Pro Ser Pro
            325                 330                 335

Tyr Ser Pro Tyr Val Gly Ala Pro Leu Thr Pro Ala Trp Pro Ala Gly
            340                 345                 350

Pro Phe Glu Thr Pro Val Leu His Ser Leu Gln Ser Arg Ala Gly Ala
            355                 360                 365

Pro Leu Pro Val Pro Arg Gly Pro Ser Ala Asp Leu Leu Glu Asp Leu
        370                 375                 380

Ser Glu Ser Arg Glu Cys Val Asn Cys Gly Ser Ile Gln Thr Pro Leu
385                 390                 395                 400

Trp Arg Arg Asp Gly Thr Gly His Tyr Leu Cys Asn Ala Cys Gly Leu
                405                 410                 415

Tyr Ser Lys Met Asn Gly Leu Ser Arg Pro Leu Ile Lys Pro Gln Lys
            420                 425                 430

Arg Val Pro Ser Ser Arg Arg Leu Gly Leu Ser Cys Ala Asn Cys His
        435                 440                 445

Thr Thr Thr Thr Thr Leu Trp Arg Arg Asn Ala Glu Gly Glu Pro Val
450                 455                 460

Cys Asn Ala Cys Gly Leu Tyr Met Lys Leu His Gly Val Pro Arg Pro
465                 470                 475                 480

Leu Ala Met Lys Lys Glu Gly Ile Gln Thr Arg Lys Arg Lys Pro Lys
                485                 490                 495

Asn Ile Asn Lys Ser Lys Thr Cys Ser Gly Asn Ser Asn Ser Ile
            500                 505                 510

Pro Met Thr Pro Thr Ser Thr Ser Ser Asn Ser Asp Asp Cys Ser Lys
        515                 520                 525

Asn Thr Ser Pro Thr Thr Gln Pro Thr Ala Ser Gly Ala Gly Ala Pro
        530                 535                 540

Val Met Thr Gly Ala Gly Glu Ser Thr Asn Pro Glu Asn Ser Glu Leu
545                 550                 555                 560

Lys Tyr Ser Gly Gln Asp Gly Leu Tyr Ile Gly Val Ser Leu Ala Ser
                565                 570                 575

Pro Ala Glu Val Thr Ser Ser Val Arg Pro Asp Ser Trp Cys Ala Leu
            580                 585                 590

Ala Leu Ala
        595

<210> SEQ ID NO 14
<211> LENGTH: 3785
<212> TYPE: DNA
<213> ORGANISM: Homo sapiens

<400> SEQUENCE: 14
agttccgacc cacagcctgg cacccttcgg cgagcgctgt tgtttaggg ctcggtgagt     60 ccaatcagga gcccaggctg cagttttccg gcagagcagt aagaggcgcc tcctctctcc    120
tttttattca ccagcagcgc ggcgcagacc ccggactcgc gctcgcccgc tggcgccctc    180
ggcttctctc cgcgcctggg agcaccctcc gccgcggccg ttctccatgc gcagcgcccg    240
cccgaggagc tagacgtcag cttggagcgg cgccggaccg tggatggcct tgactgacgg    300
cggctggtgc ttgccgaagc gcttcggggc cgcgggtgcg gacgccagcg actccagagc    360
ctttccagcg cgggagccct ccacgccgcc ttccccatc tcttcctcgt cctcctcctg     420

| | |
|---|---|
| ctcccggggc ggagagcggg gccccggcgg cgccagcaac tgcggacgc ctcagctcga | 480 |
| cacggaggcg gcggccggac ccccggcccg ctcgctgctg ctcagttcct acgcttcgca | 540 |
| tcccttcggg gctccccacg gaccttcggc gcctggggtc gcgggccccg ggggcaacct | 600 |
| gtcgagctgg gaggacttgc tgctgttcac tgacctcgac caagccgcga ccgccagcaa | 660 |
| gctgctgtgg tccagccgcg gcgccaagct gagccccttc gcacccgagc agccggagga | 720 |
| gatgtaccag accctcgccg ctctctccag ccagggtccg gccgcctacg acggcgcgcc | 780 |
| cggcggcttc gtgcactctg cggccgcggc ggcagcagcc gcggcggcgg ccagctcccc | 840 |
| ggtctacgtg cccaccaccc gcgtgggttc catgctgccc ggcctaccgt accacctgca | 900 |
| ggggtcgggc agtgggccag ccaaccacgc gggcggcgcg ggcgcgcacc ccggctggcc | 960 |
| tcaggcctcg gccgacagcc ctccatacgc cagcggaggc ggcgcggctg gcggcggggc | 1020 |
| cgcggggcct ggcggcgctg gctcagccgc ggcgcacgtc tcggcgcgct cccctactc | 1080 |
| tcccagcccg cccatggcca acggcgccgc gcgggagccg ggaggctacg cggcggcggg | 1140 |
| cagtgggggc gcgggaggcg tgagcggcgg cggcagtagc ctggcggcca tgggcggccg | 1200 |
| cgagccccag tacagctcgc tgtcggccgc gcggccgctg aacgggacgt accaccacca | 1260 |
| ccaccaccac caccaccacc atccgagccc ctactcgccc tacgtggggg cgccactgac | 1320 |
| gcctgcctgg cccgccggac ccttcgagac cccggtgctg cacagcctgc agagccgcgc | 1380 |
| cggagccccg ctcccggtgc cccggggtcc cagtgcagac ctgctggagg acctgtccga | 1440 |
| gagccgcgag tgcgtgaact gcggctccat ccagacgccg ctgtggcggc gggacggcac | 1500 |
| cggccactac ctgtgcaacg cctgcgggct ctacagcaag atgaacggcc tcagccggcc | 1560 |
| cctcatcaag ccgcagaagc gcgtgcccttc atcacggcgg cttggattgt cctgtgccaa | 1620 |
| ctgtcacacc acaactacca ccttatggcg cagaaacgcc gagggtgaac ccgtgtgcaa | 1680 |
| tgcttgtgga ctctacatga aactccatgg ggtgcccaga ccacttgcta tgaaaaaaga | 1740 |
| gggaattcaa accaggaaac gaaaacctaa gaacataaat aaatcaaaga cttgctctgg | 1800 |
| taatagcaat aattccattc ccatgactcc aacttccacc tcttctaact cagatgattg | 1860 |
| cagcaaaaat acttccccca caacacaacc tacagcctca gggcgggtg ccccggtgat | 1920 |
| gactggtgcg ggagagagca ccaatcccga gaacagcgag ctcaagtatt cgggtcaaga | 1980 |
| tgggctctac ataggcgtca gtctcgcctc gccggccgaa gtcacgtcct ccgtgcgacc | 2040 |
| ggattcctgg tgcgccctgg ccctggcctg agcccacgcc gccaggaggc agggagggct | 2100 |
| ccgccgcggg cctcactcca ctcgtgtctg cttttgtgca gcggtccaga cagtggcgac | 2160 |
| tgcgctgaca gaacgtgatt ctcgtgcctt tattttgaaa gagatgtttt cccaagagg | 2220 |
| cttgctgaaa gagtgagaga agatggaagg gaagggccag tgcaactggg cgcttgggcc | 2280 |
| actccagcca gcccgcctcc ggggcggacc ctgctccact tccagaagcc aggactagga | 2340 |
| cctgggcctt gcctgctatg gaatattgag agagattttt taaaaaagat tttgcatttt | 2400 |
| gtccaaaatc atgtgcttct tctgatcaat tttggttgtt ccagaatttc ttcataccttt | 2460 |
| ttccacatcc agatttcatg tgcgttcatg gagaagatca cttgaggcca tttggtacac | 2520 |
| atctctggag gctgagtcgg ttcatgaggt ctcttatcaa aaatattact cagttttgcaa | 2580 |
| gactgcattg taactttaac atacactgtg actgacgttt ctcaaagttc atattgtgtg | 2640 |
| gctgatctga agtcagtcgg aatttgtaaa cagggtagca aacaagatat ttttcttcca | 2700 |
| tgtatacaat aattttttta aaaagtgcaa tttgcgttgc agcaatcagt gttaaatcat | 2760 |

-continued

```
ttgcataaga tttaacagca ttttttataa tgaatgtaaa catttttaact taatggtact    2820
taaaataatt taaagaaaaa atgttaactt agacattctt atgcttcttt tacaactaca    2880
tcccatttta tatttccaat tgttaaagaa aaatatttca agaacaaatc ttctctcagg    2940
aaaattgcct ttctctattt gttaagaatt tttatacaag aacaccaata taccccettt    3000
atttttactgt ggaatatgtg ctggaaaaat tgcaacaaca ctttactacc taacggatag    3060
catttgtaaa tactctaggt atctgtaaac actctgatga agtctgtata gtgtgactaa    3120
cccacaggca ggttggttta cattaatttt ttttttttgaa tgggatgtcc tatggaaacc    3180
tatttcacca gagttttaaa aataaaaagg gtattgttt gtcttctgta cagtgagttc    3240
cttcccttt caaagctttc ttttttatgct gtatgtgact atagatattc atataaaaca    3300
agtgcacgtg aagtttgcaa aatgctttaa ggccttcctt tcaaagcata gtccttttgg    3360
agccgttttg tacctttat accttggctt atttgaagtt gacacatggg gttagttact    3420
actctccatg tgcattgggg acagttttta taagtgggaa ggactcagta ttattatatt    3480
tgagatgata agcattttgt ttgggaacaa tgcttaaaaa tattccagaa agttcagatt    3540
ttttttcttt gtgaatgaaa tatattctgg cccacgaaca gggcgatttc ctttcagttt    3600
tttccttttg caacgtgcct tgaagtctca agctcacct gaggttgcag acgttacccc    3660
caacagaaga taggtagaaa tgattccagt ggcctctttg tattttcttc attgttgagt    3720
agatttcagg aaatcaggag gtgtttcaca atacagaatg atggccttta actgtgaaaa    3780
aaaaa                                                                 3785
```

<210> SEQ ID NO 15
<211> LENGTH: 394
<212> TYPE: PRT
<213> ORGANISM: Homo sapiens

<400> SEQUENCE: 15

```
Met Lys Arg Gln Asn Val Arg Thr Leu Ala Leu Ile Val Cys Thr Phe
1               5                   10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
        35                  40                  45

Arg Ala Arg Tyr Asn Leu Ser Gln Gly Gly Tyr Glu Glu Leu Glu Arg
    50                  55                  60

Val Val Leu Arg Leu Lys Pro His Lys Ala Gly Val Gln Trp Arg Phe
65                  70                  75                  80

Ala Gly Ser Phe Tyr Phe Ala Ile Thr Val Ile Thr Thr Ile Gly Tyr
                85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190
```

```
Cys Phe Ile Thr Leu Thr Thr Ile Gly Phe Gly Asp Tyr Val Ala Leu
            195                 200                 205
Gln Lys Asp Gln Ala Leu Gln Thr Gln Pro Gln Tyr Val Ala Phe Ser
        210                 215                 220
Phe Val Tyr Ile Leu Thr Gly Leu Thr Val Ile Gly Ala Phe Leu Asn
225                 230                 235                 240
Leu Val Val Leu Arg Phe Met Thr Met Asn Ala Glu Asp Glu Lys Arg
                245                 250                 255
Asp Ala Glu His Arg Ala Leu Leu Thr Arg Asn Gly Gln Ala Gly Gly
            260                 265                 270
Gly Gly Gly Gly Ser Ala His Thr Thr Asp Thr Ala Ser Ser Thr
        275                 280                 285
Ala Ala Ala Gly Gly Gly Phe Arg Asn Val Tyr Ala Glu Val Leu
        290                 295                 300
His Phe Gln Ser Met Cys Ser Cys Leu Trp Tyr Lys Ser Arg Glu Lys
305                 310                 315                 320
Leu Gln Tyr Ser Ile Pro Met Ile Ile Pro Arg Asp Leu Ser Thr Ser
                325                 330                 335
Asp Thr Cys Val Glu Gln Ser His Ser Ser Pro Gly Gly Gly Arg
            340                 345                 350
Tyr Ser Asp Thr Pro Ser Arg Arg Cys Leu Cys Ser Gly Ala Pro Arg
        355                 360                 365
Ser Ala Ile Ser Ser Val Ser Thr Gly Leu His Ser Leu Ser Thr Phe
        370                 375                 380
Arg Gly Leu Met Lys Arg Arg Ser Ser Val
385                 390

<210> SEQ ID NO 16
<211> LENGTH: 3978
<212> TYPE: DNA
<213> ORGANISM: Homo sapiens

<400> SEQUENCE: 16
ggcggcggcg gcggcggcgg ccccgggcgc tgagcgggtg cccggcgcgg agagcggcga      60
gcgcagccat gccccaggcc gcctccgggg cagcagcagc ggcggccggg gccgaggcgc     120
gggccggggg cgccgggggg ccgcggcggg cccgggcggg acgatgaagc ggcagaacgt     180
gcgcacgctg gcgctcatcg tgtgcacctt cacctacctg ctggtgggcg ccgcggtctt     240
cgacgcgctg gagtcggagc ccgagctgat cgagcggcag cggctggagc tgcggcagca     300
ggagctgcgg gcgcgctaca acctcagcca gggcggctac gaggagctgg agcgcgtcgt     360
gctgcgcctc aagccgcaca aggccggcgt gcagtggcgc ttcgccggct ccttctactt     420
cgccatcacc gtcatcacca ccatcggcta cgggcacgcg gcacccagca cggatggcgg     480
caaggtgttc tgcatgttct acgcgctgct gggcatcccg ctcacgctcg tcatgttcca     540
gagcctgggc gagcgcatca acaccttggt gaggtacctg ctgcaccgcg ccaagaaggg     600
gctgggcatg cggcgcgccg acgtgtccat ggccaacatg gtgctcatcg gcttcttctc     660
gtgcatcagc acgctgtgca tcggcgccgc cgccttctcc cactacgagc actggaccct     720
cttccaggcc tactactact gcttcatcac cctcaccacc atcggcttcg gcgactacgt     780
ggcgctgcag aaggaccagg ccctgcagac gcagccgcag tacgtggcct tcagcttcgt     840
ctacatcctt acgggcctca cggtcatcgg cgccttcctc aacctcgtgg tgctgcgctt     900
catgaccatg aacgccgagg acgagaagcg cgacgccgag caccgcgcgc tgctcacgcg     960
```

```
caacgggcag gcgggcggcg gcggaggggg tggcagcgcg cacactacgg acaccgcctc    1020
atccacggcg gcagcgggcg gcggcggctt ccgcaacgtc tacgcggagg tgctgcactt    1080
ccagtccatg tgctcgtgcc tgtggtacaa gagccgcgag aagctgcagt actccatccc    1140
catgatcatc ccgcgggacc tctccacgtc cgacacgtgc gtggagcaga gccactcgtc    1200
gccgggaggg ggcggccgct acagcgacac gccctcgcga cgctgcctgt gcagcggggc    1260
gccacgctcc gccatcagct cggtgtccac gggtctgcac agcctgtcca ccttccgcgg    1320
cctcatgaag cgcaggagct ccgtgtgact gccccgaggg gcctggagca cctggggggcg   1380 cgggcggggg acccctgctg ggaggccagg agactgcccc tgctgccttc tgcccagtgg    1440
gaccccgcac aacatccctc accactctcc cccagcaccc ccatctccga ctgtgcctgc    1500
ttgcaccagc cggcaggagg ccgggctctg aggacccctg ggcccccat cggagccctg     1560 caaattccga gaaatgtgaa acttggtggg gtcagggagg aaaggcagaa gctgggagcc    1620
tcccttccct ttgaaaatct aagaagctcc cagtcctcag agaccctgct ggtacccaga    1680
cccccacctt cggaggggac ttcatgttcc gtgtacgttt gcatctctat ttatacctct    1740
gtcctgctag gtctcccacc ttcccttggt tccaaaagcc agggtgtcta tgtccaagtc    1800
acccctactc agccccactc cccttcctca tccccagctg tgtctcccaa cctcccttcg    1860
tgttgttttg catggctttg cagttatgga gaaagtggaa acccagcagt ccctaaagct    1920
ggtccccaga aagcaggaca gaaagaagga gggacaggca ggcagcagga ggggcgagct    1980
gggaggcagg aggcagcggc ctgtcagtct gcagaatggt cgcactggag gttcaagcta    2040
actggcctcc agccacattc tcatagcagg taggacttca gccttccaga cactgccctt    2100
agaatctgga acagaagact tcagactcac cataattgct gataattacc cactcttaaa    2160
tttgtcgagt gatttttagc ctctgaaaac tctatgctgg ccactgattc ctttgagtct    2220
cacaaaaccc tacttaggtc atcagggcag gagttctcac tcccatttta cagatgagaa    2280
tactgaggcc tggacaggtg aagtgaccag agagcaaaag gcaagggggt ggggctggg     2340 tgcagtggct cacacctgta ttcccaacac ttttggaggc tgaggttgga ggattgcttg    2400
agcccaggaa tttgagacca gcctaggtga catagtgaga ccccatctct acaaaaaata    2460
aaaaattaac caggtgtggt ggcacgtgcc tgggagtccc agcgacttgg gaggctgagg    2520
tgggaggatt gtttgagcct gggaggtcga ggctgtagtg agccctgatt gcaccactgt    2580
actccagcct gggtgacagg gcaagaccct gtctcaaaaa aaaaaaaaaa aatggcaaag    2640
ggagacaaga gcccagcctg cttgttgcta gccaaagtgt tctttccttc cagcttggcc    2700
tgctcttaaa agcaaagctc ctgcagtgta catcctggca ttgtgtggct acctgggttt    2760
taaaccagaa tcgaagtcc cggatcagag ggcactgctg aggttcagcc tcttctcttc     2820
ttggccagga ggcagcagct ctgaatgggc ccctgaggct gcacaggggc ctttgtcact    2880
ggggcgcatg cttacaaaca gtgcagttct tgggaccgag gtaagcaggg ctgggtctca    2940
tggcagaaag gccaggatct ggggctctag gaatttggga attgggcaga gtggccaaga    3000
aagctggcag gcatatccta tgggacatca cacctggcac cattgtcatt gttggtgcct    3060
gtgtcccaag tagctagtga taagctgagg ctgcagcaag aaacaccctt ccaggtgggg    3120
ggagtttgga ccagaggtgc cctctgccca ccacacctgc aacccagaag cccagatgga    3180
acgcagctga cgaaggtgat gcttgaggct cacttttggg gccccacagc tggagccggt    3240
ataatgactg ggacaacatc aagggggtgga tgaggggcct ctcctcccgc aacactgcct    3300
```

```
tcccatgctg ttccctgcc agctccttaa cactgccgac caaggccagc cctggcattc    3360
agggaaattg gagggcagca cccgtagggt ggccagcctc aggcccccacc ccagctgtgt    3420
cctctagtct ctggggaccc ctggggggaa gaagtctacc ctgcttgtga gtcccgtctc    3480
agtgtggagg aactggctgc acgtgggacc tgaaggtgcc ctctgtgttt atgttggggg    3540
tggggggca gtgctggctg cctctgtcct gtgtgtgacc ctgccctcga agggtcctgt    3600
cctgtcagtc ccgagggagc cacaaccaaa gctgcggaga gaaggtgggg aagggtgcag    3660
aatggccgtg gggcacagcg tggcagactg ttcagtctct gctgggtctt cctagggac    3720
ctggaaggcc agtgttgctt ccccctcact ccctttcact gcaggcagcc tctctgcttc    3780
cccaatgcct tatgcctggg cacactgcca cagaatatgc aatatgtgtg ggtgaccatg    3840
ccctcacgac cacaccccca ccccgggcag ccccggact ccaaaggtcg tggctgccac    3900
agcctccctc agctcttcct gcctatctgt cttcacactg agaatggcgc ccaataaatg    3960
ctatccacgg agaccagg                                                  3978
```

<210> SEQ ID NO 17
<211> LENGTH: 676
<212> TYPE: PRT
<213> ORGANISM: Homo sapiens

<400> SEQUENCE: 17

```
Met Ala Ala Ser Ser Pro Pro Arg Ala Glu Arg Lys Arg Trp Gly
1               5                   10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
        35                  40                  45

Ala Leu Tyr Ala Pro Ile Ala Pro Gly Ala Pro Gly Pro Ala Pro Pro
    50                  55                  60

Ala Ser Pro Ala Ala Pro Ala Ala Pro Pro Val Ala Ser Asp Leu Gly
65                  70                  75                  80

Pro Arg Pro Pro Val Ser Leu Asp Pro Arg Val Ser Ile Tyr Ser Thr
                85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
    130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Arg Leu Arg
            180                 185                 190

Phe Ala Arg Lys Pro Ile Ser Ile Ile Asp Leu Ile Val Val Val Ala
        195                 200                 205

Ser Met Val Val Leu Cys Val Gly Ser Lys Gly Gln Val Phe Ala Thr
    210                 215                 220

Ser Ala Ile Arg Gly Ile Arg Phe Leu Gln Ile Leu Arg Met Leu His
225                 230                 235                 240

Val Asp Arg Gln Gly Gly Thr Trp Arg Leu Leu Gly Ser Val Val Phe
                245                 250                 255
```

```
Ile His Arg Gln Glu Leu Ile Thr Thr Leu Tyr Ile Gly Phe Leu Gly
            260                 265                 270

Leu Ile Phe Ser Ser Tyr Phe Val Tyr Leu Ala Glu Lys Asp Ala Val
            275                 280                 285

Asn Glu Ser Gly Arg Val Glu Phe Gly Ser Tyr Ala Asp Ala Leu Trp
            290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                325                 330                 335

Ile Ser Phe Phe Ala Leu Pro Ala Gly Ile Leu Gly Ser Gly Phe Ala
            340                 345                 350

Leu Lys Val Gln Gln Lys Gln Arg Gln Lys His Phe Asn Arg Gln Ile
            355                 360                 365

Pro Ala Ala Ala Ser Leu Ile Gln Thr Ala Trp Arg Cys Tyr Ala Ala
            370                 375                 380

Glu Asn Pro Asp Ser Ser Thr Trp Lys Ile Tyr Ile Arg Lys Ala Pro
385                 390                 395                 400

Arg Ser His Thr Leu Leu Ser Pro Ser Pro Lys Pro Lys Lys Ser Val
                405                 410                 415

Val Val Lys Lys Lys Lys Phe Lys Leu Asp Lys Asp Asn Gly Val Thr
            420                 425                 430

Pro Gly Glu Lys Met Leu Thr Val Pro His Ile Thr Cys Asp Pro Pro
            435                 440                 445

Glu Glu Arg Arg Leu Asp His Phe Ser Val Asp Gly Tyr Asp Ser Ser
450                 455                 460

Val Arg Lys Ser Pro Thr Leu Leu Glu Val Ser Met Pro His Phe Met
465                 470                 475                 480

Arg Thr Asn Ser Phe Ala Glu Asp Leu Asp Leu Glu Gly Glu Thr Leu
                485                 490                 495

Leu Thr Pro Ile Thr His Ile Ser Gln Leu Arg Glu His His Arg Ala
            500                 505                 510

Thr Ile Lys Val Ile Arg Arg Met Gln Tyr Phe Val Ala Lys Lys Lys
            515                 520                 525

Phe Gln Gln Ala Arg Lys Pro Tyr Asp Val Arg Asp Val Ile Glu Gln
530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
            580                 585                 590

Asn Arg Val Glu Asp Lys Val Thr Gln Leu Asp Gln Arg Leu Ala Leu
            595                 600                 605

Ile Thr Asp Met Leu His Gln Leu Leu Ser Leu His Gly Gly Ser Thr
            610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
            660                 665                 670
```

Asp Glu Gly Ser
         675

<210> SEQ ID NO 18
<211> LENGTH: 3262
<212> TYPE: DNA
<213> ORGANISM: Homo sapiens

<400> SEQUENCE: 18

| | | | | | |
|---|---|---|---|---|---|
| gcggcggggc | tggcagcagt | ggctgcccgc | actgcgcccg | gcgctcgcc | ttcgctgcag | 60 |
| ctcccggtgc | cgccgctcgg | gccggccccc | cggcaggccc | tcctcgttat | ggccgcggcc | 120 |
| tcctccccgc | ccagggccga | gaggaagcgc | tggggttggg | gccgcctgcc | aggcgcccgg | 180 |
| cggggcagcg | cgggcctggc | caagaagtgc | cccttctcgc | tggagctggc | ggagggcggc | 240 |
| ccggcgggcg | gcgcgctcta | cgcgcccatc | gcgcccggcg | ccccaggtcc | cgcgcccct | 300 |
| gcgtccccgg | ccgcgcccgc | cgcgccccca | gttgcctccg | accttggccc | gcggccgccg | 360 |
| gtgagcctag | acccgcgcgt | ctccatctac | agcacgcgcc | gcccggtgtt | ggcgcgcacc | 420 |
| cacgtccagg | gccgcgtcta | caacttcctc | gagcgtccca | ccggctggaa | atgcttcgtt | 480 |
| taccacttcg | ccgtcttcct | catcgtcctg | gtctgcctca | tcttcagcgt | gctgtccacc | 540 |
| atcgagcagt | atgccgccct | ggccacgggg | actctcttct | ggatggagat | cgtgctggtg | 600 |
| gtgttcttcg | gacggagta | cgtggtccgc | tctggtccg | ccggctgccg | cagcaagtac | 660 |
| gtgggcctct | gggggcggct | cgctttgcc | cggaagccca | tttccatcat | cgacctcatc | 720 |
| gtggtcgtgg | cctccatggt | ggtcctctgc | gtgggctcca | aggggcaggt | gtttgccacg | 780 |
| tcggccatca | ggggcatccg | cttcctgcag | atcctgagga | tgctacacgt | cgaccgccag | 840 |
| ggaggcacct | ggaggctcct | gggctccgtg | gtcttcatcc | accgccagga | gctgataacc | 900 |
| accctgtaca | tcggcttcct | gggcctcatc | ttctcctcgt | actttgtgta | cctggctgag | 960 |
| aaggacgcgg | tgaacgagtc | aggccgcgtg | gagttcggca | gctacgcaga | tgcgctgtgg | 1020 |
| tgggggtgg | tcacagtcac | caccatcggc | tatgggaca | aggtgcccca | gacgtgggtc | 1080 |
| gggaagacca | tcgcctcctg | cttctctgtc | tttgccatct | ccttctttgc | gctcccagcg | 1140 |
| gggattcttg | gctcggggtt | tgccctgaag | gtgcagcaga | agcagaggca | gaagcacttc | 1200 |
| aaccggcaga | tcccgcggc | agcctcactc | attcagaccg | catggaggtg | ctatgctgcc | 1260 |
| gagaaccccg | actcctccac | ctggaagatc | tacatccgga | aggccccccg | gagccacact | 1320 |
| ctgctgtcac | ccagccccaa | acccaagaag | tctgtggtgg | taaagaaaaa | aaagttcaag | 1380 |
| ctggacaaag | acaatggggt | gactcctgga | gagaagatgc | tcacagtccc | ccatatcacg | 1440 |
| tgcgacccc | cagaagagcg | gcggctggac | cacttctctg | tcgacggcta | tgacagttct | 1500 |
| gtaaggaaga | gccaacact | gctggaagtg | agcatgcccc | atttcatgag | aaccaacagc | 1560 |
| ttcgccgagg | acctggacct | ggaaggggag | actctgctga | cacccatcac | ccacatctca | 1620 |
| cagctgcggg | aacaccatcg | ggccaccatt | aaggtcattc | gacgcatgca | gtactttgtg | 1680 |
| gccaagaaga | aattccagca | agcgcggaag | ccttacgatg | tgcgggacgt | cattgagcag | 1740 |
| tactcgcagg | gccacctcaa | cctcatggtg | cgcatcaagg | agctgcagag | gaggctggac | 1800 |
| cagtccattg | ggaagccctc | actgttcatc | tccgtctcag | aaaagagcaa | ggatcgcggc | 1860 |
| agcaacacga | tcggcgcccg | cctgaaccga | gtagaagaca | aggtgacgca | gctggaccag | 1920 |
| aggctggcac | tcatcaccga | catgcttcac | cagctgctct | ccttgcacgg | tggcagcacc | 1980 |
| cccggcagcg | gcggcccccc | cagagagggc | ggggcccaca | tcacccagcc | ctgcggcagt | 2040 |

```
ggcggctccg tcgaccctga gctcttcctg cccagcaaca ccctgcccac ctacgagcag    2100
ctgaccgtgc ccaggagggg ccccgatgag gggtcctgag gaggggatgg ggctggggga    2160
tgggcctgag tgagagggga ggccaagagt ggccccacct ggccctctct gaaggaggcc    2220
acctcctaaa aggcccagag agaagagccc cactctcaga ggccccaata ccccatggac    2280
catgctgtct ggcacagcct gcacttgggg gctcagcaag gccacctctt cctggccggt    2340
gtggggcccc cgtctcaggt ctgagttgtt accccaagcg ccctggcccc cacatggtga    2400
tgttgacatc actggcatgg tggttgggac ccagtggcag ggcacagggc ctggcccatg    2460
tatggccagg aagtagcaca ggctgagtgc aggcccaccc tgcttggccc aggggcttc     2520 ctgagggag acagagcaac ccctggaccc cagcctcaaa tccaggaccc tgccaggcac     2580
aggcagggca ggaccagccc acgctgacta cagggccgcc ggcaataaaa gcccaggagc    2640
ccatttggag ggcctgggcc tggctccctc actctcagga aatgctgacc catgggcagg    2700
agactgtgga gactgctcct gagccccag cttccagcag gagggacagt ctcaccattt      2760
ccccagggca cgtggttgag tgggggaac gcccacttcc ctgggttaga ctgccagctc     2820
ttcctagctg gagaggagcc ctgcctctcc gcccctgagc ccactgtgcg tggggctccc    2880
gcctccaacc cctcgcccag tcccagcagc cagccaaaca cacagaaggg gactgccacc    2940 tcccttgcc agctgctgag ccgcagagaa gtgacggttc ctacacagga caggggttcc     3000
ttctgggcat tacatcgcat agaaatcaat aatttgtggt gatttggatc tgtgttttaa    3060
tgagtttcac agtgtgattt tgattattaa ttgtgcaagc ttttcctaat aaacgtggag    3120
aatcacaggc tgggctgggc actgctctca ccttggttcc tggggcatcc atggggtctc    3180
tcacagacag gaccctgca gttcccctgg aagcagtgcc caggtggctg tggaatagga     3240
acgctaaaaa aaaaaaaaaa aa                                             3262
```

<210> SEQ ID NO 19
<211> LENGTH: 907
<212> TYPE: PRT
<213> ORGANISM: Homo sapiens

<400> SEQUENCE: 19

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160
```

```
Leu His Ser Leu Arg His Leu Trp Leu Asp Asp Asn Ala Leu Thr Glu
            165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
            195                 200                 205

Leu Ser Ser Leu Val Val Leu His Leu His Asn Asn Arg Ile His Ser
            210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
            245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
            275                 280                 285

Tyr Asp Asn Pro Ile Gln Phe Val Gly Arg Ser Ala Phe Gln His Leu
            290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
            325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
            355                 360                 365

Ser Phe Ser Val Cys Gln Lys Leu Gln Lys Ile Asp Leu Arg His Asn
            370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
            405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
            435                 440                 445

Lys Leu Thr Gly Asn His Ala Leu Gln Ser Leu Ile Ser Ser Glu Asn
450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
            485                 490                 495

Lys Gly Asp Asn Ser Ser Met Asp Asp Leu His Lys Lys Asp Ala Gly
            500                 505                 510

Met Phe Gln Ala Gln Asp Glu Arg Asp Leu Glu Asp Phe Leu Leu Asp
            515                 520                 525

Phe Glu Glu Asp Leu Lys Ala Leu His Ser Val Gln Cys Ser Pro Ser
            530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
            565                 570                 575
```

```
Leu Val Thr Ser Thr Val Phe Arg Ser Pro Leu Tyr Ile Ser Pro Ile
            580                 585                 590

Lys Leu Leu Ile Gly Val Ile Ala Ala Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Val Phe Leu Leu Thr
                645                 650                 655

Leu Ala Ala Leu Glu Arg Gly Phe Ser Val Lys Tyr Ser Ala Lys Phe
            660                 665                 670

Glu Thr Lys Ala Pro Phe Ser Ser Leu Lys Val Ile Leu Leu Cys
        675                 680                 685

Ala Leu Leu Ala Leu Thr Met Ala Ala Val Pro Leu Leu Gly Gly Ser
    690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Val Lys His Ile
        755                 760                 765

Ala Leu Leu Leu Phe Thr Asn Cys Ile Leu Asn Cys Pro Val Ala Phe
    770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905
```

<210> SEQ ID NO 20
<211> LENGTH: 4625
<212> TYPE: DNA
<213> ORGANISM: Homo sapiens

<400> SEQUENCE: 20

```
aaaaaacgag cgtgcaagca gagatgctgc tccacaccgc tcaggccgcg agcagcagca      60
aggcgcaccg ccactgtcgc cgctgcagcc agggctgctc cgaaggccgg cgtggcggca     120
accggcacct ctgtccccgc cgcgcttctc ctcgccgccc acgccgtggg gtcaggaacg     180
cggcgtctgg cgctgcagac gcccgctgag ttgcagaagc ccacggagcg gcgcccggcg     240
```

```
cgccacggcc cgtagcagtc cggtgctgct ctccgcccgc gtccggctcg tggcccccta    300
cttcgggcac catggacacc tcccggctcg gtgtgctcct gtccttgcct gtgctgctgc    360
agctggcgac cgggggcagc tctcccaggt ctggtgtgtt gctgaggggc tgccccacac    420
actgtcattg cgagcccgac ggcaggatgt tgctcagggt ggactgctcc gacctggggc    480
tctcggagct gccttccaac ctcagcgtct tcacctccta cctagacctc agtatgaaca    540
acatcagtca gctgctcccg aatcccctgc ccagtctccg cttcctggag gagttacgtc    600
ttgcgggaaa cgctctgaca tacattccca agggagcatt cactggcctt acagtctta     660 aagttcttat gctgcagaat aatcagctaa gacacgtacc cacagaagct ctgcagaatt    720
tgcgaagcct tcaatccctg cgtctggatg ctaaccacat cagctatgtg cccccaagct    780
gtttcagtgg cctgcattcc ctgaggcacc tgtggctgga tgacaatgcg ttaacagaaa    840
tccccgtcca ggcttttaga agtttatcgg cattgcaagc catgaccttg gccctgaaca    900
aaatacacca cataccagac tatgcctttg gaaacctctc cagcttggta gttctacatc    960
tccataacaa tagaatccac tccctgggaa agaaatgctt tgatgggctc cacagcctag   1020
agactttaga tttaaattac aataaccttg atgaattccc cactgcaatt aggacactct   1080
ccaaccttaa agaactagga tttcatagca acaatatcag gtcgataccc gagaaagcat   1140
ttgtaggcaa cccttctctt attacaaatac atttctatga caatcccatc cagtttgttg   1200
ggagatctgc ttttcaacat ttacctgaac taagaacact gactctgaat ggtgcctcac   1260
aaataactga atttcctgat ttaactggaa ctgcaaacct ggagagtctg actttaactg   1320
gagcacagat ctcatctctt cctcaaaccg tctgcaatca gttacctaat ctccaagtgc   1380
tagatctgtc ttacaaccta ttagaagatt tacccagttt ttcagtctgc caaaagcttc   1440
agaaaattga cctaagacat aatgaaatct acgaaattaa agttgacact ttccagcagt   1500
tgcttagcct ccgatcgctg aatttggctt ggaacaaaat tgctattatt caccccaatg   1560
cattttccac tttgccatcc ctaataaagc tggacctatc gtccaacctc ctgtcgtctt   1620
ttcctataac tgggttacat ggtttaactc acttaaaatt aacaggaaat catgccttac   1680
agagcttgat atcatctgaa aactttccag aactcaaggt tatagaaatg ccttatgctt   1740
accagtgctg tgcatttgga gtgtgtgaga atgcctataa gatttctaat caatggaata   1800
aaggtgacaa cagcagtatg gacgaccttc ataagaaaga tgctggaatg tttcaggctc   1860
aagatgaacg tgaccttgaa gatttcctgc ttgactttga ggaagacctg aaagcccttc   1920
attcagtgca gtgttcacct tccccaggcc ccttcaaacc tgtgaacac ctgcttgatg    1980 gctggctgat cagaattgga gtgtggacca tagcagttct ggcacttact tgtaatgctt   2040
tggtgacttc aacagttttc agatcccctc tgtacatttc ccccattaaa ctgttaattg   2100
gggtcatcgc agcagtgaac atgctcacgg gagtctccag tgccgtgctg gctggtgtgg   2160
atgcgttcac ttttggcagc tttgcacgac atggtgcctg gtgggagaat ggggttggtt   2220
gccatgtcat tggttttttg tccattttg cttcagaatc atctgttttc ctgcttactc      2280
tggcagccct ggagcgtggg ttctctgtga atattctgc aaaatttgaa acgaaagctc     2340
cattttctag cctgaaagta atcattttgc tctgtgccct gctggccttg accatggccg   2400
cagttcccct gctgggtggc agcaagtatg gcgcctcccc tctctgcctg cctttgcctt   2460 ttgggggagcc cagcaccatg ggctacatgg tcgctctcat cttgctcaat tccctttgct   2520
tcctcatgat gaccattgcc tacaccaagc tctactgcaa tttggacaag ggagacctgg   2580
agaatatttg ggactgctct atggtaaaac acattgccct gttgctcttc accaactgca   2640
```

```
tcctaaactg ccctgtggct ttcttgtcct tctcctcttt aataaacctt acatttatca    2700
gtcctgaagt aattaagttt atccttctgg tggtagtccc acttcctgca tgtctcaatc    2760
cccttctcta catcttgttc aatcctcact ttaaggagga tctggtgagc ctgagaaagc    2820
aaacctacgt ctggacaaga tcaaaacacc caagcttgat gtcaattaac tctgatgatg    2880
tcgaaaaaca gtcctgtgac tcaactcaag ccttggtaac ctttaccagc tccagcatca    2940
cttatgacct gcctcccagt tccgtgccat caccagctta tccagtgact gagagctgcc    3000
atctttcctc tgtggcattt gtcccatgtc tctaattaat atgtgaagga aatgttttc    3060 aaaggttgag aacctgaaaa tgtgagattg agtatatcag agcagtaatt aataagaaga    3120
gctgaggtga aactcggttt aaaaaccaaa aagaatctc tcagttagta agaaaaggct    3180
gaaaacctct tgatacttga gagtgaatat aagtctaaat gctgctttgt ataatttgtt    3240
cagctaaggg atagatcgat cacactattt aagtgagccc agatcaaaaa agcagattga    3300
aattttcttt agaaaagatt ctccatgatt tgaattgcat tctctttaaa ctcaccaatg    3360
taatcatttt gggaggaggg agaacccact tgctttccaa atgggtttat ttaaacccac    3420
aaactcaaga ggttgttggg ggaattagga aaataagggt tttcaatgac ctacattgct    3480
aggtagaggc tgtgatccat gggatttcat tctaatgacc atgtgaagat gtttgagtcc    3540
tcctttgcct ttcctcagaa agaatccttc taaggcacaa atcccttaga tggataatgt    3600
aaggtattgt taactcactc atattgagat cattttaga gataccaggt tttatgtatc    3660
agcactagat ggttccaccc tcatgggata aaactgctta caagtatttt gaaagaaaaa    3720
ctgaccaaaa ttcttaaatt gttactaagg caatcatgca caggtgacgt atgtcttatc    3780
tgatttgttt ttaactcctt ggtgcccaaa gctcagaagg gaattccact gccagcaatg    3840
aacatacctg gaaagaaag taagcaatct gggattttt ttctgggtta gtaaagaatt    3900
tttgcaataa gttttatcag ttgattcaaa ctgatgtgca tcttaatgat caaatgtgca    3960
cattacataa attaagtcca ctgatacaac ttcttacaca tgtatctcta gtagctctgg    4020
caaacccaat atctgacacc actttggact caagagactc agtaacgtat tatcctgttt    4080
atttagcttg gttttagctg tgttctctct ggataaccca cttgatgtta ggaacattac    4140
ttctctgctt attccatatt aatactgtgt taggtatttt aagaagcaag ttattaaata    4200
agaaaagtca agtattaat tcttaccttc tattatccta tattagcttc aatacatcca    4260
aaccaaatgg ctgttaggta gatttatttt tatataagca tgtttatttt gatcagatgt    4320
tttaacttgg atttgaaaaa atacatttat gagatgtttt ataagatgtg taaatataga    4380
actgtattta ttactatagt aaaggttcag taacattaag gaccatgata atgataataa    4440
accttgtaca gtggcatatt ctttgattta tattgtgttt ctctgcccat tttctttaaa    4500
ttcattaact gtatatatgt aaatatatag tacttgtaaa tagattccaa atttgctttt    4560
ctattgggta aaaataaat ttgtaataaa atgtgtgact atgaaacaaa aaaaaaaaa    4620 aaaaa    4625
```

<210> SEQ ID NO 21
<211> LENGTH: 332
<212> TYPE: PRT
<213> ORGANISM: Homo sapiens

<400> SEQUENCE: 21

```
Met Ala Thr Leu Lys Asp Gln Leu Ile Tyr Asn Leu Leu Lys Glu Glu
1               5                   10                  15
```

```
Gln Thr Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80

Lys Asp Tyr Asn Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Asp Leu Gly Thr Asp Lys Asp Lys
    210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Val Ser Thr Met Ile Lys Gly Leu Tyr Gly Ile Lys Asp Asp Val Phe
        275                 280                 285

Leu Ser Val Pro Cys Ile Leu Gly Gln Asn Gly Ile Ser Asp Leu Val
290                 295                 300

Lys Val Thr Leu Thr Ser Glu Glu Ala Arg Leu Lys Lys Ser Ala
305                 310                 315                 320

Asp Thr Leu Trp Gly Ile Gln Lys Glu Leu Gln Phe
                325                 330
```

<210> SEQ ID NO 22
<211> LENGTH: 2226
<212> TYPE: DNA
<213> ORGANISM: Homo sapiens

<400> SEQUENCE: 22

```
gtctgccggt cggttgtctg gctgcgcgcg ccacccgggc ctctccagtg ccccgcctgg      60
ctcggcatcc accccagcc cgactcacac gtgggttccc gcacgtccgc cggcccccc     120 cgctgacgtc agcatagctg ttccacttaa ggccctccc gcgcccagct cagagtgctg    180
cagccgctgc cgccgattcc ggatctcatt gccacgcgcc cccgacgacc gcccgacgtg    240
cattcccgat tccttttggt tccaagtcca atatggcaac tctaaaggat cagctgattt    300
```

```
ataatcttct aaaggaagaa cagacccccc agaataagat tacagttgtt ggggttggtg      360
ctgttggcat ggcctgtgcc atcagtatct taatgaagga cttggcagat gaacttgctc      420
ttgttgatgt catcgaagac aaattgaagg gagagatgat ggatctccaa catggcagcc      480
ttttccttag aacaccaaag attgtctctg gcaaagacta taatgtaact gcaaactcca      540
agctggtcat tatcacggct ggggcacgtc agcaagaggg agaaagccgt cttaatttgg      600
tccagcgtaa cgtgaacatc tttaaattca tcattcctaa tgttgtaaaa tacagcccga      660
actgcaagtt gcttattgtt tcaaatccag tggatatctt gacctacgtg gcttggaaga      720
taagtggttt tcccaaaaac cgtgttattg aagcggttg  caatctggat tcagcccgat      780
tccgttacct aatgggggaa aggctgggag ttcacccatt aagctgtcat gggtgggtcc      840
ttggggaaca tggagattcc agtgtgcctg tatggagtgg aatgaatgtt gctggtgtct      900
ctctgaagac tctgcaccca gatttaggga ctgataaaga taaggaacag tggaaagagg      960
ttcacaagca ggtggttgag agtgcttatg aggtgatcaa actcaaaggc tacacatcct     1020
gggctattgg actctctgta gcagatttgg cagagagtat aatgaagaat cttaggcggg     1080
tgcacccagt ttccaccatg attaagggtc tttacggaat aaaggatgat gtcttcctta     1140
gtgttccttg cattttggga cagaatggaa tctcagacct tgtgaaggtg actctgactt     1200
ctgaggaaga ggcccgtttg aagaagagtg cagatacact tgggggatc  caaaaggagc     1260 tgcaatttta aagtcttctg atgtcatatc atttcactgt ctaggctaca acaggattct     1320
aggtggaggt tgtgcatgtt gtccttttta tctgatctgt gattaaagca gtaatatttt     1380
aagatggact gggaaaaaca tcaactcctg aagttagaaa taagaatggt ttgtaaaatc     1440
cacagctata tcctgatgct ggatggtatt aatcttgtgt agtcttcaac tggttagtgt     1500
gaaatagttc tgccacctct gacgcaccac tgccaatgct gtacgtactg catttgcccc     1560
ttgagccagg tggatgttta ccgtgtgtta tataacttcc tggctccttc actgaacatg     1620
cctagtccaa catttttttcc cagtgagtca catcctggga tccagtgtat aaatccaata     1680
tcatgtcttg tgcataattc ttccaaagga tcttattttg tgaactatat cagtagtgta     1740
cattaccata taatgtaaaa agatctacat acaaacaatg caaccaacta tccaagtgtt     1800
ataccaacta aaacccccaa taaaccttga acagtgacta ctttggttaa ttcattatat     1860
taagatataa agtcataaag ctgctagtta ttatattaat ttggaaatat taggctattc     1920
ttgggcaacc ctgcaacgat tttttctaac agggatatta ttgactaata gcagaggatg     1980
taatagtcaa ctgagttgta ttggtaccac ttccattgta agtcccaaag tattatatat     2040
ttgataataa tgctaatcat aattggaaag taacattcta tatgtaaatg taaaatttat     2100
ttgccaactg aatataggca atgatagtgt gtcactatag gaacacaga ttttttgagat     2160 cttgtcctct ggaagctggt aacaattaaa aacaatctta aggcagggaa aaaaaaaaa      2220 aaaaaa                                                                2226
```

<210> SEQ ID NO 23
<211> LENGTH: 353
<212> TYPE: PRT
<213> ORGANISM: Homo sapiens

<400> SEQUENCE: 23

```
Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30
```

```
Lys Glu Pro Pro Glu Ala Glu Arg Phe Cys His Arg Leu Pro Pro Gly
             35                  40                  45

Ser Leu Ser Ser Thr Pro Leu Ser Thr Pro Cys Ser Ser Val Pro Ser
 50                  55                  60

Ser Pro Ser Phe Cys Ala Pro Ser Pro Gly Thr Gly Gly Gly Gly Gly
 65                  70                  75                  80

Ala Gly Gly Gly Gly Ser Ser Gln Ala Gly Gly Ala Pro Gly Pro
                 85                  90                  95

Pro Ser Gly Gly Pro Gly Ala Val Gly Gly Thr Ser Gly Lys Pro Ala
                100                 105                 110

Leu Glu Asp Leu Tyr Trp Met Ser Gly Tyr Gln His His Leu Asn Pro
            115                 120                 125

Glu Ala Leu Asn Leu Thr Pro Glu Asp Ala Val Glu Ala Leu Ile Gly
130                 135                 140

Ser Gly His His Gly Ala His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
            195                 200                 205

Gly Gly Ala Gly His Gly Gly Ala Gly His His Val Arg Leu Glu
            210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
                260                 265                 270

Phe Lys Arg Val Gln Gln Arg His Ile Leu Glu Ser Glu Lys Cys Gln
            275                 280                 285

Leu Gln Ser Gln Val Glu Gln Leu Lys Leu Glu Val Gly Arg Leu Ala
            290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335

Pro Pro Gln Ala Gly Pro Gly Gly Ala Lys Gly Thr Ala Asp Phe Phe
            340                 345                 350

Leu
```

<210> SEQ ID NO 24
<211> LENGTH: 2373
<212> TYPE: DNA
<213> ORGANISM: Homo sapiens

<400> SEQUENCE: 24

```
gcgcggccgg gcgcgggccc cgggcgatgg ccgcggagct ggcgatgggc gccgagctgc    60
ccagcagccc gctggccatc gagtacgtca acgacttcga cctgatgaag ttcgaggtga   120
agaaggagcc tcccgaggcc gagcgcttct gccaccgcct gccgccaggc tcgctgtcct   180
cgacgccgct cagcacgccc tgctcctccg tgccctcctc gccagcttc tgcgcgccca    240
```

```
gcccgggcac cggcggcggc ggcggcgcgg ggggcggcgg cggctcgtct caggccgggg      300
gcgcccccgg gccgccgagc gggggccccg gcgccgtcgg gggcacctcg gggaagccgg      360
cgctggagga tctgtactgg atgagcggct accagcatca cctcaacccc gaggcgctca      420
acctgacgcc cgaggacgcg gtggaggcgc tcatcggcag cggccaccac ggcgcgcacc      480
acggcgcgca ccacccggcg gccgccgcag cctacgaggc tttccgcggc ccgggcttcg      540
cgggcggcgg cggagcggac gacatgggcg ccggccacca ccacggcgcg caccacgccg      600
cccaccatca ccacgccgcc caccaccacc accaccacca ccaccaccat ggcggcgcgg      660
gacacggcgg tggcgcgggc cacccgtgc gcctggagga gcgcttctcc gacgaccagc      720
tggtgtccat gtcggtgcgc gagctgaacc ggcagctccg cggcttcagc aaggaggagg      780
tcatccggct caagcagaag cggcgcacgc tcaagaaccg cggctacgcg cagtcctgcc      840
gcttcaagcg ggtgcagcag cggcacattc tggagagcga aagtgccaa ctccagagcc      900
aggtggagca gctgaagctg gaggtggggc gcctggccaa agagcgggac ctgtacaagg      960
agaaatacga gaagctggcg ggccggggcg gccccgggag cgcgggcggg gccggtttcc     1020
cgcgggagcc ttcgccgccg caggccggtc ccggcggggc caagggcacg gccgacttct     1080
tcctgtaggc gccggacccc gagcccgcgc cgccgtcgcc ggggacaagt cgcgcaggc     1140
ctctcggggc ctcggctcgg actccgcggt acaggacgtg gacaccaggc ccggccggc     1200
cgtgctggcc ccggtgccaa gtctgcgggc gcgggctgg aggccccttc gctcccggtc     1260
cccgttcgcg cgcgtcggcc cgggtcgccg tcctgaggtt gagcggagaa cggtgatttc     1320
taaggaaact tgagccaggt ctaacttctt tccaagcgtc cgcttgtaca tacgttgaac     1380
gtggttctcc gttcccacct tcgccctgcc agcctagagg accgcgctg ccgtcccttc     1440
ccgggtggcc cctgcctgcc cccgccctcc ttcgttctct tctcagcctc ctttccttg     1500
ccttttttaa cttcccctcc ccgttttaaa atcggtctta ttttcgaagt atttataatt     1560
attatgcttg gtgattagaa aagaaaacct tggaggaagc cccttctttc cccagccggg     1620
gtccgccctc agtcgcgagt cacagcatga gtcgctcgcc aggagggcc cggcccctgc     1680
ctgcccccttc cccgcttgcc cccgaccctg ctaccgcgt tccttggagg tcgaagccag     1740
ggacgtcacc cgtgctgtgt ccaggcctgc tgtcctacta tgctcaaccg ggggtggggg     1800
gagggggtg agtcctgtgc tcagtcgggt ggggctggc ccggatcccg agctgctgtc     1860
tctctatgca ccagaacata tctgtaactc ctggggaaat acatcttgtt ttaaccttca     1920
agagaagtga aagaaaaaag taatgcacag tatttctagc agaaaatttt ttttttaag     1980
aggaggcttg ggccagagcc ttctggcatg gggcgggtgg agaaagtgtt tttatttaa     2040
tttaaattgt gtttcgtttt gtttgtggaa tctttcttta atgcttcgtc gctctttgga     2100
ctagccggga gagagggcga ggaggcgggt gctccaggcc ctgtaggctg ggccaggcgc     2160
ctggggatc tgcccgtttt cggaggccct caggggccat cagtgggatt ccagccgctc     2220
cacacccctc ccctgagcac tcggagtgga aggcgcgccg actcgttgaa agttttgttg     2280
tgtagttggt tttcgttgag ttcttttttc atttgctacg aaactgagaa aagaaaaaa     2340
atacacaaaa taaatctgtt cagatccaag tca                                  2373
```

<210> SEQ ID NO 25
<211> LENGTH: 1939
<212> TYPE: PRT
<213> ORGANISM: Homo sapiens

<400> SEQUENCE: 25

```
Met Thr Asp Ala Gln Met Ala Asp Phe Gly Ala Ala Gln Tyr Leu
1               5                   10                  15

Arg Lys Ser Glu Lys Glu Arg Leu Glu Ala Gln Thr Arg Pro Phe Asp
            20                  25                  30

Ile Arg Thr Glu Cys Phe Val Pro Asp Asp Lys Glu Glu Phe Val Lys
            35                  40                  45

Ala Lys Ile Leu Ser Arg Glu Gly Lys Val Ile Ala Glu Thr Glu
    50                  55                  60

Asn Gly Lys Thr Val Thr Val Lys Glu Asp Gln Val Leu Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Phe Asn Leu Lys Glu Arg Tyr Ala Ala Trp
                100                 105                 110

Met Ile Tyr Thr Tyr Ser Gly Leu Phe Cys Val Thr Val Asn Pro Tyr
            115                 120                 125

Lys Trp Leu Pro Val Tyr Asn Ala Glu Val Val Ala Ala Tyr Arg Gly
            130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
                180                 185                 190

Gln Tyr Phe Ala Ser Ile Ala Ala Ile Gly Asp Arg Gly Lys Lys Asp
            195                 200                 205

Asn Ala Asn Ala Asn Lys Gly Thr Leu Glu Asp Gln Ile Ile Gln Ala
210                 215                 220

Asn Pro Ala Leu Glu Ala Phe Gly Asn Ala Lys Thr Val Arg Asn Asp
225                 230                 235                 240

Asn Ser Ser Arg Phe Gly Lys Phe Ile Arg Ile His Phe Gly Ala Thr
            245                 250                 255

Gly Lys Leu Ala Ser Ala Asp Ile Glu Thr Tyr Leu Leu Glu Lys Ser
            260                 265                 270

Arg Val Ile Phe Gln Leu Lys Ala Glu Arg Asn Tyr His Ile Phe Tyr
            275                 280                 285

Gln Ile Leu Ser Asn Lys Lys Pro Glu Leu Leu Asp Met Leu Leu Val
            290                 295                 300

Thr Asn Asn Pro Tyr Asp Tyr Ala Phe Val Ser Gln Gly Glu Val Ser
305                 310                 315                 320

Val Ala Ser Ile Asp Asp Ser Glu Glu Leu Met Ala Thr Asp Ser Ala
            325                 330                 335

Phe Asp Val Leu Gly Phe Thr Ser Glu Glu Lys Ala Gly Val Tyr Lys
            340                 345                 350

Leu Thr Gly Ala Ile Met His Tyr Gly Asn Met Lys Phe Lys Gln Lys
            355                 360                 365

Gln Arg Glu Glu Gln Ala Glu Pro Asp Gly Thr Glu Asp Ala Asp Lys
            370                 375                 380

Ser Ala Tyr Leu Met Gly Leu Asn Ser Ala Asp Leu Leu Lys Gly Leu
385                 390                 395                 400

Cys His Pro Arg Val Lys Val Gly Asn Glu Tyr Val Thr Lys Gly Gln
                405                 410                 415
```

-continued

Ser Val Gln Gln Val Tyr Tyr Ser Ile Gly Ala Leu Ala Lys Ala Val
            420                 425                 430

Tyr Glu Lys Met Phe Asn Trp Met Val Thr Arg Ile Asn Ala Thr Leu
            435                 440                 445

Glu Thr Lys Gln Pro Arg Gln Tyr Phe Ile Gly Val Leu Asp Ile Ala
        450                 455                 460

Gly Phe Glu Ile Phe Asp Phe Asn Ser Phe Glu Gln Leu Cys Ile Asn
465                 470                 475                 480

Phe Thr Asn Glu Lys Leu Gln Gln Phe Asn His His Met Phe Val
                485                 490                 495

Leu Glu Gln Glu Glu Tyr Lys Lys Glu Gly Ile Glu Trp Thr Phe Ile
            500                 505                 510

Asp Phe Gly Met Asp Leu Gln Ala Cys Ile Asp Leu Ile Glu Lys Pro
            515                 520                 525

Met Gly Ile Met Ser Ile Leu Glu Glu Glu Cys Met Phe Pro Lys Ala
            530                 535                 540

Thr Asp Met Thr Phe Lys Ala Lys Leu Tyr Asp Asn His Leu Gly Lys
545                 550                 555                 560

Ser Asn Asn Phe Gln Lys Pro Arg Asn Ile Lys Gly Lys Gln Glu Ala
                565                 570                 575

His Phe Ser Leu Ile His Tyr Ala Gly Thr Val Asp Tyr Asn Ile Leu
            580                 585                 590

Gly Trp Leu Glu Lys Asn Lys Asp Pro Leu Asn Glu Thr Val Val Ala
            595                 600                 605

Leu Tyr Gln Lys Ser Ser Leu Lys Leu Met Ala Thr Leu Phe Ser Ser
            610                 615                 620

Tyr Ala Thr Ala Asp Thr Gly Asp Ser Gly Lys Ser Lys Gly Gly Lys
625                 630                 635                 640

Lys Lys Gly Ser Ser Phe Gln Thr Val Ser Ala Leu His Arg Glu Asn
                645                 650                 655

Leu Asn Lys Leu Met Thr Asn Leu Arg Thr Thr His Pro His Phe Val
            660                 665                 670

Arg Cys Ile Ile Pro Asn Glu Arg Lys Ala Pro Gly Val Met Asp Asn
            675                 680                 685

Pro Leu Val Met His Gln Leu Arg Cys Asn Gly Val Leu Glu Gly Ile
        690                 695                 700

Arg Ile Cys Arg Lys Gly Phe Pro Asn Arg Ile Leu Tyr Gly Asp Phe
705                 710                 715                 720

Arg Gln Arg Tyr Arg Ile Leu Asn Pro Val Ala Ile Pro Glu Gly Gln
                725                 730                 735

Phe Ile Asp Ser Arg Lys Gly Thr Glu Lys Leu Leu Ser Ser Leu Asp
            740                 745                 750

Ile Asp His Asn Gln Tyr Lys Phe Gly His Thr Lys Val Phe Phe Lys
            755                 760                 765

Ala Gly Leu Leu Gly Leu Leu Glu Glu Met Arg Asp Glu Arg Leu Ser
        770                 775                 780

Arg Ile Ile Thr Arg Met Gln Ala Gln Ala Arg Gly Gln Leu Met Arg
785                 790                 795                 800

Ile Glu Phe Lys Lys Ile Val Glu Arg Arg Asp Ala Leu Leu Val Ile
                805                 810                 815

Gln Trp Asn Ile Arg Ala Phe Met Gly Val Lys Asn Trp Pro Trp Met
            820                 825                 830

Lys Leu Tyr Phe Lys Ile Lys Pro Leu Leu Lys Ser Ala Glu Thr Glu

```
                835                 840                 845
Lys Glu Met Ala Thr Met Lys Glu Glu Phe Gly Arg Ile Lys Glu Thr
                850                 855                 860

Leu Glu Lys Ser Glu Ala Arg Arg Lys Glu Leu Glu Glu Lys Met Val
865                 870                 875                 880

Ser Leu Leu Gln Glu Lys Asn Asp Leu Gln Leu Gln Val Gln Ala Glu
                    885                 890                 895

Gln Asp Asn Leu Asn Asp Ala Glu Glu Arg Cys Asp Gln Leu Ile Lys
                900                 905                 910

Asn Lys Ile Gln Leu Glu Ala Lys Val Lys Glu Met Asn Glu Arg Leu
            915                 920                 925

Glu Asp Glu Glu Glu Met Asn Ala Glu Leu Thr Ala Lys Lys Arg Lys
930                 935                 940

Leu Glu Asp Glu Cys Ser Glu Leu Lys Lys Asp Ile Asp Asp Leu Glu
945                 950                 955                 960

Leu Thr Leu Ala Lys Val Glu Lys Glu Lys His Ala Thr Glu Asn Lys
                965                 970                 975

Val Lys Asn Leu Thr Glu Glu Met Ala Gly Leu Asp Glu Ile Ile Ala
            980                 985                 990

Lys Leu Thr Lys Glu Lys Lys Ala  Leu Gln Glu Ala His  Gln Gln Ala
            995                 1000                1005

Leu Asp Asp Leu Gln Val Glu  Glu Asp Lys Val Asn  Ser Leu Ser
    1010                1015                1020

Lys Ser Lys Val Lys Leu Glu  Gln Gln Val Asp Asp  Leu Glu Gly
    1025                1030                1035

Ser Leu Glu Gln Glu Lys Lys  Val Arg Met Asp Leu  Glu Arg Ala
    1040                1045                1050

Lys Arg Lys Leu Glu Gly Asp  Leu Lys Leu Thr Gln  Glu Ser Ile
    1055                1060                1065

Met Asp Leu Glu Asn Asp Lys  Leu Gln Leu Glu Glu  Lys Leu Lys
    1070                1075                1080

Lys Lys Glu Phe Asp Ile Asn  Gln Gln Asn Ser Lys  Ile Glu Asp
    1085                1090                1095

Glu Gln Val Leu Ala Leu Gln  Leu Gln Lys Lys Leu  Lys Glu Asn
    1100                1105                1110

Gln Ala Arg Ile Glu Glu Leu  Glu Glu Glu Leu Glu  Ala Glu Arg
    1115                1120                1125

Thr Ala Arg Ala Lys Val Glu  Lys Leu Arg Ser Asp  Leu Ser Arg
    1130                1135                1140

Glu Leu Glu Glu Ile Ser Glu  Arg Leu Glu Glu Ala  Gly Gly Ala
    1145                1150                1155

Thr Ser Val Gln Ile Glu Met  Asn Lys Lys Arg Glu  Ala Glu Phe
    1160                1165                1170

Gln Lys Met Arg Arg Asp Leu  Glu Glu Ala Thr Leu  Gln His Glu
    1175                1180                1185

Ala Thr Ala Ala Ala Leu Arg  Lys Lys His Ala Asp  Ser Val Ala
    1190                1195                1200

Glu Leu Gly Glu Gln Ile Asp  Asn Leu Gln Arg Val  Lys Gln Lys
    1205                1210                1215

Leu Glu Lys Glu Lys Ser Glu  Phe Lys Leu Glu Leu  Asp Asp Val
    1220                1225                1230

Thr Ser Asn Met Glu Gln Ile  Ile Lys Ala Lys Ala  Asn Leu Glu
    1235                1240                1245
```

```
Lys Val Ser Arg Thr Leu Glu Asp Gln Ala Asn Glu Tyr Arg Val
    1250                1255                1260

Lys Leu Glu Glu Ala Gln Arg Ser Leu Asn Asp Phe Thr Thr Gln
    1265                1270                1275

Arg Ala Lys Leu Gln Thr Glu Asn Gly Glu Leu Ala Arg Gln Leu
    1280                1285                1290

Glu Glu Lys Glu Ala Leu Ile Ser Gln Leu Thr Arg Gly Lys Leu
    1295                1300                1305

Ser Tyr Thr Gln Gln Met Glu Asp Leu Lys Arg Gln Leu Glu Glu
    1310                1315                1320

Glu Gly Lys Ala Lys Asn Ala Leu Ala His Ala Leu Gln Ser Ala
    1325                1330                1335

Arg His Asp Cys Asp Leu Leu Arg Glu Gln Tyr Glu Glu Glu Thr
    1340                1345                1350

Glu Ala Lys Ala Glu Leu Gln Arg Val Leu Ser Lys Ala Asn Ser
    1355                1360                1365

Glu Val Ala Gln Trp Arg Thr Lys Tyr Glu Thr Asp Ala Ile Gln
    1370                1375                1380

Arg Thr Glu Glu Leu Glu Glu Ala Lys Lys Lys Leu Ala Gln Arg
    1385                1390                1395

Leu Gln Asp Ala Glu Ala Val Glu Ala Val Asn Ala Lys Cys
    1400                1405                1410

Ser Ser Leu Glu Lys Thr Lys His Arg Leu Gln Asn Glu Ile Glu
    1415                1420                1425

Asp Leu Met Val Asp Val Glu Arg Ser Asn Ala Ala Ala Ala Ala
    1430                1435                1440

Leu Asp Lys Lys Gln Arg Asn Phe Asp Lys Ile Leu Ala Glu Trp
    1445                1450                1455

Lys Gln Lys Tyr Glu Glu Ser Gln Ser Glu Leu Glu Ser Ser Gln
    1460                1465                1470

Lys Glu Ala Arg Ser Leu Ser Thr Glu Leu Phe Lys Leu Lys Asn
    1475                1480                1485

Ala Tyr Glu Glu Ser Leu Glu His Leu Glu Thr Phe Lys Arg Glu
    1490                1495                1500

Asn Lys Asn Leu Gln Glu Glu Ile Ser Asp Leu Thr Glu Gln Leu
    1505                1510                1515

Gly Glu Gly Gly Lys Asn Val His Glu Leu Glu Lys Val Arg Lys
    1520                1525                1530

Gln Leu Glu Val Glu Lys Leu Glu Leu Gln Ser Ala Leu Glu Glu
    1535                1540                1545

Ala Glu Ala Ser Leu Glu His Glu Glu Gly Lys Ile Leu Arg Ala
    1550                1555                1560

Gln Leu Glu Phe Asn Gln Ile Lys Ala Glu Ile Glu Arg Lys Leu
    1565                1570                1575

Ala Glu Lys Asp Glu Glu Met Glu Gln Ala Lys Arg Asn His Gln
    1580                1585                1590

Arg Val Val Asp Ser Leu Gln Thr Ser Leu Asp Ala Glu Thr Arg
    1595                1600                1605

Ser Arg Asn Glu Val Leu Arg Val Lys Lys Lys Met Glu Gly Asp
    1610                1615                1620

Leu Asn Glu Met Glu Ile Gln Leu Ser His Ala Asn Arg Met Ala
    1625                1630                1635
```

Ala Glu Ala Gln Lys Gln Val Lys Ser Leu Gln Ser Leu Leu Lys
1640                1645                1650

Asp Thr Gln Ile Gln Leu Asp Asp Ala Val Arg Ala Asn Asp Asp
1655                1660                1665

Leu Lys Glu Asn Ile Ala Ile Val Glu Arg Arg Asn Asn Leu Leu
1670                1675                1680

Gln Ala Glu Leu Glu Glu Leu Arg Ala Val Val Glu Gln Thr Glu
1685                1690                1695

Arg Ser Arg Lys Leu Ala Glu Gln Glu Leu Ile Glu Thr Ser Glu
1700                1705                1710

Arg Val Gln Leu Leu His Ser Gln Asn Thr Ser Leu Ile Asn Gln
1715                1720                1725

Lys Lys Lys Met Glu Ser Asp Leu Thr Gln Leu Gln Ser Glu Val
1730                1735                1740

Glu Glu Ala Val Gln Glu Cys Arg Asn Ala Glu Glu Lys Ala Lys
1745                1750                1755

Lys Ala Ile Thr Asp Ala Ala Met Met Ala Glu Glu Leu Lys Lys
1760                1765                1770

Glu Gln Asp Thr Ser Ala His Leu Glu Arg Met Lys Lys Asn Met
1775                1780                1785

Glu Gln Thr Ile Lys Asp Leu Gln His Arg Leu Asp Glu Ala Glu
1790                1795                1800

Gln Ile Ala Leu Lys Gly Gly Lys Lys Gln Leu Gln Lys Leu Glu
1805                1810                1815

Ala Arg Val Arg Glu Leu Glu Gly Glu Leu Glu Ala Glu Gln Lys
1820                1825                1830

Arg Asn Ala Glu Ser Val Lys Gly Met Arg Lys Ser Glu Arg Arg
1835                1840                1845

Ile Lys Glu Leu Thr Tyr Gln Thr Glu Glu Asp Lys Lys Asn Leu
1850                1855                1860

Leu Arg Leu Gln Asp Leu Val Asp Lys Leu Gln Leu Lys Val Lys
1865                1870                1875

Ala Tyr Lys Arg Gln Ala Glu Glu Ala Glu Glu Gln Ala Asn Thr
1880                1885                1890

Asn Leu Ser Lys Phe Arg Lys Val Gln His Glu Leu Asp Glu Ala
1895                1900                1905

Glu Glu Arg Ala Asp Ile Ala Glu Ser Gln Val Asn Lys Leu Arg
1910                1915                1920

Ala Lys Ser Arg Asp Ile Gly Ala Lys Gln Lys Met His Asp Glu
1925                1930                1935

Glu

<210> SEQ ID NO 26
<211> LENGTH: 5941
<212> TYPE: DNA
<213> ORGANISM: Homo sapiens

<400> SEQUENCE: 26
agatagagag actcctgcgg cccagattct tcaggattct ccgtgaaggg ataaccaggg      60
gaagcaccaa gatgaccgat gcccagatgg ctgactttgg ggcagcggcc cagtacctcc     120
gcaagtcaga gaaggagcgt ctagaggccc agacccggcc ctttgacatt cgcactgagt     180
gcttcgtgcc cgatgacaag gaagagtttg tcaaagccaa gatttgtcc cgggagggag     240 gcaaggtcat tgctgaaacc gagaatggga agacggtgac tgtgaaggag gaccaggtgt     300

-continued

| | |
|---|---|
| tgcagcagaa cccacccaag ttcgacaaga ttgaggacat ggccatgctg accttcctgc | 360 |
| acgagcccgc ggtgcttttc aacctcaagg agcgctacgc ggcctggatg atatatacct | 420 |
| actcgggcct cttctgtgtc actgtcaacc cctacaagtg gctgccggtg tacaatgccg | 480 |
| aggtggtggc cgcctaccgg ggcaagaaga ggagtgaggc cccgccccac atcttctcca | 540 |
| tctccgacaa cgcctatcag tacatgctga cagatcggga gaaccagtcc atcctcatca | 600 |
| cgggagaatc cggggcgggg aagactgtga acaccaagcg tgtcatccag tactttgcca | 660 |
| gcattgcagc cataggtgac cgtggcaaga aggacaatgc caatgcgaac aagggcaccc | 720 |
| tggaggacca gatcatccag gccaaccccg ctctggaggc cttcggcaat gccaagactg | 780 |
| tccggaacga caactcctcc cgctttggga aattcattag gatccacttt ggggccactg | 840 |
| gaaagctggc ttctgcagac atagagacct acctgctgga aagtcccgg gtgatcttcc | 900 |
| agctgaaagc tgagagaaac taccacatct ctaccagat tctgtccaac aagaagccgg | 960 |
| agttgctgga catgctgctg gtcaccaaca atccctacga ctacgccttc gtgtctcagg | 1020 |
| gagaggtgtc cgtggcctcc attgatgact ccgaggagct catggccacc gatagtgcct | 1080 |
| ttgacgtgct gggcttcact tcagaggaga agctggcgt ctacaagctg acgggagcca | 1140 |
| tcatgcacta cgggaacatg aagttcaagc agaagcagcg ggaggagcag gcggagccag | 1200 |
| acggcaccga agatgctgac aagtcggcct acctcatggg gctgaactca gctgacctgc | 1260 |
| tcaaggggct gtgccaccct cgggtgaaag tgggcaacga gtatgtcacc aaggggcaga | 1320 |
| gcgtgcagca ggtgtactac tccatcgggg ctctggccaa ggcagtgtat gagaagatgt | 1380 |
| tcaactggat ggtgacgcgc atcaacgcca ccctggagac caagcagcca cgccagtact | 1440 |
| tcataggagt cctggacatc gctggcttcg agatcttcga cttcaacagc tttgagcagc | 1500 |
| tctgcatcaa cttcaccaac gagaagctgc agcagttctt caaccaccac atgttcgtgc | 1560 |
| tggagcagga ggagtacaag aaggagggca ttgagtggac attcattgac tttggcatgg | 1620 |
| acctgcaggc ctgcattgac ctcatcgaga agcccatggg catcatgtcc atcctggagg | 1680 |
| aggagtgcat gttccccaag gccactgaca tgaccttcaa ggccaagctg tacgacaacc | 1740 |
| acctgggcaa gtccaacaat ttccagaagc cacgcaacat caagggggaag caggaagccc | 1800 |
| acttctccct gatccactac gccggcactg tggactacaa catcctgggc tggctggaaa | 1860 |
| aaaacaagga tcctctcaac gagactgttg tggccctgta ccagaagtcc tccctcaagc | 1920 |
| tcatggccac tctcttctcc tcctacgcaa ctgccgatac tggggacagt ggtaaaagca | 1980 |
| aaggaggcaa gaaaaagggc tcatccttcc agacggtgtc ggctctccac cgggaaaatc | 2040 |
| tcaacaagct aatgaccaac ctgaggacca cccatcctca ctttgtgcgt tgcatcatcc | 2100 |
| ccaatgagcg gaaggctcca gggtgatgg acaaccccct ggtcatgcac cagctgcgct | 2160 |
| gcaatggcgt gctggagggc atccgcatct gcaggaaggg cttccccaac cgcatcctct | 2220 |
| acggggactt ccggcagagg tatcgcatcc tgaacccagt ggccatccct gagggacagt | 2280 |
| tcattgatag caggaagggg acagagaagc tgctcagctc tctggacatt gatcacaacc | 2340 |
| agtacaagtt tggccacacc aaggtgttct tcaaggcagg gctgcttggg ctgctggagg | 2400 |
| agatgcggga tgagaggctg agccgcatca tcacgcgcat gcaggcccaa gcccggggcc | 2460 |
| agctcatgcg cattgagttc aagaagatag tggaacgcag ggatgccctg ctggtaatcc | 2520 |
| agtggaacat tcgggccttc atgggggtca agaattggcc ctggatgaag ctctacttca | 2580 |
| agatcaagcc gctgctgaag agcgcagaga cggagaagga gatggccacc atgaaggaag | 2640 |

```
agttcgggcg catcaaagag acgctggaga agtccgaggc tcgccgcaag gagctggagg    2700
agaagatggt gtccctgctg caggagaaga atgacctgca gctccaagtg caggcggaac    2760
aagacaacct caatgatgct gaggagcgct gcgaccagct gatcaaaaac aagattcagc    2820
tggaggccaa agtaaaggag atgaatgaga ggctggagga tgaggaggag atgaacgcgg    2880
agctcactgc caagaagcgc aagctggaag acgagtgctc agagctcaag aaggacattg    2940
atgacctgga gctgacactg gccaaggtgg agaaggagaa gcatgcaaca gagaacaagg    3000
tgaagaacct aacagaggag atggctgggc tggatgaaat catcgctaag ctgaccaagg    3060
agaagaaagc tctacaagag gcccatcagc aggccctgga tgaccttcag gttgaggaag    3120
acaaggtcaa cagcctgtcc aagtctaagg tcaagctgga gcagcaggtg gatgatctgg    3180
agggatccct agagcaagag aagaaggtgc gcatggacct ggagcgagca aagcggaaac    3240
tggagggcga cctgaagctg acccaggaga gcatcatgga cctggaaaat gataaactgc    3300
agctggaaga aaagcttaag aagaaggagt ttgacattaa tcagcagaac agtaagattg    3360
aggatgagca ggtgctggcc cttcaactac agaagaaact gaaggaaaac caggcacgca    3420
tcgaggagct ggaggaggag ctggaggccg agcgcaccgc cagggctaag gtggagaagc    3480
tgcgctcaga cctgtctcgg gagctggagg agatcagcga gcggctggaa gaggccggcg    3540
gggccacgtc cgtgcagatc gagatgaaca agaagcgcga ggccgagttc cagaagatgc    3600
ggcgggacct ggaggaggcc acgctgcagc acgaggccac tgccgcggcc ctgcgcaaga    3660
agcacgccga cagcgtggcc gagctgggcg agcagatcga caacctgcag cgggtgaagc    3720
agaagctgga aaggagaag agcgagttca gctggagct ggatgacgtc acctccaaca    3780
tggagcagat catcaaggcc aaggcaaacc tggagaaagt gtctcggacg ctggaggacc    3840
aggccaatga gtaccgcgtg aagctagaag aggcccaacg ctccctcaat gatttcacca    3900
cccagcgagc caagctgcag accgagaatg agagttggc ccggcagcta gaggaaaagg    3960
aggcgctaat ctcgcagctg acccggggga agctctctta tcccagcaa atggaggacc    4020
tcaaaaggca gctggaggag gagggcaagg cgaagaacgc cctggcccat gcactgcagt    4080
cggcccggca tgactgcgac ctgctgcggg agcagtacga ggaggagaca gaggccaagg    4140
ccgagctgca gcgcgtcctg tccaaggcca actcggaggt ggcccagtgg aggaccaagt    4200
atgagacgga cgccattcag cggactgagg agctcgaaga ggccaaaaag aagctggccc    4260
agcggctgca ggatgccgag gaggccgtgg aggctgttaa tgccaagtgc tcctcactgg    4320
agaagaccaa gcaccggcta cagaatgaga tagaggactt gatggtggac gtagagcgct    4380
ccaatgctgc tgctgcagcc ctggacaaga agcagagaaa ctttgacaag atcctggccg    4440
agtggaagca gaagtatgag gagtcgcagt ctgagctgga gtcctcacag aaggaggctc    4500
gctcccctcag cacagagctc ttcaagctca gaacgcctca cgaggagtcc ctggagcacc    4560
tagagacctt caagcgggag aacaagaacc ttcaggagga aatctcggac cttactgagc    4620
agctaggaga aggaggaaag aatgtgcatg agctggaaag ggtccgcaaa cagctggagg    4680
tggagaagct ggagctgcag tcagccctgg aggaggcaga ggcctccctg gagcacgagg    4740
agggcaagat cctccgggcc cagctagagt tcaaccagat caaggcagag atcgagcgga    4800
agctggcaga gaaggacgag gagatggaac aggccaagcg caaccaccag cgggtggtgg    4860
actcgctgca gacctccctg gatgcagaga cacgcagccg caacgaggtc ctgagggtga    4920
agaagaagat ggaaggagac ctcaatgaga tggagatcca gctcagccac gccaaccgca    4980
tggctgccga ggcccagaag caagtcaaga gcctccagag cttgctgaag gacacccaga    5040
```

-continued

```
tccagctgga cgatgcggtc cgtgccaacg acgacctgaa ggagaacatc gccatcgtgg   5100
agcggcgcaa caacctgctg caggctgagc tggaggagct gcgtgccgtg gtggagcaga   5160
cagagcggtc ccggaagctg gcggagcagg agctgattga gaccagcgag cgggtgcagc   5220
tgctgcattc ccagaacacc agcctcatca accagaagaa gaagatggag tcggatctga   5280
cccagctcca gtcggaagtg gaggaggcag tgcaggagtg cagaaacgcc gaggagaagg   5340
ccaagaaggc catcacggat gccgccatga tggcagagga gctgaagaag gagcaggaca   5400
ccagcgccca cctggagcgc atgaagaaga acatggagca gaccattaag gacctgcagc   5460
accggctgga cgaggccgag cagatcgccc tcaaggagg caagaagcag ctgcagaagc   5520
tggaagcgcg ggtgcgggag ctggagggtg agctggaggc cgagcagaag cgcaacgcag   5580
agtcggtgaa gggcatgagg aagagcgagc ggcgcatcaa ggagctcacc taccagacag   5640
aggaagacaa aaagaacctg ctgcggctac aggacctggt ggacaagctg caactgaagg   5700
tcaaggccta caagcgccag gccgaggagg cggaggagca agccaacacc aacctgtcca   5760
agttccgcaa ggtgcagcat gagctggatg aggcagagga gcgggcggac atcgctgagt   5820
cccaggtcaa caagcttcga gccaagagcc gtgacattgg tgccaagcaa aaaatgcacg   5880
atgaggagtg acactgcctc gggaacctca ctcttgccaa cctgtaataa atatgagtgc   5940
c                                                                  5941
```

<210> SEQ ID NO 27
<211> LENGTH: 175
<212> TYPE: PRT
<213> ORGANISM: Homo sapiens

<400> SEQUENCE: 27

Met Ala Ser Arg Lys Ala Gly Thr Arg Gly Lys Val Ala Ala Thr Lys
1               5                   10                  15

Gln Ala Gln Arg Gly Ser Ser Asn Val Phe Ser Met Phe Glu Gln Ala
                20                  25                  30

Gln Ile Gln Glu Phe Lys Glu Ala Phe Ser Cys Ile Asp Gln Asn Arg
            35                  40                  45

Asp Gly Ile Ile Cys Lys Ala Asp Leu Arg Glu Thr Tyr Ser Gln Leu
        50                  55                  60

Gly Lys Val Ser Val Pro Glu Glu Leu Asp Ala Met Leu Gln Glu
65                  70                  75                  80

Gly Lys Gly Pro Ile Asn Phe Thr Val Phe Leu Thr Leu Phe Gly Glu
                85                  90                  95

Lys Leu Asn Gly Thr Asp Pro Glu Glu Ala Ile Leu Ser Ala Phe Arg
                100                 105                 110

Met Phe Asp Pro Ser Gly Lys Gly Val Val Asn Lys Asp Glu Phe Lys
            115                 120                 125

Gln Leu Leu Leu Thr Gln Ala Asp Lys Phe Ser Pro Ala Glu Val Glu
        130                 135                 140

Gln Met Phe Ala Leu Thr Pro Met Asp Leu Ala Gly Asn Ile Asp Tyr
145                 150                 155                 160

Lys Ser Leu Cys Tyr Ile Ile Thr His Gly Asp Glu Lys Glu Glu
                165                 170                 175

<210> SEQ ID NO 28
<211> LENGTH: 619
<212> TYPE: DNA
<213> ORGANISM: Homo sapiens

<400> SEQUENCE: 28

```
tctgcagaga gaatggccag caggaaggcg gggacccggg gcaaggtggc agccaccaag    60
caggcccaac gtggttcttc aacgtctttt ccatgtttg aacaagccca gatacaggag   120
ttcaaagaag ccttcagctg tatcgaccag aatcgtgatg catcatctg caaggcagac   180
ctgagggaga cctactccca gctggggaag gtgagtgtcc cagaggagga gctggacgcc   240
atgctgcaag agggcaaggg ccccatcaac ttcaccgtct tcctcacgct ctttggggag   300
aagctcaatg ggacagaccc cgaggaagcc atcctgagtg ccttccgcat gtttgacccc   360
agcggcaaag gggtggtgaa caaggatgag ttcaagcagc ttctcctgac ccaggcagac   420
aagttctctc cagctgaggt ggagcagatg ttcgccctga cacccatgga cctggcgggg   480
aacatcgact acaagtcact gtgctacatc atcacccatg gagacgagaa agaggaatga   540
ggggcagggc caggcccacg ggggggcacc tcaataaact ctgttgcaaa attggaaaaa   600
aaaaaaaaaa aaaaaaaaa                                               619
```

<210> SEQ ID NO 29
<211> LENGTH: 5179
<212> TYPE: PRT
<213> ORGANISM: Homo sapiens

<400> SEQUENCE: 29

```
Met Gly Leu Pro Leu Ala Arg Leu Ala Ala Val Cys Leu Ala Leu Ser
1               5                   10                  15

Leu Ala Gly Gly Ser Glu Leu Gln Thr Glu Gly Arg Thr Arg Asn His
            20                  25                  30

Gly His Asn Val Cys Ser Thr Trp Gly Asn Phe His Tyr Lys Thr Phe
        35                  40                  45

Asp Gly Asp Val Phe Arg Phe Pro Gly Pro Cys Asp Tyr Asn Phe Ala
    50                  55                  60

Ser Asp Cys Arg Gly Ser Tyr Lys Glu Phe Ala Val His Leu Lys Arg
65                  70                  75                  80

Gly Pro Gly Gln Ala Glu Ala Pro Ala Gly Val Glu Ser Ile Leu Leu
                85                  90                  95

Thr Ile Lys Asp Asp Thr Ile Tyr Leu Thr Arg His Leu Ala Val Leu
            100                 105                 110

Asn Gly Ala Val Val Ser Thr Pro His Tyr Ser Pro Gly Leu Leu Ile
        115                 120                 125

Glu Lys Ser Asp Ala Tyr Thr Lys Val Tyr Ser Arg Ala Gly Leu Thr
    130                 135                 140

Leu Met Trp Asn Arg Glu Asp Ala Leu Met Leu Glu Leu Asp Thr Lys
145                 150                 155                 160

Phe Arg Asn His Thr Cys Gly Leu Cys Gly Asp Tyr Asn Gly Leu Gln
                165                 170                 175

Ser Tyr Ser Glu Phe Leu Ser Asp Gly Val Leu Phe Ser Pro Leu Glu
            180                 185                 190

Phe Gly Asn Met Gln Lys Ile Asn Gln Pro Asp Val Val Cys Glu Asp
        195                 200                 205

Pro Glu Glu Glu Val Ala Pro Ala Ser Cys Ser Glu His Arg Ala Glu
    210                 215                 220

Cys Glu Arg Leu Leu Thr Ala Glu Ala Phe Ala Asp Cys Gln Asp Leu
225                 230                 235                 240

Val Pro Leu Glu Pro Tyr Leu Arg Ala Cys Gln Gln Asp Arg Cys Arg
```

```
            245                 250                 255
Cys Pro Gly Gly Asp Thr Cys Val Cys Ser Thr Val Ala Glu Phe Ser
            260                 265                 270

Arg Gln Cys Ser His Ala Gly Gly Arg Pro Gly Asn Trp Arg Thr Ala
            275                 280                 285

Thr Leu Cys Pro Lys Thr Cys Pro Gly Asn Leu Val Tyr Leu Glu Ser
            290                 295                 300

Gly Ser Pro Cys Met Asp Thr Cys Ser His Leu Glu Val Ser Ser Leu
305                 310                 315                 320

Cys Glu Glu His Arg Met Asp Gly Cys Phe Cys Pro Glu Gly Thr Val
                325                 330                 335

Tyr Asp Asp Ile Gly Asp Ser Gly Cys Val Pro Val Ser Gln Cys His
                340                 345                 350

Cys Arg Leu His Gly His Leu Tyr Thr Pro Gly Gln Glu Ile Thr Asn
                355                 360                 365

Asp Cys Glu Gln Cys Val Cys Asn Ala Gly Arg Trp Val Cys Lys Asp
            370                 375                 380

Leu Pro Cys Pro Gly Thr Cys Ala Leu Glu Gly Gly Ser His Ile Thr
385                 390                 395                 400

Thr Phe Asp Gly Lys Thr Tyr Thr Phe His Gly Asp Cys Tyr Tyr Val
                405                 410                 415

Leu Ala Lys Gly Asp His Asn Asp Ser Tyr Ala Leu Leu Gly Glu Leu
                420                 425                 430

Ala Pro Cys Gly Ser Thr Asp Lys Gln Thr Cys Leu Lys Thr Val Val
                435                 440                 445

Leu Leu Ala Asp Lys Lys Lys Asn Val Val Phe Lys Ser Asp Gly
450                 455                 460

Ser Val Leu Leu Asn Glu Leu Gln Val Asn Leu Pro His Val Thr Ala
465                 470                 475                 480

Ser Phe Ser Val Phe Arg Pro Ser Ser Tyr His Ile Met Val Ser Met
                485                 490                 495

Ala Ile Gly Val Arg Leu Gln Val Gln Leu Ala Pro Val Met Gln Leu
                500                 505                 510

Phe Val Thr Leu Asp Gln Ala Ser Gln Gly Gln Val Gln Gly Leu Cys
                515                 520                 525

Gly Asn Phe Asn Gly Leu Glu Gly Asp Phe Lys Thr Ala Ser Gly
            530                 535                 540

Leu Val Glu Ala Thr Gly Ala Gly Phe Ala Asn Thr Trp Lys Ala Gln
545                 550                 555                 560

Ser Thr Cys His Asp Lys Leu Asp Trp Leu Asp Asp Pro Cys Ser Leu
                565                 570                 575

Asn Ile Glu Ser Ala Asn Tyr Ala Glu His Trp Cys Ser Leu Leu Lys
                580                 585                 590

Lys Thr Glu Thr Pro Phe Gly Arg Cys His Ser Ala Val Asp Pro Ala
                595                 600                 605

Glu Tyr Tyr Lys Arg Cys Lys Tyr Asp Thr Cys Asn Cys Gln Asn Asn
            610                 615                 620

Glu Asp Cys Leu Cys Ala Ala Leu Ser Ser Tyr Ala Arg Ala Cys Thr
625                 630                 635                 640

Ala Lys Gly Val Met Leu Trp Gly Trp Arg Glu His Val Cys Asn Lys
                645                 650                 655

Asp Val Gly Ser Cys Pro Asn Ser Gln Val Phe Leu Tyr Asn Leu Thr
                660                 665                 670
```

```
Thr Cys Gln Gln Thr Cys Arg Ser Leu Ser Glu Ala Asp Ser His Cys
        675                 680                 685

Leu Glu Gly Phe Ala Pro Val Asp Gly Cys Gly Cys Pro Asp His Thr
    690                 695                 700

Phe Leu Asp Glu Lys Gly Arg Cys Val Pro Leu Ala Lys Cys Ser Cys
705                 710                 715                 720

Tyr His Arg Gly Leu Tyr Leu Glu Ala Gly Asp Val Val Arg Gln
                725                 730                 735

Glu Glu Arg Cys Val Cys Arg Asp Gly Arg Leu His Cys Arg Gln Ile
            740                 745                 750

Arg Leu Ile Gly Gln Ser Cys Thr Ala Pro Lys Ile His Met Asp Cys
        755                 760                 765

Ser Asn Leu Thr Ala Leu Ala Thr Ser Lys Pro Arg Ala Leu Ser Cys
    770                 775                 780

Gln Thr Leu Ala Ala Gly Tyr Tyr His Thr Glu Cys Val Ser Gly Cys
785                 790                 795                 800

Val Cys Pro Asp Gly Leu Met Asp Asp Gly Arg Gly Gly Cys Val Val
                805                 810                 815

Glu Lys Glu Cys Pro Cys Val His Asn Asn Asp Leu Tyr Ser Ser Gly
            820                 825                 830

Ala Lys Ile Lys Val Asp Cys Asn Thr Cys Thr Cys Lys Arg Gly Arg
        835                 840                 845

Trp Val Cys Thr Gln Ala Val Cys His Gly Thr Cys Ser Ile Tyr Gly
    850                 855                 860

Ser Gly His Tyr Ile Thr Phe Asp Gly Lys Tyr Tyr Asp Phe Asp Gly
865                 870                 875                 880

His Cys Ser Tyr Val Ala Val Gln Asp Tyr Cys Gly Gln Asn Ser Ser
                885                 890                 895

Leu Gly Ser Phe Ser Ile Ile Thr Glu Asn Val Pro Cys Gly Thr Thr
            900                 905                 910

Gly Val Thr Cys Ser Lys Ala Ile Lys Ile Phe Met Gly Arg Thr Glu
        915                 920                 925

Leu Lys Leu Glu Asp Lys His Arg Val Val Ile Gln Arg Asp Glu Gly
    930                 935                 940

His His Val Ala Tyr Thr Thr Arg Glu Val Gly Gln Tyr Leu Val Val
945                 950                 955                 960

Glu Ser Ser Thr Gly Ile Ile Val Ile Trp Asp Lys Arg Thr Thr Val
                965                 970                 975

Phe Ile Lys Leu Ala Pro Ser Tyr Lys Gly Thr Val Cys Gly Leu Cys
            980                 985                 990

Gly Asn Phe Asp His Arg Ser Asn  Asn Asp Phe Thr Thr Arg Asp His
        995                 1000                1005

Met Val  Val Ser Ser Glu Leu  Asp Phe Gly Asn Ser  Trp Lys Glu
        1010                1015                1020

Ala Pro  Thr Cys Pro Asp Val  Ser Thr Asn Pro Glu  Pro Cys Ser
        1025                1030                1035

Leu Asn  Pro His Arg Arg Ser  Trp Ala Glu Lys Gln  Cys Ser Ile
        1040                1045                1050

Leu Lys  Ser Ser Val Phe Ser  Ile Cys His Ser Lys  Val Asp Pro
        1055                1060                1065

Lys Pro  Phe Tyr Glu Ala Cys  Val His Asp Ser Cys  Ser Cys Asp
        1070                1075                1080
```

```
Thr Gly Gly Asp Cys Glu Cys Phe Cys Ser Ala Val Ala Ser Tyr
    1085            1090            1095

Ala Gln Glu Cys Thr Lys Glu Gly Ala Cys Val Phe Trp Arg Thr
    1100            1105            1110

Pro Asp Leu Cys Pro Ile Phe Cys Asp Tyr Tyr Asn Pro Pro His
    1115            1120            1125

Glu Cys Glu Trp His Tyr Glu Pro Cys Gly Asn Arg Ser Phe Glu
    1130            1135            1140

Thr Cys Arg Thr Ile Asn Gly Ile His Ser Asn Ile Ser Val Ser
    1145            1150            1155

Tyr Leu Glu Gly Cys Tyr Pro Arg Cys Pro Lys Asp Arg Pro Ile
    1160            1165            1170

Tyr Glu Glu Asp Leu Lys Lys Cys Val Thr Ala Asp Lys Cys Gly
    1175            1180            1185

Cys Tyr Val Glu Asp Thr His Tyr Pro Pro Gly Ala Ser Val Pro
    1190            1195            1200

Thr Glu Glu Thr Cys Lys Ser Cys Val Cys Thr Asn Ser Ser Gln
    1205            1210            1215

Val Val Cys Arg Pro Glu Glu Gly Lys Ile Leu Asn Gln Thr Gln
    1220            1225            1230

Asp Gly Ala Phe Cys Tyr Trp Glu Ile Cys Gly Pro Asn Gly Thr
    1235            1240            1245

Val Glu Lys His Phe Asn Ile Cys Ser Ile Thr Thr Arg Pro Ser
    1250            1255            1260

Thr Leu Thr Thr Phe Thr Thr Ile Thr Leu Pro Thr Thr Pro Thr
    1265            1270            1275

Thr Phe Thr Thr Thr Thr Thr Thr Thr Pro Thr Ser Ser Thr
    1280            1285            1290

Val Leu Ser Thr Thr Pro Lys Leu Cys Cys Leu Trp Ser Asp Trp
    1295            1300            1305

Ile Asn Glu Asp His Pro Ser Ser Gly Ser Asp Asp Gly Asp Arg
    1310            1315            1320

Glu Thr Phe Asp Gly Val Cys Gly Ala Pro Glu Asp Ile Glu Cys
    1325            1330            1335

Arg Ser Val Lys Asp Pro His Leu Ser Leu Glu Gln Leu Gly Gln
    1340            1345            1350

Lys Val Gln Cys Asp Val Ser Val Gly Phe Ile Cys Lys Asn Glu
    1355            1360            1365

Asp Gln Phe Gly Asn Gly Pro Phe Gly Leu Cys Tyr Asp Tyr Lys
    1370            1375            1380

Ile Arg Val Asn Cys Cys Trp Pro Met Asp Lys Cys Ile Thr Thr
    1385            1390            1395

Pro Ser Pro Pro Thr Thr Thr Pro Ser Pro Pro Thr Ser Thr
    1400            1405            1410

Thr Thr Leu Pro Pro Thr Thr Thr Pro Ser Pro Pro Thr Thr Thr
    1415            1420            1425

Thr Thr Thr Pro Pro Pro Thr Thr Pro Ser Pro Pro Ile Thr
    1430            1435            1440

Thr Thr Thr Thr Pro Pro Pro Thr Thr Pro Ser Pro Pro Ile
    1445            1450            1455

Ser Thr Thr Thr Thr Pro Pro Pro Thr Thr Thr Pro Ser Pro Pro
    1460            1465            1470

Thr Thr Thr Pro Ser Pro Pro Thr Thr Thr Pro Ser Pro Pro Thr
```

-continued

```
            1475                1480                1485
Thr Thr Thr Thr Thr Pro Pro Pro Thr Thr Thr Pro Ser Pro Pro
        1490                1495                1500
Thr Thr Thr Pro Ile Thr Pro Pro Ala Ser Thr Thr Thr Leu Pro
        1505                1510                1515
Pro Thr Thr Thr Pro Ser Pro Pro Thr Thr Thr Thr Thr Thr Pro
        1520                1525                1530
Pro Pro Thr Thr Thr Pro Ser Pro Pro Thr Thr Thr Pro Ile Thr
        1535                1540                1545
Pro Pro Thr Ser Thr Thr Thr Leu Pro Pro Thr Thr Thr Pro Ser
        1550                1555                1560
Pro Pro Pro Thr Thr Thr Thr Thr Pro Pro Thr Thr Thr Thr Pro
        1565                1570                1575
Ser Pro Pro Thr Thr Thr Thr Pro Ser Pro Pro Thr Ile Thr Thr
        1580                1585                1590
Thr Thr Pro Pro Pro Thr Thr Thr Pro Ser Pro Pro Thr Thr Thr
        1595                1600                1605
Thr Thr Thr Pro Pro Pro Thr Thr Thr Pro Ser Pro Pro Thr Thr
        1610                1615                1620
Thr Pro Ile Thr Pro Pro Thr Ser Thr Thr Thr Leu Pro Pro Thr
        1625                1630                1635
Thr Thr Pro Ser Pro Pro Pro Thr Thr Thr Thr Thr Pro Pro Pro
        1640                1645                1650
Thr Thr Thr Pro Ser Pro Pro Thr Thr Thr Thr Pro Ser Pro Pro
        1655                1660                1665
Ile Thr Thr Thr Thr Thr Pro Pro Pro Thr Thr Thr Pro Ser Ser
        1670                1675                1680
Pro Ile Thr Thr Thr Pro Ser Pro Pro Thr Thr Thr Met Thr Thr
        1685                1690                1695
Pro Ser Pro Thr Thr Thr Pro Ser Ser Pro Ile Thr Thr Thr Thr
        1700                1705                1710
Thr Pro Ser Ser Thr Thr Thr Pro Ser Pro Pro Pro Thr Thr Met
        1715                1720                1725
Thr Thr Pro Ser Pro Thr Thr Thr Pro Ser Pro Pro Thr Thr Thr
        1730                1735                1740
Met Thr Thr Leu Pro Pro Thr Thr Thr Ser Ser Pro Leu Thr Thr
        1745                1750                1755
Thr Pro Leu Pro Pro Ser Ile Thr Pro Pro Thr Phe Ser Pro Phe
        1760                1765                1770
Ser Thr Thr Thr Pro Thr Thr Pro Cys Val Pro Leu Cys Asn Trp
        1775                1780                1785
Thr Gly Trp Leu Asp Ser Gly Lys Pro Asn Phe His Lys Pro Gly
        1790                1795                1800
Gly Asp Thr Glu Leu Ile Gly Asp Val Cys Gly Pro Gly Trp Ala
        1805                1810                1815
Ala Asn Ile Ser Cys Arg Ala Thr Met Tyr Pro Asp Val Pro Ile
        1820                1825                1830
Gly Gln Leu Gly Gln Thr Val Val Cys Asp Val Ser Val Gly Leu
        1835                1840                1845
Ile Cys Lys Asn Glu Asp Gln Lys Pro Gly Gly Val Ile Pro Met
        1850                1855                1860
Ala Phe Cys Leu Asn Tyr Glu Ile Asn Val Gln Cys Cys Glu Cys
        1865                1870                1875
```

```
Val Thr Gln Pro Thr Thr Met Thr Thr Thr Thr Glu Asn Pro
1880            1885            1890

Thr Pro Pro Thr Thr Thr Pro Ile Thr Thr Thr Thr Val Thr
1895            1900            1905

Pro Thr Pro Thr Pro Thr Gly Thr Gln Thr Pro Thr Thr Pro
1910            1915            1920

Ile Thr Thr Thr Thr Thr Val Thr Pro Thr Pro Thr Pro Thr Gly
1925            1930            1935

Thr Gln Thr Pro Thr Thr Thr Pro Ile Thr Thr Thr Thr Val
1940            1945            1950

Thr Pro Thr Pro Thr Pro Thr Gly Thr Gln Thr Pro Thr Thr Thr
1955            1960            1965

Pro Ile Thr Thr Thr Thr Thr Val Thr Pro Thr Pro Thr Pro Thr
1970            1975            1980

Gly Thr Gln Thr Pro Thr Thr Thr Pro Ile Thr Thr Thr Thr
1985            1990            1995

Val Thr Pro Thr Pro Thr Pro Thr Gly Thr Gln Thr Pro Thr Thr
2000            2005            2010

Thr Pro Ile Thr Thr Thr Thr Thr Val Thr Pro Thr Pro Thr Pro
2015            2020            2025

Thr Gly Thr Gln Thr Pro Thr Thr Thr Pro Ile Thr Thr Thr
2030            2035            2040

Thr Val Thr Pro Thr Pro Thr Pro Thr Gly Thr Gln Thr Pro Thr
2045            2050            2055

Thr Thr Pro Ile Thr Thr Thr Thr Thr Val Thr Pro Thr Pro Thr
2060            2065            2070

Pro Thr Gly Thr Gln Thr Pro Thr Thr Thr Pro Ile Thr Thr Thr
2075            2080            2085

Thr Thr Val Thr Pro Thr Pro Thr Pro Thr Gly Thr Gln Thr Pro
2090            2095            2100

Thr Thr Thr Pro Ile Thr Thr Thr Thr Thr Val Thr Pro Thr Pro
2105            2110            2115

Thr Pro Thr Gly Thr Gln Thr Pro Thr Thr Thr Pro Ile Thr Thr
2120            2125            2130

Thr Thr Thr Val Thr Pro Thr Pro Thr Pro Thr Gly Thr Gln Thr
2135            2140            2145

Pro Thr Thr Thr Pro Ile Thr Thr Thr Thr Thr Val Thr Pro Thr
2150            2155            2160

Pro Thr Pro Thr Gly Thr Gln Thr Pro Thr Thr Thr Pro Ile Thr
2165            2170            2175

Thr Thr Thr Thr Val Thr Pro Thr Pro Thr Pro Thr Gly Thr Gln
2180            2185            2190

Thr Pro Thr Thr Thr Pro Ile Thr Thr Thr Thr Thr Val Thr Pro
2195            2200            2205

Thr Pro Thr Pro Thr Gly Thr Gln Thr Pro Thr Thr Thr Pro Ile
2210            2215            2220

Thr Thr Thr Thr Thr Val Thr Pro Thr Pro Thr Pro Thr Gly Thr
2225            2230            2235

Gln Thr Pro Thr Thr Thr Pro Ile Thr Thr Thr Thr Thr Val Thr
2240            2245            2250

Pro Thr Pro Thr Pro Thr Gly Thr Gln Thr Pro Thr Thr Thr Pro
2255            2260            2265
```

-continued

```
Ile Thr Thr Thr Thr Thr Val Thr Pro Thr Pro Thr Pro Thr Gly
    2270            2275            2280
Thr Gln Thr Pro Thr Thr Thr Pro Ile Thr Thr Thr Thr Thr Val
    2285            2290            2295
Thr Pro Thr Pro Thr Pro Thr Gly Thr Gln Thr Pro Thr Thr Thr
    2300            2305            2310
Pro Ile Thr Thr Thr Thr Thr Val Thr Pro Thr Pro Thr Pro Thr
    2315            2320            2325
Gly Thr Gln Thr Pro Thr Thr Thr Pro Ile Thr Thr Thr Thr Thr
    2330            2335            2340
Val Thr Pro Thr Pro Thr Pro Thr Gly Thr Gln Thr Pro Thr Thr
    2345            2350            2355
Thr Pro Ile Thr Thr Thr Thr Thr Val Thr Pro Thr Pro Thr Pro
    2360            2365            2370
Thr Gly Thr Gln Thr Pro Thr Thr Thr Pro Ile Thr Thr Thr Thr
    2375            2380            2385
Thr Val Thr Pro Thr Pro Thr Pro Thr Gly Thr Gln Thr Pro Thr
    2390            2395            2400
Thr Thr Pro Ile Thr Thr Thr Thr Thr Val Thr Pro Thr Pro Thr
    2405            2410            2415
Pro Thr Gly Thr Gln Thr Pro Thr Thr Thr Pro Ile Thr Thr Thr
    2420            2425            2430
Thr Thr Val Thr Pro Thr Pro Thr Pro Thr Gly Thr Gln Thr Pro
    2435            2440            2445
Thr Thr Thr Pro Ile Thr Thr Thr Thr Thr Val Thr Pro Thr Pro
    2450            2455            2460
Thr Pro Thr Gly Thr Gln Thr Pro Thr Thr Thr Pro Ile Thr Thr
    2465            2470            2475
Thr Thr Thr Val Thr Pro Thr Pro Thr Pro Thr Gly Thr Gln Thr
    2480            2485            2490
Pro Thr Thr Thr Pro Ile Thr Thr Thr Thr Thr Val Thr Pro Thr
    2495            2500            2505
Pro Thr Pro Thr Gly Thr Gln Thr Pro Thr Thr Thr Pro Ile Thr
    2510            2515            2520
Thr Thr Thr Val Thr Pro Thr Pro Thr Pro Thr Gly Thr Gln
    2525            2530            2535
Thr Pro Thr Thr Thr Pro Ile Thr Thr Thr Thr Thr Val Thr Pro
    2540            2545            2550
Thr Pro Thr Pro Thr Gly Thr Gln Thr Pro Thr Thr Thr Pro Ile
    2555            2560            2565
Thr Thr Thr Thr Val Thr Pro Thr Pro Thr Pro Thr Gly Thr
    2570            2575            2580
Gln Thr Pro Thr Thr Thr Pro Ile Thr Thr Thr Thr Thr Val Thr
    2585            2590            2595
Pro Thr Pro Thr Pro Thr Gly Thr Gln Thr Pro Thr Thr Thr Pro
    2600            2605            2610
Ile Thr Thr Thr Thr Val Thr Pro Thr Pro Thr Pro Thr Gly
    2615            2620            2625
Thr Gln Thr Pro Thr Thr Thr Pro Ile Thr Thr Thr Thr Thr Val
    2630            2635            2640
Thr Pro Thr Pro Thr Pro Thr Gly Thr Gln Thr Pro Thr Thr Thr
    2645            2650            2655
Pro Ile Thr Thr Thr Thr Thr Val Thr Pro Thr Pro Thr Pro Thr
```

-continued

```
              2660                2665                2670

Gly Thr Gln Thr Pro Thr Thr Thr Pro Ile Thr Thr Thr Thr
    2675                2680                2685

Val Thr Pro Thr Pro Thr Pro Thr Gly Thr Gln Thr Pro Thr Thr
    2690                2695                2700

Thr Pro Ile Thr Thr Thr Thr Thr Val Thr Pro Thr Pro Thr Pro
    2705                2710                2715

Thr Gly Thr Gln Thr Pro Thr Thr Pro Ile Thr Thr Thr Thr
    2720                2725                2730

Thr Val Thr Pro Thr Pro Thr Pro Thr Gly Thr Gln Thr Pro Thr
    2735                2740                2745

Thr Thr Pro Ile Thr Thr Thr Thr Thr Val Thr Pro Thr Pro Thr
    2750                2755                2760

Pro Thr Gly Thr Gln Thr Pro Thr Thr Thr Pro Ile Thr Thr Thr
    2765                2770                2775

Thr Thr Val Thr Pro Thr Pro Thr Pro Thr Gly Thr Gln Thr Pro
    2780                2785                2790

Thr Thr Thr Pro Ile Thr Thr Thr Thr Thr Val Thr Pro Thr Pro
    2795                2800                2805

Thr Pro Thr Gly Thr Gln Thr Pro Thr Thr Thr Pro Ile Thr Thr
    2810                2815                2820

Thr Thr Thr Val Thr Pro Thr Pro Thr Pro Thr Gly Thr Gln Thr
    2825                2830                2835

Pro Thr Thr Thr Pro Ile Thr Thr Thr Thr Thr Val Thr Pro Thr
    2840                2845                2850

Pro Thr Pro Thr Gly Thr Gln Thr Pro Thr Thr Thr Pro Ile Thr
    2855                2860                2865

Thr Thr Thr Val Thr Pro Thr Pro Thr Pro Thr Gly Thr Gln
    2870                2875                2880

Thr Pro Thr Thr Thr Pro Ile Thr Thr Thr Thr Thr Val Thr Pro
    2885                2890                2895

Thr Pro Thr Pro Thr Gly Thr Gln Thr Pro Thr Thr Thr Pro Ile
    2900                2905                2910

Thr Thr Thr Thr Val Thr Pro Thr Pro Thr Pro Thr Gly Thr
    2915                2920                2925

Gln Thr Pro Thr Thr Thr Pro Ile Thr Thr Thr Thr Thr Val Thr
    2930                2935                2940

Pro Thr Pro Thr Pro Thr Gly Thr Gln Thr Pro Thr Thr Thr Pro
    2945                2950                2955

Ile Thr Thr Thr Thr Thr Val Thr Pro Thr Pro Thr Pro Thr Gly
    2960                2965                2970

Thr Gln Thr Pro Thr Thr Thr Pro Ile Thr Thr Thr Thr Thr Val
    2975                2980                2985

Thr Pro Thr Pro Thr Pro Thr Gly Thr Gln Thr Pro Thr Thr Thr
    2990                2995                3000

Pro Ile Thr Thr Thr Thr Thr Val Thr Pro Thr Pro Thr Pro Thr
    3005                3010                3015

Gly Thr Gln Thr Pro Thr Thr Thr Pro Ile Thr Thr Thr Thr Thr
    3020                3025                3030

Val Thr Pro Thr Pro Thr Pro Thr Gly Thr Gln Thr Pro Thr Thr
    3035                3040                3045

Thr Pro Ile Thr Thr Thr Thr Thr Val Thr Pro Thr Pro Thr Pro
    3050                3055                3060
```

-continued

```
Thr Gly Thr Gln Thr Pro Thr Thr Pro Ile Thr Thr Thr Thr
    3065             3070             3075

Thr Val Thr Pro Thr Pro Thr Pro Thr Gly Thr Gln Thr Pro Thr
    3080             3085             3090

Thr Thr Pro Ile Thr Thr Thr Thr Thr Val Thr Pro Thr Pro Thr
    3095             3100             3105

Pro Thr Gly Thr Gln Thr Pro Thr Thr Pro Ile Thr Thr Thr
    3110             3115             3120

Thr Thr Val Thr Pro Thr Pro Thr Pro Thr Gly Thr Gln Thr Pro
    3125             3130             3135

Thr Thr Thr Pro Ile Thr Thr Thr Thr Thr Val Thr Pro Thr Pro
    3140             3145             3150

Thr Pro Thr Gly Thr Gln Thr Pro Thr Thr Thr Pro Ile Thr Thr
    3155             3160             3165

Thr Thr Thr Val Thr Pro Thr Pro Thr Pro Thr Gly Thr Gln Thr
    3170             3175             3180

Pro Thr Thr Thr Pro Ile Thr Thr Thr Thr Thr Val Thr Pro Thr
    3185             3190             3195

Pro Thr Pro Thr Gly Thr Gln Thr Pro Thr Thr Thr Pro Ile Thr
    3200             3205             3210

Thr Thr Thr Thr Val Thr Pro Thr Pro Thr Pro Thr Gly Thr Gln
    3215             3220             3225

Thr Pro Thr Thr Thr Pro Ile Thr Thr Thr Thr Thr Val Thr Pro
    3230             3235             3240

Thr Pro Thr Pro Thr Gly Thr Gln Thr Pro Thr Thr Thr Pro Ile
    3245             3250             3255

Thr Thr Thr Thr Thr Val Thr Pro Thr Pro Thr Pro Thr Gly Thr
    3260             3265             3270

Gln Thr Pro Thr Thr Thr Pro Ile Thr Thr Thr Thr Thr Val Thr
    3275             3280             3285

Pro Thr Pro Thr Pro Thr Gly Thr Gln Thr Pro Thr Thr Thr Pro
    3290             3295             3300

Ile Thr Thr Thr Thr Thr Val Thr Pro Thr Pro Thr Pro Thr Gly
    3305             3310             3315

Thr Gln Thr Pro Thr Thr Thr Pro Ile Thr Thr Thr Thr Thr Val
    3320             3325             3330

Thr Pro Thr Pro Thr Pro Thr Gly Thr Gln Thr Pro Thr Thr Thr
    3335             3340             3345

Pro Ile Thr Thr Thr Thr Thr Val Thr Pro Thr Pro Thr Pro Thr
    3350             3355             3360

Gly Thr Gln Thr Pro Thr Thr Thr Pro Ile Thr Thr Thr Thr Thr
    3365             3370             3375

Val Thr Pro Thr Pro Thr Pro Thr Gly Thr Gln Thr Pro Thr Thr
    3380             3385             3390

Thr Pro Ile Thr Thr Thr Thr Thr Val Thr Pro Thr Pro Thr Pro
    3395             3400             3405

Thr Gly Thr Gln Thr Pro Thr Thr Thr Pro Ile Thr Thr Thr Thr
    3410             3415             3420

Thr Val Thr Pro Thr Pro Thr Pro Thr Gly Thr Gln Thr Pro Thr
    3425             3430             3435

Thr Thr Pro Ile Thr Thr Thr Thr Thr Val Thr Pro Thr Pro Thr
    3440             3445             3450
```

```
Pro Thr Gly Thr Gln Thr Pro Thr Thr Thr Pro Ile Thr Thr Thr
    3455            3460                3465
Thr Thr Val Thr Pro Thr Pro Thr Pro Thr Gly Thr Gln Thr Pro
    3470            3475                3480
Thr Thr Thr Pro Ile Thr Thr Thr Thr Thr Val Thr Pro Thr Pro
    3485            3490                3495
Thr Pro Thr Gly Thr Gln Thr Pro Thr Thr Thr Pro Ile Thr Thr
    3500            3505                3510
Thr Thr Thr Val Thr Pro Thr Pro Thr Pro Thr Gly Thr Gln Thr
    3515            3520                3525
Pro Thr Thr Thr Pro Ile Thr Thr Thr Thr Thr Val Thr Pro Thr
    3530            3535                3540
Pro Thr Pro Thr Gly Thr Gln Thr Pro Thr Thr Thr Pro Ile Thr
    3545            3550                3555
Thr Thr Thr Val Thr Pro Thr Pro Thr Pro Thr Gly Thr Gln
    3560            3565                3570
Thr Pro Thr Thr Thr Pro Ile Thr Thr Thr Thr Thr Val Thr Pro
    3575            3580                3585
Thr Pro Thr Pro Thr Gly Thr Gln Thr Pro Thr Thr Thr Pro Ile
    3590            3595                3600
Thr Thr Thr Thr Val Thr Pro Thr Pro Thr Pro Thr Gly Thr
    3605            3610                3615
Gln Thr Pro Thr Thr Thr Pro Ile Thr Thr Thr Thr Thr Val Thr
    3620            3625                3630
Pro Thr Pro Thr Pro Thr Gly Thr Gln Thr Pro Thr Thr Thr Pro
    3635            3640                3645
Ile Thr Thr Thr Thr Val Thr Pro Thr Pro Thr Pro Thr Gly
    3650            3655                3660
Thr Gln Thr Pro Thr Thr Thr Pro Ile Thr Thr Thr Thr Thr Val
    3665            3670                3675
Thr Pro Thr Pro Thr Pro Thr Gly Thr Gln Thr Pro Thr Thr Thr
    3680            3685                3690
Pro Ile Thr Thr Thr Thr Thr Val Thr Pro Thr Pro Thr Pro Thr
    3695            3700                3705
Gly Thr Gln Thr Pro Thr Thr Thr Pro Ile Thr Thr Thr Thr Thr
    3710            3715                3720
Val Thr Pro Thr Pro Thr Pro Thr Gly Thr Gln Thr Pro Thr Thr
    3725            3730                3735
Thr Pro Ile Thr Thr Thr Thr Thr Val Thr Pro Thr Pro Thr Pro
    3740            3745                3750
Thr Gly Thr Gln Thr Pro Thr Thr Thr Pro Ile Thr Thr Thr Thr
    3755            3760                3765
Thr Val Thr Pro Thr Pro Thr Pro Thr Gly Thr Gln Thr Pro Thr
    3770            3775                3780
Thr Thr Pro Ile Thr Thr Thr Thr Thr Val Thr Pro Thr Pro Thr
    3785            3790                3795
Pro Thr Gly Thr Gln Thr Pro Thr Thr Thr Pro Ile Thr Thr Thr
    3800            3805                3810
Thr Thr Val Thr Pro Thr Pro Thr Pro Thr Gly Thr Gln Thr Pro
    3815            3820                3825
Thr Thr Thr Pro Ile Thr Thr Thr Thr Thr Val Thr Pro Thr Pro
    3830            3835                3840
Thr Pro Thr Gly Thr Gln Thr Pro Thr Thr Thr Pro Ile Thr Thr
```

-continued

```
            3845                3850                3855
Thr Thr Thr Val Thr Pro Thr Pro Thr Pro Thr Gly Thr Gln Thr
        3860                3865                3870
Pro Thr Thr Thr Pro Ile Thr Thr Thr Thr Val Thr Pro Thr
    3875                3880                3885
Pro Thr Pro Thr Gly Thr Gln Thr Pro Thr Thr Thr Pro Ile Thr
    3890                3895                3900
Thr Thr Thr Thr Val Thr Pro Thr Pro Thr Pro Thr Gly Thr Gln
    3905                3910                3915
Thr Pro Thr Thr Thr Pro Ile Thr Thr Thr Thr Val Thr Pro
    3920                3925                3930
Thr Pro Thr Pro Thr Gly Thr Gln Thr Pro Thr Thr Thr Pro Ile
    3935                3940                3945
Thr Thr Thr Thr Thr Val Thr Pro Thr Pro Thr Pro Thr Gly Thr
    3950                3955                3960
Gln Thr Pro Thr Thr Thr Pro Ile Thr Thr Thr Thr Thr Val Thr
    3965                3970                3975
Pro Thr Pro Thr Pro Thr Gly Thr Gln Thr Pro Thr Thr Thr Pro
    3980                3985                3990
Ile Thr Thr Thr Thr Thr Val Thr Pro Thr Pro Thr Pro Thr Gly
    3995                4000                4005
Thr Gln Thr Pro Thr Thr Thr Pro Ile Thr Thr Thr Thr Thr Val
    4010                4015                4020
Thr Pro Thr Pro Thr Pro Thr Gly Thr Gln Thr Pro Thr Thr Thr
    4025                4030                4035
Pro Ile Thr Thr Thr Thr Thr Val Thr Pro Thr Pro Thr Pro Thr
    4040                4045                4050
Gly Thr Gln Thr Pro Thr Thr Thr Pro Ile Thr Thr Thr Thr Thr
    4055                4060                4065
Val Thr Pro Thr Pro Thr Pro Thr Gly Thr Gln Thr Pro Thr Thr
    4070                4075                4080
Thr Pro Ile Thr Thr Thr Thr Thr Val Thr Pro Thr Pro Thr Pro
    4085                4090                4095
Thr Gly Thr Gln Thr Pro Thr Thr Pro Ile Thr Thr Thr Thr Thr
    4100                4105                4110
Thr Val Thr Pro Thr Pro Thr Pro Thr Gly Thr Gln Thr Pro Thr
    4115                4120                4125
Thr Thr Pro Ile Thr Thr Thr Thr Thr Val Thr Pro Thr Pro Thr
    4130                4135                4140
Pro Thr Gly Thr Gln Thr Pro Thr Thr Pro Ile Thr Thr Thr
    4145                4150                4155
Thr Thr Val Thr Pro Thr Pro Thr Pro Thr Gly Thr Gln Thr Pro
    4160                4165                4170
Thr Thr Thr Pro Ile Thr Thr Thr Thr Val Thr Pro Thr Pro
    4175                4180                4185
Thr Pro Thr Gly Thr Gln Thr Gly Pro Pro Thr His Thr Ser Thr
    4190                4195                4200
Ala Pro Ile Ala Glu Leu Thr Thr Ser Asn Pro Pro Glu Ser
    4205                4210                4215
Ser Thr Pro Gln Thr Ser Arg Ser Thr Ser Ser Pro Leu Thr Glu
    4220                4225                4230
Ser Thr Thr Leu Leu Ser Thr Leu Pro Pro Ala Ile Glu Met Thr
    4235                4240                4245
```

Ser Thr Ala Pro Pro Ser Thr Pro Thr Ala Pro Thr Thr Thr Ser
4250                4255                4260

Gly Gly His Thr Leu Ser Pro Pro Pro Ser Thr Thr Thr Ser Pro
4265                4270                4275

Pro Gly Thr Pro Thr Arg Gly Thr Thr Thr Gly Ser Ser Ser Ala
4280                4285                4290

Pro Thr Pro Ser Thr Val Gln Thr Thr Thr Thr Ser Ala Trp Thr
4295                4300                4305

Pro Thr Pro Thr Pro Leu Ser Thr Pro Ser Ile Ile Arg Thr Thr
4310                4315                4320

Gly Leu Arg Pro Tyr Pro Ser Ser Val Leu Ile Cys Cys Val Leu
4325                4330                4335

Asn Asp Thr Tyr Tyr Ala Pro Gly Glu Glu Val Tyr Asn Gly Thr
4340                4345                4350

Tyr Gly Asp Thr Cys Tyr Phe Val Asn Cys Ser Leu Ser Cys Thr
4355                4360                4365

Leu Glu Phe Tyr Asn Trp Ser Cys Pro Ser Thr Pro Ser Pro Thr
4370                4375                4380

Pro Thr Pro Ser Lys Ser Thr Pro Thr Pro Ser Lys Pro Ser Ser
4385                4390                4395

Thr Pro Ser Lys Pro Thr Pro Gly Thr Lys Pro Pro Glu Cys Pro
4400                4405                4410

Asp Phe Asp Pro Pro Arg Gln Glu Asn Glu Thr Trp Trp Leu Cys
4415                4420                4425

Asp Cys Phe Met Ala Thr Cys Lys Tyr Asn Asn Thr Val Glu Ile
4430                4435                4440

Val Lys Val Glu Cys Glu Pro Pro Pro Met Pro Thr Cys Ser Asn
4445                4450                4455

Gly Leu Gln Pro Val Arg Val Glu Asp Pro Asp Gly Cys Cys Trp
4460                4465                4470

His Trp Glu Cys Asp Cys Tyr Cys Thr Gly Trp Gly Asp Pro His
4475                4480                4485

Tyr Val Thr Phe Asp Gly Leu Tyr Tyr Ser Tyr Gln Gly Asn Cys
4490                4495                4500

Thr Tyr Val Leu Val Glu Glu Ile Ser Pro Ser Val Asp Asn Phe
4505                4510                4515

Gly Val Tyr Ile Asp Asn Tyr His Cys Asp Pro Asn Asp Lys Val
4520                4525                4530

Ser Cys Pro Arg Thr Leu Ile Val Arg His Glu Thr Gln Glu Val
4535                4540                4545

Leu Ile Lys Thr Val His Met Met Pro Met Gln Val Gln Val Gln
4550                4555                4560

Val Asn Arg Gln Ala Val Ala Leu Pro Tyr Lys Lys Tyr Gly Leu
4565                4570                4575

Glu Val Tyr Gln Ser Gly Ile Asn Tyr Val Val Asp Ile Pro Glu
4580                4585                4590

Leu Gly Val Leu Val Ser Tyr Asn Gly Leu Ser Phe Ser Val Arg
4595                4600                4605

Leu Pro Tyr His Arg Phe Gly Asn Asn Thr Lys Gly Gln Cys Gly
4610                4615                4620

Thr Cys Thr Asn Thr Thr Ser Asp Asp Cys Ile Leu Pro Ser Gly
4625                4630                4635

-continued

| | | | | | | | | | | | |
|---|---|---|---|---|---|---|---|---|---|---|---|
|Glu|Ile|Val|Ser|Asn|Cys|Glu|Ala|Ala|Ala|Asp|Gln|Trp|Leu|Val|
| |4640| | | |4645| | | |4650| | | | | |
|Asn|Asp|Pro|Ser|Lys|Pro|His|Cys|Pro|His|Ser|Ser|Ser|Thr|Thr|
| |4655| | | |4660| | | |4665| | | | | |
|Lys|Arg|Pro|Ala|Val|Thr|Val|Pro|Gly|Gly|Gly|Lys|Thr|Thr|Pro|
| |4670| | | |4675| | | |4680| | | | | |
|His|Lys|Asp|Cys|Thr|Pro|Ser|Pro|Leu|Cys|Gln|Leu|Ile|Lys|Asp|
| |4685| | | |4690| | | |4695| | | | | |
|Ser|Leu|Phe|Ala|Gln|Cys|His|Ala|Leu|Val|Pro|Pro|Gln|His|Tyr|
| |4700| | | |4705| | | |4710| | | | | |
|Tyr|Asp|Ala|Cys|Val|Phe|Asp|Ser|Cys|Phe|Met|Pro|Gly|Ser|Ser|
| |4715| | | |4720| | | |4725| | | | | |
|Leu|Glu|Cys|Ala|Ser|Leu|Gln|Ala|Tyr|Ala|Ala|Leu|Cys|Ala|Gln|
| |4730| | | |4735| | | |4740| | | | | |
|Gln|Asn|Ile|Cys|Leu|Asp|Trp|Arg|Asn|His|Thr|His|Gly|Ala|Cys|
| |4745| | | |4750| | | |4755| | | | | |
|Leu|Val|Glu|Cys|Pro|Ser|His|Arg|Glu|Tyr|Gln|Ala|Cys|Gly|Pro|
| |4760| | | |4765| | | |4770| | | | | |
|Ala|Glu|Glu|Pro|Thr|Cys|Lys|Ser|Ser|Ser|Gln|Gln|Asn|Asn|
| |4775| | | |4780| | | |4785| | | | | |
|Thr|Val|Leu|Val|Glu|Gly|Cys|Phe|Cys|Pro|Glu|Gly|Thr|Met|Asn|
| |4790| | | |4795| | | |4800| | | | | |
|Tyr|Ala|Pro|Gly|Phe|Asp|Val|Cys|Val|Lys|Thr|Cys|Gly|Cys|Val|
| |4805| | | |4810| | | |4815| | | | | |
|Gly|Pro|Asp|Asn|Val|Pro|Arg|Glu|Phe|Gly|Glu|His|Phe|Glu|Phe|
| |4820| | | |4825| | | |4830| | | | | |
|Asp|Cys|Lys|Asn|Cys|Val|Cys|Leu|Glu|Gly|Gly|Ser|Gly|Ile|Ile|
| |4835| | | |4840| | | |4845| | | | | |
|Cys|Gln|Pro|Lys|Arg|Cys|Ser|Gln|Lys|Pro|Val|Thr|His|Cys|Val|
| |4850| | | |4855| | | |4860| | | | | |
|Glu|Asp|Gly|Thr|Tyr|Leu|Ala|Thr|Glu|Val|Asn|Pro|Ala|Asp|Thr|
| |4865| | | |4870| | | |4875| | | | | |
|Cys|Cys|Asn|Ile|Thr|Val|Cys|Lys|Cys|Asn|Thr|Ser|Leu|Cys|Lys|
| |4880| | | |4885| | | |4890| | | | | |
|Glu|Lys|Pro|Ser|Val|Cys|Pro|Leu|Gly|Phe|Glu|Val|Lys|Ser|Lys|
| |4895| | | |4900| | | |4905| | | | | |
|Met|Val|Pro|Gly|Arg|Cys|Cys|Pro|Phe|Tyr|Trp|Cys|Glu|Ser|Lys|
| |4910| | | |4915| | | |4920| | | | | |
|Gly|Val|Cys|Val|His|Gly|Asn|Ala|Glu|Tyr|Gln|Pro|Gly|Ser|Pro|
| |4925| | | |4930| | | |4935| | | | | |
|Val|Tyr|Ser|Ser|Lys|Cys|Gln|Asp|Cys|Val|Cys|Thr|Asp|Lys|Val|
| |4940| | | |4945| | | |4950| | | | | |
|Asp|Asn|Asn|Thr|Leu|Leu|Asn|Val|Ile|Ala|Cys|Thr|His|Val|Pro|
| |4955| | | |4960| | | |4965| | | | | |
|Cys|Asn|Thr|Ser|Cys|Ser|Pro|Gly|Phe|Glu|Leu|Met|Glu|Ala|Pro|
| |4970| | | |4975| | | |4980| | | | | |
|Gly|Glu|Cys|Cys|Lys|Lys|Cys|Glu|Gln|Thr|His|Cys|Ile|Ile|Lys|
| |4985| | | |4990| | | |4995| | | | | |
|Arg|Pro|Asp|Asn|Gln|His|Val|Ile|Leu|Lys|Pro|Gly|Asp|Phe|Lys|
| |5000| | | |5005| | | |5010| | | | | |
|Ser|Asp|Pro|Lys|Asn|Asn|Cys|Thr|Phe|Phe|Ser|Cys|Val|Lys|Ile|
| |5015| | | |5020| | | |5025| | | | | |
|His|Asn|Gln|Leu|Ile|Ser|Ser|Val|Ser|Asn|Ile|Thr|Cys|Pro|Asn|

```
                    5030              5035              5040
Phe Asp Ala Ser Ile Cys Ile Pro Gly Ser Ile Thr Phe Met Pro
    5045              5050              5055
Asn Gly Cys Cys Lys Thr Cys Thr Pro Arg Asn Glu Thr Arg Val
    5060              5065              5070
Pro Cys Ser Thr Val Pro Val Thr Thr Glu Val Ser Tyr Ala Gly
    5075              5080              5085
Cys Thr Lys Thr Val Leu Met Asn His Cys Ser Gly Ser Cys Gly
    5090              5095              5100
Thr Phe Val Met Tyr Ser Ala Lys Ala Gln Ala Leu Asp His Ser
    5105              5110              5115
Cys Ser Cys Cys Lys Glu Glu Lys Thr Ser Gln Arg Glu Val Val
    5120              5125              5130
Leu Ser Cys Pro Asn Gly Gly Ser Leu Thr His Thr Tyr Thr His
    5135              5140              5145
Ile Glu Ser Cys Gln Cys Gln Asp Thr Val Cys Gly Leu Pro Thr
    5150              5155              5160
Gly Thr Ser Arg Arg Ala Arg Arg Ser Pro Arg His Leu Gly Ser
    5165              5170              5175
Gly
```

<210> SEQ ID NO 30
<211> LENGTH: 15720
<212> TYPE: DNA
<213> ORGANISM: Homo sapiens

<400> SEQUENCE: 30

```
caacccacac cgcccctgcc agccaccatg gggctgccac tagcccgcct ggcggctgtg    60
tgcctggccc tgtctttggc aggggctcg gagctccaga cagagggcag aacccgaaac   120
cacggccaca acgtctgcag cacctggggc aacttccact acaagacctt cgacggggac   180
gtcttccgct tccccggccc ctgcgactac aacttcgcct ccgactgccg aggctcctac   240
aaggaatttg ctgtgcacct gaagcggggt ccgggccagg ctgaggcccc cgccggggtg   300
gagtccatcc tgctgaccat caaggatgac accatctacc tcacccgcca cctggctgtg   360
cttaacgggg ccgtggtcag caccccgcac tacagccccg ggctgctcat tgagaagagc   420
gatgcctaca ccaaagtcta ctcccgcgcc ggcctcaccc tcatgtggaa ccggaggat   480
gcactcatgc tggagctgga cactaagttc cggaaccaca cctgtggcct ctgcggggac   540
tacaacggcc tgcagagcta ttcagaattc ctctctgacg gcgtgctctt cagtcccctg   600
gagtttggga acatgcagaa gatcaaccag cccgatgtgg tgtgtgagga tcccgaggag   660
gaggtggccc ccgcatcctg ctccgagcac cgcgccgagt gtgagaggct gctgaccgcc   720
gaggccttcg cggactgtca ggacctggtg ccgctggagc cgtatctgcg cgcctgccag   780
caggaccgct gccggtgccc gggcggtgac acctgcgtct gcagcaccgt ggccgagttc   840
tcccgccagt gctcccacgc cggcggccgg cccgggaact ggaggaccgc cacgctctgc   900
cccaagacct gccccgggaa cctggtgtac ctggagagcg gctcgccctg catggacacc   960
tgctcacacc tggaggtgag cagcctgtgc gaggagcacc gcatggacgg ctgtttctgc  1020
ccagaaggca ccgtatatga cgacatcggg gacagtggct gcgttcctgt gagccagtgc  1080
cactgcaggc tgcacggaca cctgtacaca ccgggccagg agatcaccaa tgactgcgag  1140
cagtgtgtct gtaacgctgg ccgctggggt gtgcaaagacc tgccctgccc cggcacctgt  1200
```

| | |
|---|---|
| gccctggaag gcggctccca catcaccacc ttcgatggga agacgtacac cttccacggg | 1260 |
| gactgctact atgtcctggc caagggtgac cacaacgatt cctacgctct cctgggcgag | 1320 |
| ctggccccct gtggctccac agacaagcag acctgcctga agacggtggt gctgctggct | 1380 |
| gacaagaaga agaatgtggt ggtcttcaag tccgatggca gtgtactgct caacgagctg | 1440 |
| caggtgaacc tgccccacgt gaccgcgagc ttctctgtct tccgcccgtc ttcctaccac | 1500 |
| atcatggtga gcatggccat tggcgtccgg ctgcaggtgc agctggcccc agtcatgcaa | 1560 |
| ctctttgtga cactggacca ggcctcccag gggcaggtgc agggcctctg cgggaacttc | 1620 |
| aacggcctgg aaggtgacga cttcaagacg gccagcgggc tggtggaggc cacggggggcc | 1680 |
| ggctttgcca acacctggaa ggcacagtca acctgccatg acaagctgga ctggttggac | 1740 |
| gatccctgct ccctgaacat cgagagcgcc aactacgccg agcactggtg ctccctcctg | 1800 |
| aagaagacag agacccccdtt tggcaggtgc cactcggctg tggaccctgc tgagtattac | 1860 |
| aagaggtgca aatatgacac gtgtaactgt cagaacaatg aggactgcct gtgcgccgcc | 1920 |
| ctgtcctcct acgcgcgcgc ctgcaccgcc aagggcgtca tgctgtgggg ctggcgggag | 1980 |
| catgtctgca acaaggatgt gggctcctgc cccaactcgc aggtcttcct gtacaacctg | 2040 |
| accacctgcc agcagacctg ccgctccctc tccgaggccg acagccactg tctcgagggc | 2100 |
| tttgcgcctg tggacggctg cggctgcccct gaccacacct tcctggacga aagggccgc | 2160 |
| tgcgtacccc tggccaagtg ctcctgttac caccgcggtc tctacctgga ggcggggac | 2220 |
| gtggtcgtca ggcaggaaga acgatgtgtg tgccgggatg gcggctgca ctgtaggcag | 2280 |
| atccggctga tcgccagag ctgcacggcc ccaaagatcc acatgactg cagcaacctg | 2340 |
| actgcactgg ccacctcgaa gccccgagcc ctcagctgcc agacgctggc cgccggctat | 2400 |
| taccacacag agtgtgtcag tggctgtgtg tgccccgacg ggctgatgga tgacggccgg | 2460 |
| ggtggctgcg tggtggagaa ggaatgccct tgcgtccata caacgacct gtattcttcc | 2520 |
| ggcgccaaga tcaaggtgga ctgcaatacc tgcacctgca agagaggacg ctgggtgtgc | 2580 |
| acccaggctg tgtgccatgg cacctgctcc atttacggga gtggccacta catcaccttt | 2640 |
| gacgggaagt actacgactt tgacggacac tgctcctacg tggctgttca ggactactgc | 2700 |
| ggccagaact cctcactggg ctcattcagc atcatcaccg agaacgtccc ctgtggcact | 2760 |
| acgggcgtca cctgctccaa ggccatcaag atcttcatgg ggaggacgga gctgaagttg | 2820 |
| gaagacaagc accgtgtggt gatccagcgt gatgagggtc accacgtggc ctacaccacg | 2880 |
| cgggaggtgg gccagtacct ggtggtggag tccagcacgg gcatcatcgt catctgggac | 2940 |
| aagaggacca ccgtgttcat caagctggct ccctcctaca agggcaccgt gtgtggcctg | 3000 |
| tgtgggaact tgaccaccg ctccaacaac gacttcacca cgcgggacca catggtggtg | 3060 |
| agcagcgagc tggacttcgg gaacagctgg aaggaggccc ccacctgccc agatgtgagc | 3120 |
| accaaccccg agccctgcag cctgaacccg caccgccgct cctgggccga gaagcagtgc | 3180 |
| agcatcctca aaagcagcgt gttcagcatc tgccacagca aggtggaccc caagcccttc | 3240 |
| tacgaggcct gtgtgcacga ctcgtgctcc tgtgacacgg gtggggactg tgagtgcttc | 3300 |
| tgctctgccg tggcctccta cgcccaggag tgtaccaaag agggggcctg cgtgttctgg | 3360 |
| aggacgccgg acctgtgccc catattctgc gactactaca accctccgca tgagtgtgag | 3420 |
| tggcactatg agccatgtgg gaaccggagc ttcgagacct gcaggaccat caatggcatc | 3480 |
| cactccaaca tctccgtgtc ctacctggag ggctgctacc cccggtgccc caaggacagg | 3540 |
| cccatctatg aggaggatct gaagaagtgt gtcactgcag acaagtgtgg ctgctatgtc | 3600 |

```
gaggacaccc actacccacc tggagcatcg gttcccaccg aggagacctg caagtcctgc    3660
gtgtgtacca actcctccca agtcgtctgc aggccgagg aaggaaagat tcttaaccag     3720
acccaggatg gcgccttctg ctactgggag atctgtggcc ccaacgggac ggtggagaag    3780
cacttcaaca tctgttccat tacgacacgc ccgtccaccc tgaccacctt caccaccatc    3840
accctcccca ccaccccac caccttcacc actaccacca ccaccaccac cccgacctcc     3900
agcacagttt tatcaacaac tccgaagctg tgctgcctct ggtctgactg gatcaatgag    3960
gaccacccca gcagtggcag cgacgacggt gaccgagaaa catttgatgg ggtctgcggg    4020
gccctgagg acatcgagtg caggtcggtc aaggatcccc acctcagctt ggagcagcta    4080
ggccagaagg tgcagtgtga tgtctctgtt gggttcattt gcaagaatga agaccagttt    4140
ggaaatggac catttggact gtgttacgac tacaagatac gtgtcaattg ttgctggccc    4200
atggataagt gtatcaccac tcccagccct ccaactacca ctcccagccc tccaccaacc    4260
agcacgacca cccttccacc aaccaccacc cccagccctc caaccaccac cacaaccacc    4320
cctccaccaa ccaccacccc cagccctcca ataaccacca cgaccacccc tccaccaacc    4380
accactccca gccctccaat aagcaccaca accacccctc caccaaccac cactcccagc    4440
cctccaacca ccactcccag ccctccaacc accactccca gccctccaac aaccaccaca    4500
accacccctc caccaaccac cactcccagc cctccaacga ctacgcccat cactccacca    4560
gccagcacta ccacccttcc accaaccacc actcccagcc ctccaacaac caccacaacc    4620
acccctccac caaccaccac tcccagtcct ccaacgacta cgccatcac tccaccaacc     4680
agcactacta cccttccacc aaccaccact cccagccctc caccaaccac cacaaccacc    4740
cctccaccaa ccaccactcc cagccctcca acaaccacca ctcccagtcc tccaacaatc    4800
accacaacca ccctccacc aaccaccact cccagccctc caacaacgac cacaaccacc     4860
cctccaccaa ccaccactcc cagccctcca acgactacac ccatcactcc accaaccagc    4920
actaccaccc ttccaccaac caccactccc agccctccac caaccaccac aaccacccct    4980
ccaccaacca ccactcccag ccctccaaca accaccactc cagccctcc aataaccacc     5040
acaaccaccc ctcaccaaac caccactccc agctctccaa taaccaccac tcccagccct    5100
ccaacaacca ccatgaccac cccttcacca accaccaccc cagctctcc aataaccacc     5160
acaaccaccc cttcctcaac taccactccc agccctccac caaccaccat gaccacccct    5220
tcaccaacca ccactcccag ccctccaaca accaccatga ccacccttcc accaaccacc    5280
acttccagcc tctaacaac tactcctcta cctccatcaa taactcctcc tacattttca    5340
ccattctcaa cgacaacccc tactacccca tgcgtgcctc tctgcaattg gactggctgg    5400
ctggattctg gaaacccaa ctttcacaaa ccaggtggag acacagaatt gattggagac    5460
gtctgtggac caggctgggc agctaacatc tcttgcagag ccaccatgta tcctgatgtt    5520
cccattggac agcttggaca aacagtggtg tgtgatgtct ctgtggggct gatatgcaaa    5580
aatgaagacc aaaagccagg tggggtcatc cctatggcct tctgcctcaa ctacgagatc    5640
aacgttcagt gctgtgagtg tgtcacccaa cccaccacca tgacaaccac caccacagag    5700
aacccaactc cgccaaccac gacacccatc accaccacca ctacggtgac cccaacccca    5760
acacccaccg gcacacagac cccaaccacg acacccatca ccaccaccac tacggtgacc    5820
ccaaccccaa cacccaccgg cacacagacc caaccacga cacccatcac caccaccact    5880
acggtgaccc caacccaac acccaccggc acacagaccc aaccacgac acccatcacc     5940
```

```
accaccacta cggtgacccc aaccccaaca cccaccggca cacagacccc aaccacgaca    6000
cccatcacca ccaccactac ggtgacccca accccaacac ccaccggcac acagacccca    6060
accacgacac ccatcaccac caccactacg gtgaccccaa ccccaacacc caccggcaca    6120
cagaccccaa ccacgacacc catcaccacc accactacgg tgaccccaac cccaacaccc    6180
accggcacac agaccccaac cacgacaccc atcaccacca ccactacggt gaccccaacc    6240
ccaacaccca ccggcacaca gaccccaacc acgacaccca tcaccaccac cactacggtg    6300
accccaaccc caacacccac cggcacacag accccaacca cgacacccat caccaccacc    6360
actacggtga ccccaacccc aacacccacc ggcacacaga ccccaaccac gacacccatc    6420
accaccacca ctacggtgac cccaacccca cacccaccg gcacacagac cccaaccacg    6480
acacccatca ccaccaccac tacggtgacc ccaaccccaa cacccaccgg cacacagacc    6540
ccaaccacga cacccatcac caccaccact acggtgaccc caaccccaac acccaccggc    6600
acacagaccc caaccacgac acccatcacc accaccacta cggtgacccc aaccccaaca    6660
cccaccggca cacagacccc aaccacgaca cccatcacca ccaccactac ggtgacccca    6720
accccaacac ccaccggcac acagacccca accacgacac ccatcaccac caccactacg    6780
gtgaccccaa ccccaacacc caccggcaca cagaccccaa ccacgacacc catcaccacc    6840
accactacgg tgaccccaac cccaacaccc accggcacac agaccccaac cacgacaccc    6900
atcaccacca ccactacggt gaccccaacc ccaacaccca ccggcacaca gaccccaacc    6960
acgacaccca tcaccaccac cactacggtg accccaaccc caacacccac cggcacacag    7020
accccaacca cgacacccat caccaccacc actacggtga ccccaacccc aacacccacc    7080
ggcacacaga ccccaaccac gacacccatc accaccacca ctacggtgac cccaacccca    7140
acacccaccg gcacacagac cccaaccacg acacccatca ccaccaccac tacggtgacc    7200
ccaaccccaa cacccaccgg cacacagacc ccaaccacga cacccatcac caccaccact    7260
acggtgaccc caaccccaac acccaccggc acacagaccc caaccacgac acccatcacc    7320
accaccacta cggtgacccc aaccccaaca cccaccggca cacagacccc aaccacgaca    7380
cccatcacca ccaccactac ggtgacccca accccaacac ccaccggcac acagacccca    7440
accacgacac ccatcaccac caccactacg gtgaccccaa ccccaacacc caccggcaca    7500
cagaccccaa ccacgacacc catcaccacc accactacgg tgaccccaac cccaacaccc    7560
accggcacac agaccccaac cacgacaccc atcaccacca ccactacggt gaccccaacc    7620
ccaacaccca ccggcacaca gaccccaacc acgacaccca tcaccaccac cactacggtg    7680
accccaaccc caacacccac cggcacacag accccaacca cgacacccat caccaccacc    7740
actacggtga ccccaacccc aacacccacc ggcacacaga ccccaaccac gacacccatc    7800
accaccacca ctacggtgac cccaacccca cacccaccg gcacacagac cccaaccacg    7860
acacccatca ccaccaccac tacggtgacc ccaaccccaa cacccaccgg cacacagacc    7920
ccaaccacga cacccatcac caccaccact acggtgaccc caaccccaac acccaccggc    7980
acacagaccc caaccacgac acccatcacc accaccacta cggtgacccc aaccccaaca    8040
cccaccggca cacagacccc aaccacgaca cccatcacca ccaccactac ggtgacccca    8100
accccaacac ccaccggcac acagacccca accacgacac ccatcaccac caccactacg    8160
gtgaccccaa ccccaacacc caccggcaca cagaccccaa ccacgacacc catcaccacc    8220
accactacgg tgaccccaac cccaacaccc accggcacac agaccccaac cacgacaccc    8280
atcaccacca ccactacggt gaccccaacc ccaacaccca ccggcacaca gaccccaacc    8340
```

```
acgacaccca tcaccaccac cactacggtg accccaaccc caacacccac cggcacacag    8400
accccaacca cgacacccat caccaccacc actacggtga ccccaacccc aacacccacc    8460
ggcacacaga ccccaaccac gacacccatc accaccacca ctacggtgac cccaaccccca   8520
acacccaccg gcacacagac cccaaccacg acacccatca ccaccaccac tacggtgacc    8580
ccaaccccaa cacccaccgg cacacagacc caaccacga cacccatcac caccaccact    8640
acggtgaccc caaccccaac acccaccggc acacagaccc caaccacgac acccatcacc    8700
accaccacta cggtgacccc aaccccaaca cccaccggca cacagacccc aaccacgaca    8760
cccatcacca ccaccactac ggtgacccca accccaacac ccaccggcac acagacccca   8820
accacgacac ccatcaccac caccactacg gtgacccccaa ccccaacacc caccggcaca   8880
cagaccccaa ccacgacacc catcaccacc accactacgg tgaccccaac cccaacaccc    8940
accggcacac agaccccaac cacgacaccc atcaccacca ccactacggt gaccccaacc    9000
ccaacaccca ccggcacaca gaccccaacc acgacaccca tcaccaccac cactacggtg    9060
accccaaccc caacacccac cggcacacag accccaacca cgacacccat caccaccacc    9120
actacggtga ccccaacccc aacacccacc ggcacacaga ccccaaccac gacacccatc    9180
accaccacca ctacggtgac cccaacccca acacccaccg gcacacagac cccaaccacg    9240
acacccatca ccaccaccac tacggtgacc ccaaccccaa cacccaccgg cacacagacc    9300
ccaaccacga cacccatcac caccaccact acggtgaccc caaccccaac acccaccggc    9360
acacagaccc caaccacgac acccatcacc accaccacta cggtgacccc aaccccaaca    9420
cccaccggca cacagacccc aaccacgaca cccatcacca ccaccactac ggtgacccca    9480
accccaacac ccaccggcac acagacccca accacgacac ccatcaccac caccactacg    9540
gtgacccccaa ccccaacacc caccggcaca cagaccccaa ccacgacacc catcaccacc    9600
accactacgg tgaccccaac cccaacaccc accggcacac agaccccaac cacgacaccc    9660
atcaccacca ccactacggt gaccccaacc ccaacaccca ccggcacaca gaccccaacc    9720
acgacaccca tcaccaccac cactacggtg accccaaccc caacacccac cggcacacag    9780
accccaacca cgacacccat caccaccacc actacggtga ccccaacccc aacacccacc    9840
ggcacacaga ccccaaccac gacacccatc accaccacca ctacggtgac cccaacccca    9900
acacccaccg gcacacagac cccaaccacg acacccatca ccaccaccac tacggtgacc    9960
ccaaccccaa cacccaccgg cacacagacc caaccacga cacccatcac caccaccact   10020
acggtgaccc caaccccaac acccaccggc acacagaccc caaccacgac acccatcacc   10080
accaccacta cggtgacccc aaccccaaca cccaccggca cacagacccc aaccacgaca   10140
cccatcacca ccaccactac ggtgacccca accccaacac ccaccggcac acagacccca   10200
accacgacac ccatcaccac caccactacg gtgaccccaa ccccaacacc caccggcaca   10260
cagaccccaa ccacgacacc catcaccacc accactacgg tgaccccaac cccaacaccc   10320
accggcacac agaccccaac cacgacaccc atcaccacca ccactacggt gaccccaacc   10380
ccaacaccca ccggcacaca gaccccaacc acgacaccca tcaccaccac cactacggtg   10440
accccaaccc caacacccac cggcacacag accccaacca cgacacccat caccaccacc   10500
actacggtga ccccaacccc aacacccacc ggcacacaga ccccaaccac gacacccatc   10560
accaccacca ctacggtgac cccaacccca acacccaccg gcacacagac cccaaccacg   10620
acacccatca ccaccaccac tacggtgacc ccaaccccaa cacccaccgg cacacagacc   10680
```

```
ccaaccacga cacccatcac caccaccact acggtgaccc caaccccaac acccaccggc    10740
acacagaccc caaccacgac acccatcacc accaccacta cggtgacccc aaccccaaca    10800
cccaccggca cacagacccc aaccacgaca cccatcacca ccaccactac ggtgacccca    10860
accccaacac ccaccggcac acagacccca accacgacac ccatcaccac caccactacg    10920
gtgaccccaa ccccaacacc caccggcaca cagacccaa ccacgacacc catcaccacc    10980
accactacgg tgaccccaac cccaacaccc accggcacac agaccccaac cacgacaccc    11040
atcaccacca ccactacggt gaccccaacc caacaccca ccggcacaca gaccccaacc    11100
acgacaccca tcaccaccac cactacggtg accccaaccc caacacccac cggcacacag    11160
accccaacca cgacacccat caccaccacc actacggtga ccccaacccc acacccacc     11220
ggcacacaga ccccaaccac gacacccatc accaccacca ctacggtgac cccaaacccca   11280
acacccaccg gcacacagac cccaaccacg acacccatca ccaccaccac tacggtgacc    11340
ccaaccccaa cacccaccgg cacagacc ccaaccacga cacccatcac caccaccact      11400
acggtgaccc caaccccaac acccaccggc acagaccc caaccacgac acccatcacc      11460
accaccacta cggtgacccc aaccccaaca cccaccggca cagaccccc aaccacgaca     11520
cccatcacca ccaccactac ggtgacccca accccaacac ccaccggcac acagacccca    11580
accacgacac ccatcaccac caccactacg gtgaccccaa ccccaacacc caccggcaca    11640
cagacccaa ccacgacacc catcaccacc accactacgg tgaccccaac cccaacaccc     11700
accggcacac agaccccaac cacgacaccc atcaccacca ccactacggt gaccccaacc    11760
caacaccca ccggcacaca gaccccaacc acgacaccca tcaccaccac cactacggtg     11820
accccaaccc caacacccac cggcacacag accccaacca cgacacccat caccaccacc    11880
actacggtga ccccaacccc aacacccacc ggcacacaga ccccaaccac gacacccatc    11940
accaccacca ctacggtgac cccaaccca acacccaccg gcacacagac cccaaccacg     12000
acacccatca ccaccaccac tacggtgacc ccaaccccaa cacccaccgg cacacagacc    12060
ccaaccacga cacccatcac caccaccact acggtgaccc caaccccaac acccaccggc    12120
acacagaccc caaccacgac acccatcacc accaccacta cggtgacccc aaccccaaca    12180
cccaccggca cacagacccc aaccacgaca cccatcacca ccaccactac ggtgacccca    12240
accccaacac ccaccggcac acagacccca accacgacac ccatcaccac caccactacg    12300
gtgaccccaa ccccaacacc caccggcaca cagacccaa ccacgacacc catcaccacc     12360
accactacgg tgaccccaac cccaacaccc accggcacac agaccccaac cacgacaccc    12420
atcaccacca ccactacggt gaccccaacc caacaccca ccggcacaca gaccccaacc     12480
acgacaccca tcaccaccac cactacggtg accccaaccc caacacccac cggcacacag    12540
accccaacca cgacacccat caccaccacc actacggtga ccccaacccc aacacccacc    12600
ggcacacaga ccgggcccc cacccacaca agcacagcac cgattgctga gttgaccaca     12660
tccaatcctc cgcctgagtc ctcaaccct cagacctctc ggtccacctc ttccctctc      12720
acggagtcaa ccacccttct gagtacccta ccacctgcca ttgagatgac cagcacggcc    12780
ccaccctcca cacccacggc acccacgacc acgagcggag ccacacact gtctccaccg     12840
cccagcacca ccacgtcccc tccaggcacc cccactcgcg gtaccacgac tgggtcatct    12900
tcagccccca cccccagcac tgtgcagacg accaccacca gtgcctggac ccccacgccg    12960
accccactct ccacacccag catcatcagg accacaggcc tgaggcccta cccttcctct    13020
gtgcttatct gctgtgtcct gaacgacacc tactacgcac caggtgagga ggtgtacaac    13080
```

```
ggcacatacg gagacacctg ttatttcgtc aactgctcac tgagctgtac gttggagttc    13140
tataactggt cctgcccatc cacgccctcc ccaacaccca cgccctccaa gtcgacgccc    13200
acgccttcca agccatcgtc cacgccctcc aagccgacgc ccggcaccaa gccccccgag    13260
tgcccagact ttgatcctcc cagacaggag aacgagactt ggtggctgtg cgactgcttc    13320
atggccacgt gcaagtacaa caacacggtg gagatcgtga aggtggagtg tgagccgccg    13380
cccatgccca cctgctccaa cggcctccaa cccgtgcgcg tcgaggaccc cgacggctgc    13440
tgctggcact gggagtgcga ctgctactgc acgggctggg gcgacccgca ctatgtcacc    13500
ttcgacggac tctactacag ctaccagggc aactgcacct acgtgctggt ggaggagatc    13560
agcccctccg tggacaactt cggagtttac atcgacaact accactgcga tcccaacgac    13620
aaggtgtcct gcccccgcac cctcatcgtc gccacgaga cccaggaggt gctgatcaag    13680
accgtgcata tgatgcccat gcaggtgcag gtgcaggtga acaggcaggc ggtggcactg    13740
ccctacaaga agtacgggct ggaggtgtac cagtctggca tcaactacgt ggtggacatc    13800
cccgagctgg gtgtcctcgt ctcctacaat ggcctgtcct tctccgtcag gctgccctac    13860
caccggtttg gcaacaacac caagggccag tgtggcacct gcaccaacac cacctccgac    13920
gactgcattc tgcccagcgg ggagatcgtc tccaactgtg aggctgcggc tgaccagtgg    13980
ctggtgaacg acccctccaa gccacactgc ccccacagca gctccacgac caagcgcccg    14040
gccgtcactg tgcccggggg cggtaaaacg accccacaca aggactgcac cccatctccc    14100
ctctgccagc tcatcaagga cagcctgttt gcccagtgcc acgcactggt gccccgcag    14160 cactactacg atgcctgcgt gttcgacagc tgcttcatgc cgggctcgag cctggagtgc    14220
gccagtctgc aggcctacgc agccctctgt gcccagcaga acatctgcct cgactggcgg    14280
aaccacacgc atggggcctg cttggtggag tgcccatctc acagggagta ccaggcctgt    14340
ggccctgcag aagagcccac gtgcaaatcc agctcctccc agcagaacaa cacagtcctg    14400
gtggaaggct gcttctgtcc tgagggcacc atgaactacg ctcctggctt tgatgtctgc    14460
gtgaagacct cgggctgtgt gggacctgac aatgtgccca gagagtttgg ggagcacttc    14520
gagttcgact gcaagaactg tgtctgcctg gagggtggaa gtggcatcat ctgccaaccc    14580
aagaggtgca gccagaagcc cgttacccac tgcgtggaag acggcaccta cctcgccacg    14640
gaggtcaacc ctgccgacac ctgctgcaac attaccgtct gcaagtgcaa caccagcctg    14700
tgcaaagaga agccctccgt gtgcccgctg ggattcgaag tgaagagcaa gatggtgcct    14760
ggaaggtgct gtccttttcta ctggtgtgag tccaagggggg tgtgtgttca cgggaatgct    14820
gagtaccagc ccggttctcc agtttattcc tccaagtgcc aggactgcgt gtgcacggac    14880
aaggtggaca acaacaccct gctcaacgtc atcgcctgca cccacgtgcc ctgcaacacc    14940
tcctgcagcc ctggcttcga actcatggag gccccggggg agtgctgtaa gaagtgtgaa    15000
cagacgcact gtatcatcaa acggcccgac aaccagcacg tcatcctgaa gcccggggac    15060
ttcaagagcg acccgaagaa caactgcaca ttcttcagct gcgtgaagat ccacaaccag    15120
ctcatctcgt ccgtctccaa catcacctgc cccaactttg atgccagcat ttgcatcccg    15180
ggctccatca cattcatgcc caatggatgc tgcaagacct gcacccctcg caatgagacc    15240
agggtgccct gctccaccgt ccccgtcacc acggaggttt cgtacgccgg ctgcaccaag    15300
accgtcctca tgaatcattg ctccgggtcc tgcgggacat ttgtcatgta ctcggccaag    15360
gcccaggccc tggaccacag ctgctcctgc tgcaaagagg agaaaaccag ccagcgtgag    15420
```

```
gtggtcctga gctgccccaa tggcggctcg ctgacacaca cctacaccca catcgagagc    15480
tgccagtgcc aggacaccgt ctgcgggctc cccaccggca cctcccgccg ggcccggcgc    15540
tcccctaggc atctggggag cgggtgagcg ggtgggcac agccccttc actgccctcg     15600 acagctttac ctcccccgga ccctctgagc ctcctaagct cggcttcctc tcttcagata    15660
tttattgtct gagtctttgt tcagtccttg ctttccaata ataaactcag ggggacatgc    15720
```

<210> SEQ ID NO 31
<211> LENGTH: 324
<212> TYPE: PRT
<213> ORGANISM: Homo sapiens

<400> SEQUENCE: 31

```
Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Arg Lys Pro Arg Val Leu
    130                 135                 140

Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175

Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
        195                 200                 205

Pro Pro Pro Pro Pro Ala Arg Arg Ile Ala Val Pro Val Leu Val
    210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
            260                 265                 270

Ala Tyr Pro Ala Gly Pro Ser Pro Ala Gln Pro Ala Thr Ala Ala Ala
        275                 280                 285

Asn Asn Asn Phe Val Asn Phe Gly Val Gly Asp Leu Asn Ala Val Gln
    290                 295                 300

Ser Pro Gly Ile Pro Gln Ser Asn Ser Gly Val Ser Thr Leu His Gly
305                 310                 315                 320

Ile Arg Ala Trp
```

<210> SEQ ID NO 32
<211> LENGTH: 1669
<212> TYPE: DNA
<213> ORGANISM: Homo sapiens

<400> SEQUENCE: 32

```
gctcctgtca tcgaggcccc tggcccaatg gcaggctgag tcccctcct ctggcctggt      60
cccgcctctc ctgccccttg tgctcagcgc tacctgctgc ccggacacat ccagagctgg    120
ccgacgggtg cgcgggcggg cggcggcacc atgcaggaa gctgccaggg gccgtgggca     180
gcgccgcttt ctgccgccca cctggcgctg tgagactggc gctgccacca tgttccccag    240
ccctgctctc acgcccacgc ccttctcagt caaagacatc ctaaacctgg aacagcagca    300
gcgcagcctg gctgccgccg gagagctctc tgcccgcctg gaggcgaccc tggcgccctc    360
ctcctgcatg ctggccgcct tcaagccaga ggcctacgct gggcccgagg cggctgcgcc    420
gggcctccca gagctgcgcg cagagctggg ccgcgcgcct tcaccggcca agtgtgcgtc    480
tgcctttccc gccgccccg ccttctatcc acgtgcctac agcgaccccg acccagccaa    540
ggacccctaga gccgaaaaga aagagctgtg cgcgctgcag aaggcggtgg agctggagaa    600
gacagaggcg gacaacgcgg agcggccccg ggcgcgacgg cggaggaagc cgcgcgtgct    660
cttctcgcag gcgcaggtct atgagctgga gcggcgcttc aagcagcagc ggtacctgtc    720
ggcccccgaa cgcgaccagc tggccagcgt gctgaaactc acgtccacgc aggtcaagat    780
ctggttccag aaccggcgct acaagtcaa gcggcagcgg caggaccaga ctctggagct    840
ggtggggctg ccccgccgc cgccgccgcc tgcccgcagg atcgcggtgc cagtgctggt    900
gcgcgatggc aagccatgcc tagggggactc ggcgccctac gcgcctgcct acggcgtggg    960
cctcaatccc tacggttata acgcctaccc cgcctatccg ggttacggcg gcgcggcctg   1020
cagccctggc tacagctgca ctgccgctta ccccgccggg cctccccag cgcagccggc   1080
cactgccgcc gccaacaaca acttcgtgaa cttcggcgtc ggggacttga atgcggttca   1140
gagccccggg attccgcaga gcaactcggg agtgtccacg ctgcatggta tccgagcctg   1200
gtagggaagg gacccgcgtg gcgcgaccct gaccgatccc acctcaacag ctccctgact   1260
ctcgggggga gaaggggctc ccaacatgac cctgagtccc ctggattttg cattcactcc   1320
tgcgagacc taggaactt ttctgtccca cgcgcgttg tcttgcgca cgggagagtt       1380
tgtggcggcg attatgcagc gtgcaatgag tgatcctgca gcctggtgtc ttagctgtcc   1440
ccccaggagt gccctccgag agtccatggg cacccccggt tggaactggg actgagctcg   1500
ggcacgcagg gcctgagatc tggccgccca ttccgcgagc cagggccggg cgcccgggcc   1560
tttgctatct cgccgtcgcc cgcccacgca cccacccgta tttatgtttt tacctattgc   1620
tgtaagaaat gacgatcccc ttcccattaa agagagtgcg ttgaccccg               1669
```

<210> SEQ ID NO 33
<211> LENGTH: 356
<212> TYPE: PRT
<213> ORGANISM: Homo sapiens

<400> SEQUENCE: 33

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Leu Glu Ala Met Asn Ala
    35                  40                  45

Glu Glu Asp Ser Leu Arg Asn Gly Gly Glu Glu Asp Glu Asp Glu
50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
            115                 120                 125

Pro Cys Tyr Ser Lys Thr Gln Lys Leu Ser Lys Ile Glu Thr Leu Arg
130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
            195                 200                 205

Thr Ala Ser Ala Ser Phe Pro Val His Pro Tyr Ser Tyr Gln Ser Pro
210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
            275                 280                 285

Pro Ser Ala Glu Phe Glu Lys Asn Tyr Ala Phe Thr Met His Tyr Pro
290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355

<210> SEQ ID NO 34
<211> LENGTH: 3002
<212> TYPE: DNA
<213> ORGANISM: Homo sapiens

<400> SEQUENCE: 34
ggggaggagg ggagaacggg gagcgcacag cctggacgcg tgcgcaggcg tcaggcgcat      60
agacctgcta gcccctcagc tagcggcccc gcccgcgctt agcatcacta actgggctat     120
ataacctgag cgcccgcgcg gccacgacac gaggaattcg cccacgcagg aggcgcggcg     180
tccggaggcc ccagggttat gagactatca ctgctcagga cctactaaca acaaggaaa     240

```
tcgaaacatg accaaatcgt acagcgagag tgggctgatg ggcgagcctc agccccaagg    300
tcctccaagc tggacagacg agtgtctcag ttctcaggac gaggagcacg aggcagacaa    360
gaaggaggac gacctcgaag ccatgaacgc agaggaggac tcactgagga acggggaga    420 ggaggaggac gaagatgagg acctggaaga ggaggaagaa gaggaagagg aggatgacga    480
tcaaaagccc aagagacgcg gccccaaaaa gaagaagatg actaaggctc gcctggagcg    540
ttttaaattg agacgcatga aggctaacgc ccgggagcgg aaccgcatgc acggactgaa    600
cgcggcgcta gacaacctgc gcaaggtggt gccttgctat tctaagacgc agaagctgtc    660
caaaatcgag actctgcgct tggccaagaa ctacatctgg gctctgtcgg agatcctgcg    720
ctcaggcaaa agcccagacc tggtctcctt cgttcagacg ctttgcaagg cttatccca    780 acccaccacc aacctggttg cgggctgcct gcaactcaat cctcggactt ttctgcctga    840
gcagaaccag gacatgcccc cccacctgcc gacggccagc gcttccttcc ctgtacaccc    900
ctactcctac cagtcgcctg ggctgccag tccgccttac ggtaccatgg acagctccca    960
tgtcttccac gttaagcctc cgccgcacgc ctacagcgca gcgctggagc ccttctttga   1020
aagccctctg actgattgca ccagcccttc ctttgatgga cccctcagcc cgccgctcag   1080
catcaatggc aacttctctt tcaaaacacga accgtccgcc gagtttgaga aaattatgc   1140 ctttaccatg cactatcctg cagcgacact ggcaggggcc caaagccacg gatcaatctt   1200
ctcaggcacc gctgccctc gctgcgagat ccccatagac aatattatgt ccttcgatag   1260
ccattcacat catgagcgag tcatgagtgc ccagctcaat gccatatttc atgattagag   1320
gcacgccagt ttcaccattt ccgggaaacg aacccactgt gcttacagtg actgtcgtgt   1380
ttacaaaagg cagccctttg ggtactactg ctgcaaagtg caaatactcc aagcttcaag   1440
tgatatatgt atttattgtc attactgcct ttggaagaaa cagggatca aagttcctgt   1500 tcaccttatg tattattttc tatagctctt ctatttaaaa ataaaaaaa tacagtaaag   1560 tttaaaaaat acaccacgaa tttggtgtgg ctgtattcag atcgtattaa ttatctgatc   1620
gggataacaa atcacaagc aataattagg atctatgcaa ttttaaact agtaatgggc   1680 caattaaaat atatataaat atatatttt caaccagcat tttactactt gttacctttc   1740
ccatgctgaa ttattttgtt gtgattttgt acagaatttt taatgacttt ttataatgtg   1800
gatttcctat tttaaaacca tgcagcttca tcaattttta tacatatcag aaaagtagaa   1860
ttatatctaa tttatacaaa ataatttaac taatttaaac cagcagaaaa gtgcttagaa   1920
agttattgtg ttgccttagc acttctttcc tctccaattg taaaaaaaaa aaaaaaaaa   1980 aaaaaaaaaa aaaattgca caatttgagc aattcatttc actttaaagt ctttccgtct   2040
ccctaaaata aaaaccagaa tcataatttt caagagaaga aaaattaag agatacattc   2100 cctatcaaaa catatcaatt caacacatta cttgcacaag cttgtatata catattataa   2160
ataaatgcca acatacccttt ctttaaatca aaagctgctt gactatcaca tacaatttgc   2220
actgttactt tttagtctttt tactcctttg cattccatga ttttacagag aatctgaagc   2280
tattgatgtt tccagaaaat ataaatgcat gattttatac atagtcacaa aaatggtggt   2340
ttgtcatata ttcatgtaat aaatctgagc ctaaatctaa tcaggttgtt aatgttggga   2400
tttatatcta tagtagtcaa ttagtacagt agcttaaata aattcaaacc atttaattca   2460
taattagaac aatagctatt gcatgtaaaa tgcagtccag aataagtgct gtttgagatg   2520
tgatgctggt accactggaa tcgatctgta ctgtaatttt gtttgtaatc ctgtatatta   2580
tggtgtaatg cacaatttag aaaacattca tccagttgca ataaaatagt attgaaagtg   2640
```

-continued

```
agagcaattg ttgcatttct tcttaaaggg attctgtttt tattttttggg gaaagtagtt     2700 gcttttttgc tgagttaaaa aatactaaac actatatgta gaataaaaga aagaaaaaa      2760 gtttaccttg gcatatgctc ttgtctgttt atcttgcaca gggagtcacc agttctatgt     2820
agataatgaa aagacctaac tgatatttca ttatttggaa tatgggactg gacggcagta    2880
caaacagtgt gttttttttct ttgttttaag tggcttagcc tttaggtttt ttatttccat   2940
ttttaaaaat gattgttaca tgttttcttc tattttcttt tttaaaaggt ggatttttaat   3000 aa                                                                   3002
```

```
<210> SEQ ID NO 35
<211> LENGTH: 367
<212> TYPE: PRT
<213> ORGANISM: Homo sapiens

<400> SEQUENCE: 35

Met Leu Ala Val Gly Ala Met Glu Gly Thr Arg Gln Ser Ala Phe Leu
1               5                   10                  15

Leu Ser Ser Pro Leu Ala Ala Leu His Ser Met Ala Glu Met Lys
                20                  25                  30

Thr Pro Leu Tyr Pro Ala Ala Tyr Pro Pro Leu Pro Ala Gly Pro Pro
            35                  40                  45

Ser Ser Ser Ser Ser Ser Ser Ser Ser Pro Ser Pro Pro Leu
        50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
                85                  90                  95

Gly Ile Asn Asp Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Ser Ser Ala Ser Ala Ala Ala Ala Ala Ala
    130                 135                 140

Ala Ala Ala Ala Ala Ser Ser Pro Ala Gly Leu Leu Ala Gly Leu
145                 150                 155                 160

Pro Arg Phe Ser Ser Leu Ser Pro Pro Pro Pro Pro Gly Leu Tyr
                165                 170                 175

Phe Ser Pro Ser Ala Ala Ala Val Ala Ala Val Gly Arg Tyr Pro Lys
            180                 185                 190

Pro Leu Ala Glu Leu Pro Gly Arg Thr Pro Ile Phe Trp Pro Gly Val
        195                 200                 205

Met Gln Ser Pro Pro Trp Arg Asp Ala Arg Leu Ala Cys Thr Pro His
    210                 215                 220

Gln Gly Ser Ile Leu Leu Asp Lys Asp Gly Lys Arg Lys His Thr Arg
225                 230                 235                 240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
        275                 280                 285

Thr Lys Trp Arg Lys Lys His Ala Ala Glu Met Ala Thr Ala Lys Lys
    290                 295                 300
```

Lys Gln Asp Ser Glu Thr Glu Arg Leu Lys Gly Ala Ser Glu Asn Glu
305                 310                 315                 320

Glu Glu Asp Asp Tyr Asn Lys Pro Leu Asp Pro Asn Ser Asp Asp
            325                 330                 335

Glu Lys Ile Thr Gln Leu Leu Lys His Lys Ser Ser Gly Gly
        340                 345                 350

Gly Gly Gly Leu Leu Leu His Ala Ser Glu Pro Glu Ser Ser Ser
            355                 360                 365

<210> SEQ ID NO 36
<211> LENGTH: 1116
<212> TYPE: DNA
<213> ORGANISM: Homo sapiens

<400> SEQUENCE: 36

```
cgtgggatgt tagcggtggg ggcaatggag ggcacccggc agagcgcatt cctgctcagc      60
agccctcccc tggccgccct gcacagcatg gccgagatga agaccccgct gtaccctgcc     120
gcgtatcccc cgctgcctgc cggccccccc tcctcctcgt cctcgtcgtc gtcctcctcg     180
tcgccctccc cgcctctggg cacccacaac ccaggcggcc tgaagccccc ggccacgggg     240
gggctctcat ccctcggcag ccccccgcag cagctctcgg ccgccacccc acacggcatc     300
aacgatatcc tgagccggcc ctccatgccc gtggcctcgg gggccgccct gcctccgcc     360
tcgccctccg gttcctcctc ctcctcttcc tcgtccgcct ctgcctcctc cgcctctgcc     420
gccgccgcgg ctgctgccgc ggccgcagcc gccgcctcat ccccggcggg gctgctggcc     480
ggactgccac gctttagcag cctgagcccg ccgccgccgc cgcccgggct ctacttcagc     540
cccagcgccg cggccgtggc cgccgtgggc cggtacccca gccgctggc tgagctgcct     600
ggccggacgc ccatcttctg gccggagtg atgcagagcc cgccctggag ggacgcacgc     660
ctggcctgta cccctcatca aggatccatt ttgttggaca agacgggaa gagaaaacac     720
acgagaccca cttttttccgg acagcagatc ttcgccctgg agaagacttt cgaacaaaca     780
aaatacttgg cggggcccga gagggctcgt ttggcctatt cgttgggat gacagagagt     840
caggtcaagg tctggttcca gaaccgccgg accaagtgga ggaagaagca cgctgccgag     900
atggccacgg ccaagaagaa gcaggactcg gagacagagc gcctcaaggg ggcctcggag     960
aacgaggaag aggacgacga ctacaataag cctctggatc ccaactcgga cgacgagaaa    1020
atcacgcagc tgttgaagaa gcacaagtcc agcagcggcg gcggcggcgg cctcctactg    1080
cacgcgtccg agccggagag ctcatcctga acgccg                              1116
```

<210> SEQ ID NO 37
<211> LENGTH: 353
<212> TYPE: PRT
<213> ORGANISM: Homo sapiens

<400> SEQUENCE: 37

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

```
Ser Pro Ser Phe Cys Ala Pro Ser Pro Gly Thr Gly Gly Gly Gly Gly
 65                  70                  75                  80

Ala Gly Gly Gly Gly Ser Ser Gln Ala Gly Gly Ala Pro Gly Pro
             85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
            115                 120                 125

Glu Ala Leu Asn Leu Thr Pro Glu Asp Ala Val Ala Leu Ile Gly
            130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly
            165                 170                 175

Ala Asp Asp Met Gly Ala Gly His His His Gly Ala His His Ala Ala
            180                 185                 190

His His His His Ala Ala His His His His His His His His
            195                 200                 205

Gly Gly Ala Gly His Gly Gly Ala Gly His His Val Arg Leu Glu
            210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Val Ile Arg Leu Lys
            245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
            275                 280                 285

Leu Gln Ser Gln Val Glu Gln Leu Lys Leu Glu Val Gly Arg Leu Ala
            290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
            325                 330                 335

Pro Pro Gln Ala Gly Pro Gly Gly Ala Lys Gly Thr Ala Asp Phe Phe
            340                 345                 350

Leu

<210> SEQ ID NO 38
<211> LENGTH: 2058
<212> TYPE: DNA
<213> ORGANISM: Homo sapiens

<400> SEQUENCE: 38
gggtccttca ggtaggaggt cctgggtgac tttggaagtc cgtagtgtct cattgcagat      60
aatttttagc ttagggcctg gtggctaggt cggttctctc ctttccagtc ggagacctct     120
gccgcaaaca tgctccgcca gatcatcggt caggccaaga agcatccgag cttgatcccc     180
ctctttgtat ttattggaac tggagctact ggagcaacac tgtatctctt gcgtctggca     240
ttgttcaatc cagatgtttg ttgggacaga ataacccag agccctggaa caaactgggt      300
cccaatgatc aatacaagtt ctactcagtg aatgtggatt acagcaagct gaagaaggaa     360
cgtccagatt tctaaatgaa atgtttcact ataacgctgc tttagaatga aggtcttcca     420
gaagccacat ccgcacaatt ttccacttaa ccaggaaata tttctcctct aaatgcatga     480
```

```
aatcatgttg gagatctcta ttgtaatctc tattggagat tacaatgatt aaatcaataa    540
ataactgaaa cttgatatgt gtcactttt tatgctgaaa gtatgctctg aactttagag    600
tataggaaat taactattag aatttaaaga atttcttgaa tttctgtagt ttgaaaatac    660
gactttaagc tgctttagta aaacacttcc attttgtgta tagactgttg gtaacttcac    720
tagagcatac ataacaactg gaactggaaa ttatacaaaa gtaaattggg aaggatactc    780
cagcatctga cactggcaaa atggaaacct ttgagtttct cttactggct gttgaagtgt    840
gtgcagtttt taacaatggt ttttacttgg catctctttg ttgtgatttt caaggttata    900
agttgctttg gtcctaggat tgaagttgaa atctgagttt atcagtgcta accatggtgc    960
tagtagtcaa gagatcttga aattttggc tgctgagtct tggtgcaggg tgcaggtttt   1020
cttttctttt ttcttttttt tttttttgag atagtctctg tcacccaggc tggagtgcag   1080
tggtacaaac atggatcact gcagcctcta cctcccgggc ttaagtgatc ctcctgcctc   1140
agcccctaag tagccgggac tacaggtatg tgccaccatg cccagttaat ttttgtaatt   1200
tttttagag acagggtttt gccatgttgc ccaggctggt ctcaaactct tgagctcaag   1260
cgatccattc tcctcagcct cccagggtgc tgggattaca ggcgtgagcc attgcgctta   1320
gccatggtgc aggttttcaa aggccaggaa gtatattcat aattttaaga tggggaatat   1380
agcaagtttt cacataggtg tgtgtaagtc atcacatcat agaaacttga ggaattcagt   1440
gacattaatt ttggattttc atacgtaagt atacaattaa atgtttacag ggtagtagaa   1500
gcacatttta aatgtcagga actgaactaa gtatttgaat tacgtggatt atctcaaaaa   1560
ttttgaaatt gttaaacgag ttgaattact tgaattcatt ctgttagtca aatggtggat   1620
atttacaccc atgtagtttt gaatttagag tgtgtagagt gttttcagtt accagactcc   1680
atgcttttac ctcctatgtg tcaggtataa tttgaacctc taagaacagg gtttctcaac   1740
cttgccactg ttgactattt ctgaaagaca gtttggttta gcagaccatc ccatgcgctt   1800
tagcttgttt agtagctaac ttgggctctg ccactacaga caaaaagcac tctttccctc   1860
caattcccac aggctatgag aagaatggag acattaccaa atgtccattg gtgggcaaaa   1920
ttgcttcatt cctacctctg ttgagaatta ctctagatcc tttggcacaa attacctcaa   1980
agtttaaaat tgtgtaaaca aacagtgtgt catgtaattg aaaaacatta agcaactcca   2040
aataaatgct acattaag                                                 2058
```

<210> SEQ ID NO 39
<211> LENGTH: 343
<212> TYPE: PRT
<213> ORGANISM: Homo sapiens

<400> SEQUENCE: 39

Met Asn Gln Leu Gly Gly Leu Phe Val Asn Gly Arg Pro Leu Pro Leu
1               5                   10                  15

Asp Thr Arg Gln Gln Ile Val Arg Leu Ala Val Ser Gly Met Arg Pro
            20                  25                  30

Cys Asp Ile Ser Arg Ile Leu Lys Val Ser Asn Gly Cys Val Ser Lys
        35                  40                  45

Ile Leu Gly Arg Tyr Tyr Arg Thr Gly Val Leu Glu Pro Lys Gly Ile
    50                  55                  60

Gly Gly Ser Lys Pro Arg Leu Ala Thr Pro Pro Val Val Ala Arg Ile
65                  70                  75                  80

Ala Gln Leu Lys Gly Glu Cys Pro Ala Leu Phe Ala Trp Glu Ile Gln

```
                85                  90                  95
Arg Gln Leu Cys Ala Glu Gly Leu Cys Thr Gln Asp Lys Thr Pro Ser
            100                 105                 110

Val Ser Ser Ile Asn Arg Val Leu Arg Ala Leu Gln Glu Asp Gln Gly
        115                 120                 125

Leu Pro Cys Thr Arg Leu Arg Ser Pro Ala Val Leu Ala Pro Ala Val
    130                 135                 140

Leu Thr Pro His Ser Gly Ser Glu Thr Pro Arg Gly Thr His Pro Gly
145                 150                 155                 160

Thr Gly His Arg Asn Arg Thr Ile Phe Ser Pro Ser Gln Ala Glu Ala
                165                 170                 175

Leu Glu Lys Glu Phe Gln Arg Gly Gln Tyr Pro Asp Ser Val Ala Arg
            180                 185                 190

Gly Lys Leu Ala Thr Ala Thr Ser Leu Pro Glu Asp Thr Val Arg Val
        195                 200                 205

Trp Phe Ser Asn Arg Arg Ala Lys Trp Arg Arg Gln Glu Lys Leu Lys
    210                 215                 220

Trp Glu Met Gln Leu Pro Gly Ala Ser Gln Gly Leu Thr Val Pro Arg
225                 230                 235                 240

Val Ala Pro Gly Ile Ile Ser Ala Gln Gln Ser Pro Gly Ser Val Pro
                245                 250                 255

Thr Ala Ala Leu Pro Ala Leu Glu Pro Leu Gly Pro Ser Cys Tyr Gln
            260                 265                 270

Leu Cys Trp Ala Thr Ala Pro Glu Arg Cys Leu Ser Asp Thr Pro Pro
        275                 280                 285

Lys Ala Cys Leu Lys Pro Cys Trp Gly His Leu Pro Gln Pro Asn
    290                 295                 300

Ser Leu Asp Ser Gly Leu Leu Cys Leu Pro Cys Pro Ser His Cys
305                 310                 315                 320

His Leu Ala Ser Leu Ser Gly Ser Gln Ala Leu Leu Trp Pro Gly Cys
                325                 330                 335

Pro Leu Leu Tyr Gly Leu Glu
            340

<210> SEQ ID NO 40
<211> LENGTH: 2010
<212> TYPE: DNA
<213> ORGANISM: Homo sapiens

<400> SEQUENCE: 40
caaagactca cccgtgagcc agctctcaaa gaaagcagct tgcgttgaca gcctgggggc    60
agcaaggatg cagtctccca ggagaggatg cactcggtgg tgggaagcca ggctggaggg   120
gcctgagtga ccctctccac aggcgggcag ggcagtggga gaggtggtgt gtggatacct   180
ctgtctcacg cccagggatc agcagcatga accagcttgg ggggctcttt gtgaatggcc   240
ggcccctgcc tctggatacc cggcagcaga ttgtgcggct agcagtcagt ggaatgcggc   300
cctgtgacat ctcacggatc cttaaggtat ctaatggctg tgtgagcaag atcctagggc   360
gttactaccg cacaggtgtc ttggagccaa agggcattgg gggaagcaag ccacggctgg   420
ctacaccccc tgtggtggct cgaattgccc agctgaaggg tgagtgtcca gccctctttg   480
cctgggaaat ccaacgccag ctttgtgctg aagggctttg cacccaggac aagactccca   540
gtgtctcctc catcaaccga gtcctgcggg cattacagga ggaccaggga ctaccgtgca   600
cacggctcag gtcaccagct gttttggctc cagctgtcct cactccccat agtggctctg   660
```

```
agactccccg gggtacccac ccagggaccg gccaccggaa tcggactatc ttctccccaa      720
gccaagcaga ggcactggag aaagagttcc agcgtgggca gtatcctgat tcagtggccc      780
gtggaaagct ggctactgcc acctctctgc ctgaggacac ggtgagggtc tggttttcca      840
acagaagagc caaatggcgt cggcaagaga agctcaagtg gaaatgcag ctgccaggtg       900
cttcccaggg gctgactgta ccaagggttg ccccaggaat catctctgca cagcagtccc      960
ctggcagtgt gcccacagca gccctgcctg ccctggaacc actgggtccc tcctgctatc     1020
agctgtgctg ggcaacagca ccagaaaggt gtctgagtga caccccacct aaagcctgtc     1080
tcaagccctg ctggggccac ttgccccac agccgaattc cctggactca ggactgcttt     1140
gccttccttg cccttcctcc cactgtcacc tggccagtct tagtggctct caggccctgc     1200
tctggcctgg ctgcccacta ctgtatggct tggaatgagg caggagtggg aaggagatgg     1260
catagagaag atctaatacc atcctgccca ttgtccttac cgtcctgccc atacagactg     1320
tggctccttc ctccttcctg tgattgctcc ctcctgtgtg gacgttgcct ggccctgcct     1380
cgatgcctct ctggcgcatc acctgattgg aggggctggt aaagcaacac ccacccactt     1440
ctcacactag ccttaagagg cctccactca gcagtaataa aagctgtttt tattagcagt     1500
agttctgttg tccatcatgt tttccctatg agcaccccta tgcccactct aatattcaac     1560
aattatagac aatttgccct atcatttatt tacatctatg tatctaccat ctaatctatg     1620
catgtatgta ggcaatacat gtatctaaac aatgtatttg tcaatgcatc aatttaccta     1680
ctctatgtat gcatctatat gtgtattatg tatgcgtgca tgcgtgcgcg cacacacaca     1740
cacacacaca cacactgaca ttatatcatg gcattttatt cctaaatctt ccagcatgca     1800
tccccaaaaa acaagaaact tgtcttacat aatcacaata atatatccac atctaagaaa     1860
atttactgta acttcttaat ctaagaaaat tatgtatttt tgtcatatgt attttgtcat     1920
atgtattttg tatttgcata tgtatttttgt atttgcatat gtattttgt catagcagca     1980
aacagagtga aatgccattt ttcatattct                                      2010
```

<210> SEQ ID NO 41
<211> LENGTH: 286
<212> TYPE: PRT
<213> ORGANISM: Homo sapiens

<400> SEQUENCE: 41

```
Met Gly Ala Asp Gly Met Tyr Asp Lys Leu Arg Met Leu Asn Gly Gln
1               5                   10                  15

Thr Gly Ser Trp Gly Thr Arg Pro Gly Trp Tyr Pro Gly Thr Ser Val
            20                  25                  30

Pro Gly Gln Pro Thr Gln Asp Gly Cys Gln Gln Glu Gly Gly Gly
        35                  40                  45

Glu Asn Thr Asn Ser Ile Ser Ser Asn Gly Glu Asp Ser Asp Glu Ala
    50                  55                  60

Gln Met Arg Leu Gln Leu Lys Arg Lys Leu Gln Arg Asn Arg Thr Ser
65                  70                  75                  80

Phe Thr Gln Glu Gln Ile Glu Ala Leu Glu Lys Glu Phe Glu Arg Thr
                85                  90                  95

His Tyr Pro Asp Val Phe Ala Arg Glu Arg Leu Ala Ala Lys Ile Asp
                100                 105                 110

Leu Pro Glu Ala Arg Ile Gln Val Trp Phe Ser Asn Arg Arg Ala Lys
            115                 120                 125
```

```
Trp Arg Arg Glu Glu Lys Leu Arg Asn Gln Arg Arg Gln Ala Ser Asn
    130                 135                 140
Thr Pro Ser His Ile Pro Ile Ser Ser Ser Phe Ser Thr Ser Val Tyr
145                 150                 155                 160
Gln Pro Ile Pro Gln Pro Thr Thr Pro Val Ser Ser Phe Thr Ser Gly
                165                 170                 175
Ser Met Leu Gly Arg Thr Asp Thr Ala Leu Thr Asn Thr Tyr Ser Ala
            180                 185                 190
Leu Pro Pro Met Pro Ser Phe Thr Met Ala Asn Asn Leu Pro Met Gln
        195                 200                 205
Pro Pro Val Pro Ser Gln Thr Ser Ser Tyr Ser Cys Met Leu Pro Thr
    210                 215                 220
Ser Pro Ser Val Asn Gly Arg Ser Tyr Asp Thr Tyr Thr Pro Pro His
225                 230                 235                 240
Met Gln Thr His Met Asn Ser Gln Pro Met Gly Thr Ser Gly Thr Thr
                245                 250                 255
Ser Thr Gly Leu Ile Ser Pro Gly Val Ser Val Pro Val Gln Val Pro
            260                 265                 270
Gly Ser Glu Pro Asp Met Ser Gln Tyr Trp Pro Arg Leu Gln
        275                 280                 285

<210> SEQ ID NO 42
<211> LENGTH: 6732
<212> TYPE: DNA
<213> ORGANISM: Homo sapiens

<400> SEQUENCE: 42
cttttcaatt agccttccat gcatgatccg gagcgacttc cgcctatttc cagaaattaa      60
gctcaaactt gacgtgcagc tagttttatt ttaaagacaa atgtcagaga ggctcatcat     120
attttccccc ctcttctata tttggagctt atttattgct aagaagctca ggctcctggc     180
gtcaatttat cagtaggctc caaggagaag agaggagagg agaggagagc tgaacaggga     240
gccacgtctt ttcctgggag ggctgctatc taagtcgggg ctgcaggtca cagcggagtg     300
aatcagctcg gtggtgtctt tgtcaacggg cggccactgc cggactccac ccggcagaag     360
attgtagagc tagctcacag cggggcccgg ccgtgcgaca tttcccgaat tctgcagacc     420
catgcagatg caaaagtcca agtgctggac aatcaaaacg tgtccaacgg atgtgtgagt     480
aaaattctgg gcaggtatta cgagactggc tccatcagac ccagggcaat cggtggtagt     540
aaaccgagag tagcgactcc agaagttgta agcaaaatag cccagtataa gcgggagtgc     600
ccgtccatct ttgcttggga atccgagaca agattactgt ccgaggggt ctgtaccaac      660
gataacatac caagcgtgtc atcaataaac agagttcttc gcaacctggc tagcgaaaag     720
caacagatgg gcgcagacgg catgtatgat aaactaagga tgttgaacgg gcagaccgga     780
agctggggca cccgcccctgg ttggtatccg gggacttcgg tgccagggca acctacgcaa     840
gatggctgcc agcaacagga aggaggggga gagaatacca actccatcag ttccaacgga     900
gaagattcag atgaggctca aatgcgactt cagctgaagc ggaagctgca agaaatcga      960
acatccttta cccaagagca aattgaggcc ctggagaaag agtttgagag aacccattat    1020
ccagatgtgt ttgcccgaga aagactagca gccaaaatag atctacctga gcaagaata    1080
caggtatggt tttctaatcg aagggccaaa tggagaagag aagaaaaact gaggaatcag    1140
agaagacagg ccagcaacac acctagtcat attcctatca gcagtagttt cagcaccagt    1200
gtctaccaac caattccaca acccaccaca ccggtttcct ccttcacatc tggctccatg    1260
```

```
ttgggccgaa cagacacagc cctcacaaac acctacagcg ctctgccgcc tatgcccagc    1320
ttcaccatgg caaataacct gcctatgcaa cccccagtcc ccagccagac ctcctcatac    1380
tcctgcatgc tgcccaccag cccttcggtg aatgggcgga gttatgatac ctacaccccc    1440
ccacatatgc agacacacat gaacagtcag ccaatgggca cctcgggcac cacttcaaca    1500
ggactcattt cccctggtgt gtcagttcca gttcaagttc ccggaagtga acctgatatg    1560
tctcaatact ggccaagatt acagtaaaaa aaaaaaaaaa aaaaaaagg aaaggaaata    1620 ttgtgttaat tcagtcagtg actatgggga cacaacagtt gagctttcag gaaagaaaga    1680
aaaatggctg ttagagccgc ttcagttcta caattgtgtc ctgtattgta ccactgggga    1740
aggaatggac ttgaaacaag gacctttgta tacagaaggc acgatatcag ttggaacaaa    1800
tcttcatttt ggtatccaaa cttttattca ttttggtgta ttatttgtaa atgggcattt    1860
gtatgttata atgaaaaaaa gaacaatgta gactggatgg atgtttgatc tgtgttggtc    1920
atgaagttgt tttttttttt tttaaaaaga aaaccatgat caacaagctt tgccacgaat    1980
ttaagagttt tatcaagata tatcgaatac ttctacccat ctgttcatag tttatggact    2040
gatgttccaa gtttgtatca ttcctttgca tataattaaa cctggaacaa catgcactag    2100
atttatgtca gaaatatctg ttggttttcc aaaggttgtt aacagatgaa gtttatgtgc    2160
aaaaaagggt aagatataaa ttcaaggaag aaaaaaagtt gatagctaaa aggtagagtg    2220
tgtcttcgat ataatccaat ttgttttatg tcaaaatgta agtatttgtc ttccctagaa    2280
atcctcagaa tgatttctat aataaagtta atttcattta tatttgacaa gaatatagat    2340
gttttataca cattttcatg caatcatacg tttctttttt ggccagcaaa agttaattgt    2400
tcttagatat agttgtatta ctgttcacgg tccaatcatt ttgtgcatct agagttcatt    2460
cctaatcaat taaaagtgct tgcaagagtt ttaaacttaa gtgttttgaa gttgttcaca    2520
actacatatc aaaattaacc attgttgatt gtaaaaaacc atgccaaagc ctttgtattt    2580
cctttattat acagttttct ttttaacctt atagtgtggt gttacaaatt ttatttccat    2640
gttagatcaa cattctaaac caatggttac tttcacacac actctgtttt acatcctgat    2700
gatcctaaaa aaataatcct tatagatacc ataaatcaaa aacgtgttag aaaaaaattc    2760
cacttacagc agggtgtaga tctgtgccca tttatacccca caacatatat acaaaatggt    2820
aacatttccc agttagccat ttaattctaa agctcaaagt ctagaaataa tttaaaaatg    2880
caacaagcga ttagctagga attgtttttt gaattaggac tggcatttc aatctgggca     2940 gatttccatt gtcagcctat ttcaacaatg atttcactga agtatattca aaagtagatt    3000
tcttaaagga gactttctga aagctgttgc cttttcaaa taggccctct ccctttctg      3060 tctccctccc ctttgcacaa gaggcatcat ttcccattga accactacag ctgttcccat    3120
ttgaatcttg ctttctgtgc ggttgtggat ggttggaggg tggagggggg atgttgcatg    3180
tcaaggaata atgagcacag acacatcaac agacaacaac aaagcagact gtgactggcc    3240
ggtgggaatt aaaggccttc agtcattggc agcttaagcc aaacattccc aaatctatga    3300
agcagggccc attgttggtc agttgttatt tgcaatgaag cacagttctg atcatgttta    3360
aagtggaggc acgcagggca ggagtgcttg agcccaagca aaggatggaa aaaaataagc    3420
ctttgttggg taaaaaagga ctgtctgaga cttctttg ttctgtgcaa catataagtc       3480
aatacagata agtcttcctc tgcaaacttc actaaaagc ctgggggttc tggcagtcta     3540
gattaaaatg cttgcacatg cagaaacctc tggggacaaa gacacacttc cactgaatta    3600
```

| | |
|---|---|
| tactctgctt taaaaaaatc cccaaaagca aatgatcaga aatgtagaaa ttaatggaag | 3660 |
| gatttaaaca tgaccttctc gttcaatatc tactgttttt tagttaagga attacttgtg | 3720 |
| aacagataat tgagattcat tgctccggca tgaaatatac taataatttt attccaccag | 3780 |
| agttgctgca catttggaga caccttccta agttgcagtt tttgtatgtg tgcatgtagt | 3840 |
| tttgttcagt gtcagcctgc actgcacagc agcacatttc tgcaggggag tgagcacaca | 3900 |
| tacgcactgt tggtacaatt gccggtgcag acatttctac ctcctgacat tttgcagcct | 3960 |
| acattccctg agggctgtgt gctgagggaa ctgtcagaga agggctatgt gggagtgcat | 4020 |
| gccacagctg ctggctggct tacttcttcc ttctcgctgg ctgtaatttc caccacggtc | 4080 |
| aggcagccag ttccggccca cggttctgtt gtgtagacag cagagacttt ggagacccgg | 4140 |
| atgtcgcacg ccaggtgcaa gaggtgggaa tgggagaaaa ggagtgacgt gggagcggag | 4200 |
| ggtctgtatg tgtgcacttg ggcacgtata tgtgtgctct gaaggtcagg attgccaggg | 4260 |
| caaagtagca cagtctggta tagtctgaag aagcggctgc tcagctgcag aagccctctg | 4320 |
| gtccggcagg atgggaacgg ctgccttgcc ttctgcccac ccctaggga catgagctgt | 4380 |
| ccttccaaac agagctccag gcactctctt ggggacagca tggcaggctc tgtgtggtag | 4440 |
| cagtgcctgg gagttggcct tttactcatt gttgaaataa ttttgttta ttatttattt | 4500 |
| aacgatacat atatttatat atttatcaat ggggtatctg cagggatgtt ttgacaccat | 4560 |
| cttccaggat ggagattatt tgtgaagact tcagtagaat cccaggacta aacgtctaaa | 4620 |
| ttttttctcc aaacttgact gacttgggaa accaggtga atagaataag agctgaatgt | 4680 |
| tttaagtaat aaacgttcaa actgctctaa gtaaaaaaat gcattttact gcaatgaatt | 4740 |
| tctagaatat ttttccccca aagctatgcc tcctaaccct taaatggtga caactggtt | 4800 |
| tcttgctaca gctcactgcc atttcttctt actatcatca ctaggtttcc taagattcac | 4860 |
| tcatacagta ttatttgaag attcagcttt gttctgtgaa tgtcatctta ggattgtgtc | 4920 |
| tatattcttt tgcttatttc tttttactct gggcctctca tactagtaag atttaaaaa | 4980 |
| gccttttctt ctctgtatgt ttggctcacc aaggcgaaat atatattctt ctcttttca | 5040 |
| tttctcaaga ataaacctca tctgctttt tgttttctg tgttttggct tggtactgaa | 5100 |
| tgactcaact gctcggtttt aaagttcaaa gtgtaagtac ttagggttag tactgcttat | 5160 |
| ttcaataatg ttgacggtga ctatctttgg aaagcagtaa catgctgtct tagaaatgac | 5220 |
| attaataatg ggcttaaaca aatgaatagg ggggtccccc cactctcctt ttgtatgcct | 5280 |
| atgtgtgtct gatttgttaa aagatggaca gggaattgat tgcagagtgt cgcttccttc | 5340 |
| taaagtagtt ttattttgtc tactgttagt atttaaagat cctggaggtg gacataagga | 5400 |
| ataaatggaa gagaaaagta gatattgtat ggtggctact aaaaggaaat tcaaaaagtc | 5460 |
| ttagaacccg agcacctgag caaactgcag tagtcaaaat atttatctca tgttaaagaa | 5520 |
| aggcaaatct agtgtaagaa atgagtacca tatagggttt tgaagttcat atactagaaa | 5580 |
| cacttaaaag atatcatttc agatattacg tttggcattg ttcttaagta tttatatctt | 5640 |
| tgagtcaagc tgataattaa aaaaaatctg ttaatggagt gtatatttca taatgtatca | 5700 |
| aaatggtgtc tatacctaag gtagcattat tgaagagaga tatgtttatg tagtaagtta | 5760 |
| ttaacataat gagtaacaaa taatgtttcc agaagaaagg aaaacacatt ttcagagtgc | 5820 |
| gttttttatca gaggaagaca aaaatacaca cccctctcca gtagcttatt tttacaaagc | 5880 |
| cggcccagtg aattagaaaa acaaagcact tggatatgat ttttgaaaag cccaggtaca | 5940 |
| cttattattc aaaatgcact tttactgagt ttgaaaagtt tctttatat ttaaaataag | 6000 |

-continued

```
ggttcaaata tgcatattca attttatag tagttatcta tttgcaaagc atatattaac    6060
tagtaattgg ctgttaattt tatagacatg gtagccaggg aagtatatca atgacctatt    6120
aagtattttg acaagcaatt tacatatctg atgacctcgt atctctttt  cagcaagtca    6180 aatgctatgt aattgttcca ttgtgtgttg tataaaatga atcaacacgg taagaaaaag    6240
gttagagtta ttaaaataat aaactgacta aaatactcat ttgaatttat tcagaatgtt    6300
cataatgctt tcaaggaca tagcagagct tttgtggagt atccgcacaa cattatttat     6360
tatctatgga ctaaatcaat tttttgaagt tgctttaaaa tttaaaagca cctttgctta    6420
atataaagcc ctttaatttt aactgacaga tcaattctga aactttattt tgaaaagaaa    6480
atggggaaga atctgtgtct ttagaattaa aagaaatgaa aaaataaac  ccgacattct    6540 aaaaaaatag aataagaaac ctgattttta gtactaatga aatagcgggt gacaaaatag    6600
ttgtcttttt gattttgatc acaaaaaata aactggtagt gacaggatat gatggagaga    6660
tttgacatcc tggcaaatca ctgtcattga ttcaattatt ctaattctga ataaaagctg    6720
tatacagtaa aa                                                        6732
```

<210> SEQ ID NO 43
<211> LENGTH: 283
<212> TYPE: PRT
<213> ORGANISM: Homo sapiens

<400> SEQUENCE: 43

```
Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125

Ala Trp Lys Gly Gln Trp Ala Gly Gly Ala Tyr Ala Ala Glu Pro Glu
    130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
        195                 200                 205

Arg Gly Gly Gly Thr Ala Val Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240
```

```
Pro Pro Pro Pro Gly Gly Ala Val Pro Pro Ala Ala Pro Val Ala Ala
                245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
        275                 280

<210> SEQ ID NO 44
<211> LENGTH: 2573
<212> TYPE: DNA
<213> ORGANISM: Homo sapiens

<400> SEQUENCE: 44
gggtggcgcc gggagtggga acgccacaca gtgccaaatc cccggctcca gctcccgact    60
cccggctccc ggctcccggc tcccggtgcc caatcccggg ccgcagccat gaacggcgag   120
gagcagtact acgcggccac gcagctttac aaggacccat gcgcgttcca gcgaggcccg   180
gcgccggagt tcagcgccag ccccctgcg tgcctgtaca tgggccgcca gccccgccg    240 ccgccgccgc accgttccc tggcgccctg ggcgcgctgg agcagggcag ccccccggac    300
atctccccgt acgaggtgcc ccccctcgcc gacgaccccg cggtggcgca ccttcaccac   360
cacctcccgg ctcagctcgc gctccccac ccgcccgccg ggcccttccc ggagggagcc    420 gagccgggc tcctggagga gcccaaccgc gtccagctgc cttcccatg atgaagtct    480 accaaagctc acgcgtggaa aggccagtgg gcaggcggcg cctacgctgc ggagccggag   540
gagaacaagc ggacgcgcac ggcctacacg cgcgcacagc tgctagagct ggagaaggag   600
ttcctattca acaagtacat ctcacggccg cgccgggtgg agctggctgt catgttgaac   660
ttgaccgaga gacacatcaa gatctggttc caaaaccgcc gcatgaagtg gaaaaaggag   720
gaggacaaga gcgcggcgg cgggacagct gtcggggtg gcggggtcgc ggagcctgag    780
caggactgcg ccgtgacctc cggcgaggag cttctggcgc tgccgccgcc gccgcccccc   840
ggaggtgctg tgccgcccgc tgccccgtt gccgcccgag agggccgcct gccgcctggc    900
cttagcgcgt cgccacagcc ctccagcgtc gcgcctcggc ggccgcagga accacgatga    960
gaggcaggag ctgctcctgg ctgagggct tcaaccactc gccgaggagg agcagagggc   1020
ctaggaggac cccgggcgtg gaccaccgc cctggcagtt gaatgggcg gcaattgcgg   1080 ggcccacctt agaccgaagg ggaaaacccg ctctctcagg cgcatgtgcc agttggggcc   1140
ccgcgggtag atgccggcag gccttccgga agaaaaagag ccattggttt ttgtagtatt   1200
ggggccctct tttagtgata ctggattggc gttgtttgtg gctgttgcgc acatccctgc   1260
cctcctacag cactccacct tgggacctgt ttagagaagc cggctcttca agacaatgg    1320 aaactgtacc atacacattg gaaggctccc taacacacac agcggggaag ctgggccgag   1380
taccttaatc tgccataaag ccattcttac tcgggcgacc cctttaagtt tagaaataat   1440
tgaaaggaaa tgtttgagtt ttcaaagatc ccgtgaaatt gatgccagtg gaatacagtg   1500
agtcctcctc ttcctcctcc tcctcttccc cctcccttc ctcctcctcc tcttcttttc    1560
cctcctcttc ctcttcctcc tgctctcctt cctcccct cctcttttcc ctcctcttcc    1620
tcttcctcct gctctccttt cctcccctc ctctttctcc tcctctcct cttcttcccc    1680 ctcctctccc tcctcctctt cttccccctc ctctccctcc tcctcttctt ctccctcctc   1740
ttcctcttcc tcctcttcca cgtgctctcc tttcctcccc ctcctcttgc tccccttctt   1800 cccgtcctc ttcctcctcc tcctcttctt ctccctcctc ttcctcctcc tctttcttcc   1860
```

```
tgacctcttt ctttctcctc ctcctccttc tacctcccct tctcatccct cctcttcctc    1920
ttctctagct gcacacttca ctactgcaca tcttataact tgcaccccct tcttctgagg    1980
aagagaacat cttgcaaggc agggcgagca gcggcagggc tggcttagga gcagtgcaag    2040
agtccctgtg ctccagttcc acactgctgg cagggaaggc aaggggggac gggcctggat    2100 ctggggtga gggagaaaga tggacccctg ggtgaccact aaaccaaaga tattcggaac    2160
tttctattta ggatgtggac gtaattcctg ttccgaggta gaggctgtgc tgaagacaag    2220
cacagtggcc tggtgcgcct tggaaaccaa caactattca cgagccagta tgaccttcac    2280
atctttagaa attatgaaaa cgtatgtgat tggagggttt ggaaaaccag ttatcttatt    2340
taacatttta aaaattacct aacagttatt tacaaacagg tctgtgcatc ccaggtctgt    2400
cttcttttca aggtctgggc cttgtgctcg ggttatgttt gtgggaaatg cttaataaat    2460
actgataata tgggaagaga tgaaaactga ttctcctcac tttgtttcaa acctttctgg    2520
cagtgggatg attcgaattc acttttaaaa ttaaattagc gtgttttgtt ttg           2573
```

<210> SEQ ID NO 45
<211> LENGTH: 328
<212> TYPE: PRT
<213> ORGANISM: Homo sapiens

<400> SEQUENCE: 45

```
Met Asp Ala Val Leu Leu Glu His Phe Pro Gly Gly Leu Asp Ala Phe
1               5                   10                  15

Pro Ser Ser Tyr Phe Asp Glu Asp Phe Phe Thr Asp Gln Ser Ser
            20                  25                  30

Arg Asp Pro Leu Glu Asp Gly Asp Glu Leu Leu Ala Asp Glu Gln Ala
        35                  40                  45

Glu Val Glu Phe Leu Ser His Gln Leu His Glu Tyr Cys Tyr Arg Asp
    50                  55                  60

Gly Ala Cys Leu Leu Leu Gln Pro Ala Pro Ala Ala Pro Leu Ala
65                  70                  75                  80

Leu Ala Pro Pro Ser Ser Gly Gly Leu Gly Glu Pro Asp Asp Gly Gly
                85                  90                  95

Gly Gly Gly Tyr Cys Cys Glu Thr Gly Ala Pro Pro Gly Gly Phe Pro
            100                 105                 110

Tyr Ser Pro Gly Ser Pro Ser Cys Leu Ala Tyr Pro Cys Ala Gly
        115                 120                 125

Ala Ala Val Leu Ser Pro Gly Ala Arg Leu Arg Gly Leu Ser Gly Ala
    130                 135                 140

Ala Ala Ala Ala Arg Arg Arg Arg Val Arg Ser Glu Ala Glu
145                 150                 155                 160

Leu Gln Gln Leu Arg Gln Ala Ala Asn Val Arg Glu Arg Arg Met
                165                 170                 175

Gln Ser Ile Asn Asp Ala Phe Glu Gly Leu Arg Ser His Ile Pro Thr
            180                 185                 190

Leu Pro Tyr Glu Lys Arg Leu Ser Lys Val Asp Thr Leu Arg Leu Ala
        195                 200                 205

Ile Gly Tyr Ile Asn Phe Leu Ser Glu Leu Val Gln Ala Asp Leu Pro
    210                 215                 220

Leu Arg Gly Gly Gly Ala Gly Gly Cys Gly Gly Pro Gly Gly Gly
225                 230                 235                 240

Arg Leu Gly Gly Asp Ser Pro Gly Ser Gln Ala Gln Lys Val Ile Ile
```

```
                245                 250                 255
Cys His Arg Gly Thr Arg Ser Pro Ser Pro Ser Asp Pro Asp Tyr Gly
            260                 265                 270

Leu Pro Pro Leu Ala Gly His Ser Leu Ser Trp Thr Asp Glu Lys Gln
        275                 280                 285

Leu Lys Glu Gln Asn Ile Ile Arg Thr Ala Lys Val Trp Thr Pro Glu
    290                 295                 300

Asp Pro Arg Lys Leu Asn Ser Lys Ser Ser Phe Asn Asn Ile Glu Asn
305                 310                 315                 320

Glu Pro Pro Phe Glu Phe Val Ser
                325

<210> SEQ ID NO 46
<211> LENGTH: 1339
<212> TYPE: DNA
<213> ORGANISM: Homo sapiens

<400> SEQUENCE: 46
atggacgcgg tgttgctgga gcacttcccc gggggcctag acgcctttcc ttcttcgtac      60
ttcgacgagg acgacttctt caccgaccag tcttcacggg accccctgga ggacggcgat     120
gagctgctgg cggacgagca ggccgaggtg gagttcctta gccaccagct ccacgagtac     180
tgctaccgcg acggggcgtg cctgctgctg cagcccgcgc cccggccgc cccgctagcg      240 ctcgccccgc cgtcctcggg gggcctcggt gagccagacg acgcggcgg cggcggctac      300 tgctgcgaga cggggcgcc cccaggcggc ttcccctact cgcccggctc gccgccctcg      360
tgcctggcct acccgtgcgc cggggcggca gtactgtctc ccggggcgcg gctgcgcggc      420
ctgagcggag cggcggctgc ggcgcgcgg cgccggcggc gggtgcgctc cgaggcggag      480
ctgcagcagc tgcggcaggc ggccaacgtg cgcgagcggc ggcgcatgca gtccatcaac      540
gacgccttcg aggggctgcg ctcgcacatc cccacgctgc cctacagaa gcgcctctcc      600 aaggtggaca cgctgcgcct ggccatcggc tacatcaact cctcagcga gctcgtgcag      660 gccgacctgc ccttgcgcgg cggtggcgcg ggcggctgcg gggggccggg cggcggcggg      720
cgcctgggcg gggacagccc gggcagccag gcccagaagg tcatcatctg ccatcggggc      780
acccggtccc cctcccccag cgaccctgat tatggcctcc ctcccctagc aggacactct      840
ctctcatgga ctgatgaaaa acaactcaag gaacaaaata ttatccgaac agccaaagtc      900
tggaccccag aggaccccag aaaactcaac agcaaatctt ccttcaacaa catagaaaac      960
gaaccaccat ttgagtttgt gtcctgagaa gtcccagact cggctgaaga tctgattatg     1020
tctctgtgca tattgtacat gtaaatatct ataatgtaaa tgtaatttaa gaatcaaatt     1080
tttcgaatgg caatcaactg tttattattt atctatttat tatcctgttg agttgatgaa     1140
atagatgatt tcttttttaaa tatataattt ataaactta tcctgatttt ctgaaaatat      1200
gcaatagcct atgattttcc tgaactctgt gttgttggga gaactctggc cagaaaacgt     1260
cctgcttatt tattgccaga tatggtttat ttctaagcgt tgtcaataaa tgctatttac     1320 acctttttcct gaaaaaaaa                                                  1339

<210> SEQ ID NO 47
<211> LENGTH: 1555
<212> TYPE: DNA
<213> ORGANISM: Homo sapiens

<400> SEQUENCE: 47
```

```
cggcgatggc cccactcgga tacttcttac tcctctgcag cctgaagcag gctctgggca    60
gctacccgat ctggtggtcg ctggctgttg ggccacagta ttcctccctg ggctcgcagc   120
ccatcctgtg tgccagcatc ccgggcctgg tccccaagca gctccgcttc tgcaggaact   180
acgtggagat catgcccagc gtggccgagg catcaagat tggcatccag gagtgccagc   240
accagttccg cggccgccgg tggaactgca ccaccgtcca cgacagcctg gccatcttcg   300
ggcccgtgct ggacaaagct accagggagt cggcctttgt ccacgccatt gcctcagccg   360
gtgtggcctt tgcagtgaca cgctcatgtg cagaaggcac ggccgccatc tgtggctgca   420
gcagccgcca ccagggctca ccaggcaagg gctggaagtg gggtggctgt agcgaggaca   480
tcgagtttgg tgggatggtg tctcgggagt cgccgacgc ccgggagaac cggccagatg   540
cccgctcagc catgaaccgc acaacaacg aggctgggcg ccaggccatc gccagccaca   600
tgcacctcaa gtgcaagtgc cacgggctgt cgggcagctg cgaggtgaag acatgctggt   660
ggtcgcaacc cgacttccgc gccatcggtg acttcctcaa ggacaagtac gacagcgcct   720
cggagatggt ggtggagaag caccgggagt cccgcggctg gtggagacc ctgcggccgc   780
gctacaccta cttcaaggtg cccacggagc gcgacctggt ctactacgag gcctcgccca   840
acttctgcga gcccaaccct gagacgggct ccttcggcac gcgcgaccgc acctgcaacg   900
tcagctcgca cggcatcgac ggctgcgacc tgctgtgctg cggccgcggc cacaacgcgc   960
gagcggagcg gcgccgggag aagtgccgct gcgtgttcca ctggtgctgc tacgtcagct  1020
gccaggagtg cacgcgcgtc tacgacgtgc acacctgcaa gtaggcaccg gccgcggctc  1080
cccctggacg gggcgggccc tgcctgaggg tgggcttttc cctgggtgga gcaggactcc  1140
cacctaaacg gggcagtact cctccctggg ggcgggactc ctccctgggg gtggggctcc  1200
tacctggggg cagaactcct acctgaaggc agggctcctc cctggagcta gtgtctcctc  1260
tctggtggct gggctgctcc tgaatgaggc ggagctccag gatggggagg ggctctgcgt  1320
tggcttctcc ctggggacgg ggctcccctg acagaggcg gggctacaga ttgggcgggg  1380
cttctcttgg gtgggacagg gcttctcctg cggggggcgag gcccctccca gtaagggcgt  1440
ggctctgggt gggcggggca ctaggtaggc ttctacctgc aggcggggct cctcctgaag  1500
gaggcgggc tctaggatgg ggcacggctc tggggtaggc tgctccctga gggcg        1555
```

<210> SEQ ID NO 48
<211> LENGTH: 385
<212> TYPE: PRT
<213> ORGANISM: Homo sapiens

<400> SEQUENCE: 48

```
Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
                20                  25                  30

Ser Ser Leu Gly Ser Gln Pro Ile Leu Cys Ala Ser Ile Pro Gly Leu
            35                  40                  45

Val Pro Lys Gln Leu Arg Phe Cys Arg Asn Tyr Val Glu Ile Met Pro
        50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
```

|   | 100 |   |   |   | 105 |   |   |   | 110 |   |   |
|---|---|---|---|---|---|---|---|---|---|---|---|
| His | Ala | Ile | Ala | Ser | Ala | Gly | Val | Ala | Phe | Ala | Val |
|   |   |   | 115 |   |   |   | 120 |   |   |   | 125 |
| Thr | Arg | Ser | Cys | Ala | Glu | Gly | Thr | Ala | Ala | Ile | Cys |
|   |   |   | 130 |   |   |   | 135 |   |   |   | 140 |
| Gly | Cys | Ser | Ser | Arg | His | Gln | Gly | Ser | Pro | Gly | Lys |
| 145 |   |   |   |   | 150 |   |   |   |   | 155 |   |
| Gly | Trp | Lys | Trp | Gly | Gly | Cys | Ser | Glu | Asp | Ile | Glu |
|   |   |   |   |   |   |   |   |   |   |   | 160 |
| Phe | Gly | Gly | Met | Val | Ser | Arg | Glu | Phe | Ala | Asp | Ala |
|   |   |   |   | 165 |   |   |   |   | 170 |   |   |
| Arg | Glu | Asn | Arg | Pro | Asp | Ala | Arg | Ser | Ala | Met | Asn |
|   |   |   | 175 |   |   |   | 180 |   |   |   | 185 |
| Arg | His | Asn | Asn | Glu | Ala | Gly | Arg | Gln | Ala | Ile | Ala |
|   |   |   |   |   | 190 |   |   |   |   | 195 |   |
| Ser | His | Met | His | Leu | Lys | Cys | Lys | Cys | His | Gly | Leu |
|   |   |   | 200 |   |   |   | 205 |   |   |   |   |
| Ser | Gly | Ser | Cys | Glu | Val | Lys | Thr | Cys | Trp | Trp | Ser |
|   | 210 |   |   |   |   | 215 |   |   |   |   | 220 |
| Gln | Pro | Asp | Phe | Arg | Ala | Ile | Gly | Asp | Phe | Leu | Lys |
|   |   |   |   | 225 |   |   |   |   | 230 |   |   |
| Asp | Lys | Tyr | Asp | Ser | Ala | Ser | Glu | Met | Val | Val | Glu |
|   |   |   | 235 |   |   |   | 240 |   |   |   |   |
| Lys | His | Arg | Glu | Ser | Arg | Gly | Trp | Val | Glu | Thr | Leu |
|   | 245 |   |   |   |   | 250 |   |   |   |   | 255 |
| Arg | Pro | Arg | Tyr | Thr | Tyr | Phe | Lys | Val | Pro | Thr | Glu |
|   |   |   | 260 |   |   |   | 265 |   |   |   |   |
| Arg | Asp | Leu | Val | Tyr | Tyr | Glu | Ala | Ser | Pro | Asn | Phe |
|   | 270 |   |   |   |   | 275 |   |   |   |   | 280 |
| Cys | Glu | Pro | Asn | Pro | Glu | Thr | Gly | Ser | Phe | Gly | Thr |
|   |   |   | 285 |   |   |   |   |   | 290 |   |   |
| Arg | Asp | Arg | Thr | Cys | Asn | Val | Ser | Ser | His | Gly | Ile |
|   |   | 295 |   |   |   |   | 300 |   |   |   |   |
| Asp | Gly | Cys | Asp | Leu | Leu | Cys | Cys | Gly | Arg | Gly | His |
| 305 |   |   |   |   | 310 |   |   |   |   | 315 |   |
| Asn | Ala | Arg | Ala | Glu | Arg | Arg | Arg | Glu | Lys | Cys | Arg |
|   |   |   | 320 |   |   |   |   | 325 |   |   |   |
| Cys | Val | Phe | His | Trp | Cys | Cys | Tyr | Val | Ser | Cys | Gln |
|   | 330 |   |   |   |   | 335 |   |   |   |   | 340 |
| Glu | Cys | Thr | Arg | Val | Tyr | Asp | Val | His | Thr | Cys | Lys |
|   |   |   |   | 345 |   |   |   |   | 350 |   |   |
| Asn | Pro | Gly | Ser | Arg | Ala | Gly | Asn | Ser | Ala | His | Gln |
|   |   | 355 |   |   |   |   | 360 |   |   |   |   |
| Pro | Pro | His | Pro | Gln | Pro | Pro | Val | Arg | Phe | His | Pro |
| 365 |   |   |   |   | 370 |   |   |   |   | 375 |   |
| Pro | Leu | Arg | Ala | Gly | Lys | Val | Pro |   |   |   |   |
|   |   |   | 380 |   |   |   | 385 |   |   |   |   |

<210> SEQ ID NO 49
<211> LENGTH: 1056
<212> TYPE: DNA
<213> ORGANISM: Homo sapiens

<400> SEQUENCE: 49

| atgagtcccc | gctcgtgcct | gcgttcgctg | cgcctcctcg | tcttcgccgt | cttctcagcc | 60 |
| gccgcgagca | actggctgta | cctggccaag | ctgtcgtcgg | tggggagcat | ctcagaggag | 120 |
| gagacgtgcg | agaaactcaa | gggcctgatc | cagaggcagg | tgcagatgtg | caagcggaac | 180 |
| ctggaagtca | tggactcggt | gcgccgcggt | gcccagctgg | ccattgagga | gtgccagtac | 240 |
| cagttccgga | accggcgctg | gaactgctcc | acactcgact | ccttgccgt | cttcggcaag | 300 |
| gtggtgacgc | aagggattcg | ggaggcggcc | ttggtgtacg | ccatctcttc | ggcaggtgtg | 360 |
| gcctttgcag | tgacgcgggc | gtgcagcagt | ggggagctgg | agaagtgcgg | ctgtgacagg | 420 |
| acagtgcatg | gggtcagccc | acagggcttc | cagtggtcag | gatgctctga | caacatcgcc | 480 |

```
tacggtgtgg ccttctcaca gtcgtttgtg gatgtgcggg agagaagcaa gggggcctcg    540
tccagcagag ccctcatgaa cctccacaac aatgaggccg gcaggaaggc catcctgaca    600
cacatgcggg tggaatgcaa gtgccacggg gtgtcaggct cctgtgaggt aaagacgtgc    660
tggcgagccg tgccgccctt ccgccaggtg ggtcacgcac tgaaggagaa gtttgatggt    720
gccactgagg tggagccacg ccgcgtgggc tcctccaggg cactggtgcc acgcaacgca    780
cagttcaagc cgcacacaga tgaggacttg gtgtacttgg agcctagccc cgacttctgt    840
gagcaggaca tgcgcagcgg cgtgctgggc acgaggggcc gcacatgcaa caagacgtcc    900
aaggccatcg acggctgtga gctgctgtgc tgtggccgcg gcttccacac ggcgcaggtg    960
gagctggctg aacgctgcag ctgcaaattc cactggtgct gcttcgtcaa gtgccggcag   1020
tgccagcggc tcgtggagtt gcacacgtgc cgatga                             1056
```

<210> SEQ ID NO 50
<211> LENGTH: 351
<212> TYPE: PRT
<213> ORGANISM: Homo sapiens

<400> SEQUENCE: 50

```
Met Ser Pro Arg Ser Cys Leu Arg Ser Leu Arg Leu Leu Val Phe Ala
1               5                   10                  15

Val Phe Ser Ala Ala Ala Ser Asn Trp Leu Tyr Leu Ala Lys Leu Ser
            20                  25                  30

Ser Val Gly Ser Ile Ser Glu Glu Thr Cys Glu Lys Leu Lys Gly
        35                  40                  45

Leu Ile Gln Arg Gln Val Gln Met Cys Lys Arg Asn Leu Glu Val Met
    50                  55                  60

Asp Ser Val Arg Arg Gly Ala Gln Leu Ala Ile Glu Glu Cys Gln Tyr
65                  70                  75                  80

Gln Phe Arg Asn Arg Arg Trp Asn Cys Ser Thr Leu Asp Ser Leu Pro
                85                  90                  95

Val Phe Gly Lys Val Val Thr Gln Gly Ile Arg Glu Ala Ala Leu Val
            100                 105                 110

Tyr Ala Ile Ser Ser Ala Gly Val Ala Phe Ala Val Thr Arg Ala Cys
        115                 120                 125

Ser Ser Gly Glu Leu Glu Lys Cys Gly Cys Asp Arg Thr Val His Gly
    130                 135                 140

Val Ser Pro Gln Gly Phe Gln Trp Ser Gly Cys Ser Asp Asn Ile Ala
145                 150                 155                 160

Tyr Gly Val Ala Phe Ser Gln Ser Phe Val Asp Val Arg Glu Arg Ser
                165                 170                 175

Lys Gly Ala Ser Ser Arg Ala Leu Met Asn Leu His Asn Asn Glu
            180                 185                 190

Ala Gly Arg Lys Ala Ile Leu Thr His Met Arg Val Glu Cys Lys Cys
        195                 200                 205

His Gly Val Ser Gly Ser Cys Glu Val Lys Thr Cys Trp Arg Ala Val
    210                 215                 220

Pro Pro Phe Arg Gln Val Gly His Ala Leu Lys Glu Lys Phe Asp Gly
225                 230                 235                 240

Ala Thr Glu Val Glu Pro Arg Arg Val Gly Ser Ser Arg Ala Leu Val
                245                 250                 255

Pro Arg Asn Ala Gln Phe Lys Pro His Thr Asp Glu Asp Leu Val Tyr
            260                 265                 270
```

Leu Glu Pro Ser Pro Asp Phe Cys Glu Gln Asp Met Arg Ser Gly Val
            275                 280                 285

Leu Gly Thr Arg Gly Arg Thr Cys Asn Lys Thr Ser Lys Ala Ile Asp
        290                 295                 300

Gly Cys Glu Leu Leu Cys Cys Gly Arg Gly Phe His Thr Ala Gln Val
305                 310                 315                 320

Glu Leu Ala Glu Arg Cys Ser Cys Lys Phe His Trp Cys Cys Phe Val
                325                 330                 335

Lys Cys Arg Gln Cys Gln Arg Leu Val Glu Leu His Thr Cys Arg
            340                 345                 350

<210> SEQ ID NO 51
<211> LENGTH: 1143
<212> TYPE: DNA
<213> ORGANISM: Homo sapiens

<400> SEQUENCE: 51

| | |
|---|---|
| atgaagaagt ccattggaat attaagccca ggagttgctt tggggatggc tggaagtgca | 60 |
| atgtcttcca agttcttcct agtggctttg gccatatttt tctccttcgc ccaggttgta | 120 |
| attgaagcca attcttggtg gtcgctaggt atgaataacc ctgttcagat gtcagaagta | 180 |
| tatattatag gagcacagcc tctctgcagc caactggcag gactttctca aggacagaag | 240 |
| aaactgtgcc acttgtatca ggaccacatg cagtacatcg agaaggcgc gaagacaggc | 300 |
| atcaaagaat gccagtatca attccgacat cgaaggtgga actgcagcac tgtggataac | 360 |
| acctctgttt ttggcagggt gatgcagata ggcagccgcg agacggcctt cacatacgcg | 420 |
| gtgagcgcag caggggtggt gaacgccatg agccgggcgt gccgcgaggg cgagctgtcc | 480 |
| acctgcggct gcagccgcgc cgcgcgcccc aaggacctgc cgcgggactg gctctggggc | 540 |
| ggctgcggcg acaacatcga ctatggctac cgctttgcca aggagttcgt ggacgcccgc | 600 |
| gagcgggagc gcatccacgc caagggctcc tacgagagtg ctcgcatcct catgaacctg | 660 |
| cacaacaacg aggccggccg caggacggtg tacaacctgg ctgatgtggc ctgcaagtgc | 720 |
| catggggtgt ccggctcatg tagcctgaag acatgctggc tgcagctggc agacttccgc | 780 |
| aaggtgggtg atgccctgaa ggagaagtac gacagcgcgg cggccatgcg gctcaacagc | 840 |
| cggggcaagt tggtacaggt caacagccgc ttcaactcgc ccaccacaca agacctggtc | 900 |
| tacatcgacc ccagccctga ctactgcgtg cgcaatgaga gcaccggctc gctgggcacg | 960 |
| cagggccgcc tgtgcaacaa gacgtcggag ggcatggatg gctgcgagct catgtgctgc | 1020 |
| ggccgtggct acgaccagtt caagaccgtg cagacggagc gctgccactg caagttccac | 1080 |
| tggtgctgct acgtcaagtg caagaagtgc acggagatcg tggaccagtt tgtgtgcaag | 1140 |
| tag | 1143 |

<210> SEQ ID NO 52
<211> LENGTH: 380
<212> TYPE: PRT
<213> ORGANISM: Homo sapiens

<400> SEQUENCE: 52

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
            20                  25                  30

Phe Phe Ser Phe Ala Gln Val Val Ile Glu Ala Asn Ser Trp Trp Ser

-continued

```
                35                  40                  45
Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380
```